(12) United States Patent
Chen et al.

(10) Patent No.: US 8,877,742 B2
(45) Date of Patent: Nov. 4, 2014

(54) COMPOUNDS

(75) Inventors: Deborah W. Chen, Singapore (SG); Sarah Duncan, Singapore (SG); Nigel Paul King, Singapore (SG); Kiew Ching Lee, Singapore (SG); Sing Yeung Mak, Singapore (SG); Dean Andrew Rivers, Singapore (SG)

(73) Assignee: GlaxoSmithKline Intellectual Property Limited, Brentford, Middlesex (GB)

( * ) Notice: Subject to any disclaimer, the term of this patent is extended or adjusted under 35 U.S.C. 154(b) by 0 days.

(21) Appl. No.: 14/119,900

(22) PCT Filed: Jun. 8, 2012

(86) PCT No.: PCT/US2012/041442
§ 371 (c)(1),
(2), (4) Date: Jan. 27, 2014

(87) PCT Pub. No.: WO2012/170752
PCT Pub. Date: Dec. 13, 2012

(65) Prior Publication Data
US 2014/0155375 A1   Jun. 5, 2014

Related U.S. Application Data

(60) Provisional application No. 61/495,462, filed on Jun. 10, 2011.

(51) Int. Cl.
*C07D 471/04*   (2006.01)
*C07D 498/04*   (2006.01)

(52) U.S. Cl.
USPC ............. 514/210.18; 514/300; 514/253.04; 514/211.09; 514/230.5; 514/252.04; 514/210.21; 514/234.5; 546/113; 544/362; 544/105; 544/127; 544/238

(58) Field of Classification Search
USPC ............. 514/210.18, 300, 253.04, 211.09, 514/230.5, 252.04, 210.21, 213.01, 234.5; 546/113; 544/362, 105, 238, 127
See application file for complete search history.

(56) References Cited

U.S. PATENT DOCUMENTS 6,335,342 B1 * 1/2002 Longo et al. ............. 514/254.09
2010/0035917 A1   2/2010 Bamborough et al.

FOREIGN PATENT DOCUMENTS

| EP | 2166010 A1 | 3/2010 |
| WO | WO 2007/002433 A1 | 1/2007 |
| WO | WO 2007/081690 A2 | 7/2007 |

* cited by examiner

*Primary Examiner* — Niloofar Rahmani
(74) *Attorney, Agent, or Firm* — Haiyan Chen; William M Majarian; Carl W Battle

(57) ABSTRACT

The present invention relates to novel NADPH oxidase II inhibitors and their use in the treatment of diseases mediated by the NADPH oxidase enzymes.

14 Claims, No Drawings

COMPOUNDS

This application is a 371 of International Application No. PCT/US2012/041442, filed 8 Jun. 2012, which claims the benefit of U.S. Provisional Application No. 61/495,462, filed 10 Jun. 2011, which are incorporated herein in their entireties.

The present invention relates to novel NADPH oxidase II inhibitors and their use in the treatment of diseases mediated by the NADPH oxidase enzymes.

BACKGROUND OF THE INVENTION

Reactive oxygen species (ROS) are oxygen-derived small molecules including oxygen radicals such as superoxide, hydroxyl, peroxyl and alkoxyl. Through interactions with a variety of target molecules including small molecules as well as nucleic acids, proteins, lipids and carbohydrates, ROS play an important role in the regulation of diverse physiological processes. However, ROS can also irreversibly destroy or alter the function of target molecules. Excessive exposure to ROS induces oxidative stress and causes genetic mutations. ROS have been identified as a major contributor of cellular damage (Bedard & Krause (2007) *Physiol. Rev.* 87:245-313).

The NADPH oxidases (NOX) are transmembrane proteins that transport electrons across biological membranes to generate ROS from oxygen. Unlike other cellular elements such as mitochondria which generate ROS as a byproduct, the NOX enzymes generate ROS as their primary function. Seven members of the NOX family have been identified: NOX1 to NOX5, Duox1 and Duox2 (Bedard & Krause (2007) *Physiol. Rev.* 87:245-313).

NOX2, which was first identified in phagocytic cells and is often referred to as the phagocytic NOX, is also expressed in a variety of other cell types including neurons, cardiomyocytes, skeletal muscle myocytes, hepatocytes, endothelial cell and hematopoietic stem cells. Mutations in the human NOX2 gene cause chronic granulomatous disease (CGD), an immune disorder characterized by the inability of phagocytes to produce bacteria-destroying ROS. NOX2 deficient mice, which display pathological features similar to that of CGD patients, have been widely used as animal models (Sorce & Krause (2009) *Antioxid. Redox. Signal.* 11:2481-2504).

ROS overproduction by NOX2 has been implicated in the pathogenesis of a variety of central nervous system diseases including amyotrophic lateral sclerosis, Parkinson's disease, Alzheimer's disease, multiple sclerosis and Huntington's disease. Amyotrophic lateral sclerosis (ALS) is a progressive neurodegenerative disease that affects motor neurons. Although the cause of ALS is largely unknown, oxidative stress is believed to play a crucial role in the development of ALS. Studies have shown that NOX2 was activated in the spinal cords of ALS patients and mutant SOD1 transgenic mice, which develops motor neuron degeneration comparable to those observed in ALS patients (Wu et al. (2006) *Proc. Natl. Acad. Sci. U.S.A.* 103:12132-12137). Recent studies in which mutant SOD1 mice were crossed with NOX2-deficient mice showed that NOX2 deficiency delayed neurodegeneration and increased lifespan of SOD1 mice, suggesting that NOX2 may play an important role in ALS pathogenesis (Marden et al. (2007) *J. Clin. Invest.* 117:2913-2919; Wu et al. (2006) *Proc. Natl. Acad. Sci. U.S.A.* 103:12132-12137). Parkinson's disease (PD) is a neurodegenerative disease characterized by progressive degeneration of dopaminergic neurons in the substantia nigra. Oxidative stress is believed to play an important role in the degeneration of dopaminergic neurons. Studies have shown that administration of lipopolysaccharide (LPS) resulted in the release of proinflammatory factors, the activation of NOX2 and the degeneration of dopaminergic neurons (Iravani et al. (2005) *Eur. J. Neurosci.* 22: 317-330; Qin et al. (2004) *J. Biol. Chem.* 279:1415-1421). In addition, NOX2 deficient mice were shown to be significantly protected against loss of dopaminergic neurons compared to wild-type mice (Qin et al. (2004) *J. Biol. Chem.* 279:1415-1421). The data thus suggest that NOX2 activation plays an important role in the loss of dopaminergic neurons in PD. NOX2 has also been implicated in the development of Alzheimer's disease (AD). Studies have shown that in the brain of AD patients, markers of oxidative stress increased with severity of the disease and NOX2 is activated (de la Monte & Wands (2006) *J. Alzheimers. Dis.* 9:167-181; Shimohama et al. (2000) *Biochem. Biophys. Res. Commun.* 273:5-9). In addition, studies in which the Tg2576 mice (an animal model of AD) were crossed with NOX2 deficient mice showed that oxidative stress and cerebrovascular dysfunction do not occur in Tg2576 mice deficient in NOX2 (Park et al. (2005) *J. Neurosci.* 25:1769-1777). There is also evidence that NOX2 is involved in the pathogenesis of multiple sclerosis (Sorce & Krause (2009) *Antioxid. Redox. Signal.* 11:2481-2504) and Huntington's disease (Stack et al. (2008) *Ann. N.Y. Acad. Sci.* 1147:79-92).

ROS overproduction by NOX2 has also been implicated in the pathogenesis of spinal cord injury (Kim et al. (2010) *Proc. Natl. Acad. Sci. U.S.A.* 107:14851-14856) and traumatic brain injury (Dohi et al. (2010) *J. Neuroinflamm.* 7:41). In addition, ROS overproduction by NOX2 has been implicated in the pathogenesis of ocular diseases including diabetic retinopathy (Al-Shabrawey et al. (2008) *IOVS* 49:3231-3238; 3239-3244).

ROS overproduction by NOX2 has also been implicated in the pathogenesis of a number of cardiovascular diseases including hypertension, atherosclerosis, cardiac hypertrophy and cardiac fibrosis. Studies have shown renovascular hypertension was significantly reduced in the NOX2 deficient mice (Jung et al. (2004) *Circulation* 109: 1795-1801). Human atherosclerotic plaques have been found to express large amounts of NOX2 (Zhou et al. (2006) *Hypertension* 47:81-86). Studies have also shown that NOX2 plays an important role in angiotensin II-induced cardiac hypertrophy and cardiac fibrosis (Bendall et al. (2002) *Circulation* 105:293-296; Johar et al. (2006) *FASEB J.* 20:1546-1548). In addition, ROS production by NOX2 is also believed to be involved in the pathogenesis of stroke. Studies have shown that brain injury resulted from stroke induced in NOX2 deficient mice was significantly less than that in the wild-type mice (Walder et al. (1997) *Stroke* 28:2252-2258).

ROS overproduction has also been implicated in the pathogenesis of a number of reproduction diseases such as prostate cancer and preeclampsia (Lim et al. (2005) *Prostate* 62: 200-7; Cui et al. (2006) *Placenta* 27: 422-31), the pathogenesis of liver diseases such as hepatic carcinogenesis, non-alcoholic fatty liver disease, liver ischemia, liver necrosis, liver reperfusion injury (Sancho et al. (2010) *J. Biol. Chem.* 285:24815-24); the pathogenesis of kidney diseases such as diabetic nephropathy, chronic renal failure and acute renal failure (Fu et al. (2010) *Am. J. Nephrol.* 32:581-9).

One approach to the treatment of those diseases associated with ROS overproduction is to search for compounds that inhibit NOX enzymes including NOX2.

SUMMARY OF THE INVENTION

The invention is directed to novel NOX2 inhibitors and their use in the treatment of diseases mediated by NOX enzymes including NOX2. Specifically, the invention is directed to compounds according to Formula (I).

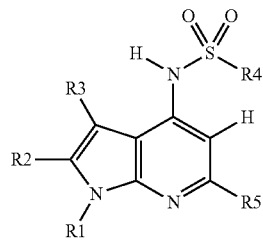

Formula (I)

wherein R1, R2, R3, R4 and R5 are defined below, and to pharmaceutically-acceptable salts thereof.

In another aspect, this invention provides the compounds of Formula (I) for use in the treatment of diseases mediated by NOX enzymes including NOX2. Examples of such diseases include neurodegenerative diseases such as amyotrophic lateral sclerosis, Parkinson's disease, Alzheimer's disease and Huntington's disease; neuroinflammatory diseases such as multiple sclerosis; cardiovascular diseases such as hypertension, atherosclerosis, cardiac hypertrophy, cardiac fibrosis and stroke; ocular diseases such as diabetic macular edema, diabetic retinopathy, age-related macular degeneration and glaucoma; spinal cord injury; traumatic brain injury; reproduction diseases such as prostate cancer and preeclampsia; liver diseases such as hepatic carcinogenesis, non-alcoholic fatty liver disease, liver ischemia, liver necrosis, liver reperfusion injury; kidney diseases such as diabetic nephropathy, chronic renal failure and acute renal failure. In yet another aspect, the invention is directed to methods of treating such diseases.

DETAILED DESCRIPTION OF THE INVENTION

Terms and Definitions

In describing the invention, chemical elements are identified in accordance with the Periodic Table of the Elements.

"Alkoxy" refers to the group —O—R where R is alkyl having the specified number of member atoms. Examples of alkoxy include methoxy, ethoxy and propoxy.

"Alkyl" refers to a monovalent saturated hydrocarbon chain having the specified number of member atoms. For example, C1-C6 alkyl refers to an alkyl group having from 1 to 6 member atoms. Alkyl groups may be optionally substituted with one or more substituent as defined herein. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

"Cycloalkyl" refers to a saturated hydrocarbon ring having the specified number of member atoms. Cycloalkyl groups are monocyclic ring systems. For example, C3-C6 cycloalkyl refers to a cycloalkyl group having from 3 to 6 member atoms. Cycloalkyl groups may be optionally substituted with one or more substituent as defined herein. Cycloalkyl includes cyclopropyl, cyclobutyl, cyclopentyl, and cyclohexyl.

"Enantiomerically enriched" refers to products whose enantiomeric excess is greater than zero. For example, enantiomerically enriched refers to products whose enantiomeric excess is greater than 50% ee, greater than 75% ee, and greater than 90% ee.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 99% ee or greater.

"Half-life" refers to the time required for half of a quantity of a substance to be converted to another chemically distinct species in vitro or in vivo.

"Halo" refers to the halogen radicals fluoro, chloro, bromo, and iodo.

"Heteroaryl" refers to an aromatic ring containing from 1 to 4 heteroatoms as member atoms in the ring. Heteroaryl groups containing more than one heteroatom may contain different heteroatoms. Heteroaryl groups may be optionally substituted with one or more substituent as defined herein. Heteroaryl groups are monocyclic ring systems or are fused or bridged bicyclic ring systems. Monocyclic heteroaryl rings have from 5 to 7 member atoms. Bicyclic heteroaryl rings have from 7 to 11 member atoms. Bicyclic heteroaryl rings include those rings wherein phenyl and a monocyclic heterocycloalkyl ring are attached forming a fused, spiro, or bridged bicyclic ring system, and those rings wherein a monocyclic heteroaryl ring and a monocyclic cycloalkyl, cycloalkenyl, heterocycloalkyl, or heteroaryl ring are attached forming a fused, spiro, or bridged bicyclic ring system. Heteroaryl includes pyrrolyl, pyrazolyl, imidazolyl, oxazolyl, isoxazolyl, oxadiazolyl, thiazolyl, isothiazolyl, thiadiazolyl, furanyl, furazanyl, thienyl, triazolyl, pyridinyl, pyrimidinyl, pyridazinyl, pyrazinyl, triazinyl, tetrazinyl, tetrazolyl, indolyl, isoindolyl, indolizinyl, indazolyl, indolinyl, isoindolinyl, purinyl, quinolinyl, isoquinolinyl, quinoxalinyl, quinazolinyl, pteridinyl, cinnolinyl, benzimidazolyl, benzopyranyl, benzoxazolyl, benzisoxazolyl, benzofuranyl, isobenzofuranyl, benzothiazolyl, benzisothiazolyl, benzothienyl, furopyridinyl, benzomorpholinyl, tetrahydroquinolinyl and naphthyridinyl.

"Heteroatom" refers to a nitrogen, sulphur, or oxygen atom.

"Heterocycloalkyl" refers to a saturated or unsaturated ring containing from 1 to 2 heteroatoms as member atoms in the ring. However, heterocycloalkyl rings are not aromatic. Heterocycloalkyl groups containing more than one heteroatom may contain different heteroatoms. Heterocycloalkyl groups may be optionally substituted with one or more substituent as defined herein. Heterocycloalkyl groups are monocyclic ring systems containing from 4 to 7 member atoms. In certain embodiments, heterocycloalkyl is saturated. In other embodiments, heterocycloalkyl is unsaturated but not aromatic. Heterocycloalkyl includes pyrrolidinyl, tetrahydrofuranyl, dihydrofuranyl, pyranyl, tetrahydropyranyl, dihydropyranyl, tetrahydrothienyl, pyrazolidinyl, oxazolidinyl, thiazolidinyl, piperidinyl, homopiperidinyl, piperazinyl, morpholinyl, thiamorpholinyl, azepinyl, 1,3-dioxolanyl, 1,3-dioxanyl, 1,4-dioxanyl, 1,3-oxathiolanyl, 1,3-oxathianyl, 1,3-dithianyl, azetidinyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group, such as alkyl, alkenyl, alkynyl, aryl, cycloalkyl, cycloalkenyl, heterocycloalkyl, or heteroaryl, may be unsubstituted, or the group may be substituted with one or more substituent as defined.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

"Substituted" in reference to a group indicates that one or more hydrogen atom attached to a member atom within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituent, one or more (as appropriate) member atom within the group may be substituted. In addition, a single member atom within the group may be substituted with more than one substituent as long as such substitution is in accordance with the permitted valence of the atom. Suitable substituents are defined herein for each substituted or optionally substituted group.

Compounds

The present invention provides, in a first aspect, a compound of Formula (I) or a pharmaceutically acceptable salt thereof

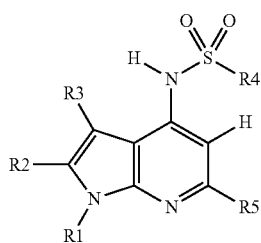

Formula (I)

wherein:
R1 is selected from the group consisting of:
 H,
 C1-C6 alkyl optionally substituted with cycloalkyl or C1-C3 alkoxy substituted with trimethylsilyl,
 $(CH_2)_k$NRaRa, wherein Ra is optionally substituted with halo or NRaRa,
 $(CH_2)_m$Rb, wherein Rb is optionally substituted with C1-C3 alkyl, C1-C3 alkoxy or C(O)ORa, and
 benzyl optionally substituted with C1-C3 alkoxy, halo or C1-C3 alkyl;
R2 is selected from the group consisting of:
 H, halo, CN, $(CH_2)_n$NRaRa, C(O)NRaRa, C(O)ORa, NRaC(O)Ra, $(CH_2)_s$ORa,
 C1-C6 alkyl optionally substituted with Rb,
 indoline optionally substituted with C1-C3 alkyl or halo,
 C2-C6 alkynyl optionally substituted with OH, C1-C3 alkoxy, NRaRa or Rb,
 $(CH_2)_n$Rb, wherein Rb is optionally substituted with C1-C3 alkyl,
 C(O)Rb, wherein Rb is optionally substituted with C1-C3 alkyl,
 $(CH_2)_n$Rc wherein Rc is optionally substituted with one or more substituents selected from the group consisting of C1-C3 alkoxy, C1-C3 alkyl, NRaRa and halo, and
 $(CH_2)_n$Rd wherein Rd is optionally substituted with one or more substituents selected from the group consisting of C1-C3 alkoxy, C1-C3 alkyl, NRaRa and halo;
R3 is selected from the group consisting of:
 H,
 indoline, wherein said indoline is optionally substituted with one or more substituents selected from the group consisting of 1) C1-C6 alkyl optionally substituted with C3-C5 cycloalkyl or halo, 2) cycloalkyl substituted with C1-C3 alkyl, 3) halo, 4) C1-C3 alkoxy, 5) $(CH_2)_t$OH, and 6) =O,
 indole optionally substituted with one or more 1) C1-C3 alkyl optionally substituted with halo, 2) halo, or 3) C1-C3 alkoxy,
 indazole optionally substituted with C1-C3 alkyl or halo,
 $(CH_2)_t$Rc wherein Rc is optionally substituted with one or more substituents selected from the group consisting of:
 1) Rb optionally substituted with C1-C3 alkyl, C(O)ORa or =O,
 2) C1-C3 alkoxy,
 3) C1-C4 alkyl optionally substituted with one to three F,
 4) $(CH_2)_t$NRaC(O)ORa,
 5) $(CH_2)_t$NRaRa,
 6) halo,
 7) —S—$CH_3$,
 8) —S(O)$CH_3$, and
 9) Rd,
 $(CH_2)_t$Rd wherein Rd is optionally substituted with one or more substituents selected from the group consisting of C1-C4 alkyl, C1-C3 alkoxy, halo, Rb, and $(CH_2)_t$NRaRa optionally substituted with dimethylamino;
R4 is selected from the group consisting of:
 C1-C3 alkyl optionally substituted with cycloalkyl,
 C3-C5 cycloalkyl,
 Rb optionally substituted with one or more substituents selected from the group consisting of: 1) C1-C3 alkyl, 2) halo, 3) $(CH_2)_v$NRaRa, 4) $(CH_2)_v$CF$_3$, 5) C(O)CH$_3$ and 6) benzylcarboxylate,
 Rc optionally substituted with one or more substituents selected from the group consisting of: 1) halo, 2) CN, 3) C1-C3 alkoxy, 4) Rb optionally substituted with C1-C3 alkyl, and 5) $(CH_2)_v$NRaRa, and
 Rd optionally substituted with one or more substituents selected from the group consisting of: 1) C1-C3 alkyl, 2) C1-C3 alkoxy, 3) CF$_3$, 4) halo, and 5) Rb optionally substituted with C1-C3 alkyl;
R5 is H, C1-C3 alkyl or halo;
each Ra is C1-C6 alkyl, C3-C5 cycloalkyl or H;
each Rb is heterocycloalkyl;
each Rc is phenyl;
each Rd is heteroaryl;
s is 1 or 2;
k is 2 or 3;
m is 0, 1, 2 or 3;
n is 0, 1, 2 or 3;
t is 0, 1, 2 or 3; and
v is 0, 1, 2 or 3.

In one embodiment, the invention relates to the compounds of Formula (I), wherein
R1 is H or C1-C3 alkyl;
R2 is H or methyl;

R3 is selected from the group consisting of:
  indoline optionally substituted with one or two substituents selected from the group consisting of 1) C1-C3 alkyl, 2) halo, and 3) C1-C3 alkoxy,
  phenyl optionally substituted with one or two substituents selected from the group consisting of 1) heterocycloalkyl, 2) NRaRa, and halo, and
  heteroaryl optionally substituted with C1-C3 alkyl or heterocycloalkyl.
R4 is selected from the group consisting of:
  heterocycloalkyl optionally substituted with C1-C3 alkyl,
  heteroaryl optionally substituted with C1-C3 methyl, and
  phenyl;
R5 is H; and
Ra is H or C1-C3 alkyl.

In one embodiment, this invention also relates to compounds of any of the above embodiments, wherein R1 is methyl. In one embodiment, this invention also relates to compounds of any of the above embodiments, wherein R1 is ethyl. In one embodiment, this invention also relates to compounds of any of the above embodiments, wherein R1 is isopropyl. In one embodiment, this invention also relates to compounds of any of the above embodiments, wherein R1 is H.

In one embodiment, this invention also relates to compounds of any of the above embodiments, wherein R2 is H. In one embodiment, this invention also relates to compounds of any of the above embodiments, wherein R2 is methyl. In one embodiment, this invention also relates to compounds of any of the above embodiments, wherein R2 is methylindolin. In one embodiment, this invention also relates to compounds of any of the above embodiments, wherein R2 is C(O)OCH$_3$ or COOH.

In one embodiment, this invention also relates to compounds of any of the above embodiments, wherein R3 is indoline. In one embodiment, this invention also relates to compounds of any of the above embodiments, wherein R3 is methylindolin, dimethylindolin or fluoro-methylindolin. In one embodiment, this invention also relates to compounds of any of the above embodiments, wherein R3 is methoxy-dimethylindol. In one embodiment, this invention also relates to compounds of any of the above embodiments, wherein R3 is (pyrrolidin-1-yl)phenyl or fluoro-(pyrrolidin-1-yl)phenyl. In one embodiment, this invention also relates to compounds of any of the above embodiments, wherein R3 is dimethylaminophenyl. In one embodiment, this invention also relates to compounds of any of the above embodiments, wherein R3 is (pyrrolidin-1-yl)pyridazin. In one embodiment, this invention also relates to compounds of any of the above embodiments, wherein R3 is a bicyclic heteroaryl ring optionally substituted with methyl.

In one embodiment, this invention also relates to compounds of any of the above embodiments, wherein R4 is methylpiperidinyl or isopropylpiperidinyl. In one embodiment, this invention also relates to compounds of any of the above embodiments, wherein R4 is phenyl or pyridinyl. In one embodiment, this invention also relates to compounds of any of the above embodiments, wherein R4 is methylpyrazol or methylpyridinyl. In one embodiment, this invention also relates to compounds of any of the above embodiments, wherein R4 is a bicyclic heteroaryl ring optionally substituted with methyl.

In one embodiment, this invention also relates to compounds of any of the above embodiments, wherein R5 is H. In one embodiment, this invention also relates to compounds of any of the above embodiments, wherein R5 is methyl.

The present invention provides, in yet another aspect, a compound of Formula (II) or a pharmaceutically acceptable salt thereof.

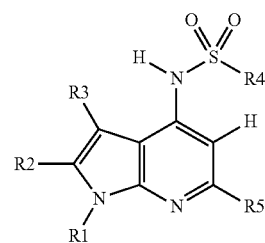

Formula (II)

wherein:
R1 is selected from the group consisting of:
  H,
  C1-C6 alkyl optionally substituted with cycloalkyl or C1-C3 alkoxy substituted with trimethylsilyl,
  (CH$_2$)$_k$NRaRa, wherein Ra is optionally substituted with halo or NRaRa,
  (CH$_2$)$_m$Rb, wherein Rb is optionally substituted with C1-C3 alkyl, C1-C3 alkoxy or C(O)ORa, and
  benzyl substituted with C1-C3 alkoxy, halo or C1-C3 alkyl;
R2 is selected from the group consisting of:
  H, halo, CN, (CH$_2$)$_n$NRaRa, C(O)NRaRa, C(O)ORa, NRaC(O)Ra, (CH$_2$)$_s$ORa,
  C1-C6 alkyl optionally substituted with Rb,
  indoline optionally substituted with C1-C3 alkyl or halo,
  C2-C6 alkynyl optionally substituted with OH, C1-C3 alkoxy, NRaRa or Rb,
  (CH$_2$)$_n$Rb, wherein Rb is optionally substituted with C1-C3 alkyl,
  C(O)Rb, wherein Rb is optionally substituted with C1-C3 alkyl,
  (CH$_2$)$_n$Rc wherein Rc is optionally substituted with one or more substituents selected from the group consisting of C1-C3 alkoxy, C1-C3 alkyl, NRaRa and halo, and
  (CH$_2$)$_n$Rd wherein Rd is optionally substituted with one or more substituents selected from the group consisting of C1-C3 alkoxy, C1-C3 alkyl, NRaRa and halo;
R3 is selected from the group consisting of:
  H,
  indoline, wherein said indoline is optionally substituted with one or more substituents selected from the group consisting of 1) C1-C6 alkyl optionally substituted with C3-C5 cycloalkyl or halo, 2) cycloalkyl substituted with C1-C3 alkyl, 3) halo, and 4) C1-C3 alkoxy,
  indole optionally substituted with 1) C1-C3 alkyl optionally substituted with halo, 2) halo, or 3) C1-C3 alkoxy,
  indazole optionally substituted with C1-C3 alkyl or halo,
  (CH$_2$)$_t$Rc wherein Rc is optionally substituted with one or more substituents selected from the group consisting of:
    1) Rb optionally substituted with C1-C3 alkyl or C(O)ORa,
    2) C1-C3 alkoxy,
    3) C1-C4 alkyl optionally substituted with one to three F
    4) (CH$_2$)$_t$NRaC(O)Ra,
    5) (CH$_2$)$_t$NRaRa,
    6) halo, and
    7) oxopyrrolinyl,
  (CH$_2$)$_t$Rd wherein Rd is optionally substituted with one or more substituents selected from the group consisting of C1-C4 alkyl, C1-C3 alkoxy, halo, Rb, and (CH$_2$)$_t$NRaRa optionally substituted with dimethylamino;

R4 is selected from the group consisting of:
C1-C3 alkyl optionally substituted with cycloalkyl,
Rb optionally substituted with one or more substituents selected from the group consisting of C1-C3 alkyl, halo, $(CH_2)_v$NRaRa and benzylcarboxylate,
Rd optionally substituted with one or more substituents selected from the group consisting of C1-C3 alkyl, $CF_3$ and halo,
C3-C5 cycloalkyl, and
Rc optionally substituted with one or more substituents selected from the group consisting of: halo, CN, C1-C3 alkoxy, Rb and $(CH_2)_v$NRaRa;
R5 is H, C1-C3 alkyl or halo;
each Ra is C1-C6 alkyl, C3-C5 cycloalkyl or H;
each Rb is heterocycloalkyl;
each Rc is phenyl;
each Rd is heteroaryl;
s is 1 or 2; k is 2 or 3; m is 0, 1, 2 or 3; n is 0, 1, 2 or 3; t is 0, 1, 2 or 3; and v is 0, 1, 2 or 3.

The present invention provides, in yet another aspect, a compound of Formula (III) or a pharmaceutically acceptable salt thereof

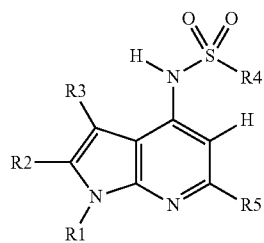

Formula (III)

wherein:
R1 is selected from the group consisting of:
H,
C1-C3 alkyl optionally substituted with C1-C3 alkoxy substituted with trimethylsilyl,
$(CH_2)_k$NRaRa,
$(CH_2)_m$Rb, wherein Rb is optionally substituted with C1-C3 alkyl or C(O)ORa, and
benzyl substituted with C1-C3 alkoxy;
R2 is selected from the group consisting of:
H,
C(O)ORa,
C1-C3 alkyl,
indoline optionally substituted with C1-C3 alkyl,
$(CH_2)_n$Rb, wherein Rb is optionally substituted with C1-C3 alkyl,
C(O)Rb, wherein Rb is optionally substituted with C1-C3 alkyl, and
$(CH_2)_n$Rd wherein Rd is optionally substituted with C1-C3 alkyl;
R3 is selected from the group consisting of:
H,
indoline, wherein said indoline is optionally substituted with one or more substituents selected from the group consisting of 1) C1-C3 alkyl optionally substituted with C3-C5 cycloalkyl and 2) halo,
indole optionally substituted with C1-C3 alkyl,
indazole optionally substituted with C1-C3 alkyl,
$(CH_2)_t$Rc wherein Rc is optionally substituted with one or more substituents selected from the group consisting of:
1) Rb optionally substituted with C1-C3 alkyl or C(O)ORa,
2) C1-C3 alkoxy,
3) C1-C4 alkyl,
4) $(CH_2)_v$NRaRa,
5) halo, and
6) oxopyrrolinyl,
$(CH_2)_t$Rd wherein Rd is optionally substituted with one or more substituents selected from the group consisting of C1-C4 alkyl, Rb optionally substituted with C1-C3 alkyl, and $(CH_2)_v$NRaRa optionally substituted with dimethylamino;
R4 is selected from the group consisting of:
Rb optionally substituted with one or more substituents selected from the group consisting of C1-C3 alkyl, halo and benzylcarboxylate,
Rd optionally substituted with one or more substituents selected from the group consisting of C1-C3 alkyl, $CF_3$ and halo,
C3-C5 cycloalkyl, and
Rc optionally substituted with one or more substituents selected from the group consisting of: halo, CN, C1-C3 alkoxy, Rb optionally substituted with C1-C3 alkyl;
R5 is H, C1-C3 alkyl or halo;
each Ra is C1-C4 alkyl, C3-C5 cycloalkyl or H;
each Rb is heterocycloalkyl;
each Rc is phenyl;
each Rd is heteroaryl;
k is 2 or 3; m is 0, 1, 2 or 3; n is 0, 1, 2 or 3; and t is 0, 1, 2 or 3.

In one embodiment, R1 is H. In another embodiment, R1 is C1-C3 alkyl.
In one embodiment, R2 is H. In another embodiment, R2 is C1-C3 alkyl.
In one embodiment, R3 is phenyl substituted with one or more substituents selected from the group consisting of pyrrolidinyl, dimethylamino and halo. In another embodiment, R3 is methylindoline or isopropylindoline optionally substituted with halo.
In one embodiment, R4 is phenyl optionally substituted with halo or CN. In another embodiment, R4 is heteroaryl optionally substituted with one or more C1-C3 alkyl. In yet another embodiment, R4 is C3-C5 cycloalkyl. In yet another embodiment, R4 is heterocycloalkyl optionally substituted with C1-C3 alkyl.
In one embodiment, R5 is H. In another embodiment, R5 is C1-C3 alkyl.
In one embodiment, R1 is methyl, ethyl or isopropyl, R2 is H or methyl, R3 is methylindoline or isopropylindoline, R4 is methylpyrazole and R5 is H.
In another embodiment, R1 is methyl or isopropyl, R2 is H, R3 is phenyl substituted with pyrrolidinyl, R4 is methylpyrazole, and R5 is H or methyl.
In yet another embodiment, R1 is methyl, R2 is H, R3 is methylindoline, R4 is C3-C5 cycloalkyl or phenyl, and R5 is H.

The meaning of any functional group or substituent thereon at any one occurrence in Formula I, or any subformula thereof, is independent of its meaning, or any other functional group's or substituent's meaning, at any other occurrence, unless stated otherwise.

The compounds according to Formula I may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in Formula I, or in any chemical structure illustrated herein, is not specified the structure is intended to encompass all individual stereoisomers and all mixtures thereof. Thus, compounds according to Formula I containing one or more chiral center may be used as racemic mixtures, enantiomerically enriched mixtures, or as enantiomerically pure individual stereoisomers.

Individual stereoisomers of a compound according to Formula I which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to Formula I may also contain double bonds or other centers of geometric asymmetry. Where the stereochemistry of a center of geometric asymmetry present in Formula I, or in any chemical structure illustrated herein, is not specified, the structure is intended to encompass the trans (E) geometric isomer, the cis (Z) geometric isomer, and all mixtures thereof.

The compounds of Formula (I) may exist as tautomers. Where tautomers exist, whether in equilibrium or predominately in one form, each tautomeric form and mixtures thereof are included in the present invention.

In certain embodiments, compounds according to Formula I may contain an acidic functional group. In certain other embodiments, compounds according to Formula I may contain a basic functional group. Thus, the skilled artisan will appreciate that pharmaceutically-acceptable salts of the compounds according to Formula I may be prepared. Indeed, in certain embodiments of the invention, pharmaceutically-acceptable salts of the compounds according to Formula I may be preferred over the respective free base or free acid because such salts may impart greater stability or solubility to the molecule thereby facilitating formulation into a dosage form. Accordingly, the invention is further directed to the use of pharmaceutically-acceptable salts of the compounds according to Formula I.

As used herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

As used herein, the term "compounds of the invention" means both the compounds according to Formula I and the pharmaceutically-acceptable salts thereof. The term "a compound of the invention" also appears herein and refers to both a compound according to Formula I and its pharmaceutically-acceptable salts.

The invention also includes various deuterated forms of the compounds of Formula (I). Each available hydrogen atom attached to a carbon atom may be independently replaced with a deuterium atom. A person of ordinary skill in the art will know how to synthesize deuterated forms of the compounds of Formula (I). Commercially available deuterated starting materials may be employed in the preparation of deuterated forms of the compounds of Formula (I), or they may be synthesized using conventional techniques employing deuterated reagents (e.g. lithium aluminum deuteride).

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The compounds of the invention have a pIC50 value of at least 4 in at least one of the suitable assays for determining the activity of a NOX2 inhibitor. Examples of such suitable assays include the fluorescence assay, the absorbance assay and the substrate depletion assay described herein.

Compound Preparation

The compounds according to Formula I are prepared using conventional organic syntheses. Suitable synthetic routes are depicted below in the following general reaction schemes. Starting materials and reagents depicted in the general reaction schemes below are commercially available or can be made from commercially available starting materials using methods known to those skilled in the art.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

Treatment of 1.5 with a compound 1.6 ($R_4$—$SO_2NH_2$) in the presence of a catalyst (such as $Pd(OAc)_2$) with a ligand (such as Xantphos) and a base (such as $Cs_2CO_3$) in a solvent

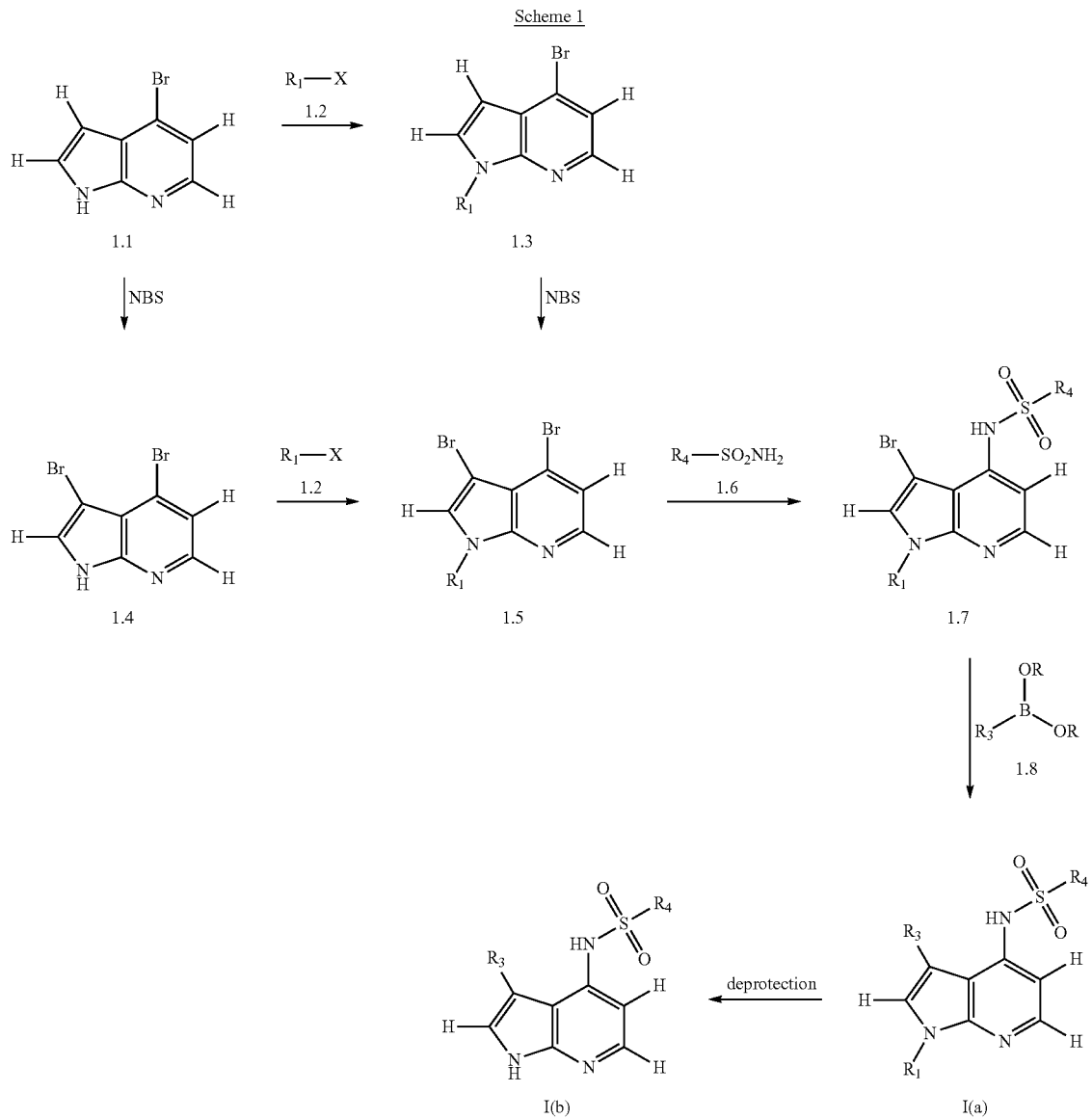

Scheme 1

Scheme 1 represents a general reaction scheme for preparing intermediates and certain compounds of Formula I. Intermediate 1.3 can be obtained by treatment of the corresponding azaindole 1.1 with compound 1.2 ($R_1$—X, wherein X is a halogen, e.g. SEMCl) in the presence of a base (such as DIPEA) in a solvent (such as DCM) at room temperature.

Intermediate 1.4 can be prepared by treatment of 1.1 with a suitable halogenating agent (such as NBS) in a solvent (such as DCM) at a temperature of 0° C.

Intermediate 1.5 can be obtained by treatment of 1.3 with a halogenating agent (such as NBS) in a solvent (such as DCM) at a temperature of 0° C. Intermediate 1.5 can also be obtained by treatment of 1.4 with 1.2 (such as SEMCl or MeI) in the presence of a base (such as DIPEA or NaH) in a solvent (such as DCM or DMF) at temperatures between 0° C. and room temperature.

(such as 1,4-dioxane) at temperatures between 100 and 120° C. (under conventional or microwave heating) can afford intermediate 1.7.

Compound I(a) can be obtained by treatment of intermediate 1.7 with compound 1.8 ($R_3$—$B(OR)_2$) in the presence of a catalyst (such as $Pd(OAc)_2$) and a ligand (such as [1,1'-biphenyl]-2-yldicyclohexylphosphine) or in the presence of a catalyst/ligand complex (such as $PdCl_2(dppf)$.DCM or $Pd(PPh_3)_4$) with a base (such as KF, CsF or $K_2HPO_4$) in a solvent (such as THF or DME) at temperatures between 50 and 120° C. (using either convention or microwave heating).

In cases where $R_1$ is a protecting group (such as SEM), this can be deprotected under appropriate conditions, utilising an acid (such as TFA or 4M HCl in 1,4-dioxane) optionally in a solvent (such as DCM) followed by further treatment with a base (such as 50% aqueous NaOH or TEM optionally in a solvent (such as THF or MeOH) as required.

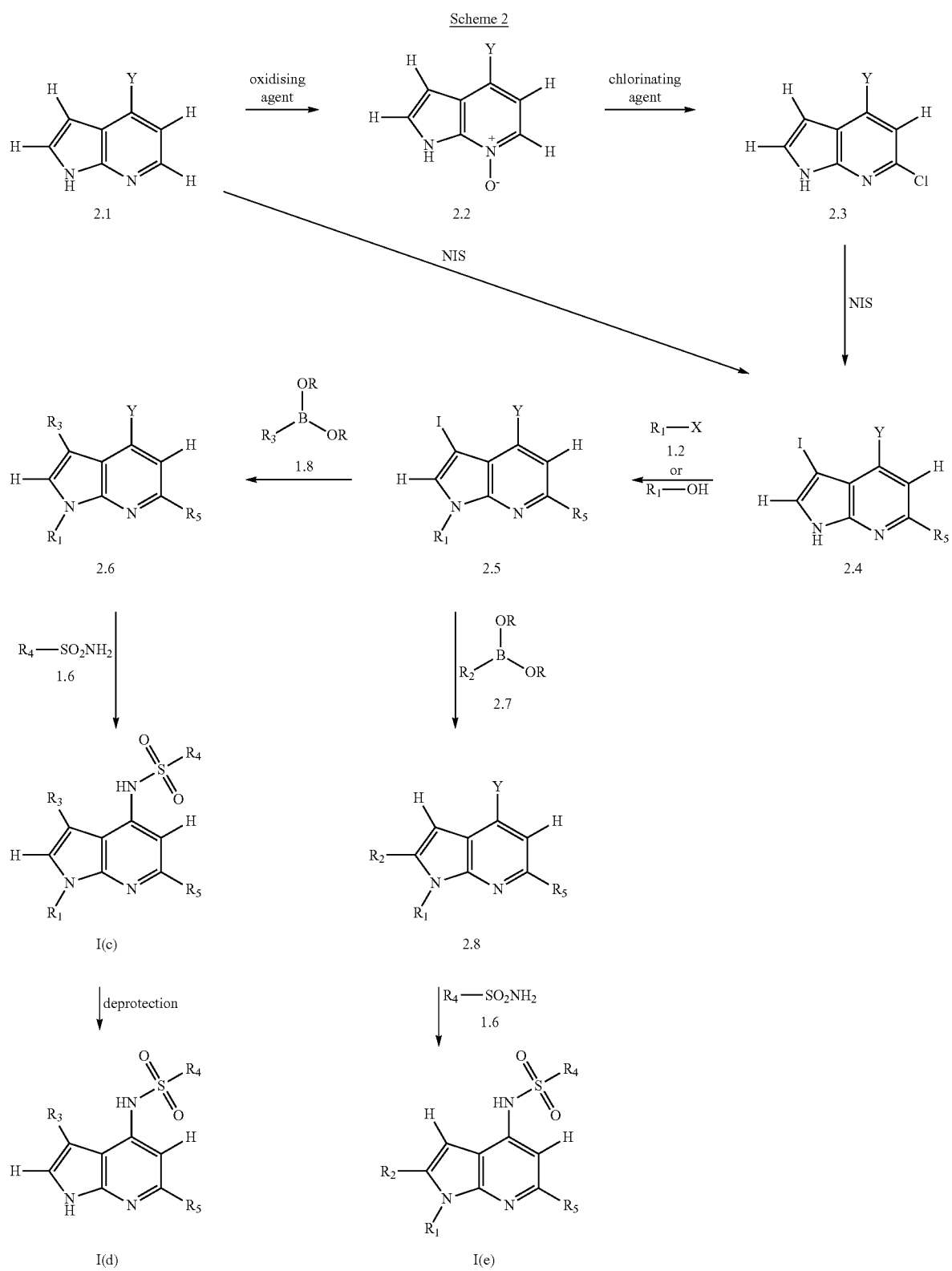

Scheme 2 represents another general scheme for preparing intermediates and certain compounds of Formula I. In Scheme 2, Y represents a halogen (such as Br or Cl) and $R_5$ represents either H or Cl.

Where $R_5$ is Cl, intermediate 2.3 can be prepared from compound 2.1. Intermediate 2.2 can be obtained by treatment of 2.1 with an oxidizing agent (such as mCPBA) in a solvent (such as diethyl ether) at temperatures between 0° C. and room temperature. Treatment of 2.2 with an appropriate reagent (such as methanesulfonyl chloride) in a solvent (such as DMF) at temperatures between 50 and 75° C. can give 2.3.

Intermediate 2.4 can be obtained by treatment of either 2.1 or 2.3 with a halogenating agent (such as NIS) in a solvent (such as chloroform, DCM or DMF) at temperatures between −40° C. and room temperature (using conventional or flow chemistry). Intermediate 2.4 can then be converted into intermediate 2.5 by various substitution reactions (such as alkylation or Mitsunobu reaction). Alkylation of 2.4 using 1.2 (such as MeI, iPrI, EtI or SEMCl) in the presence of a base (such as sodium hydride, DBU, DIPEA, $Cs_2CO_3$ or TBAI) in a solvent (such as DMF, DCM, THF or DMSO) at temperatures between 0 and 95° C. (using conventional or flow chemistry) can afford intermediate 2.5. Intermediate 2.5 can also be prepared from Mitsunobu reaction by treatment of 2.4 with an agent (such as isopropanol) in the presence of reagent (such as $PPh_3$) and an azodicarboxylate (such as DIAD) in a solvent (such as THF) at temperatures between 0° C. and room temperature.

Intermediate 2.6 can be obtained by treatment of 2.5 with 1.8 in the presence of a catalyst (such as $Pd(PPh_3)_2Cl_2$ or Pd(dppf)$Cl_2$-DCM adduct) and a base (such as $Na_2CO_3$) in a solvent (such as acetonitrile, ethanol, DMF, DCM, DME, MeOH and/or water) at temperatures between 55° C. and 100° C. (using conventional or microwave heating).

Treatment of 2.6 with a 1.6 in the presence of a catalyst (such as $Pd_2(dba)_3$ or $Pd(OAc)_2$) a ligand (such as Xantphos and/or Davephos) and a base (such as NaOtBu or $Cs_2CO_3$) in a solvent (such as 1,4-dioxane) at temperatures between 115 and 180° C. (using conventional or microwave heating) can afford compound I(c). Where $R_1$ in I(c) is a protecting group (such as SEM) this can be deprotected under appropriate conditions utilising an acid (such as 4M HCl or TFA) optionally in a solvent (such as DCM or 1,4-dioxane), followed by further treatment with a base (such as DIPEA or 50% aqueous NaOH) in a solvent (such as MeOH, THF and/or water) to give compound I(d).

Intermediate 2.8 can be obtained by treatment of 2.5 with compound 2.7 ($R_2$—B(OR)$_2$) in the presence of a catalyst (such as $Pd(PPh_3)_2Cl_2$ or PEPPSI-IPr) and a base (such as $Na_2CO_3$ or $K_3PO_4$) in a solvent (such as acetonitrile, 1,4-dioxane and/or water) at temperatures between 70 and 120° C. (using conventional or microwave heating).

Treatment of 2.8 with 1.6 in the presence of a catalyst (such as $Pd_2(dba)_3$ or $Pd(OAc)_2$), a ligand (such as Xantphos and/or Davephos) and a base (such as NaOtBu or $Cs_2CO_3$) in a solvent (such as acetonitrile or 1,4-dioxane) at temperatures between 115 and 180° C. (using conventional or microwave heating) can afford compound I(e).

Where further elaboration is required at $R_1$, $R_3$ and/or $R_4$, other reactions (such as oxidation, deprotection, substitution or reductive amination) can be performed at a suitable point in the reaction sequence to provide a desired intermediate or target compound.

Scheme 3

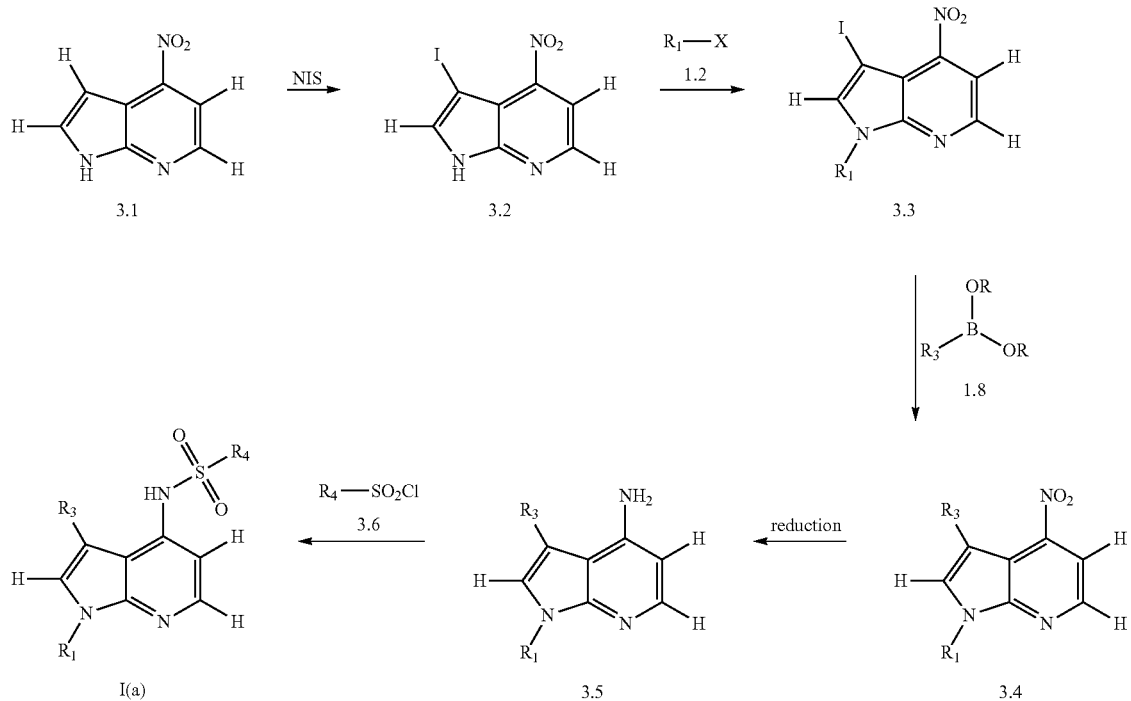

Scheme 3 represents another general scheme for preparing intermediates and certain compounds of Formula I. Intermediate 3.2 can be obtained by treatment of compound 3.1 with a halogenating agent (such as NIS) in a solvent (such as DCM) at temperatures between 0° C. and room temperature. Intermediate 3.3 can be obtained by treatment of 3.2 with 1.2 (such as MeI or iPrI) in the presence of a base (such as sodium hydride) in a solvent (such as DMF) at temperatures between 0° C. and room temperature.

Intermediate 3.4 can be obtained by treatment of 3.3 with 1.8 in the presence of a catalyst (such as $Pd(PPh_3)_2Cl_2$) and a base (such as $Na_2CO_3$) in a solvent (such as acetonitrile, DMF, water and/or DCM) at a temperature of 65° C. 3.4 can then be converted to intermediate 3.5 under appropriate conditions (such as H$_2$ with Pd/C catalyst) in a solvent (such as ethanol). Treatment of 3.5 with 3.6 (R$_4$—SO$_2$Cl) in the presence of a base (such as LiHMDS or NaOtBu) in a solvent (such as THF) at temperatures between 0° C. and room temperature can give compound I(a).
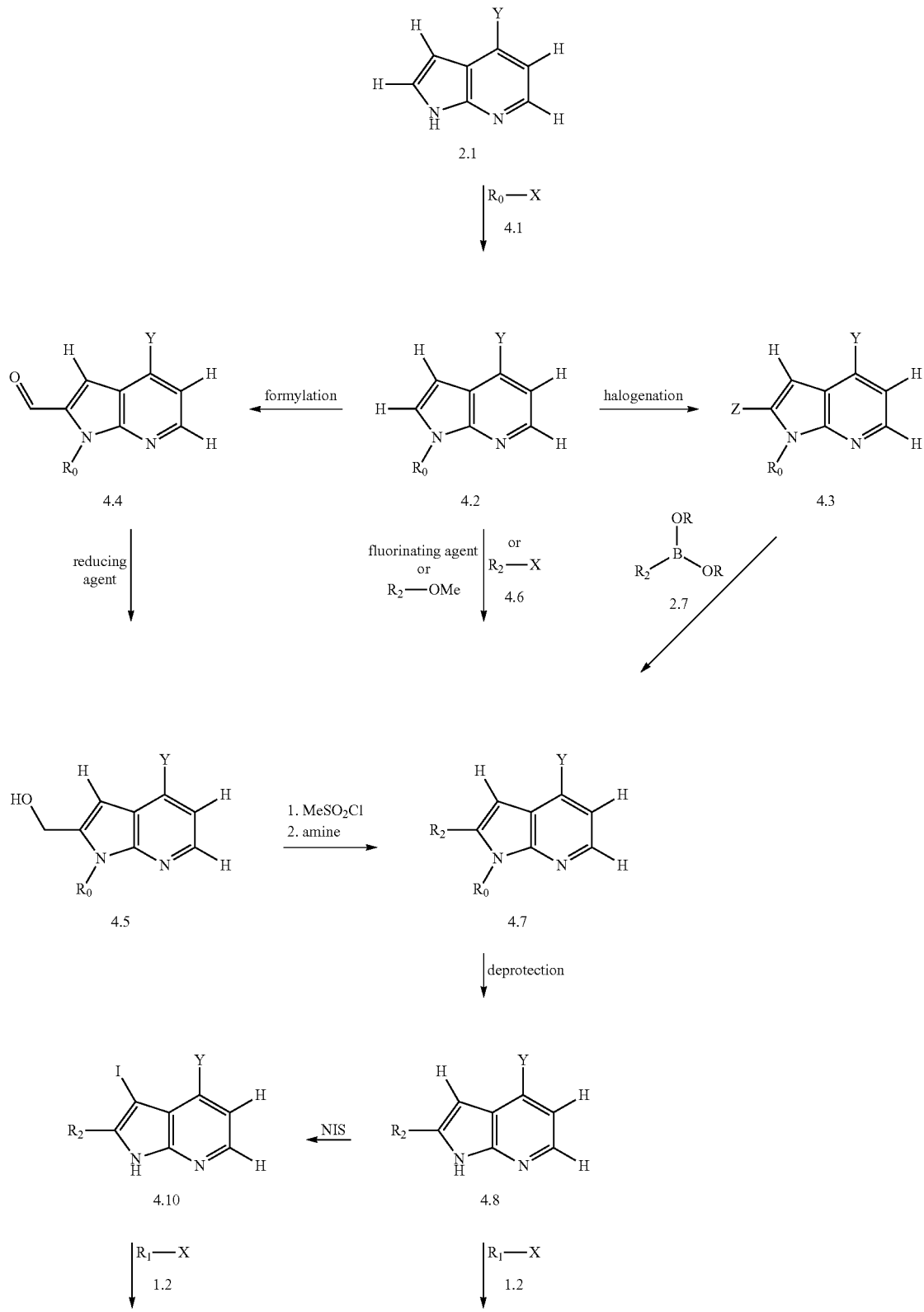

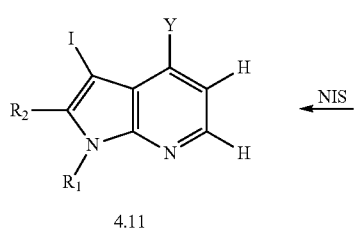

4.11

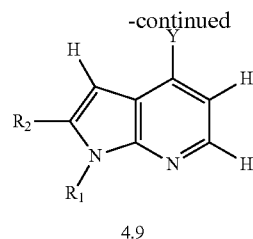

-continued 4.9

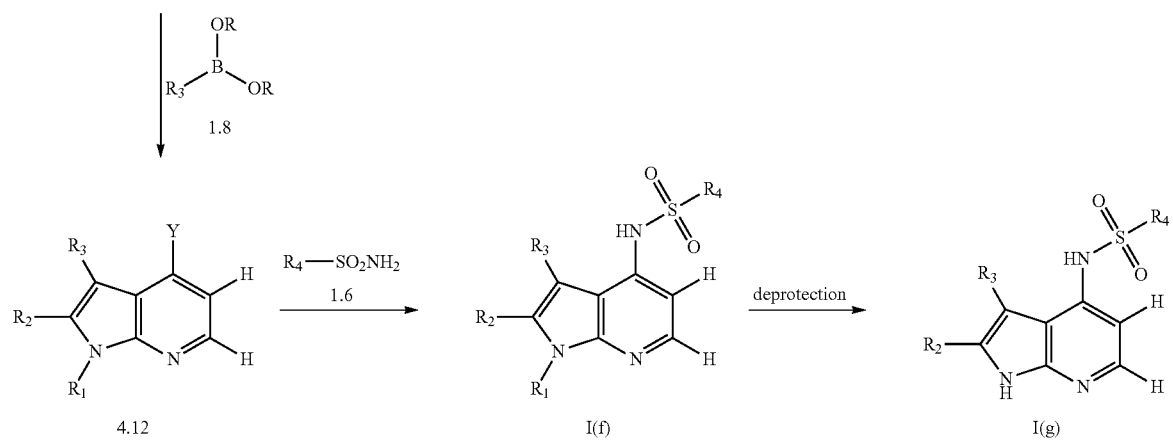

Scheme 4 represents another general reaction scheme for preparing intermediates and certain compounds of Formula I. In Scheme 4, Y and Z represent a halogen (such as Br or Cl). $R_O$ represents a protecting group (such as tosyl or phenyl sulfonyl).

Intermediate 4.2 can be obtained by treatment of 2.1 with compound 4.1 ($R_O$—X, e.g. TsCl or $PhSO_2Cl$) in the presence of a base (such as NaOtBu or NaH) in a solvent (such as DMF and/or THF) at temperatures between 0° C. and room temperature.

Intermediate 4.2 can then be converted into intermediate 4.7 by a variety of methods. Where $R_2$ is an alkyl group, 4.7 can be prepared by treatment of 4.2 with compound 4.6 ($R_2$—X, e.g. MeI) in the presence of a base (such as NaH or LDA) in a solvent (such as THF) at temperatures between −78° C. and room temperature.

Where $R_2$ is a halogen (such as F), treatment of 4.2 with an agent (such as $FN(SO_2Ph)_2$) in the presence of a base (such as LDA) in a solvent (such as THF) at a temperature of −78° C. can afford intermediate 4.7.

Where $R_2$ is an ester group, 4.7 can be prepared by treatment of 4.2 with an agent (such as $CO(OMe)_2$) in the presence of a base (such as LDA) in a solvent (such as THF) at a temperature of −78° C.

Where $R_2$ is a heterocycle, treatment of 4.2 with a halogenating agent (such as $I_2$) in the presence of a base (such as LDA) in a solvent (such as THF) at temperatures between −78 and 0° C. can afford intermediate 4.3. This can then be converted to 4.7 in the presence of 2.7 with a catalyst (such as $Pd(PPh_3)_4$) in the presence of a base (such as $K_2CO_3$) in a solvent (such as 1,4-dioxane, DMF and/or water) at temperatures between 100 and 120° C. (using conventional or microwave heating).

Where $R_2$ represents $CH_2Rb$, treatment of 4.2 with DMF in the presence of a base (such as LDA) in a solvent (such as THF) at temperatures between −78 to 0° C. can afford intermediate 4.4. This can be converted to the corresponding alcohol 4.5 utilising a reducing agent (such as $NaBH(OAc)_3$) in the presence of an acid (such as AcOH) and a solvent (such as DCM) at room temperature. Treatment of 4.5 with a reagent (such as $MeSO_2Cl$) in the presence of a base (such as DIPEA) in a solvent (such as DCM) at room temperature can afford the corresponding mesylate which can then be treated with an amine (such as morpholine) in a solvent (such as THF) at a temperature of 70° C. to afford 4.7.

Intermediate 4.8 can be obtained by deprotection of 4.7 under suitable conditions (such as 5M NaOH or $Cs_2CO_3$) in a solvent (such as MeOH or 1,4-dioxane) at temperatures between 0 and 70° C.

Treatment of 4.8 with 1.2 (such MeI) in the presence of a base (such as NaH) in a solvent (such as THF) at temperatures between 0° C. and room temperature can afford intermediate 4.9. This can then be treated with an appropriate halogenating agent (such as NIS) in a solvent (such as DCM) at temperatures between 0° C. and room temperature to afford 4.11.

Intermediate 4.8 can be converted to intermediate 4.10 in the presence of a halogenating agent (such as NIS) in a solvent (such as DCM) at temperatures between 0° C. and room temperature. Intermediate 4.10 can then be treated with 1.2 (such as MeI, $^iPrI$ or SEMCl) in the presence of a base (such as NaH or DIPEA) in a solvent (such as THF, DMF or DCM) at temperatures between 0° C. and room temperature to afford 4.11.

Intermediate 4.12 can be obtained from 4.11 by reaction with 1.8 in the presence of a catalyst (such as $Pd(PPh_3)_2Cl_2$) and a base (such as $Na_2CO_3$) in a solvent (such as MeCN, 1,4-dioxane, DMF, DCM and/or water) at temperatures between 65 and 100° C. (using conventional or microwave heating).

Compound I(f) can be obtained by treatment of 4.12 with 1.6 in the presence of a catalyst (such as $Pd_2(dba)_3$ or $Pd(OAc)_2$) with a ligand (such as Davephos or Xantphos) and a base (such as $Cs_2CO_3$) in a solvent (such as 1,4-dioxane) at temperatures between 120 and 150° C. (using conventional or microwave heating).

Where a protecting group is present at the $R_1$ position of I(f), this can be deprotected to give compound I(g) utilising appropriate conditions (such as 4M HCl or TBAF) in a solvent (such as 1,4-dioxane or THF) at temperatures between room temperature and 80° C., followed by reaction with a base (such as DIPEA) in a solvent (such as MeOH) at a temperature of 80° C. as required.

Where further elaboration is required at $R_2$, other reactions (such as deprotection, protection, alkylation, hydrolysis and amide coupling) can be performed at a suitable point in the reaction sequence to provide a desired intermediate or target compound.

presence of a base (such as LDA) in a solvent (such as THF) at temperatures between −78 and 0° C. 5.2 can then be converted to intermediate 5.3 in the presence of 2.7 with a catalyst (such as $Pd(PPh_3)_4$) in the presence of a base (such as $K_2CO_3$) in a solvent (such as 1,4-dioxane and/or water) at temperatures between 100 and 120° C. (using conventional or microwave heating).

Intermediate 5.3 can be converted to 4.11 by treatment with a halogenating agent (such as NIS) in a solvent (such as DCM) at a temperature of 0° C.

Intermediate 4.12 can be obtained from 4.11 by reaction with 1.8 in the presence of a catalyst (such as $Pd(PPh_3)_2Cl_2$)

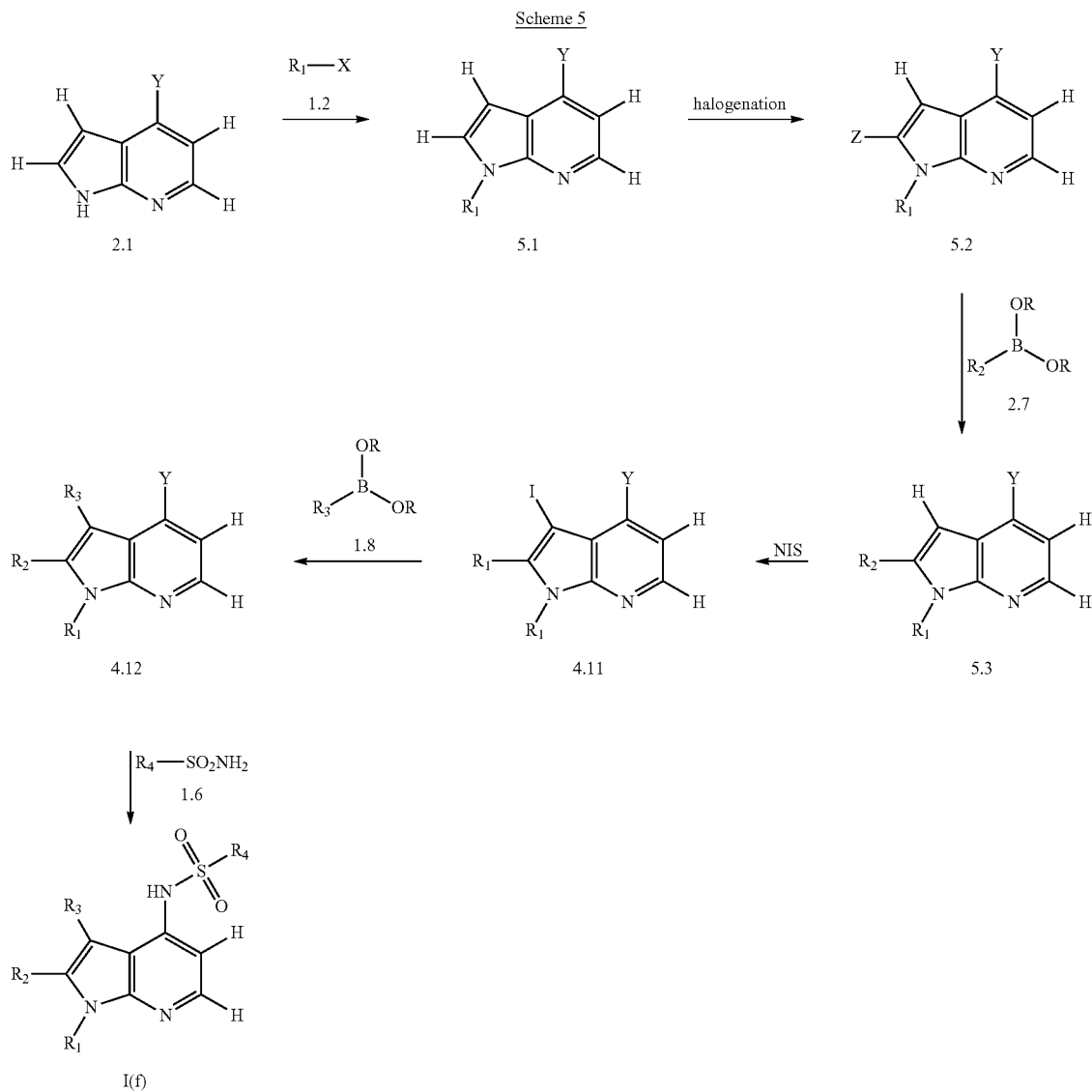

Scheme 5

Scheme 5 represents another general reaction scheme for preparing intermediates and certain compounds of Formula I. In Scheme 5, Y and Z represent a halogen (such as Br or Cl).

Intermediate 5.1 can be obtained by treatment of 2.1 with 1.2 (such as MeI) in the presence of a base (such as NaH) in a solvent (such as DMF) at temperatures between 0° C. and room temperature.

Intermediate 5.1 can then be converted into intermediate 5.2 by treatment with a halogenating agent (such as $I_2$) in the and a base (such as 2M aq $Na_2CO_3$) in a solvent (such as MeCN) at temperatures between 100 and 120° C. (using microwave heating).

Compound I(f) can be obtained by treatment of 4.12 with 1.6 in the presence of a catalyst (such as $Pd(OAc)_2$) with a ligand (such as Xantphos) and a base (such as $Cs_2CO_3$) in a solvent (such as 1,4-dioxane) at temperatures between 120 and 130° C. (using microwave heating).

Where further elaboration is required at $R_2$, other reactions (such as deprotection, protection, alkylation, hydrolysis and amide coupling) can be performed at a suitable point in the reaction sequence to provide a desired intermediate or target compound.

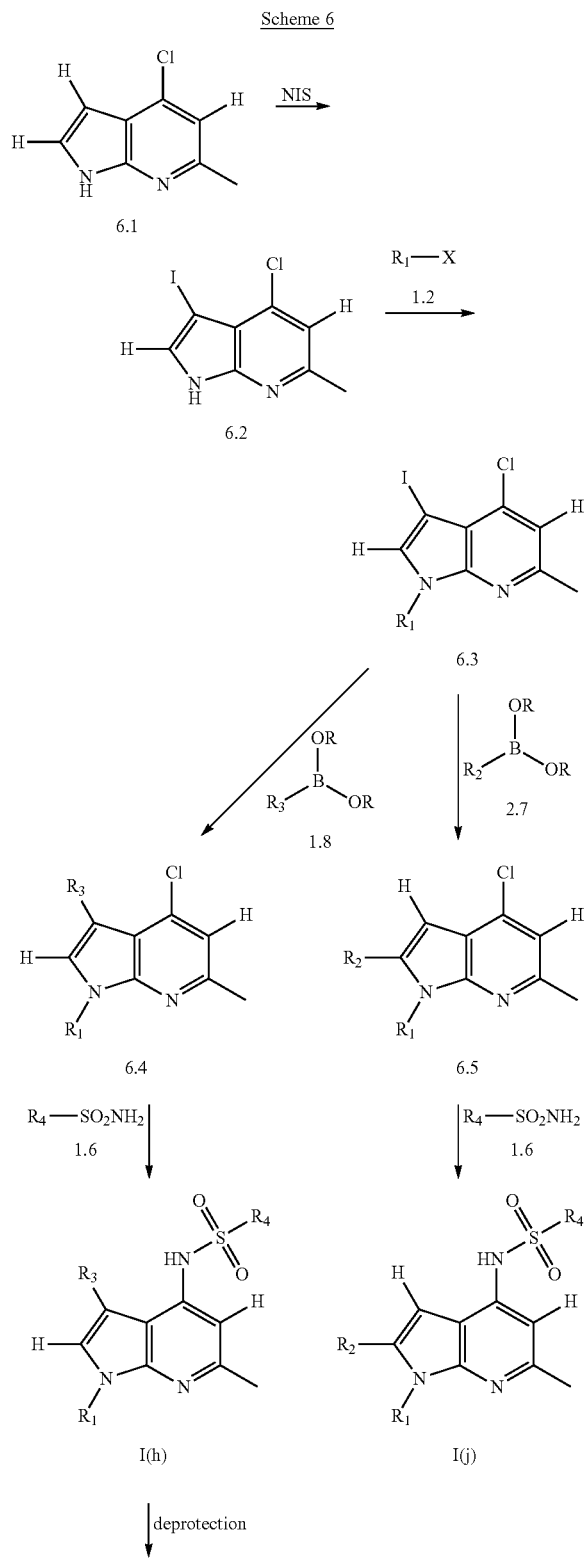

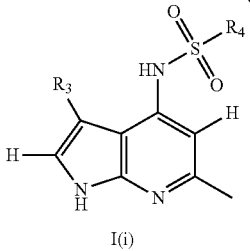

Scheme 6 represents another general reaction scheme for preparing intermediates and certain compounds of Formula I.

Intermediate 6.2 can be obtained by treatment of 6.1 with a halogenating agent (such as NIS) in a solvent (such as DCM) at temperatures between −40° C. and room temperature. Alkylation of 6.2 using 1.2 (such as MeI, iPrI or SEMCl) in the presence of a base (such as sodium hydride) in a solvent (such as DMF or THF) at temperatures between 0° C. and room temperature can afford intermediate 6.3.

Intermediate 6.4 can be obtained by treatment of 6.3 with 1.8 in the presence of a catalyst (such as $Pd(PPh_3)_2Cl_2$ or $Pd(dppf)Cl_2$-DCM adduct) and a base (such as $Na_2CO_3$) in a solvent (such as acetonitrile, ethanol, DMF, DCM, DME, MeOH and/or water) at temperatures between 55° C. and 100° C. (using conventional or microwave heating).

Treatment of 6.4 with a 1.6 in the presence of a catalyst (such as $Pd_2(dba)_3$ or $Pd(OAc)_2$), a ligand (such as Xantphos and/or Davephos) and a base (such as NaOtBu or $Cs_2CO_3$) in a solvent (such as 1,4-dioxane) at temperatures between 115 and 180° C. (using conventional or microwave heating) can afford compound I(h). Where $R_1$ in I(h) is a protecting group (such as SEM) this can be deprotected under appropriate conditions utilising an acid (such as 4M HCl or TFA) optionally in a solvent (such as DCM or 1,4-dioxane), followed by further treatment with a base (such as DIPEA or 50% aqueous NaOH) in a solvent (such as MeOH, THF and/or water) to give compound I(i).

Intermediate 6.5 can be obtained by treatment of 6.3 with compound 2.7 in the presence of a catalyst (such as $Pd(PPh_3)_2Cl_2$ or PEPPSI-IPr) and a base (such as $Na_2CO_3$ or $K_3PO_4$) in a solvent (such as acetonitrile, 1,4-dioxane and/or water) at temperatures between 70 and 120° C. (using conventional or microwave heating).

Treatment of 6.5 with 1.6 in the presence of a catalyst (such as $Pd_2(dba)_3$ or $Pd(OAc)_2$), a ligand (such as Xantphos and/or Davephos) and a base (such as NaOtBu or $Cs_2CO_3$) in a solvent (such as acetonitrile or 1,4-dioxane) at temperatures between 115 and 180° C. (using conventional or microwave heating) can afford compound I(j).

Where further elaboration is required at $R_3$ and/or $R_4$, other reactions (such as deprotection, substitution or reductive amination) can be performed at a suitable point in the reaction sequence to provide a desired intermediate or target compound.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

Abbreviations

Ac Acetate
ACN Acetonitrile
Aq Aqueous
Boc tert-Butoxycarbonyl
Bu Butyl
Davephos 2-Dicyclohexylphosphino-2'-(N,N-dimethylamino)biphenyl
dba dibenzylideneacetone
DBU 1,8-Diazabicyclo[5.4.0]undec-7-ene
DCM Dichloromethane
DIAD Diisopropyl azodicarboxylate
DIPEA N,N-Diisopropylethylamine
DME 1,2-Dimethoxyethane
DMF N,N-Dimethylformamide
DMSO Dimethyl sulfoxide
dppf 1,1'-bis(diphenylphosphino)-ferrocene
ELS Evaporative light scattering
h hour(s)
HMDS bis(trimethylsilyl)amide
HPLC High-performance liquid chromatography
I Iso
IPA Isopropanol
LCMS Liquid chromatography mass spectrometry
LDA Lithium diisopropylamide
M Molarity
mCPBA 3-Chloroperbenzoic acid
MDAP Mass-directed auto-purification
Me Methyl
MS Mass spectrometry
NBS N-Bromosuccinimide
NIS N-Iodosuccinimide
NCS N-Chlorosuccinimide
NMR nuclear magnetic resonance
PDA Photo diode array
PEPPSI-Ipr [1,3-Bis(2,6-Diisopropylphenyl)imidazol-2-ylidene](3-chloropyridyl)palladium(II) dichloride
Ph Phenyl
Pr Propyl
RT Room temperature
SEM 2-(Trimethylsilyl)ethoxymethyl
t tertiary
TBAF Tetra-n-butylammonium fluoride
TBAI Tetrabutylammonium iodide
TEA Triethylamine
TFA Trifluoroacetic acid
THF Tetrahydrofuran
Ts 4-toluenesulfonyl
Xantphos 4,5-Bis(diphenylphosphino)-9,9-dimethylxanthene All other abbreviations and symbols utilized herein are in accordance with the common usage of such abbreviations and symbols by those skilled in the chemical and biological arts.

Analytical Conditions

LCMS (A) was conducted on Waters Acquity system with a Waters column (Acquity UPLC BEH C18 2.1×5.0 mm, 1.7 μm) running a water/acetonitrile (0.05% acid or basic modifier was used) gradient over 2 minutes with a flow rate of 1 mL/min. The detectors used were a PDA (210-450 nm), MS+ (100-1700 m/z), MS− (100-1700 m/z) and ELS detector.

LCMS (B) was conducted on Agilent system with a column (Sunfire, 50×4.6 mm, 3.5 μm or XBridge, 50×4.6 mm, 3.5 μm) running a water/acetonitrile (0.01% acid modifier or 10 mM basic modifier was used) gradient over 2.7 minutes with a flow rate of 2 mL/min. The detectors used were a PDA (190-400 nm), MS+ (100-1000 m/z), MS− (100-1000 m/z) and ELS detector.

Preparative HPLC was performed on a Waters MDAP system with a Waters column (Sunfire or XBridge C18 19×150 mm or 30×100 mm, 5 μm) running a generic water/acetonitrile (0.2% acid or basic modifier was used) gradient over 15 minutes with a flow rate of 20 or 40 mL/min. The detectors used were a PDA (210-450 nm), MS+ (100-1700 m/z), MS− (100-1700 m/z) and optional ELS detector.

Chiral purity was recorded on a Waters Alliance 2695 HPLC system with a column with chiral stationary phase (Diacel Chiralpak AD-H, AS-H, IA, IB, OD-H or OJ-H, 4.6×250 mm, 5 μm) running a hexane/ethanol gradient over 20-70 minutes with a flow rate of 1 mL/min. The detector used was a PDA (190-800 nm) detector.

Preparative chiral separations were performed on a Waters auto-purification system with a column with chiral stationary phase (Diacel Chiralpak AD, AS, IA or IB; 20×250 mm, 10 μm) running a hexane/ethanol gradient over 20-60 minutes with a flow rate of 18 mL/min. The detector used was a PDA (190-800 nm) detector.

NMR spectra were performed on a Bruker Avance II 400 MHz NMR instrument. Spectra were acquired using standard Bruker pulse sequences and either a QNP or BBI (with ATM) probes.

Intermediates

D1

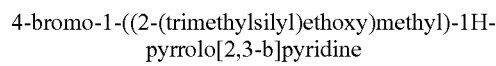

4-bromo-1-((2-(trimethylsilyl)ethoxy)methyl)-1H-pyrrolo[2,3-b]pyridine

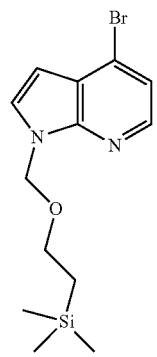 [SMILES: C[Si](C)(C)CCOCn1ccc2c(Br)ccnc21]

A mixture of 4-bromo-1H-pyrrolo[2,3-b]pyridine (1.00 g, 5.08 mmol), SEMCl (0.898 mL, 5.08 mmol) and DIPEA (1.768 mL, 10.15 mmol) in DCM (20.0 mL) was stirred at RT. After 3 nights the mixture was evaporated to dryness. The residues were purified on silica eluting with isohexane and ethyl acetate (0-100%). The appropriate fractions were combined and evaporated to dryness producing the title compound (1.65 g). LCMS (A): m/z (M+H)$^+$ 327/329, C13H19BrN2OSi requires 326/328 (basic).

D2

3,4-dibromo-1H-pyrrolo[2,3-b]pyridine

A mixture of 4-bromo-1H-pyrrolo[2,3-b]pyridine (1.00 g, 5.08 mmol) and NBS (0.918 g, 5.16 mmol) in DCM (20.0 mL) was stirred at 0° C. for 1.5 hour. The resulting suspension was filtered, washed with DCM, residue collected, dried in a 50° C. oven overnight to afford the title compound (1.014 g). LCMS (A): m/z (M+H)$^+$ 277, C7H4Br2N2 requires 276 (basic).

D3

3,4-dibromo-1-((2-(trimethylsilyl)ethoxy)methyl)-1H-pyrrolo[2,3-b]pyridine

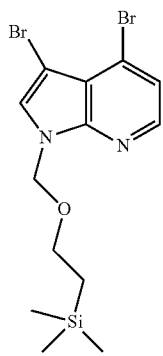 [SMILES: C[Si](C)(C)CCOCn1cc(Br)c2c(Br)ccnc21]

Method A:
A mixture of 4-bromo-1-({[2-(trimethylsilyl)ethyl]oxy}methyl)-1H-pyrrolo[2,3-b]pyridine (D1) (750 mg, 2.292 mmol) and NBS (428 mg, 2.406 mmol) in DCM (11.5 mL) was stirred at 0° C. for 1.5 hour. The mixture was partitioned between DCM (10 mL) and water (5 mL). The organic phase was separated, passed through a hydrophobic frit and evaporated to dryness. The residues were purified on silica eluting with isohexane and ethyl acetate (0-40%). The appropriate fractions were combined and evaporated to dryness producing the title compound (738 mg). LCMS (A): m/z (M+H)$^+$ 407, C13H18Br2N2OSi requires 406 (basic).

Method B:
A mixture of 3,4-dibromo-1H-pyrrolo[2,3-b]pyridine (D2) (1.014 g, 3.67 mmol), SEMCl (0.650 mL, 3.67 mmol) and DIPEA (1.280 mL, 7.35 mmol) in DCM (12.54 mL) was stirred at RT under nitrogen for overnight (17 hours). TLC showed presence of starting material. Stirring continued for 3 hours. TLC showed that the reaction has completed. The reaction mixture was taken up in DCM and purified using silica gel, eluting with ethyl acetate in cyclohexane (0 to 20%). Fractions with desired product were collected and solvent reduced in vacuo to afford the title compound (0.527 g). LCMS (A): m/z (M+H)$^+$ 407, C13H18Br2N2OSi requires 406 (basic).

D4

N-[3-bromo-1-({[2-(trimethylsilyl)ethyl]oxy}methyl)-1H-pyrrolo[2,3-b]pyridin-4-yl]-3-chlorobenzenesulfonamide

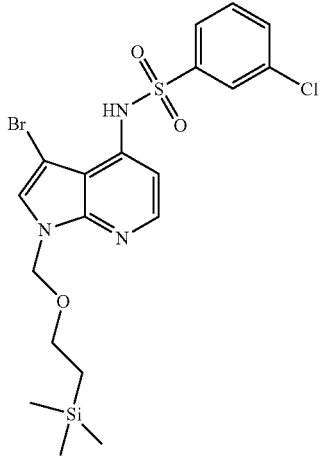 [SMILES: C[Si](C)(C)CCOCn1cc(Br)c2c(NS(=O)(=O)c3cccc(Cl)c3)ccnc21]

A mixture of 3,4-dibromo-1-({[2-(trimethylsilyl)ethyl]oxy}methyl)-1H-pyrrolo[2,3-b]pyridine (D3) (1.020 g, 2.51 mmol), xantphos (0.218 g, 0.377 mmol), palladium(II) acetate (0.042 g, 0.188 mmol), cesium carbonate (1.636 g, 5.02 mmol) and 3-chlorobenzenesulfonamide (0.602 g, 3.14 mmol) in 1,4-dioxane (15 mL) was stirred at 100° C. for ca. 3 hours. The mixture was evaporated to dryness and the residues partitioned between water (15 mL) and ethyl acetate (40 mL). The aqueous phase was separated and extracted with additional ethyl acetate (15 mL). The organic extracts were combined, washed with brine (10 mL), dried with MgSO$_4$ and evaporated to dryness. The residue was purified through silica gel, eluting with a gradient of 0-40% ethyl acetate in cyclohexane to give the title compound (407.4 mg). LCMS (A): m/z (M−H)$^-$ 514/516, C19H23BrClN3O3SSi requires 515/517 (acidic).

D5

3-chloro-N-(3-(3-(pyrrolidin-1-yl)phenyl)-1-((2-(trimethylsilyl)ethoxy)methyl)-1H-pyrrolo[2,3-b]pyridin-4-yl)benzenesulfonamide

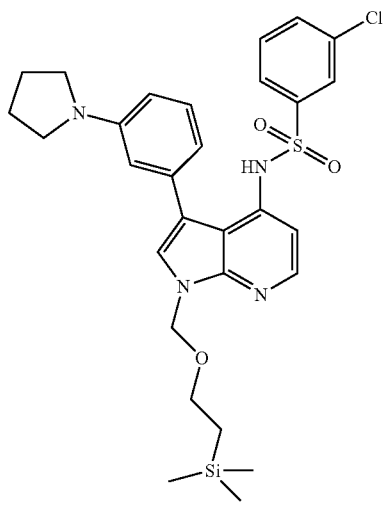 [SMILES: C[Si](C)(C)CCOCn1cc(-c2cccc(N3CCCC3)c2)c2c(NS(=O)(=O)c3cccc(Cl)c3)ccnc21]

A mixture of N-[3-bromo-1-({[2-(trimethylsilyl)ethyl]oxy}methyl)-1H-pyrrolo[2,3-b]pyridin-4-yl]-3-chlorobenzenesulfonamide (D4) (233 mg, 0.451 mmol), [3-(1-pyrrolidinyl)phenyl]boronic acid (129 mg, 0.676 mmol), cesium fluoride (205 mg, 1.352 mmol) and 1,1'-bis(diphenylphosphino)ferrocene-palladium(II)dichloride dichloromethane complex (36.8 mg, 0.045 mmol) in DME (5.706 mL) was heated in a microwave at 120° C. for 30 minutes. Additional 3-(1-pyrrolidinyl)phenyl]boronic acid (129 mg, 0.676 mmol), cesium fluoride (68.3 mg) and 1,1'-bis(diphenylphosphino)ferrocene-palladium(II)dichloride dichloromethane complex (36.8 mg, 0.045 mmol) were added into the reaction mixture and heated in a microwave at 120° C. for 1 hour. The reaction mixture was partitioned between aqueous saturated NaHCO₃ solution and ethyl acetate. The aqueous phase was separated and extracted with ethyl acetate (thrice). The organic extracts were combined, dried over phase separator. The residue was purified on silica gel, eluting with a gradient of 0-40% ethyl acetate in cyclohexane). The appropriate fractions were combined and evaporated to dryness to afford the title compound (128.1 mg). LCMS (A): m/z (M+H)⁺ 583, C29H35ClN4O3SSi requires 582 (acidic).

D6

4-bromo-3-iodo-1H-pyrrolo[2,3-b]pyridine

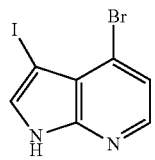 [SMILES: Brc1ccnc2[nH]cc(I)c12]

Method A:

In a round bottom flask under nitrogen gas, 4-bromo-1H-pyrrolo[2,3-b]pyridine (7.13 g, 36.2 mmol) was dissolved in DCM (250 mL) and cooled to 0° C. To this was added NIS (8.96 g, 39.8 mmol). The reaction was stirred for 1 hour at 0° C. before being quenched by the addition of saturated Na₂SO₃. The mixture was filtered over a vacuum and washed with excess DCM. The filtrate was dried under a high vacuum to give the title compound (10.181 g). LCMS (A): m/z (M+H)⁺ 323/325, C7H4BrIN2 requires 322/324 (acidic).

Method B:

A solution of NIS (5.71 g, 25.4 mmol) in DMF (40 mL) and a solution of 4-bromo-1H-pyrrolo[2,3-b]pyridine were prepared. A Vapourtec flow reactor was outfitted with a cooling apparatus and a 10 mL reactor was purged with IPA then DMF at a rate of 2 mL/min while being cooled to a temperature of −40° C. The two reagent solutions were then introduced to the flow reactor through a probe at a rate of 1 mL/min each. The solutions flowed through the reactor at −40° C. at a combined rate of 2 mL/min for a total residence time in the reactor of 5 minutes. The crude solution was collected and concentrated in vacuo. The residue was taken up in water and filtered through a filter cup. The solid was then rinsed with an excess of aqueous saturated Na₂SO₃ solution followed by water. The solid was then dried under vacuum to yield the title compound (6.027 g). Basic LCMS showed an approximate 32:1 ratio of product to isomer. LCMS (A): m/z (M+H)⁺ 323/325, C7H4BrIN2 requires 322/324 (acidic).

Method C:

Solution A=NIS (11.42 g, 50.8 mmol) in DMF (200 mL). Solution B=4-bromo-1H-pyrrolo[2,3-b]pyridine (10 g, 50.8 mmol) in DMF (200 mL). Solution A (1 mL/min) and Solution B (1 mL/min) were flowed through a Vapourtec reactor (10 mL loop) at 0° C. with a combined flow rate of 2 mL/min. The product was then collected before removing volatiles by evaporation. The residue was then taken up in H₂O (50 mL), collected by filtration, washed with saturated sodium sulphate (50 mL) and dried in vacuo for 18 hours to afford the title compound (15.4 g). LCMS (A): m/z (M+H)⁺ 323/325, C7H4BrIN2 requires 322/324 (acidic).

D7

4-bromo-3-iodo-1-methyl-1H-pyrrolo[2,3-b]pyridine

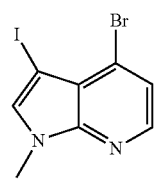

Method A:

In a round bottom flask, sodium hydride (0.533 g, 13.33 mmol) was suspended in DMF (80 mL) and cooled to 0° C. To this, at 0° C., was added a solution of 4-bromo-3-iodo-1H-pyrrolo[2,3-b]pyridine (D6) (2.87 g, 8.89 mmol) in DMF (12.00 mL) over 30 minutes. The reaction mixture was then left to stir for 15 minutes, after which, methyl iodide (0.611 mL, 9.78 mmol) was added. The reaction mixture was stirred at 0° C. for 1.5 hours, then quenched with saturated aq. NH₄Cl (80 mL), transferred to a separatory funnel and washed with brine (80 mL). The aqueous layer was washed with excess ethyl acetate (3×100 mL) and the combined organic dried over MgSO₄, filtered and concentrated in vacuo. The residue was purified on silica column eluting with ethyl acetate in cyclohexane (0-30%) to afford the title compound (2.18 g). LCMS (A): m/z (M+H)⁺ 337/339, C8H6BrIN2 requires 336/338 (acidic).

Method B:

All solvents used with the flow reactor were filtered through a filter cup prior to use. A solution of 4-bromo-3-iodo-1H-pyrrolo[2,3-b]pyridine (D6) (7.488 g, 22.22 mmol) and DBU (7.00 mL, 46.4 mmol) dissolved in DMF (94 mL) was prepared and filtered through a filter cup. In a separate vial iodomethane (5.81 mL, 93 mmol) was added through a syringe filter to the filtered DMF (94 mL). The two probes from the Vapourtec flow reactor were inserted into each two 50-mL Erlenmeyer flasks containing the reagent solutions. A Vapourtec Flow Reactor, outfitted with a 10 mL reactor, was purged with IPA at a rate of 2 mL/min for ten minutes followed by DMF at a rate of 2 mL/min for another ten minutes at RT. The two reagent solutions were then drawn into the flow reactor (1 mL/min for each pump, net flow rate of 2 mL/min, residence time of 5 minutes). The reaction was quenched by the addition of 50 mL of 2.0 M NH₃ in MeOH. Approximately 600 mL of water were then added to the solution to cause the precipitation of the product. This solid was isolated by vacuum filtration, rinsed with excess water and left to stand overnight under a vacuum to give the title compound (7.488 g). LCMS (A): m/z (M+H)+ 337/339, C8H6BrIN2 requires 336/338 (acidic).

D8

4-bromo-1-methyl-3-(1-methylindolin-6-yl)-1H-pyrrolo[2,3-b]pyridine

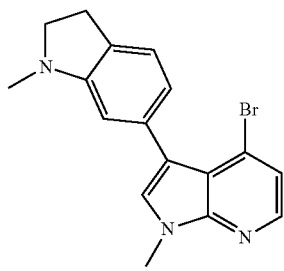 [SMILES: CN1CCc2ccc(-c3cn(C)c4nccc(Br)c34)cc21]

To a stirred solution of 4-bromo-3-iodo-1-methyl-1H-pyrrolo[2,3-b]pyridine (D7) (5 g, 14.84 mmol) and 1-methyl-6-(4,4,5,5-tetramethyl-1,3,2-dioxaborolan-2-yl)indoline (4.61 g, 17.81 mmol) in ACN (40 mL), DMF (40 mL) and DCM (20 mL) was added 2M sodium carbonate aq. solution (74.2 mL, 148 mmol). Bis(triphenylphosphine)palladium(II) chloride (1.250 g, 1.781 mmol) was then added to the solution and the resulting mixture was heated at 55° C. for ca. 1.5 hour. The reaction mixture was diluted with DCM (100 mL) and water (150 mL). The organic phase was separated and the aqueous phase was further extracted with DCM (100 mL×3). The combined organics were dried and concentrated. The residue was purified by chromatography on silica, eluting with a gradient of 0-20% ethyl acetate in cyclohexane. The corresponding fractions were combined and concentrated to give the title compound (2.48 g). LCMS (A): m/z (M+H)+ 342/344, C17H16BrN3 requires 341/343 (acidic).

D9

4-bromo-3-iodo-1-((2-(trimethylsilyl)ethoxy)methyl)-1H-pyrrolo[2,3-b]pyridine

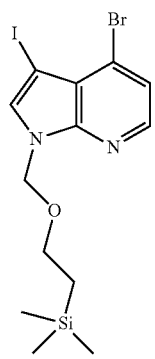 [SMILES: C[Si](C)(C)CCOCn1cc(I)c2c(Br)ccnc21]

Method A:
In a round bottom flask under N2 gas, 4-bromo-3-iodo-1H-pyrrolo[2,3-b]pyridine (D6) (7 g, 21.68 mmol) was dissolved in DMF (200 mL) and cooled to 0° C. To this was added NaH (1.300 g, 32.5 mmol). After 30 minutes of stirring, the SEMCl (4.45 mL, 23.84 mmol) was added and the reaction mixture was stirred at 0° C. for 90 minutes. The reaction was quenched with saturated NH4Cl, transferred to a separatory funnel with excess Et2O. The aqueous layer was extracted ten times with Et2O. The organics were combined, dried (MgSO4), concentrated by rotary evaporation and placed under a vacuum overnight to remove the remaining DMF. The residue was chromatographed on silica gel, eluted with a gradient of 0-30% ethyl acetate in cyclohexane affording the title compound (6.885 g). LCMS (A): m/z (M+H)+ 453/455, C13H18BrIN2OSi requires 452/454 (acidic).

Method B:
Similar to Method A with THF as solvent.

Method C:
A mixture of 4-bromo-3-iodo-1H-pyrrolo[2,3-b]pyridine (D6) (2.00 g, 6.19 mmol), SEMCl (1.151 mL, 6.50 mmol) and DIPEA (2.158 mL, 12.39 mmol) in DCM (21.07 mL) was stirred at RT. After 1 hour, an additional 0.29 mL SEMCl was added. The mixture was stirred overnight (ca. 18 hours). The mixture was evaporated to dryness. The residues were purified on silica eluting with cyclohexane and ethyl acetate (0-50%). The appropriate fractions were combined and evaporated to dryness producing the title compound (2.70 g).

D10

4-bromo-3-iodo-1-isopropyl-1H-pyrrolo[2,3-b]pyridine

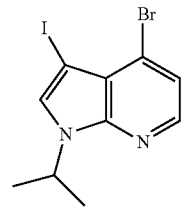

Method A:
Sodium hydride (2.403 g, 60.1 mmol) was added portionwise to a cooled mixture 4-bromo-3-iodo-1H-pyrrolo[2,3-b]pyridine (D6) (13.86 g, 42.9 mmol) in DMF (200 mL) at 0° C. and was stirred at that temperature for 15 min. 2-iodopropane (5.15 ml, 51.5 mmol) was then added and the reaction mixture was allowed to warm to RT and stirred overnight. The reaction mixture was cooled to 0° C. again and quenched with saturated NH4Cl solution (ca. 5 mL) and further diluted with water (ca. 200 mL). The aqueous layer was extracted with ethyl acetate (3×200 mL). The organic layer was dried and concentrated down. The residue was purified on silica, eluting with ethyl acetate in cyclohexane (0-10%) to give the title compound (14 g). LCMS (A): m/z (M+H)+ 365/367, C10H10BrIN2 requires 364/366 (acidic).

Method B:
To a stirred mixture of 4-bromo-3-iodo-1H-pyrrolo[2,3-b]pyridine (D6) (81 g, 251 mmol), isopropanol (21.12 mL, 276 mmol), and triphenylphosphine (72.4 g, 276 mmol) at 0° C. was added DIAD (58.5 mL, 301 mmol) and the mixture was stirred for 1 hour at this temperature. The mixture was evaporated in vacuo. To this residue was added 25% ethyl acetate/cyclohexane (400 mL) solution and formed precipitate was filtered off, rinsed with 25% ethyl acetate/cyclohexane and the filtrate was evaporated in vacuo. The residue was purified by chromatography on silica, eluting with a gradient of 0-20% ethyl acetate in cyclohexane to give a material which was crystallized with ethanol/water (1:5, 400 mL). The formed solid was filtered, washed with water and collected to give the title compound (77.09 g).

D11

4-bromo-1-isopropyl-3-(1-methylindolin-6-yl)-1H-pyrrolo[2,3-b]pyridine

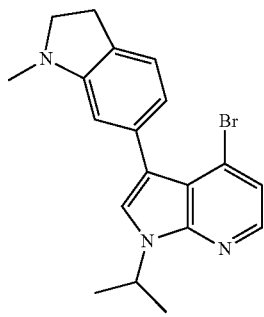 [SMILES: CC(C)n1cc(-c2ccc3c(c2)N(C)CC3)c2c(Br)ccnc21]

To a stirred suspension of 4-bromo-3-iodo-1-isopropyl-1H-pyrrolo[2,3-b]pyridine (D10) (2.5 g, 6.85 mmol) and 1-methyl-6-(4,4,5,5-tetramethyl-1,3,2-dioxaborolan-2-yl)indoline (2.130 g, 8.22 mmol) in ACN (15 mL), DMF (15.00 mL) and DCM (7.50 mL) was added 2M sodium carbonate aq. solution (34.2 mL, 68.5 mmol). Bis(triphenylphosphine)palladium(II) chloride (0.577 g, 0.822 mmol) was then added to the solution and the resulting mixture was heated at 55° C. for ca. 1 hour. Temperature was raised to 65° C. and heated for another 1 hour. The reaction was allowed to cool to RT and diluted with DCM (70 mL). The organic layer was separated and the aqueous layer was extracted with DCM (2×50 mL). The combined organics were dried and concentrated down. The residue obtained was purified on silica using 0-10% ethyl acetate/cyclohexane to afford the title compound (1.73 g). LCMS (A): m/z (M+H)$^+$ 370/372, C19H20BrN3 requires 369/371 (acidic).

D12

4-chloro-3-iodo-6-methyl-1H-pyrrolo[2,3-b]pyridine

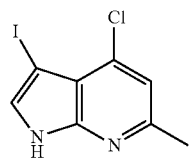

To a stirred solution of 4-chloro-6-methyl-1H-pyrrolo[2,3-b]pyridine (4.06 g, 24.37 mmol) in DCM (80 mL) at 0° C., was added NIS (6.22 g, 27.6 mmol). The reaction mixture was then warmed to RT and stirred for 18 hours. The reaction mixture was then filtered (washed with excess DCM) to give the title compound (4.01 g). LCMS (A): m/z (M+H)$^+$ 293, C8H6ClIN2 requires 292 (acidic).

D13

4-chloro-3-iodo-1,6-dimethyl-1H-pyrrolo[2,3-b]pyridine

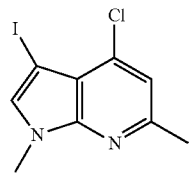

In a round bottom flask under N$_2$ gas, 4-chloro-3-iodo-6-methyl-1H-pyrrolo[2,3-b]pyridine (D12) (1.48 g, 5.06 mmol) was dissolved in THF (25 mL) and cooled to 0° C. To this was added NaH (0.405 g, 10.12 mmol) portion wise. After 30 minutes of stirring, methyl iodide (0.633 mL, 10.12 mmol) was added and the reaction mixture was stirred at 0° C. for 30 mins and at RT for 1 hour.

The reaction was quenched with saturated ammonium chloride (30 mL) and the mixture transferred to a separatory funnel with ethyl acetate (50 mL). The aqueous layer was extracted with ethyl acetate (30 mL×3). The organics were combined, dried over magnesium sulfate and concentrated. The residue was purified over normal phase chromatography eluting with ethyl acetate and cyclohexane (0-30%) to give the title compound (1.22 g). LCMS (A): m/z (M+H)$^+$ 307, C9H8ClIN2 requires 306 (acidic).

D14

4-chloro-1,6-dimethyl-3-(3-(pyrrolidin-1-yl)phenyl)-1H-pyrrolo[2,3-b]pyridine

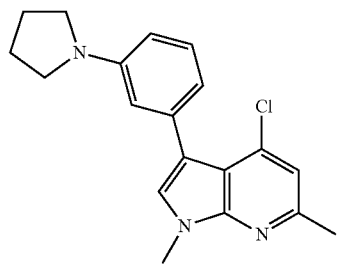 [SMILES: Cc1cc(Cl)c2c(-c3cccc(N4CCCC4)c3)cn(C)c2n1]

A mixture of 4-chloro-3-iodo-1,6-dimethyl-1H-pyrrolo[2,3-b]pyridine (D13) (500 mg, 1.631 mmol), (3-(pyrrolidin-1-yl)phenyl)boronic acid (374 mg, 1.957 mmol), bis(triphenylphosphine)palladium(II) chloride (114 mg, 0.163 mmol) and sodium carbonate (2M aq. solution) (8 mL, 16.00 mmol) was heated at 65° C. for 1 hour. The mixture was transferred to a separatory funnel with ethyl acetate (50 mL). The aqueous layer was extracted with ethyl acetate (30 mL×3). The organics were combined, dried over magnesium sulfate and concentrated. The crude was purified over normal phase chromatography eluting with ethyl acetate and cyclohexane (0-30%) to give the title compound (135 mg). LCMS (A): m/z (M+H)+ 326, C19H20ClN3 requires 325 (acidic).

D15

4-bromo-1-isopropyl-3-(3-(pyrrolidin-1-yl)phenyl)-1H-pyrrolo[2,3-b]pyridine (D15)

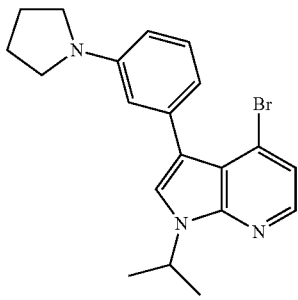 [SMILES: CC(C)n1cc(-c2cccc(N3CCCC3)c2)c2c(Br)ccnc21]

A mixture of 4-bromo-3-iodo-1-isopropyl-1H-pyrrolo[2,3-b]pyridine (D10) (2.80 g, 7.67 mmol), (3-(pyrrolidin-1-yl)phenyl)boronic acid (1.612 g, 8.44 mmol), bis(triphenylphosphine)palladium(II) chloride (0.538 g, 0.767 mmol) and 2M sodium carbonate aqueous solution (9.59 mL, 19.18 mmol) in ACN (35.0 mL) was heated at 65° C. for 2 hours and then allowed to cool to RT. The mixture was evaporated to dryness and the residue partitioned between water (50 mL) and ethyl acetate (150 mL). The aqueous phase was separated and extracted with additional ethyl acetate (100 mL). The organic extracts were combined, washed with brine (50 mL), dried with anhydrous magnesium sulfate, filtered and evaporated to dryness. The residue was purified on silica eluting with cyclohexane and ethyl acetate (0-35%) to give an impure material which was further purified on silica eluting with cyclohexane and ethyl acetate (0-25%). The appropriate fractions were combined and evaporated to dryness producing the title compound (692 mg). LCMS (A): m/z (M+H)+ 384/386, C20H22BrN3 requires 383/385 (acidic).

D16

3-iodo-4-nitro-1H-pyrrolo[2,3-b]pyridine

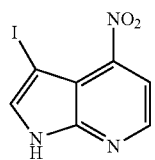 [SMILES: O=[N+]([O-])c1ccnc2[nH]cc(I)c12]

To a stirred solution of 4-nitro-1H-pyrrolo[2,3-b]pyridine (4.5 g, 27.6 mmol) in DCM (180 mL) was added NIS (6.83 g, 30.3 mmol) over 30 mins at 0° C. The resulting mixture was stirred at 0° C. for another 1 hour. The reaction mixture was concentrated. The residue was suspended in DCM (ca. 25 mL), the solid was filtered and dried in a vacuum oven to give the title compound (8.51 g). LCMS (A): m/z (M+H)+ 290, C7H4IN3O2 requires 289 (acidic).

D17

3-iodo-1-methyl-4-nitro-1H-pyrrolo[2,3-b]pyridine

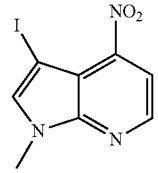

To a stirred suspension of sodium hydride (0.872 g, 21.80 mmol) in DMF (80 mL) was added 3-iodo-4-nitro-1H-pyrrolo[2,3-b]pyridine (D16) (4.2 g, 14.53 mmol) predissolved in DMF (20 mL) dropwise over 30 mins at 0° C. The reaction mixture was then left stirring at 0° C. for 15 mins. After which, methyl iodide (1.090 mL, 17.44 mmol) was added and the resulting reaction mixture was stirred at 0° C. for ca. 1 hour. The reaction mixture was quenched with ammonium chloride solution (ca. 150 mL). The aqueous phase was extracted with ethyl acetate (3×80 mL). The combined organic phases were dried and concentrated. Another batch of 3-iodo-4-nitro-1H-pyrrolo[2,3-b]pyridine (D16) (4.2 g, 14.53 mmol) was treated in the same way. The residue from both reactions were combined and purified by chromatography on silica, eluting with a gradient of 0-50% ethyl acetate in cyclohexane to give the title compound (6.4 g). The impure fractions were re-purified by chromatography on silica, eluting with a gradient of 0-30% ethyl acetate in cyclohexane to give another batch of the title compound (1.32 g). LCMS (A): m/z (M+H)+ 304, C8H6IN3O2 requires 303 (acidic).

D18

1-methyl-3-(1-methylindolin-6-yl)-4-nitro-1H-pyrrolo[2,3-b]pyridine

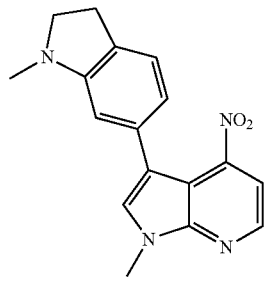 [SMILES: CN1CCc2ccc(-c3cn(C)c4nccc([N+](=O)[O-])c34)cc21]

To a stirred solution of 3-iodo-1-methyl-4-nitro-1H-pyrrolo[2,3-b]pyridine (D17) (6.2 g, 20.46 mmol) in ACN (108 mL) was added 1-methyl-6-(4,4,5,5-tetramethyl-1,3,2-dioxaborolan-2-yl)indoline (7.95 g, 30.7 mmol), bis(triphenylphosphine)palladium(II) chloride (1.436 g, 2.046 mmol) and 2M sodium carbonate aq. solution (108 mL, 217 mmol). The resulting mixture was heated at 65° C. for 1 hour. After being cooled to RT, the reaction mixture was diluted with DCM (150 mL) and water (200 mL). The organic phase was separated and the aqueous phase was further extracted with DCM (80 mL×4). The combined organics were dried and concentrated. The residue was purified by chromatography on silica, eluting with a gradient of 0-100% ethyl acetate in cyclohexane to give an impure fraction which was re-purified by chromatography on silica, eluting with a gradient of 0-20% ethyl acetate in DCM to give the title compound (3.14 g). LCMS (A): m/z (M+H)$^+$ 309, C17H16N4O2 requires 308 (acidic).

D19

1-methyl-3-(1-methylindolin-6-yl)-1H-pyrrolo[2,3-b]pyridin-4-amine

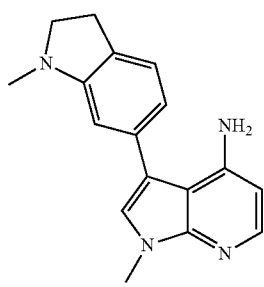 [SMILES: CN1CCc2ccc(-c3cn(C)c4nccc(N)c34)cc21]

To a stirred suspension of 1-methyl-3-(1-methylindolin-6-yl)-4-nitro-1H-pyrrolo[2,3-b]pyridine (D18) (3.1 g, 10.05 mmol) in ethanol (75 mL) was added 10% palladium on carbon (1.070 g, 1.005 mmol). The mixture was then stirred under hydrogen environment (4 bar) at RT for ca. 24 hours. Extra 10% palladium on carbon (1.070 g, 1.005 mmol) was added and the mixture was stirred under hydrogen (4 bar) at RT for another 24 hours. Additional 10% palladium on carbon (1.070 g, 1.005 mmol) was added and the mixture continued stirring under hydrogen atmosphere at RT for overnight (ca. 16 hours). The reaction mixture was filtered through celite. Washed celite with excess ethanol and the filtrate was concentrated. The residue was purified by chromatography on silica, eluting with a gradient of 0-20% MeOH in DCM to give the title compound (1.21 g). LCMS (A): m/z (M+H)$^+$ 279, C17H18N4 requires 278 (acidic).

D20

4-bromo-1-tosyl-1H-pyrrolo[2,3-b]pyridine

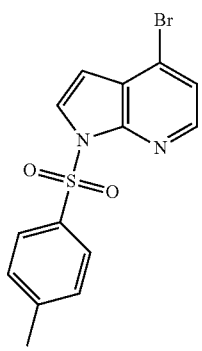 [SMILES: Cc1ccc(S(=O)(=O)n2ccc3c(Br)ccnc32)cc1]

To a stirred solution of 4-bromo-1H-pyrrolo[2,3-b]pyridine (10 g, 50.8 mmol) in THF (200 mL) and DMF (100 mL) was added sodium tert-butoxide (12.19 g, 127 mmol) and tosyl-Cl (19.35 g, 102 mmol). The whole mixture was stirred at RT for ca. 2.5 hours. The reaction mixture was quenched with saturated NH$_4$Cl solution (ca. 300 mL), extracted with ethyl acetate (150 mL×3). The combined organics were dried and concentrated. The residue was purified on normal phase chromatography eluting with a gradient of 0-50% ethyl acetate in cyclohexane. The corresponding fractions were combined and concentrated to give the title compound (16.5 g). LCMS (A): m/z (M+H)$^+$ 351/353, C14H11BrN2O2S requires 350/352 (acidic).

D21

4-bromo-2-methyl-1-tosyl-1H-pyrrolo[2,3-b]pyridine

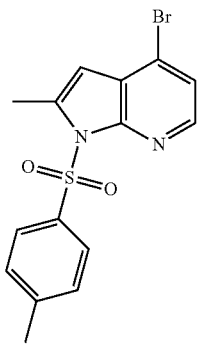 [SMILES: Cc1ccc(S(=O)(=O)n2c(C)cc3c(Br)ccnc32)cc1]

A mixture of 4-bromo-1-tosyl-1H-pyrrolo[2,3-b]pyridine (D20) (6 g, 17.08 mmol) in THF (100 ml) was cooled to −78° C. LDA (2M in THF) (21.35 mL, 42.7 mmol) was added at −78° C. and stirred at this temperature for ca. 1 hour. Iodomethane (2.136 ml, 34.2 mmol) was then added. After stirred at −78° C. for further ca. 30 min, the mixture was quenched by addition of saturated NH$_4$Cl solution (150 mL), extracted with ethyl acetate (100 mL×3). The combined organics were dried over Na$_2$SO$_4$, filtered and concentrated. The residue was purified on normal phase chromatography eluting with a gradient of 0-30% ethyl acetate in cyclohexane to give the title compound containing impurities (5.4 g). LCMS (A): m/z (M+H)$^+$ 365/367, C15H13BrN2O2S requires 364/366 (acidic).

D22

4-bromo-1-(phenylsulfonyl)-1H-pyrrolo[2,3-b]pyridine

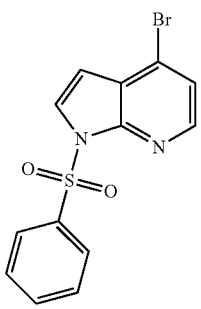 [SMILES: O=S(=O)(c1ccccc1)n1ccc2c(Br)ccnc21]

To a solution of 4-bromo-1H-pyrrolo[2,3-b]pyridine (2 g, 10.15 mmol) in DMF (50 mL) stirred at 0° C. was added sodium hydride (0.487 g, 12.18 mmol). After stirring for 30 min at 0° C., benzenesulfonyl chloride (1.570 mL, 12.18 mmol) was added to the mixture and stirred at 0° C. for 1.5 hour. The reaction was quenched with addition of saturated NH$_4$Cl aq. solution and the mixture was poured into saturated aq. NH$_4$Cl (100 mL). The mixture was extracted with ethyl acetate (20 mL×3). The organic layers were combined, washed with brine (100 mL), dried over MgSO$_4$, filtered and evaporated in vacuo. The residue was purified by chromatography on silica, eluting with a gradient of 0-25% ethyl acetate in cyclohexane to give the title compound (3.39 g). LCMS (A): m/z (M+H)$^+$ 337/339, C13H9BrN2O2S requires 336/338 (acidic).

D23

4-bromo-2-methyl-1-(phenylsulfonyl)-1H-pyrrolo[2,3-b]pyridine

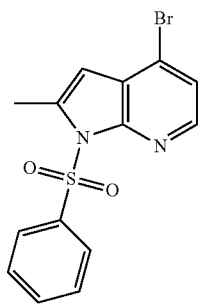 [SMILES: Cc1cc2c(Br)ccnc2n1S(=O)(=O)c1ccccc1]

To a solution of 4-bromo-1-(phenylsulfonyl)-1H-pyrrolo[2,3-b]pyridine (D22) (3.37 g, 9.99 mmol) in THF (50 mL) stirred at −35° C. was added 2M THF solution of LDA (9.99 mL, 19.99 mmol) and the mixture was stirred for 45 min at this temperature. Iodomethane (1.250 mL, 19.99 mmol) was added dropwise to the mixture and the mixture was then allowed to warm to RT over 2 hours. The reaction was quenched with addition of saturated NH$_4$Cl aq. solution and the mixture was poured into saturated NH4Cl aq. solution (100 mL). The mixture was extracted with ethyl acetate. The organic layers were combined, washed with brine (100 mL), dried over MgSO$_4$, filtered and evaporated in vacuo. The crude residue was purified by chromatography on silica, eluting with a gradient of 0-20% ethyl acetate in cyclohexane to give the title compound (2.93 g). LCMS (A): m/z (M+H)$^+$ 351/353, C14H11BrN2O2S requires 350/352 (acidic).

D24

4-bromo-2-methyl-1H-pyrrolo[2,3-b]pyridine

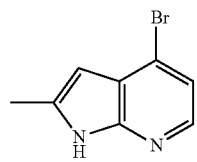

Method A:

To a stirred suspension of 4-bromo-2-methyl-1-tosyl-1H-pyrrolo[2,3-b]pyridine (D21) (5.4 g) in MeOH (100 mL) was added 5M NaOH (6.83 mL, 34.2 mmol) at RT. The whole mixture was heated at 70° C. for ca. 1.5 hour. After being cooled to RT, the reaction mixture was concentrated. The residue was taken up in ethyl acetate (80 mL) and water (150 mL). The organic layer was separated and the aqueous layer was re-extracted with ethyl acetate (80 mL×3). The combined organics were dried and concentrated to give the title compound (2.5 g). The material was carried forward without further purification.

Method B:

To a solution of 4-bromo-2-methyl-1-(phenylsulfonyl)-1H-pyrrolo[2,3-b]pyridine (D23) (2.90 g, 8.26 mmol) in 1,4-dioxane (70 mL) was added 2M aqueous solution of sodium hydroxide (20.64 mL, 41.3 mmol). The mixture was then heated at 60° C. for 13 hours. The mixture was heated at 80° C. for 4 hours. After cooling to RT, the organic layer was separated. The aqueous layer was extracted with ethyl acetate (20 mL×3). The organic layers were combined, washed with brine (100 mL), dried over MgSO$_4$, filtered and concentrated in vacuo to give the title compound (1.66 g). LCMS (A): m/z (M+H)$^+$ 211/213, C8H7BrN2 requires 210/212 (acidic).

D25

4-bromo-1,2-dimethyl-1H-pyrrolo[2,3-b]pyridine

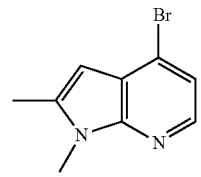

NaH (60% in oil dispersion) (1.228 g, 30.7 mmol) was suspended in THF (60 mL) and the mixture cooled to 0° C. A solution of 4-bromo-2-methyl-1H-pyrrolo[2,3-b]pyridine (D24) (3.24 g, 15.35 mmol) in THF (30.0 ml) was added dropwise to the mixture and allowed to stir at that temperature for 15 mins, after which MeI (1.440 mL, 23.03 mmol) was added dropwise. The final mixture was stirred at 0° C. for 15 min and then at RT for ca. 3 hours. The reaction mixture was quenched with NH$_4$Cl solution (ca. 100 mL), extracted with ethyl acetate (50 mL×3). The combined organics were dried over MgSO$_4$ and concentrated. The residue was purified by chromatography on silica, eluting with a gradient of 0-50% ethyl acetate in cyclohexane. The corresponding fractions were combined to give the title compound (2.18 g, approx. 47% purity) which was used without further purification in the next stage. LCMS (A): m/z (M+H)$^+$ 225/227, C9H9BrN2 requires 224/226 (acidic).

D26

4-bromo-3-iodo-2-methyl-1H-pyrrolo[2,3-b]pyridine

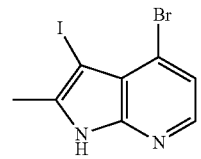

To a mixture of 4-bromo-2-methyl-1H-pyrrolo[2,3-b]pyridine (D24) (1.65 g, 7.82 mmol) in DCM (70 mL) was added NIS (1.935 g, 8.60 mmol) at 0° C. and the mixture was stirred for 1.5 hour at 0° C. The mixture was evaporated in vacuo. DCM (ca. 20 mL) was added to the residue. The formed precipitate was filtered, rinsed with DCM to give the title compound (2.45 g). LCMS (A): m/z (M+H)+ 337/339, C8H6BrIN2 requires 336/338 (acidic).

D27

4-bromo-3-iodo-1,2-dimethyl-1H-pyrrolo[2,3-b]pyridine

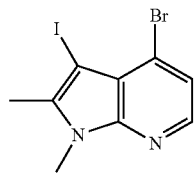

Method A:

To a solution of 4-bromo-1,2-dimethyl-1H-pyrrolo[2,3-b]pyridine (D25) (2.18 g) in DCM (65 mL) was added NIS (2.179 g, 9.69 mmol) at RT. The reaction mixture was stirred at RT for 10 mins before it was quenched with ca. 40 mL of sodium thiosulfate aqueous solution. The aqueous layer was extracted with DCM (3×50 mL). The organic layers were combined, passed through a hydrophobic frit and concentrated. The residue was purified by column chromatographyon silica gel, eluting with a gradient of 0-25% ethyl acetate in cyclohexane to give an impure material which was further purified by MDAP (acidic) to afford the title compound (590 mg). LCMS (A): m/z (M+H)+ 351/353, C9H8BrIN2 requires 350/352 (acidic).

Method B:

To a stirred suspension of sodium hydride (0.214 g, 8.90 mmol) in DMF (25 mL) was added 4-bromo-3-iodo-2-methyl-1H-pyrrolo[2,3-b]pyridine (D26) (1.5 g, 4.45 mmol) predissolved in DMF (5 mL) at 0° C. After 15 min of stirring, MeI (0.418 mL, 6.68 mmol) was added and the reaction mixture was stirred at RT for 1 hour. The reaction was quenched with saturated ammonium chloride (50 mL) and extracted with ethyl acetate (40 mL×3). The organics were combined, dried and concentrated. The residue was purified by normal phase chromatography, eluting with a gradient of 0-30% ethyl acetate and cyclohexane to give the title compound (1.4 g).

D28

4-bromo-1,2-dimethyl-3-(1-methylindolin-6-yl)-1H-pyrrolo[2,3-b]pyridine

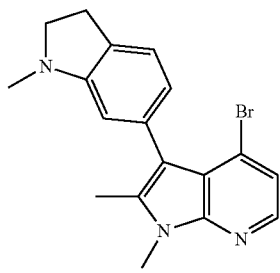 [SMILES: Cc1c(-c2ccc3c(c2)N(C)CC3)c2c(Br)ccnc2n1C]

To a solution of 4-bromo-3-iodo-1,2-dimethyl-1H-pyrrolo[2,3-b]pyridine (D27) (580 mg, 1.653 mmol) in ACN (9 mL) was added 1-methyl-6-(4,4,5,5-tetramethyl-1,3,2-dioxaborolan-2-yl)indoline (557 mg, 2.148 mmol), bis(triphenylphosphine)palladium(II) chloride (116 mg, 0.165 mmol) and 9 mL of sodium carbonate (2N aqueous solution). The reaction mixture was stirred at 65° C. for 3 hours. The reaction mixture was diluted with water (30 mL), the aqueous layer was then extracted with ethyl acetate (50 mL×3). The organic layers were combined, passed through a hydrophobic frit and concentrated. The residue was purified by column chromatography on silica gel, eluting with a gradient of 0-30% ethyl acetate in cyclohexane to give an impure material which was further purified by column chromatography on silica gel, eluting with a gradient of 0-20% ethyl acetate in cyclohexane to afford the title compound (89 mg). LCMS (A): m/z (M+H)+ 356/358, C18H18BrN3 requires 355/357 (acidic).

D29

4-bromo-1H-pyrrolo[2,3-b]pyridine 7-oxide

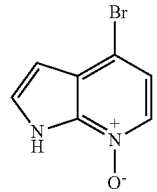

A mixture of 4-bromo-1H-pyrrolo[2,3-b]pyridine (2 g, 10.15 mmol) in diethyl ether (160 mL) was cooled to 0° C. mCPBA (3.64 g, 16.24 mmol) was added to the mixture at 0° C. After stirring for 20 min at this temperature, the mixture was allowed to warm to RT and stirred for 3 hours. The formed precipitate was filtered and washed with cold ether to give the title compound (1.978 g). LCMS (A): m/z (M+H)+ 213/215, C7H5BrN2O requires 212/214 (acidic).

D30

4-bromo-6-chloro-1H-pyrrolo[2,3-b]pyridine

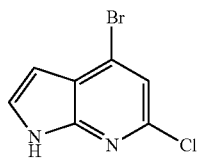

To a suspension of 4-bromo-1H-pyrrolo[2,3-b]pyridine 7-oxide (D29) (1.95 g, 9.15 mmol) in DMF (15 mL) at 50° C. was added methanesulfonyl chloride (1.783 mL, 22.88 mmol). Upon completion of the addition, the mixture was stirred at 75° C. for 1 hour. After cooling to RT, the reaction was quenched with water (25 mL). The mixture was then cooled to 0° C. and neutralised with addition of 6N sodium hydroxide solution. The ice bath was removed and the resulting slurry was stirred at RT for 3 hours. The precipitate was filtered and washed with water to give the title compound (1.88 g). This was used in the next step without further purification. LCMS (A): m/z (M+H)+ 233, C7H4BrClN2 requires 232 (acidic).

D31 tert-butyl 3-(4-bromo-3-iodo-1H-pyrrolo[2,3-b]pyridin-1-yl)azetidine-1-carboxylate

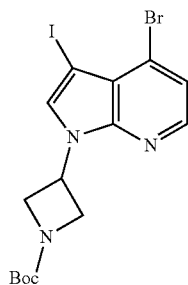 [SMILES: CC(C)(C)OC(=O)N1CC(n2cc(I)c3c(Br)ccnc32)C1]

To a mixture of 4-bromo-3-iodo-1H-pyrrolo[2,3-b]pyridine (D6) (500 mg, 1.548 mmol) and tert-butyl 3-(tosyloxy) azetidine-1-carboxylate (D100) (558 mg, 1.703 mmol) in DMSO (10 mL) was added cesium carbonate (1513 mg, 4.64 mmol). The final mixture was heated at 80° C. for 4 hours after which the temperature is increase to 95° C. and the mixture heated overnight. The reaction mixture was diluted with water (50 mL) and then extracted with ethyl acetate (50 mL×3). The combined organics were dried over magnesium sulfate and concentrated. The crude was purified on normal phase silica eluting with ethyl acetate and cyclohexane (0-50%) to give the title compound (243 mg). LCMS (A): m/z (M+H)+ 478/480, C15H17BrIN3O2 requires 477/479 (acidic).

D32 tert-butyl 3-(4-bromo-3-(5-fluoro-1-methylindolin-6-yl)-1H-pyrrolo[2,3-b]pyridin-1-yl)azetidine-1-carboxylate

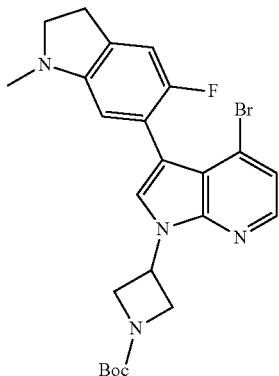 [SMILES: CN1CCc2cc(F)c(-c3cn(C4CN(C(=O)OC(C)(C)C)C4)c4nccc(Br)c34)cc21]

To a mixture of tert-butyl 3-(4-bromo-3-iodo-1H-pyrrolo[2,3-b]pyridin-1-yl)azetidine-1-carboxylate (D31) (118 mg, 0.247 mmol), 5-fluoro-1-methyl-6-(4,4,5,5-tetramethyl-1,3,2-dioxaborolan-2-yl)indoline, hydrochloride (85 mg, 0.271 mmol) in DME (2 mL) and MeOH (0.222 mL) was added bis(triphenylphosphine)palladium(II) chloride (17.32 mg, 0.025 mmol) and 2M sodium carbonate aq. solution (1.234 mL, 2.468 mmol). The mixture was stirred at 60° C. for 1 hour. The mixture was cooled to RT. Water (30 mL) was added and was extracted with ethyl acetate (3×50 mL). The combined organics were dried over magnesium sulfate, filtered and solvent removed in vacuo to give a residue which was purified on normal phase chromatography eluting with ethyl acetate in cyclohexane (0-50%) to give the title compound (84 mg). LCMS (A): m/z (M+H)+ 501/503, C24H26BrFN4O2 requires 500/502 (acidic).

D33 tert-butyl 3-(3-(5-fluoro-1-methylindolin-6-yl)-4-(phenylsulfonamido)-1H-pyrrolo[2,3-b]pyridin-1-yl) azetidine-1-carboxylate

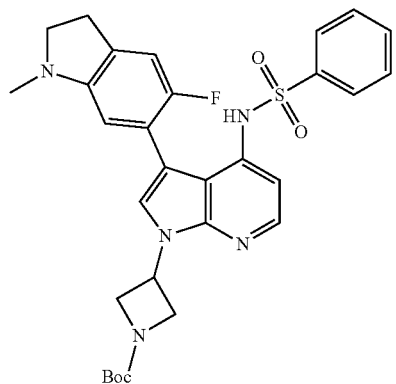 [SMILES: CN1CCc2cc(F)c(-c3cn(C4CN(C(=O)OC(C)(C)C)C4)c4nccc(NS(=O)(=O)c5ccccc5)c34)cc21]

A mixture of tert-butyl 3-(4-bromo-3-(5-fluoro-1-methylindolin-6-yl)-1H-pyrrolo[2,3-b]pyridin-1-yl)azetidine-1-carboxylate (D32) (420 mg, 0.838 mmol), benzene sulfonamide (158 mg, 1.005 mmol), xantphos (97 mg, 0.168 mmol), diacetoxypalladium (18.81 mg, 0.084 mmol), cesium carbonate (819 mg, 2.51 mmol) in 1,4-dioxane (7 mL) was refluxed at 120° C. for 3 hours. The mixture was cooled. Water (50 mL) was added and extracted with ethyl acetate (3×50 mL). The combined organics were dried over magnesium sulfate, filtered and concentrated to give a residue which was purified on normal phase silica, eluting with ethyl acetate in cyclohexane (0-50%) to give the title compound (413 mg). LCMS (A): m/z (M+H)+ 578, C30H32FN5O4S requires 577 (acidic).

D34

N-(1-(azetidin-3-yl)-3-(5-fluoro-1-methylindolin-6-yl)-1H-pyrrolo[2,3-b]pyridin-4-yl)benzenesulfonamide

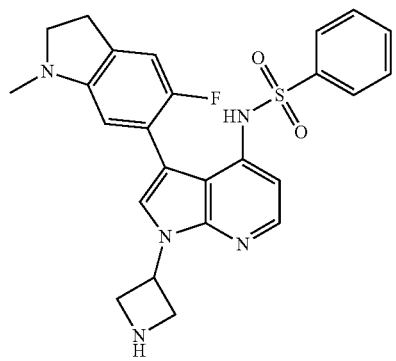 [SMILES: CN1CCc2cc(F)c(-c3cn(C4CNC4)c4nccc(NS(=O)(=O)c5ccccc5)c34)cc21]

To a solution of tert-butyl 3-(3-(5-fluoro-1-methylindolin-6-yl)-4-(phenylsulfonamido)-1H-pyrrolo[2,3-b]pyridin-1-yl)azetidine-1-carboxylate (D33) (489 mg, 0.847 mmol) in DCM (8 mL) was added 4M HCl in dioxane (4.23 mL, 16.93 mmol). The final mixture was stirred at RT for 6 hours. The mixture was concentrated in vacuo. The residue was dissolved in MeOH and passed through a SCX cartridge eluting with MeOH followed by 2M ammonia in MeOH to give the title compound (394 mg). LCMS (A): m/z (M+H)+ 478, C25H24FN5O2S requires 477 (acidic).

D35

6-(4-bromo-1-methyl-1H-pyrrolo[2,3-b]pyridin-3-yl)-4-methyl-3,4-dihydro-2H-benzo[b][1,4]oxazine

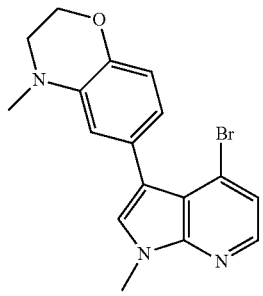 [SMILES: CN1CCOc2ccc(-c3cn(C)c4nccc(Br)c34)cc21]

To a suspension of 4-bromo-3-iodo-1-methyl-1H-pyrrolo[2,3-b]pyridine (D7) (300 mg, 0.890 mmol) and 4-methyl-6-(4,4,5,5-tetramethyl-1,3,2-dioxaborolan-2-yl)-3,4-dihydro-2H-benzo[b][1,4]oxazine (353 mg, 1.283 mmol) in ACN (2.5 mL) was added 2M sodium carbonate aqueous solution (4.72 mL, 9.43 mmol). DMF (4 mL) and DCM (3 mL) were added to aid the solubility. Then, bis(triphenylphosphine)palladium(II)chloride (81 mg, 0.116 mmol) was added and the reaction was stirred at 55° C. for 30 mins. Volatiles were removed by evaporation before partitioning between DCM and water. The organic layer was separated, dried and concentrated. The crude material was purified on silica eluting with gradient of 0-40% ethyl acetate in cyclohexane to afford the title compound (130 mg). LCMS (A): m/z (M+H)+ 358/360, C17H16BrN3O requires 357/359 (acidic).

Alternatively, to a mixture of 4-bromo-3-iodo-1-methyl-1H-pyrrolo[2,3-b]pyridine (D7) (1 g, 2.97 mmol), 4-methyl-6-(4,4,5,5-tetramethyl-1,3,2-dioxaborolan-2-yl)-3,4-dihydro-2H-benzo[b][1,4]oxazine (0.857 g, 3.12 mmol) in DME (18 mL) and MeOH (2.0 mL) was added bis(triphenylphosphine)palladium(II) chloride (0.208 g, 0.297 mmol) and 2M sodium carbonate aq. solution (14.84 mL, 29.7 mmol). The mixture was stirred at 60° C. for 1 hour. The mixture was cooled to RT and filtered. The solid was washed with excess ethyl acetate and the filtrate concentrated in vacuo. The residue aqueous was extracted with ethyl acetate (4×200 mL). The combined organics were dried over magnesium sulfate, filtered and concentrated. The residue was purified on normal phase chromatography eluting with a gradient of 0-30% ethyl acetate in cyclohexane to give the title compound (344 mg). LCMS (A): m/z (M+H)+ 358/360, C17H16BrN3O requires 357/359 (acidic).

D36

4-bromo-3-(1,2-dimethylindolin-6-yl)-1-methyl-1H-pyrrolo[2,3-b]pyridine

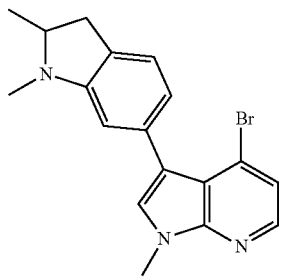 [SMILES: CC1Cc2ccc(-c3cn(C)c4nccc(Br)c34)cc2N1C]

4-Bromo-3-iodo-1-methyl-1H-pyrrolo[2,3-b]pyridine (D7) (1.1 g, 3.26 mmol), 1,2-dimethyl-6-(4,4,5,5-tetramethyl-1,3,2-dioxaborolan-2-yl)indoline (970 mg, 3.55 mmol), bis(triphenylphosphine) palladium(II) chloride (0.229 g, 0.326 mmol) and 2M sodium carbonate aqueous solution (16.32 mL, 32.6 mmol) were suspended in DMF (10 mL), ACN (10 mL) and DCM (5 mL). This was degassed under nitrogen for 10 mins before being heated to 70° C. and left stirring at this temperature for 30 mins. The reaction mixture was partitioned between ethyl acetate/water (ca. 40 mL each). The aqueous layer was separated and extracted with ethyl acetate (ca. 25 mL twice). The combined organic layer were dried over MgSO4 and concentrated. The residue was purified using chromatography on silica, eluting with a gradient of 0-40% ethyl acetate in cyclohexane to afford title compound (544 mg). LCMS (A): m/z (M+H)+ 356/358, C18H18BrN3 requires 355/357 (acidic).

D37

4-bromo-3-(5-fluoro-1-methylindolin-6-yl)-1-isopropyl-1H-pyrrolo[2,3-b]pyridine

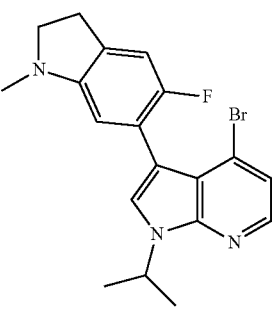 [SMILES: CC(C)n1cc(-c2cc3c(cc2F)CCN3C)c2c(Br)ccnc21]

To a stirred suspension of 4-bromo-3-iodo-1-isopropyl-1H-pyrrolo[2,3-b]pyridine (D10) (1.500 g, 4.11 mmol), 5-fluoro-1-methyl-6-(4,4,5,5-tetramethyl-1,3,2-dioxaborolan-2-yl)indoline (1.367 g, 4.93 mmol), bis(triphenylphosphine)palladium(II) chloride (0.288 g, 0.411 mmol), 2M sodium carbonate aq. solution. (20.55 mL, 41.1 mmol) in ACN (10 mL), DMF (10 mL) and DCM (5 mL) at RT was degassed under nitrogen for 10 mins. The reaction mixture was heated to 60° C. under nitrogen atmosphere for an hour. The reaction mixture was cooled to RT and partitioned between ethyl acetate/water (ca. 50 mL each). The aqeuous layer was separated and extracted with ethyl acetate (ca. 30 mL twice). The combined organic layer was dried over MgSO$_4$ and solvent removed in vacuo. The residue was purified using silica chromatography (eluted with 0-20% ethyl acetate/cyclohexane) to afford the title compound (910 mg). LCMS (A): m/z (M+H)$^+$ 388/390, C19H19BrFN3 requires 387/389 (acidic).

D38 tert-butyl 4-(N-(3-(5-fluoro-1-methylindolin-6-yl)-1-isopropyl-1H-pyrrolo[2,3-b]pyridin-4-yl)sulfamoyl)piperidine-1-carboxylate

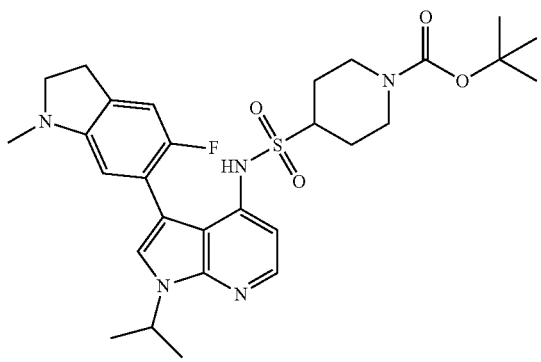 [SMILES: CC(C)n1cc(-c2cc3c(cc2F)CCN3C)c2c(NS(=O)(=O)C3CCN(C(=O)OC(C)(C)C)CC3)ccnc21]

A microwave vial was charged with tert-butyl 4-sulfamoylpiperidine-1-carboxylate (331 mg, 1.252 mmol), 4-bromo-3-(5-fluoro-1-methylindolin-6-yl)-1-isopropyl-1H-pyrrolo[2,3-b]pyridine (D37) (324 mg, 0.834 mmol), Pd2(dba)$_3$ (76 mg, 0.083 mmol), xantphos (97 mg, 0.167 mmol) and cesium carbonate (816 mg, 2.503 mmol). This was suspended in 1,4-dioxane (7 mL) and degassed under nitrogen atmosphere for 10 mins before subjected to microwave heating at 130° C. for 30 mins. The reaction mixture was filtered through celite (washing with ethyl acetate). The filtrate was removed in vacuo to give a residue which was purified using chromatography on silica (eluted with 0-20% ethyl acetate/DCM) to afford the title compound (450 mg). LCMS (A): m/z (M+H)$^+$ 572, C29H38FN5O4S requires 571 (acidic).

D39

N-(3-(5-fluoro-1-methylindolin-6-yl)-1-isopropyl-1H-pyrrolo[2,3-b]pyridin-4-yl)piperidine-4-sulfonamide, hydrochloride

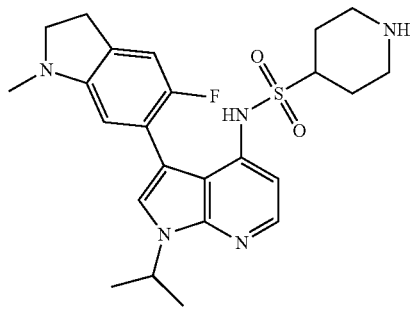 [SMILES: CC(C)n1cc(-c2cc3c(cc2F)CCN3C)c2c(NS(=O)(=O)C3CCNCC3)ccnc21]

To a stirred solution of tert-butyl 4-(N-(3-(5-fluoro-1-methylindolin-6-yl)-1-isopropyl-1H-pyrrolo[2,3-b]pyridin-4-yl)sulfamoyl)piperidine-1-carboxylate (D38) (442 mg, 0.773 mmol) in DCM (5 mL) at RT was added 4M HCl in 1,4-dioxane (1.933 mL, 7.73 mmol). The reaction mixture stirred at RT overnight. The reaction mixture was concentrated in vacuo to afford the title compound (500 mg). The material was used in next step without further purification. LCMS (A): m/z [(M−HCl)+H]$^+$ 472, C24H30FN5O2S.HCl requires 507 (acidic).

D40

2-(6-(4-bromo-1-methyl-1H-pyrrolo[2,3-b]pyridin-3-yl)-5-fluoro-1H-indol-1-yl)ethanol

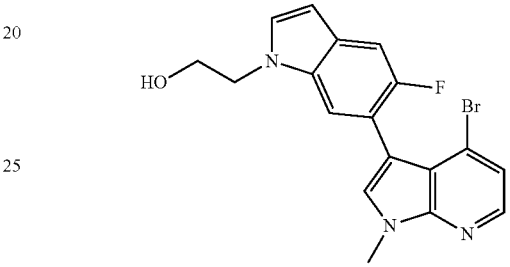

The title compound was prepared from 2-(5-fluoro-6-(4,4,5,5-tetramethyl-1,3,2-dioxaborolan-2-yl)-1H-indol-1-yl)ethanol (D79) and 4-bromo-3-iodo-1-methyl-1H-pyrrolo[2,3-b]pyridine (D7) using a similar procedure to that described for D8. LCMS (A): m/z (M+H)$^+$ 388/390, C18H15BrFN3O requires 387/389 (acidic).

D41

2-(6-(4-bromo-1-methyl-1H-pyrrolo[2,3-b]pyridin-3-yl)-5-fluoroindolin-1-yl)ethanol

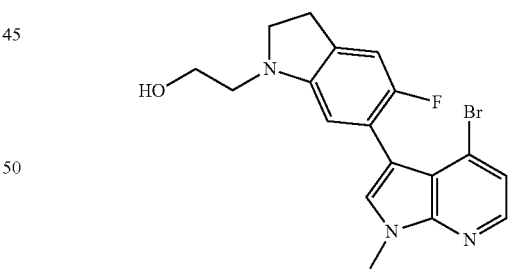

To a solution of 2-(6-(4-bromo-1-methyl-1H-pyrrolo[2,3-b]pyridin-3-yl)-5-fluoro-1H-indol-1-yl)ethanol (D40) (780 mg, 2.009 mmol) in 5 mL of acetic acid cooled in an ice bath was added sodium cyanoborohydride (189 mg, 3.01 mmol). The ice bath was removed and the reaction mixture was left to stir at RT for 1 hour. The reaction mixture was once again cooled in an ice bath then quenched and basified by the slow addition of 2N sodium carbonate aqueous solution. The aqueous layer was extracted with DCM (3×50 mL), the organic layers were combined, passed through a hydrophobic frit and concentrated. The crude was purified by column chromatography on silica gel, eluting with a gradient of 0-50% ethyl acetate in cyclohexane to afford the title compound (614 mg). LCMS (A): m/z (M+H)⁺390/392, C18H17BrFN3O requires 389/391 (acidic).

D42

4-bromo-3-(5-fluoro-1-(2-methoxyethyl)indolin-6-yl)-1-methyl-1H-pyrrolo[2,3-b]pyridine

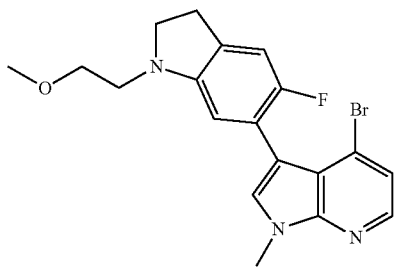 [SMILES: COCCN1CCc2cc(F)c(-c3cn(C)c4nccc(Br)c34)cc21]

To a solution of 2-(6-(4-bromo-1-methyl-1H-pyrrolo[2,3-b]pyridin-3-yl)-5-fluoroindolin-1-yl)ethanol (D41) (150 mg, 0.384 mmol) in DMSO (3 mL) was added potassium hydroxide (64.7 mg, 1.153 mmol) followed by methyl iodide (0.036 mL, 0.577 mmol). The reaction mixture was stirred at RT for 1 hour, after which an additional 0.5 eq of methyl iodide (0.012 mL) was added. The reaction mixture was stirred for an additional hour. The reaction mixture was quenched by the addition of saturated ammonium chloride aqueous solution (20 mL). The aqueous layer was extracted with DCM (3×40 mL). The organic layers were combined, passed through a hydrophobic frit and concentrated. The crude was purified by column chromatography on silica gel, eluting with a gradient of 0-40% ethyl acetate in cyclohexane to afford title compound (106 mg). LCMS (A): m/z (M+H)⁺ 404/406, C19H19BrFN3O requires 403/405 (acidic).

Preparation of Boronic Esters

Boronic acids or boronic esters were commercially available or prepared via known literature routes, unless stated below. The respective aryl bromides were prepared as detailed below and converted to their corresponding boronic esters using standard methodology similar to that described in D44.

D43 tert-butyl 4-(5-bromopyridin-3-yl)piperazine-1-carboxylate

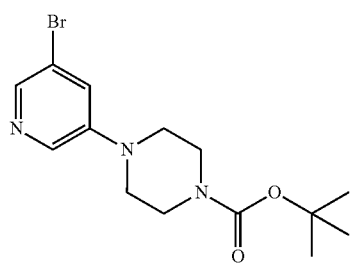 [SMILES: CC(C)(C)OC(=O)N1CCN(c2cncc(Br)c2)CC1]

To a suspension of 3,5-dibromopyridine (2 g, 8.44 mmol), 1,1-dimethylethyl 1-piperazinecarboxylate (1.572 g, 8.44 mmol), BINAP (0.210 g, 0.338 mmol) and sodium tert-butoxide (1.136 g, 11.82 mmol) in Toluene (50 mL) at RT, was added Pd₂dba₃ (0.42 g, 0.459 mmol). The reaction mixture was heated at 100° C. for 3 hours and was cooled to RT, followed by filtration through a short pad of celite (washed with ethyl acetate). The filtrate was concentrated in vacuo to give a residue, which was purified on silica gel, eluting with a gradient of 0-20% ethyl acetate in cyclohexane, to give the title compound (1.8 g). LCMS (A): m/z (M+H)⁺ 342/344, C14H20BrN3O2 requires 341/343 (acidic).

D44 tert-butyl-4-(5-(4,4,5,5-tetramethyl-1,3,2-dioxaborolan-2-yl)pyridin-3-yl)piperazine-1-carboxylate

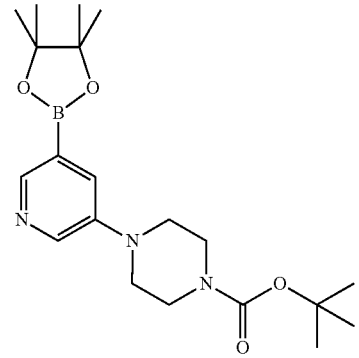 [SMILES: CC(C)(C)OC(=O)N1CCN(c2cncc(B3OC(C)(C)C(C)(C)O3)c2)CC1]

To a stirred suspension of tert-butyl 4-(5-bromopyridin-3-yl)piperazine-1-carboxylate (D43) (1.8 g, 5.26 mmol), potassium acetate (1.549 g, 15.78 mmol) and 4,4,4',4',5,5,5',5'-octamethyl-2,2'-bi-1,3,2-dioxaborolane (1.402 g, 5.52 mmol) in 1,4-Ddoxane (35 mL), was added PdCl₂(dppf)-DCM adduct (0.215 g, 0.263 mmol). The reaction mixture was stirred at 100° C. for 16 hours and was then cooled to RT before the solvent was removed in vacuo to give a residue. Water (50 mL) and DCM (100 mL) were subsequently added and the aqueous layer was separated. The organic layer was washed with water (2×50 mL), dried (phase separating column) and concentrated down. The material obtained was taken up in DCM and passed through a short plug of silica using DCM as the eluent (ca. 300 mL). The silica cartridge was then flushed with MeOH (ca. 300 mL). The methanol fraction was then concentrated down to afford the title compound (674 mg). LCMS (A): m/z (M+H)⁺ 308 corresponding to the boronic acid, C20H32BN3O4 requires 389 (acidic).

D45

1-(3-bromophenyl)azetidine

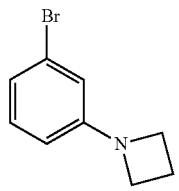 [SMILES: Brc1cccc(N2CCC2)c1]

The title compound was prepared from 1,3-dibromobenzene and azetidine using a similar procedure to that described for D43. LCMS (A): m/z (M+H)$^+$ 212/214, C9H10BrN requires 211/213 (acidic).

D46

6-chloropyridazin-4-ol

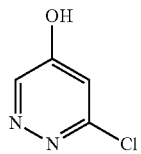

To 3,5-dichloropyridazine (200 mg, 1.342 mmol) was added 2M sodium hydroxide (1242 μL, 2.484 mmol). The reaction mixture was heated at 100° C. for 2 hours. After cooling to RT, it was acidified to pH ca. 3 using 1N HCl (ca. 1 mL). A precipitate formed was filtered and washed with water, followed by drying in the vacuum oven overnight to give the title compound (76 mg). LCMS (A): m/z (M+H)$^+$ 131, C4H3ClN2O requires 130 (acidic).

D47

6-(pyrrolidin-1-yl)pyridazin-4-ol (D35)

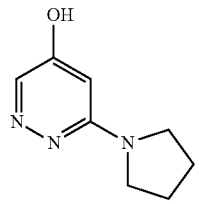 [SMILES: Oc1cnnc(N2CCCC2)c1]

In a 5 mL microwave vial, 6-chloro-4-pyridazinol (D46) (76 mg, 0.582 mmol) was dissolved in pyrrolidine (1 ml, 12.09 mmol). The reaction mixture was stirred for 30 min at 130° C. in a microwave. The reaction mixture was loaded onto the MDAP for purification (acidic conditions). The desired product recovered was triturated with DCM (1×3 mL) to afford the title compound (65 mg). LCMS (A): m/z (M+H)$^+$ 166, C8H11N3O requires 165 (acidic).

D48

5-bromo-3-(pyrrolidin-1-yl)pyridazine

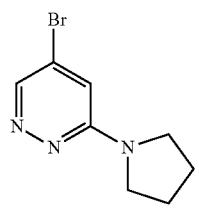

6-(1-pyrrolidinyl)-4-pyridazinol (D47) (35 mg, 0.212 mmol) was suspended in toluene (2 mL), followed by addition of phosphorus oxybromide (121 mg, 0.424 mmol). The reaction mixture was heated to 110° C. for 2 hours. The reaction was cooled to RT followed by addition of DMF (2.0 mL). The reaction was then heated at 110° C. again for 2 hours. Reaction mixture was allowed to cool to RT, and then poured onto crush ice portionwise with stirring. The mixture was neutralized with 5M NaOH and then extracted with ethyl acetate (3×20 mL). The combined organics were dried and concentrated down to give the title compound (40 mg) which was taken on to the next step without purification. LCMS (A): m/z (M+H)$^+$ 228/230, C8H10BrN3 requires 227/229 (acidic).

D49

6-bromo-4-fluoro-1-methylindoline

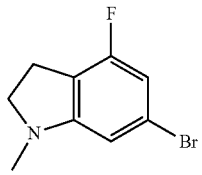

To a stirred solution of 6-bromo-4-fluoro-1H-indole (412 mg, 1.925 mmol) in acetic acid (10.600 mL) at RT was added sodium cyanoborohydride (605 mg, 9.62 mmol). Reaction mixture was stirred for 15 mins Paraformaldehyde (578 mg, 19.25 mmol) was then added and the reaction mixture was stirred at RT for 4 hours. Reaction mixture was quenched with saturated Na$_2$CO$_3$ aqueous solution (ca. 30 mL) and extracted with DCM (ca. 25 mL twice). The combined organic layers were dried over phase separator and solvent removed in vacuo. The resulting material was purified using chromatography on silica (eluted with 5-10% ethyl acetate/cyclohexane) to afford the title compound (180 mg). LCMS (A): m/z (M+H)$^+$ 230/232, C9H9BrFN requires 229/231 (acidic).

D50

8-bromo-2,3,4,5-tetrahydro-1H-benzo[b]azepine

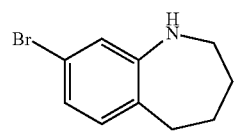

To a solution of 8-bromo-1,3,4,5-tetrahydro-2H-1-benzazepin-2-one (500 mg, 2.082 mmol) in THF (20 mL) at RT was added borane-THF complex (1M solution in THF) (5.206 mL, 5.21 mmol). The reaction mixture was refluxed for 3 hours, after which the reaction mixture was cooled in an ice bath before the addition of a further amount of borane-THF complex (1M solution in THF) (7.290 mL, 7.29 mmol). The reaction mixture was once again refluxed overnight. The reaction mixture was cooled in an ice bath before the dropwise addition of water. The aqueous layer was then extracted with diethyl ether (3×25 mL). The organic layers were combined, passed through a hydrophobic frit and concentrated. This residue was purified on silica column eluting with ethyl acetate in cyclohexane (0-15%) to afford the title compound (400 mg). LCMS (A): m/z (M+H)+ 226/228, C10H12BrN requires 225/227 (acidic).

D51

8-bromo-1-methyl-2,3,4,5-tetrahydro-1H-benzo[b]azepine

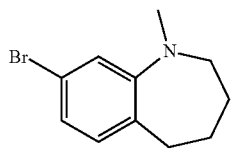

To a solution of 8-bromo-2,3,4,5-tetrahydro-1H-benzo[b]azepine (D50) (395 mg, 1.747 mmol) in 25 mL of MeOH and acetic acid (1 mL, 17.47 mmol) was added formaldehyde (37% aq solution) (0.780 mL, 10.48 mmol) and the reaction mixture stirred for 30 minutes followed by the addition of a solution of sodium cyanoborohydride (878 mg, 13.98 mmol) in MeOH (10 mL). The reaction mixture was stirred at RT for 1 hour, then basified by the slow addition of sodium hydrogen carbonate aqueous solution (ca. 50 mL). The aqueous layer was extracted with DCM (3×50 mL), the organic layers were combined, passed through a hydrophobic frit and concentrated. The residue was purified by column chromatography on silica gel, eluting with a gradient of 0-5% ethyl acetate in cyclohexane to afford the title compound (357 mg). LCMS (A): m/z (M+H)+ 240/242, C11H14BrN requires 239/241 (acidic).

D52 tert-butyl (3-bromo-2-hydroxyphenyl)carbamate

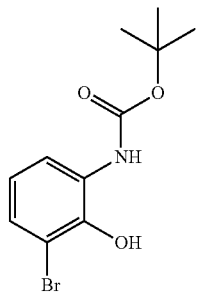 [SMILES: CC(C)(C)OC(=O)Nc1cccc(Br)c1O]

To a stirred suspension of 2-amino-6-bromophenol (2 g, 10.64 mmol) in chloroform (15 mL) at RT was added pyridine (2.58 mL, 31.9 mmol) followed by the dropwise addition of Boc-anhydride (2.96 mL, 12.76 mmol) in chloroform (5 mL). The mixture was stirred at RT for 16 hours. The reaction mixture was then quenched using 1M HCl aqueous solution (10.64 mL, 10.64 mmol), extracted with DCM, organic phase separated, dried and volatiles removed by evaporation. The residue was then purified on silica eluting with a gradient of 0-30% ethyl acetate in cyclohexane to afford the title compound (3 g). LCMS (A): m/z (M+H)+ 288/290, C11H14BrNO3 requires 287/289 (acidic).

D53 tert-butyl 9-bromo-3,4-dihydrobenzo[b][1,4]oxazepine-5(2H)-carboxylate

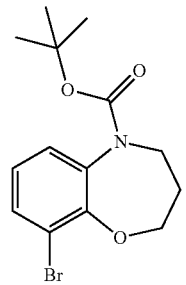 [SMILES: CC(C)(C)OC(=O)N1CCCOc2c(Br)cccc21]

To a solution of tert-butyl (3-bromo-2-hydroxyphenyl)carbamate (D52) (3 g, 10.41 mmol) in acetone (30 mL) was added 1,3-dibromopropane (3.17 mL, 31.2 mmol), K2CO3 (11.51 g, 83 mmol) and the mixture stirred at 75° C. for 16 hours. The reaction was then cooled to RT, filtered, the filtrate was evaporated. The residue was then purified on silica eluting with a gradient of 0-10% ethyl acetate in cyclohexane to afford the title compound (2.2 g). LCMS (A): m/z (M+H)+ 328/330, C14H18BrNO3 requires 327/329 (acidic).

D54 tert-butyl 7-bromo-3,4-dihydrobenzo[b][1,4]oxazepine-5(2H)-carboxylate

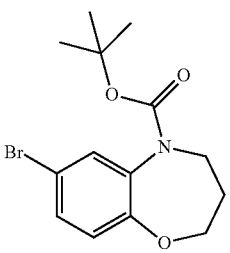 [SMILES: CC(C)(C)OC(=O)N1CCCOc2ccc(Br)cc21]

The title compound was prepared from 2-amino-4-bromophenol using a similar procedure to that described for D53. LCMS (A): m/z (M+H)+ 328/330, C14H18BrNO3 requires 327/329 (acidic).

D55

7-bromo-1-methyl-1H-pyrido[2,3-b][1,4]oxazin-2(3H)-one

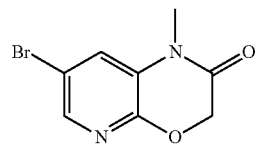

To a suspension of 7-bromo-1H-pyrido[2,3-b][1,4]oxazin-2(3H)-one (500 mg, 2.183 mmol) in acetone (8 mL) at RT was added potassium carbonate (905 mg, 6.55 mmol) followed by methyl iodide (0.341 mL, 5.46 mmol). This was heated to 60° C. under nitrogen atmosphere for 3 hours. The reaction mixture was cooled to RT, solvent removed in vacuo. The residue was partitioned between water/ethyl acetate (ca. 25 mL each). The aqueous layer was extracted with ethyl acetate (ca. 25 mL twice). The combined organic layers were dried over MgSO$_4$ and solvent removed in vacuo. The residue was purified on silica gel (eluted with 20-60% ethyl acetate/cyclohexane) to afford the title compound (334 mg). LCMS (A): m/z (M+H)$^+$ 243/245, C8H7BrN2O2 requires 242/244 (acidic).

D56

7-bromo-1-methyl-2,3-dihydro-1H-pyrido[2,3-b][1,4]oxazine

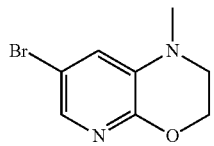

The title compound was prepared from 7-bromo-1-methyl-1H-pyrido[2,3-b][1,4]oxazin-2(3H)-one (D55) using a similar procedure to that described for D50. LCMS (A): m/z (M+H)$^+$ 229/231, C8H9BrN2O requires 228/230 (acidic).

D57 tert-butyl 4-(3-methoxy-5-(4,4,5,5-tetramethyl-1,3,2-dioxaborolan-2-yl)phenyl)piperazine-1-carboxylate

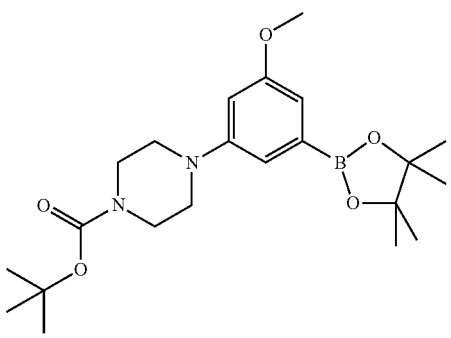 [SMILES: COc1cc(B2OC(C)(C)C(C)(C)O2)cc(N2CCN(C(=O)OC(C)(C)C)CC2)c1]

The title compound was prepared from 3,5-dibromoanisole and 1-Boc-piperazine using a similar procedure to that described for D44. LCMS (A): m/z (M+H)$^+$ 419, C22H35BN2O5 requires 418 (acidic).

D58

1-methyl-6-(4,4,5,5-tetramethyl-1,3,2-dioxaborolan-2-yl)indoline

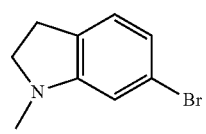

The title compound was prepared from 6-bromo-1H-indole using a similar procedure to that described for D49. LCMS (A): m/z (M+H)$^+$ 212/214, C9H10BrN requires 211/213 (acidic).

D59

1-(4-fluoro-3-(4,4,5,5-tetramethyl-1,3,2-dioxaborolan-2-yl)phenyl)pyrrolidine

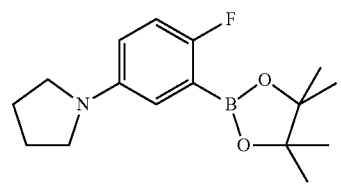 [SMILES: CC1(C)OB(c2cc(N3CCCC3)ccc2F)OC1(C)C]

The title compound was prepared from 2-bromo-1-fluoro-4-iodobenzene and pyrrolidine using a similar procedure to that described for D44. LCMS (A): m/z (M+H)$^+$ 292, C22H35BN2O5 requires 291 (acidic).

D60

1-(3-fluoro-5-(4,4,5,5-tetramethyl-1,3,2-dioxaborolan-2-yl)phenyl)pyrrolidine

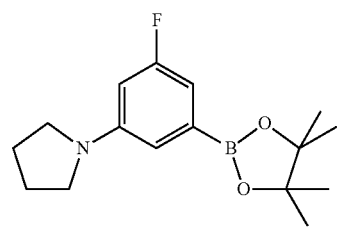 [SMILES: CC1(C)OB(c2cc(F)cc(N3CCCC3)c2)OC1(C)C]

The title compound was prepared from 1,3-dibromo-5-fluorobenzene and pyrrolidine using a similar procedure to that described for D44. LCMS (A): m/z (M+H)$^+$ 293, C22H35BN2O5 requires 291 (acidic).

D61

1-(2-fluoro-5-(4,4,5,5-tetramethyl-1,3,2-dioxaborolan-2-yl)phenyl)pyrrolidine

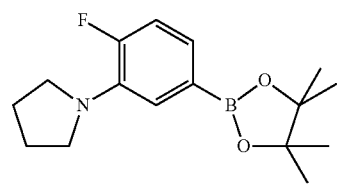 [SMILES: CC1(C)OB(c2ccc(F)c(N3CCCC3)c2)OC1(C)C]

The title compound was prepared from 4-bromo-1-fluoro-2-iodobenzene and pyrrolidine using a similar procedure to that described for D44. LCMS (A): m/z (M+H)$^+$ 292, C22H35BN2O5 requires 291 (acidic).

D62

5-bromo-2-(pyrrolidin-1-yl)thiazole

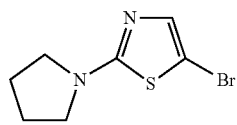 [SMILES: Brc1cnc(N2CCCC2)s1]

4 batches of 2,5-dibromo-1,3-thiazole (250 mg, 1.029 mmol), pyrrolidine (0.089 mL, 1.081 mmol) and DIPEA (0.225 mL, 1.286 mmol) in THF (2.5 mL) were heated in a microwave at 120° C. for 15 minutes. All 4 batches were combined and evaporated to dryness. The residues were purified on silica eluting with cyclohexane and ethyl acetate (0-100%). The appropriate fractions were combined and evaporated to dryness producing the title compound (260 mg). LCMS (A): m/z (M+H)$^+$ 233/235, C7H9BrN2S requires 232/234 (acidic).

D63

4-bromo-1-methylindoline

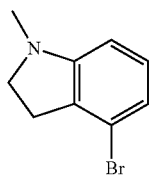

The title compound was prepared from 4-bromo-1H-indole using a similar procedure to that described for D49. LCMS (A): m/z (M+H)$^+$ 212/214, C9H10BrN requires 211/213 (acidic).

D64

6-bromo-1,5-dimethylindoline

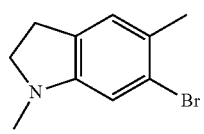

The title compound was prepared from 6-bromo-5-methyl-1H-indole using a similar procedure to that described for D49. LCMS (A): m/z (M+H)$^+$ 226/228, C10H12BrN requires 225/227 (acidic).

D65

6-bromo-5-fluoro-1-methylindoline

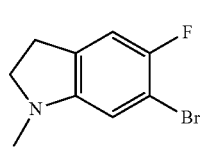

The title compound was prepared from 6-bromo-5-fluoro-1H-indole using a similar procedure to that described for D49. LCMS (A): m/z (M+H)$^+$ 230/232 C9H9BrFN requires 229/231 (acidic).

D66

2-methyl-1-(3-(4,4,5,5-tetramethyl-1,3,2-dioxaborolan-2-yl)phenyl)pyrrolidine

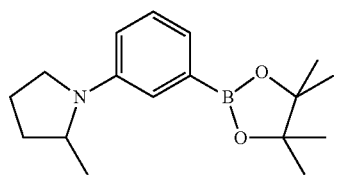 [SMILES: CC1CCCN1c1cccc(B2OC(C)(C)C(C)(C)O2)c1]

The title compound was prepared from 1,3-dibromobenzene and 2-methylpyrrolidine using a similar procedure to that described for D44. LCMS (A): m/z (M+H)$^+$ 288, C17H26BNO2 requires 287 (acidic).

D67

3-bromo-N-cyclobutyl-N-methylaniline

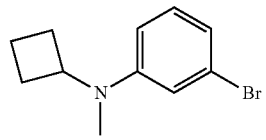

The title compound was prepared from 3-bromo-N-cyclobutylaniline using a similar procedure to that described for D51. LCMS (A): m/z (M+H)$^+$ 240/242, C11H14BrN requires 239/241 (acidic).

D68

3-bromo-N-cyclopentyl-N-methylaniline

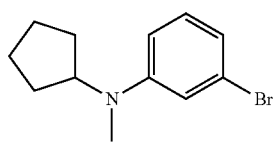

The title compound was prepared from 1,3-dibromobenzene and N-methylcyclopentanamine using a similar procedure to that described for D43. LCMS (A): m/z (M+H)+ 254/256, C$_{12}$H16BrN requires 253/255 (acidic).

D69

1-(3-bromophenyl)pyrrolidin-2-one

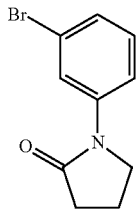

To a stirring solution of 1,3-dibromobenzene (3 g, 12.72 mmol) in 1,4-dioxane (100 mL) was added 2-pyrrolidinone (0.975 mL, 12.72 mmol), palladium(II) acetate (0.143 g, 0.636 mmol), xantphos (0.736 g, 1.272 mmol) and cesium carbonate (8.29 g, 25.4 mmol). The mixture was then heated at 100° C. overnight. The reaction mixture was diluted with ethyl acetate (100 mL). The organic phase was washed with water (100 mL). The organic phase was collected, and the aqueous phase further extracted with ethyl acetate (2×50 mL). The organic phases were combined, dried over MgSO$_4$, filtered and removed solvent under vacuo. The residue was purified on silica gel, eluting with a gradient of 0-40% ethyl acetate in cyclohexane to give the title compound (2.06 g). LCMS (A): m/z (M+H)+ 240/242, C10H10BrNO requires 239/241 (acidic).

D70

6-bromo-4-methyl-3,4-dihydro-2H-benzo[b][1,4]oxazine

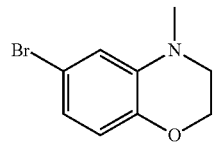

The title compound was prepared from 6-bromo-2H-1,4-benzoxazin-3(4H)-one using a similar procedure to that described for D51. LCMS (A): m/z (M+H)+ 228/230, C9H10BrNO requires 227/229 (acidic).

D71

6-bromo-1,2-dimethylindoline

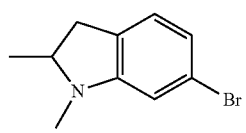

The title compound was prepared from 6-bromo-2-methyl-1H-indole using a similar procedure to that described for D49. LCMS (A): m/z (M+H)+ 226/228, C10H12BrN requires 225/227 (acidic).

D72

6-bromo-3-chloro-1H-indole

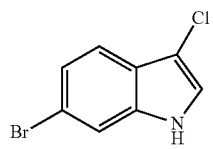 [SMILES: Clc1c[nH]c2cc(Br)ccc12]

A mixture of 6-bromo-1H-indole (850 mg, 4.34 mmol) and NCS (593 mg, 4.44 mmol) in DCM (17 mL) was stirred at 0° C. for 1.5 hour. The mixture was partitioned between saturated aqueous ammonium chloride (25 mL) and ethyl acetate (150 mL). The organic phase was separated, washed with brine (25 mL), dried with anhydrous magnesium sulfate, filtered and evaporated to dryness to give the title compound (894 mg). LCMS (A): m/z (M+H)+ 230/232, C8H5BrClN requires 229/231 (acidic).

D73

6-bromo-3-chloro-1-methyl-1H-indole

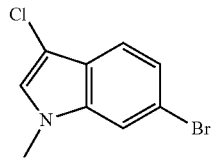

A solution of 6-bromo-3-chloro-1H-indole (D72) (894 mg, 3.88 mmol) in DMF (16 mL) was cooled to 0° C. under an atmosphere of nitrogen. Sodium hydride (60% in mineral oil) (163 mg, 4.07 mmol) was added portionwise followed by methyl iodide (0.243 mL, 3.88 mmol). The mixture was stirred for 1.5 hour, slowly allowing to warm to RT. The mixture was quenched with saturated aq. NH$_4$Cl and extracted with ethyl acetate (2×150 mL). The organic extracts were combined, dried with anhydrous sodium sulfate, filtered and evaporated to dryness. The residues were purified on silica, eluting with cyclohexane and ethyl acetate (0-50%). The appropriate fractions were combined and evaporated to dryness to give title compound (831 mg). LCMS (A): m/z (M−H)− 242/244, C9H7BrClN requires 243/245 (acidic).

D74

1-(6-bromoindolin-1-yl)-2,2,2-trifluoroethanone

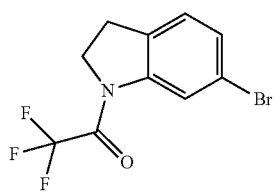 [SMILES: O=C(N1CCc2ccc(Br)cc21)C(F)(F)F]

A mixture of 6-bromoindoline (1.00 g, 5.05 mmol), 2,2,2-trifluoroacetic anhydride (0.843 mL, 6.06 mmol) and triethylamine (1.056 mL, 7.57 mmol) in DCM (25 mL) was stirred at RT for 3 hours. The mixture was partitioned between water (50 mL) and DCM (100 mL). The aqueous phase was separated and extracted with additional DCM (50 mL). The organic extracts were combined, washed with brine (25 mL), dried with anhydrous magnesium sulfate, filtered and evaporated to dryness. The residues were purified on silica eluting with cyclohexane and ethyl acetate (0-100%). The appropriate fractions were combined and evaporated to dryness producing title compound (1.40 g). LCMS (A): m/z (M+H)$^+$ 294/296, C10H7BrF3NO requires 293/295 (acidic).

D75

6-bromo-1-(2,2,2-trifluoroethyl)indoline

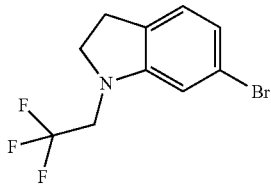 [SMILES: FC(F)(F)CN1CCc2ccc(Br)cc21]

A solution of BH3.THF (1M in THF) (6.12 mL, 6.12 mmol) was added to a solution of 1-(6-bromoindolin-1-yl)-2,2,2-trifluoroethanone (D74) (900 mg, 3.06 mmol) in dry THF (2.0 mL) stirred at 0° C. The mixture was then heated at reflux for overnight (ca. 16 hours). The reaction mixture was quenched with aqueous ammonium chloride, and was partitioned between water (25 mL) and ethyl acetate (100 mL). The aqueous phase was separated and extracted with additional ethyl acetate (100 mL). The organic extracts were combined, washed with brine (25 mL), dried with anhydrous magnesium sulfate, filtered and evaporated to dryness. The residues were purified on silica eluting with cyclohexane and ethyl acetate (0-100%). The appropriate fractions were combined and evaporated to dryness producing title compound (670 mg). LCMS (A): m/z (M+H)$^+$ 280/282, C10H9BrF3N requires 279/281 (acidic).

D76

6-bromo-5-methoxy-1,2-dimethyl-1H-indole

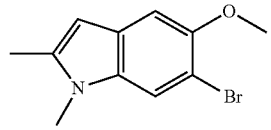

6-Bromo-5-methoxy-1,2-dimethyl-1H-indole-3-carboxylic acid (1.02 g, 3.42 mmol) was separated into two round bottom flasks (each with 500 mg of material), followed by the addition of quinoline (2 mL) in each flask. The reaction mixture was heated at 200° C. for 4 hours and was cooled to RT. The two reaction mixture was combined and loaded directly on a silica gel column, eluting with a gradient of 0-20% ethyl acetate in cyclohexane, to give title compound (435 mg). LCMS (A): m/z (M+H)$^+$ 254/256, C11H12BrNO requires 253/255 (acidic).

D77

Methyl 2-(6-bromo-5-fluoro-1H-indol-1-yl)acetate

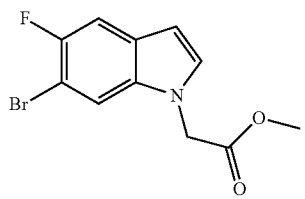 [SMILES: COC(=O)Cn1ccc2cc(F)c(Br)cc21]

6-Bromo-5-fluoro-1H-indole (10 g, 46.7 mmol) was dissolved in DMF (100 mL) and cooled to 0° C. in an ice bath before the addition of sodium hydride, 60% dispersion in mineral oil (3.74 g, 93 mmol) and methyl 2-bromoacetate (8.59 mL, 93 mmol). The ice bath was removed and the reaction mixture was stirred at RT for 1 hour. The reaction mixture was cooled with an ice bath once again then quenched with water (50 mL). The aqueous layer was extracted with DCM (3×200 mL). The organics were combined, passed through a hydrophobic frit and concentrated. The residue was purified by column chromatography on silica gel, eluting with a gradient of 0-40% ethyl acetate in cyclohexane to afford the title compound (10.209 g). LCMS (A): m/z (M+H)$^+$ 286/288, C11H9BrFNO2 requires 285/287 (acidic).

D78

2-(6-bromo-5-fluoro-1H-indol-1-yl) ethanol

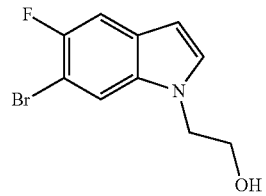 [SMILES: OCCn1ccc2cc(F)c(Br)cc21]

Methyl 2-(6-bromo-5-fluoro-1H-indol-1-yl)acetate (D77) (10.2 g, 35.7 mmol) was dissolved up in 81 mL of THF and cooled in a cardice/acetone bath before the addition of LiAlH$_4$ (2N in THF solution) (17.83 mL, 35.7 mmol). The reaction mixture was left to stir in the cardice/acetone bath for 30 mins. Whilst still in the bath the reaction mixture was quenched by the dropwise addition of saturated sodium sulfate aqueous solution. The solid formed was filtered off and washed with ethyl acetate. The filtrate was washed with brine. The organic layer was passed through a hydrophobic frit and concentrated to afford title compound (8.852 g). LCMS (A): m/z (M+H)+ 258/260, C10H9BrFNO requires 257/259 (acidic).

D79

2-(5-fluoro-6-(4,4,5,5-tetramethyl-1,3,2-dioxaborolan-2-yl)-1H-indol-1-yl)ethanol

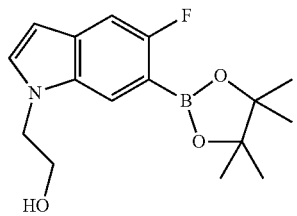 [SMILES: CC1(C)OB(c2cc3c(ccn3CCO)cc2F)OC1(C)C]

To a solution of 2-(6-bromo-5-fluoro-1H-indol-1-yl)ethanol (D78) (8.85 g, 34.3 mmol) in DME (110 mL) was added 4,4,4',4',5,5,5',5'-octamethyl-2,2'-bi(1,3,2-dioxaborolane) (9.58 g, 37.7 mmol), PdCl₂(dppf)-DCM Adduct (1.40 g, 1.715 mmol), and potassium acetate (10.10 g, 103 mmol). The reaction mixture as stirred at 100° C. for 2 hours before the addition of a further 0.5 eq of 4,4,4',4',5,5,5',5'-octamethyl-2,2'-bi(1,3,2-dioxaborolane) (4.35 g) and 0.05 eq of PdCl₂(dppf)-DCM Adduct (1.4 g). The reaction mixture was stirred for 1 additional hour. The reaction mixture was cooled to RT then filtered through celite and the celite was washed with ethyl acetate. The filtrate was concentrated. The resulting residue was purified by column chromatography on silica gel, eluting with a gradient of 0-50% ethyl acetate in cyclohexane to afford title compound (2.659 g). LCMS (A): m/z (M+H)+ 306, C16H21BFNO3 requires 305 (acidic).

D80

4-bromo-1-fluoro-2-(methoxymethoxy)benzene

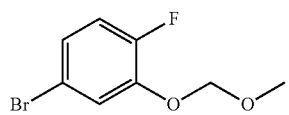

To a stirred solution of 5-bromo-2-fluorophenol (5 g, 26.2 mmol) in DMF (50 mL) at 0° C. was added sodium hydride (1.571 g, 39.3 mmol). After stirring for 10 min, chloromethyl methyl ether (2.386 mL, 31.4 mmol) was added dropwise to mixture and the mixture was then stirred for 1 hour at 0° C. The reaction was quenched with addition of saturated NH₄Cl aq. and the mixture was poured into water (150 mL). The mixture was extracted with ethyl acetate (30 mL×2). The organic layers were combined, washed with brine (100 mL), dried over MgSO₄, filtered and evaporated in vacuo. The crude residue was purified by chromatography on silica, eluting with a gradient of 0-10% ethyl acetate in cyclohexane to give the title compound (5.90 g). 1H NMR (CDCl₃, 400 MHz) δ ppm: 3.55 (3H, s), 5.24 (2H, s), 6.95-7.02 (1H, m), 7.08-7.14 (1H, m), 7.36-7.40 (1H, m).

D81

7-(4-fluoro-3-(methoxymethoxy)phenyl)-7-azabicyclo[2.2.1]heptanes

The starting material divided in 2 microwave vials. A mixture of 4-bromo-1-fluoro-2-(methoxymethoxy)benzene (D80) (500 mg, 2.127 mmol), 7-azabicyclo[2.2.1]heptane hydrochloride (370 mg, 2.77 mmol), tris(dibenzylideneacetone)dipalladium(0) (195 mg, 0.213 mmol), 2-dicyclohexylphosphino-2',4',6'-triisopropylbiphenyl (203 mg, 0.425 mmol) and sodium tert-butoxide (1022 mg, 10.64 mmol) in 1,4-dioxane (14 mL) was degassed with nitrogen and the mixture was heated at 120° C. for 30 min in a microwave. The reaction mixtures were combined, filtered through celite, washed with ethyl acetate and the filtrate was evaporated in vacuo. The crude residue was purified by chromatography on silica, eluting with a gradient of 0-10% ethyl acetate in cyclohexane to give the title compound (388.3 mg). LCMS (A): m/z (M+H)+ 252, C14H18FNO2 requires 251 (acidic).

D82

5-(7-azabicyclo[2.2.1]heptan-7-yl)-2-fluorophenol, hydrochloride

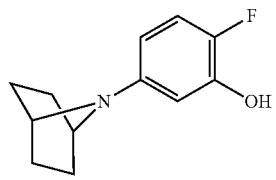 [SMILES: Oc1cc(N2C3CCC2CC3)ccc1F]

To a solution of 7-(4-fluoro-3-(methoxymethoxy)phenyl)-7-azabicyclo[2.2.1]heptane (D81) (423 mg, 1.683 mmol) in THF (10 mL) and MeOH (1 mL) was added 4M solution of HCl in 1,4-dioxane (2.104 mL, 8.42 mmol). The mixture was stirred overnight at RT. The reaction mixture was evaporated in vacuo to give the title compound (427 mg), which was carried over to next step without purification. LCMS (A): m/z [(M−HCl)+H]+ 208, C₁₂H14FNO.HCl requires 243 (acidic).

D83

5-(7-azabicyclo[2.2.1]heptan-7-yl)-2-fluorophenyl trifluoromethanesulfonate

To a stirred solution of 5-(7-azabicyclo[2.2.1]heptan-7-yl)-2-fluorophenol, hydrochloride (D82) (421 mg, 1.727 mmol) and N,N-diisopropylethylamine (0.905 mL, 5.18 mmol) in DCM (15 mL) at 0° C. was added triflic anhydride (0.350 mL, 2.073 mmol). After stirring for 30 min, the mixture was allowed to warm to RT and stirred for 2 h. The mixture was poured into water (50 mL) and extracted with DCM (10 mL×3). The organic layers were filtered through phase separator and evaporated in vacuo to give title compound (1.311 g). The material was used to next step without purification. LCMS (A): m/z (M+H)$^+$ 340, C13H13F4NO3S requires 339 (acidic).

D84

7-(4-fluoro-3-(4,4,5,5-tetramethyl-1,3,2-dioxaborolan-2-yl)phenyl)-7-azabicyclo[2.2.1]heptanes

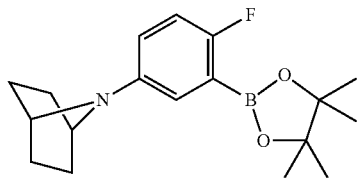 [SMILES: CC1(C)OB(c2cc(N3C4CCC3CC4)ccc2F)OC1(C)C]

The title compound was prepared from 5-(7-azabicyclo[2.2.1]heptan-7-yl)-2-fluorophenyl trifluoromethanesulfonate (D83) using a similar procedure to that described for D44. LCMS (A): m/z (M+H)$^+$ 318, C18H25BFNO2 requires 317 (acidic).

D85

2-amino-4-bromo-5-fluorobenzoic acid, hydrochloride

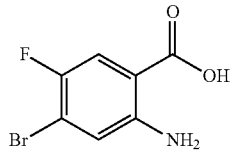

To a mixture of 4-bromo-5-fluoro-2-nitrobenzoic acid (10 g, 37.9 mmol) and HCl (70 mL, 852 mmol) in water (70 mL) was added tin(II) chloride (21.55 g, 114 mmol) and the mixture was then heated at 90° C. for 3 hours. After cooling to RT, the formed precipitate was filtered, washed with water and collected to give title compound (8.51 g). LCMS (A): m/z [(M−HCl)+H]$^+$ 234/236, C7H5BrFNO2.HCl requires 269/271 (acidic).

D86

4-bromo-2-((1-carboxyethyl)amino)-5-fluorobenzoic acid

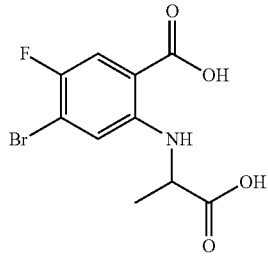 [SMILES: CC(Nc1cc(Br)c(F)cc1C(=O)O)C(=O)O]

To a mixture of 2-amino-4-bromo-5-fluorobenzoic acid, hydrochloride (D85) (1.5 g, 5.55 mmol) in water (10 mL) was added sodium hydroxide (0.444 g, 11.09 mmol) followed by potassium carbonate (1.533 g, 11.09 mmol). A solution of methyl 2-bromopropionate (0.619 mL, 5.55 mmol) in MeOH (10.00 mL) was added to the mixture and the mixture was then heated at 80° C. for 24 hours. LCMS showed reaction was not complete with remaining significant amount of starting material. Further methyl 2-bromopropionate (0.619 mL, 5.55 mmol) was added to the mixture and the mixture was then stirred for 24 hours at 80° C. 6M aqueous sodium hydroxide (4.62 mL, 27.7 mmol) was added to the mixture and the mixture was then heated at 100° C. for 1.5 h. After cooling to RT, MeOH was removed under reduced pressure. The aqueous residue was extracted with ethyl acetate (20 mL). The aqueous layer was cooled to 0° C. and was then acidified with addition of concentrated HCl. The formed precipitate was filtered, washed with water and collected to give title compound (1.78 g). LCMS (A): m/z (M+H)$^+$ 306/308, C10H9BrFNO4 requires 305/307 (acidic).

D87

1-acetyl-6-bromo-5-fluoro-2-methyl-1H-indol-3-yl acetate

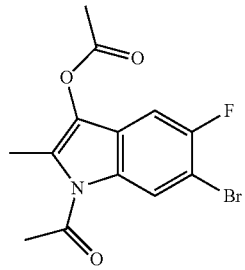 [SMILES: CC(=O)Oc1c(C)n(C(C)=O)c2cc(Br)c(F)cc12]

A mixture of 4-bromo-2-((1-carboxyethyl)amino)-5-fluorobenzoic acid (D86) (1.599 g, 5.22 mmol), sodium acetate (1.714 g, 20.90 mmol) and acetic anhydride (19.72 mL, 209 mmol) was heated at 150° C. for 30 min in a microwave. The mixture was evaporated in vacuo. The residue was diluted with DCM and poured into saturated NaHCO3 aq. (200 mL). The mixture extracted with DCM (30 mL×3). The organic layers were combined, washed with brine (100 mL), filtered through phase separator and evaporated in vacuo. The crude residue was purified by chromatography on silica, eluting with a gradient of 0-35% ethyl acetate in cyclohexane to give title compound (1.233 g). LCMS (A): m/z (M+H)$^+$ 328/330, C13H11BrFNO3 requires 327/329 (acidic).

D88

1-acetyl-6-bromo-5-fluoro-2-methylindolin-3-one

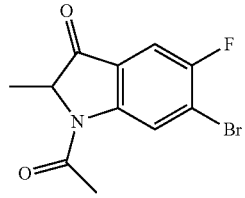 [SMILES: CC(=O)N1c2cc(Br)c(F)cc2C(=O)C1C]

To a mixture of 1-acetyl-6-bromo-5-fluoro-2-methyl-1H-indol-3-yl acetate (D87) (1.22 g, 3.72 mmol) in ethanol (15 mL) was added a solution of sodium sulfite (0.562 g, 4.46 mmol) in water (15.00 mL). The mixture was then heated at 110° C. for 2 hours. After cooling to RT, ethanol was removed under reduced pressure. The aqueous residue was poured into water (50 mL) and extracted with DCM (20 mL×3). The organic layers were combined, washed with brine (100 mL), filtered through phase separator and evaporated in vacuo. The crude residue was purified by chromatography on silica, eluting with a gradient of 0-40% ethyl acetate in cyclohexane to give title compound (769.5 mg). LCMS (A): m/z (M+H)$^+$ 286/288, C11H9BrFNO2 requires 285/287 (acidic).

D89

1-acetyl-6-bromo-5-fluoro-2,2-dimethylindolin-3-one

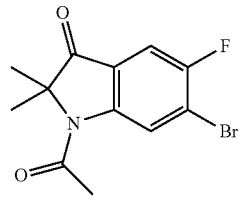 [SMILES: CC(=O)N1c2cc(Br)c(F)cc2C(=O)C1(C)C]

To a stirred mixture of 1-acetyl-6-bromo-5-fluoro-2-methylindolin-3-one (D88) (800 mg, 2.80 mmol) in THF (20 mL) at 0° C. was added sodium hydride (224 mg, 5.59 mmol). After stirring for 10 min, iodomethane (0.210 mL, 3.36 mmol) was added to the mixture. The mixture was allowed to warm to RT. The mixture was stirred for 1 hour at RT. The reaction was quenched with addition with saturated NH$_4$Cl aq. and the mixture was poured into water (100 mL). The mixture was extracted with ethyl acetate (30 mL×3). The organic layers were combined, washed with brine (100 mL), dried over MgSO$_4$, filtered and evaporated in vacuo. The crude residue was purified by chromatography on silica, eluting with a gradient of 0-30% ethyl acetate in cyclohexane to give title compound (300 mg). LCMS (A): m/z (M+H)$^+$ 300/302, C12H11BrFNO2 requires 299/301 (acidic).

D90

6-bromo-5-fluoro-2,2-dimethylindolin-3-one

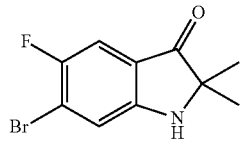

To a mixture of 1-acetyl-6-bromo-5-fluoro-2,2-dimethylindolin-3-one (D89) (297 mg, 0.990 mmol) in ethanol (3 mL) was added 2M aqueous sodium hydroxide (0.594 mL, 1.188 mmol) and the mixture was heated at 90° C. for 1 h. After cooling to RT, ethanol was evaporated in vacuo. Aqueous residue was poured into water (10 mL) and extracted with ethyl acetate (10 mL×3). The organic layers were combined, washed with brine (10 mL), dried over MgSO$_4$, filtered and evaporated in vacuo. The crude residue was purified by chromatography on silica, eluting with a gradient of 0-40% ethyl acetate in cyclohexane to give title compound (244.1 mg). LCMS (A): m/z (M+H)$^+$ 258/260, C10H9BrFNO requires 257/259 (acidic).

D91

6-bromo-5-fluoro-1,2,2-trimethylindolin-3-one

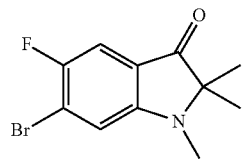

To a stirred solution of 6-bromo-5-fluoro-2,2-dimethylindolin-3-one (D90) (240 mg, 0.930 mmol) in DMF (3 mL) at 0° C. was added sodium hydride (55.8 mg, 1.395 mmol). After stirring for 10 min, iodomethane (0.116 mL, 1.860 mmol) was added to the mixture and the mixture was stirred for 30 min at 0° C. The reaction was quenched with addition of saturated NH$_4$Cl (1 mL) and the mixture was poured into water (60 mL). The mixture was extracted with ethyl acetate (10 mL×3). The organic layers were combined, washed with brine (50 mL), dried over MgSO$_4$, filtered and evaporated in vacuo. The crude residue was purified by chromatography on silica, eluting with a gradient of 0-30% ethyl acetate in cyclohexane to give the title compound (247.7 mg). LCMS (A): m/z (M+H)$^+$ 272/274, C11H11BrFNO requires 271/273 (acidic).

D92

5-fluoro-1,2,2-trimethyl-6-(4,4,5,5-tetramethyl-1,3,2-dioxaborolan-2-yl)indolin-3-one

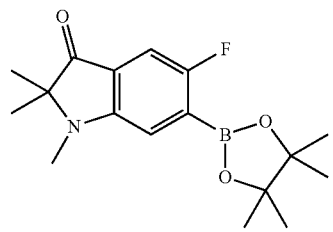

The title compound was prepared from 6-bromo-5-fluoro-1,2,2-trimethylindolin-3-one (D91) using a similar procedure to that described for D79. LCMS (A): m/z (M+H)$^+$ 238 corresponding to the boronic acid, C17H23BFNO3 requires 319 (acidic).

Preparation of Sulfonamides

Sulfonamides were commercially available or prepared using known literature routes, unless stated below. The respective sulfonyl chlorides were prepared as detailed below and converted to their corresponding sulphonamides using standard methodology similar to that described in D98.

D93

1,3-dimethyl-1H-pyrazole-4-sulfonamide

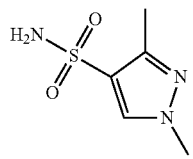

A solution of 1,3-dimethyl-1H-pyrazole-4-sulfonyl chloride (232 mg, 1.192 mmol) in THF (10.0 mL) was cooled to 0° C. and to it was added dropwise ammonium hydroxide (0.650 mL, 16.69 mmol). The reaction mixture was allowed to warm to RT and left to stir over the weekend (ca. 64 hours). The reaction mixture was concentrated in vacuo. The residues were taken up in water, then neutralized with 1M aqueous HCl (dropwise addition) to pH 5-6 and extracted with ethyl acetate (3×50 mL). The combined organics were dried over MgSO$_4$, filtered and evaporated to dryness, producing the title compound (233 mg). LCMS (A): m/z (M+H)$^+$ 176, C5H9N3O2S requires 175 (acidic).

D94

1-methyl-1H-pyrazole-3-sulfonamide

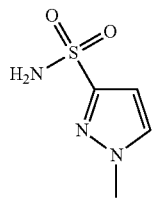

A solution of 1-methyl-1H-pyrazole-3-sulfonyl chloride (3 g, 16.61 mmol) in THF (100 mL) was cooled to 0° C. and to it was added dropwise ammonium hydroxide (6.47 mL, 166 mmol). The reaction mixture was allowed to warm to RT and left to stir for 3 hours. The reaction mixture was concentrated in vacuo. The solid formed was filtered and washed with water (2×20 mL) to give the title compound. The filtrate was extracted with ethyl acetate (3×50 mL). The combined organics were dried over magnesium sulfate, filtered and concentrated to give another batch of the title compound. Both batches were combined to give the title compound (3.27 g). LCMS (A): m/z (M+H)$^+$ 162, C4H7N3O2S requires 161 (acidic).

D95 tert-butyl 4-sulfamoylpiperidine-1-carboxylate

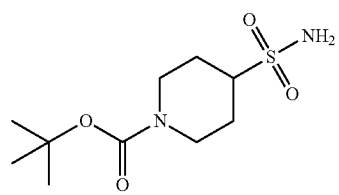 [SMILES: CC(C)(C)OC(=O)N1CCC(S(N)(=O)=O)CC1]

The title compound was prepared from tert-butyl 4-(chlorosulfonyl)piperidine-1-carboxylate using a similar procedure to that described for D94. LCMS (A): m/z (M−H)$^-$ 263, C10H20N2O4S requires 264 (acidic).

D96 tert-butyl 5-(benzylthio)isoindoline-2-carboxylate

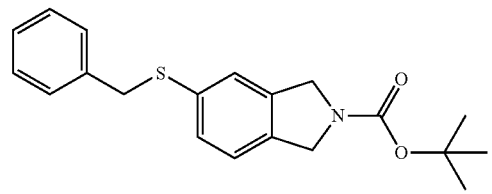 [SMILES: CC(C)(C)OC(=O)N1Cc2ccc(SCc3ccccc3)cc2C1]

To a solution of tert-butyl 5-bromoisoindoline-2-carboxylate (2 g, 6.71 mmol) in 1,4-dioxane (17.1 mL) in a round bottom flask was added Pd$_2$(dba)$_3$ (0.154 g, 0.168 mmol), xantphos (0.194 g, 0.335 mmol), DIPEA (2.343 mL, 13.41 mmol) and benzyl mercaptan (0.873 mL, 7.38 mmol) and the resulting mixture was stirred and heated at 90° C. under nitrogen for overnight. The reaction mixture was filtered through celite, rinsed with ethyl acetate and the filtrate concentrated in vacuo. The residue was purified on silica gel, eluting with ethyl acetate in cyclohexane (0-20%) to afford the title compound (2.11 g). LCMS (A): m/z [(M-tBu)+H]$^+$ 286, C20H23NO2S requires 341 (acidic).

D97 tert-butyl 5-(chlorosulfonyl)isoindoline-2-carboxylate

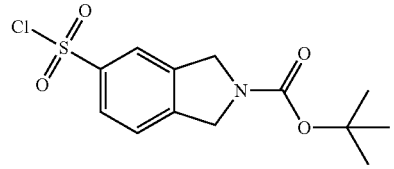 [SMILES: CC(C)(C)OC(=O)N1Cc2ccc(S(=O)(=O)Cl)cc2C1]

To a solution of tert-butyl 5-(benzylthio)isoindoline-2-carboxylate (D96) (882 mg, 2.58 mmol) in acetic acid (15 mL) and water (1.667 mL) was added NCS (1035 mg, 7.75 mmol) and the reaction mixture left to stir under nitrogen for about 30 min at RT. The reaction mixture was diluted with water (50 mL) and extracted with ethyl acetate (2×50 mL). The combined organics were dried and concentrated. The residue was purified on silica gel, eluting with a gradient of 0-25% ethyl acetate in cyclohexane to afford the title compound (400 mg). LCMS (A): m/z (M−H)$^-$ 298 (displacement of Cl by OH), C13H16ClNO4S requires 317 (acidic).

D98 tert-butyl 5-sulfamoylisoindoline-2-carboxylate

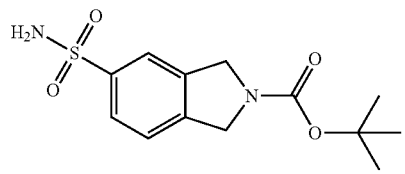 [SMILES: CC(C)(C)OC(=O)N1Cc2ccc(S(N)(=O)=O)cc2C1]

To a solution of tert-butyl 5-(chlorosulfonyl)isoindoline-2-carboxylate (D97) (400 mg, 1.259 mmol) in THF (12 mL) was added ammonium hydroxide (0.490 mL, 12.59 mmol) at 0° C. The mixture was left to stir for 1 hour at RT. The mixture was concentrated in vacuo and the residue obtained taken up in water (50 mL) and extracted with ethyl acetate (3×50 mL). The combined organics were dried and concentrated down to afford the title compound (335 mg). LCMS (A): m/z (M−H)⁻ 297, C13H18N2O4S requires 298 (acidic).

D99 tert-butyl 2-(chlorosulfonyl)-6,7-dihydropyrazolo[1,5-a]pyrazine-5(4H)-carboxylate

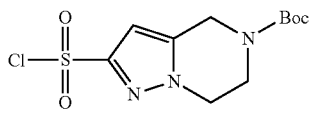 [SMILES: CC(C)(C)OC(=O)N1CCn2nc(S(=O)(=O)Cl)cc2C1]

The title compound was prepared from tert-butyl 2-bromo-6,7-dihydropyrazolo[1,5-a]pyrazine-5(4H)-carboxylate using a similar procedure to that described for D97. LCMS (A): m/z (M+H)⁺ 322, C11H16ClN3O4S requires 321 (acidic).

Preparation of Tosylates

Toslyates were prepared from the corresponding commercially available alcohols, using a method similar to that described for D100.

D100 tert-butyl 3-(tosyloxy)azetidine-1-carboxylate

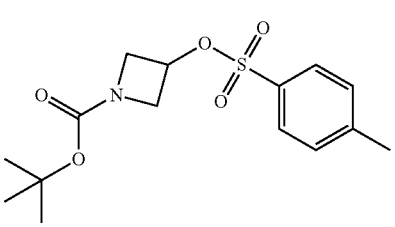 [SMILES: Cc1ccc(S(=O)(=O)OC2CN(C(=O)OC(C)(C)C)C2)cc1]

To a stirred solution of 1,1-dimethylethyl 3-hydroxy-1-azetidinecarboxylate (1.5 g, 8.66 mmol) in DCM (35 mL) at RT was added triethylamine (1.801 mL, 12.99 mmol), DMAP (0.053 g, 0.433 mmol) followed by tosyl-Cl (1.816 g, 9.53 mmol). This was stirred at RT overnight. The reaction mixture was partitioned between DCM/water (ca. 30 mL each). The aqueous layer was separated and extracted with DCM (ca. 25 mL twice). The combined organic layer was dried over MgSO₄ and solvent removed in vacuo. The residue was purified on silica gel (eluted with 0-40% ethyl acetate/cyclohexane) to afford the title compound (2.675 g). LCMS (A): m/z [(M-tBu)+H]⁺ 272, C15H21NO5S requires 327 (acidic).

Example 1

3-chloro-N-(3-(3-(pyrrolidin-1-yl)phenyl)-1H-pyrrolo[2,3-b]pyridin-4-yl)benzenesulfonamide

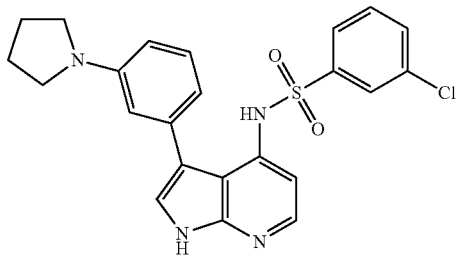 [SMILES: O=S(=O)(Nc1ccnc2[nH]cc(-c3cccc(N4CCCC4)c3)c12)c1cccc(Cl)c1]

To a solution of 3-chloro-N-[3-[3-(1-pyrrolidinyl)phenyl]-1-({[2-(trimethylsilyl)ethyl]oxy}methyl)-1H-pyrrolo[2,3-b]pyridin-4-yl]benzenesulfonamide (D5) (128.1 mg, 0.220 mmol) in DCM (1.9 mL) was added TFA (1.9 mL, 24.66 mmol) which was stirred at RT for ca. 2 hours. The reaction mixture was concentrated under reduced pressure and the residue was diluted with 10 mL of saturated sodium hydrogen carbonate, the aqueous layer was extracted with DCM (3×10 mL). The organic layers were combined, dried over MgSO₄ and concentrated. The residue was taken up in MeOH (2.5 mL) and triethylamine (0.306 mL, 2.196 mmol) was added. The reaction mixture was stirred at 70° C. for ca. 1 hour which was then concentrated under reduced pressure. The resulting residue was purified on silica gel, eluting with a gradient of 0-40% ethyl acetate/DCM to afford a material which was further purified using MDAP (acidic condition) to give material A (14.8 mg) and material B (35.4 mg). To a solution of the material B in MeOH (2.5 mL) was added triethylamine (0.306 mL, 2.196 mmol). The reaction mixture was stirred at 70° C. for ca. 3 hours which was then concentrated under reduced pressure. The residue was combined with material A and purified over silica gel (0-40% ethyl acetate/DCM) to afford the title compound (30.5 mg). LCMS (A): m/z (M+H)⁺ 453, C23H21ClN4O2S requires 452 (acidic).

Example 2

3-chloro-N-(3-(3-methoxyphenyl)-1-((2-(trimethylsilyl)ethoxy)methyl)-1H-pyrrolo[2,3-b]pyridin-4-yl)benzenesulfonamide

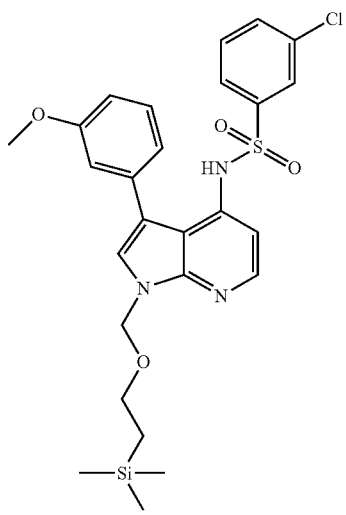 [SMILES: COc1cccc(-c2cn(COCC[Si](C)(C)C)c3nccc(NS(=O)(=O)c4cccc(Cl)c4)c23)c1]

The title compound was prepared using the procedure as described for Scheme 1. LCMS (A): m/z (M+H)⁺ 544, C26H30ClN3O4SSi requires 543 (basic).

Example 3

3-chloro-N-(3-(3-methoxyphenyl)-1H-pyrrolo[2,3-b]pyridin-4-yl)benzenesulfonamide

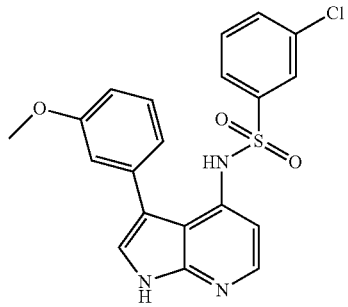 [SMILES: COc1cccc(-c2c[nH]c3nccc(NS(=O)(=O)c4cccc(Cl)c4)c23)c1]

The title compound was prepared using the procedure as described for Scheme 1. LCMS (A): m/z (M+H)+ 414, C20H16ClN3O3S requires 413 (acidic).

Example 4

3-chloro-N-(3-(m-tolyl)-1H-pyrrolo[2,3-b]pyridin-4-yl)benzenesulfonamide

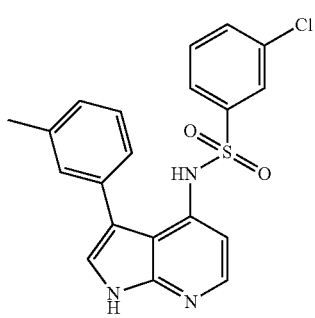 [SMILES: Cc1cccc(-c2c[nH]c3nccc(NS(=O)(=O)c4cccc(Cl)c4)c23)c1]

The title compound was prepared using the procedure as described for Scheme 1. LCMS (A): m/z (M+H)+ 398, C20H16ClN3O2S requires 397 (acidic).

Example 5

N-(3-(3-(dimethylamino)phenyl)-1H-pyrrolo[2,3-b]pyridin-4-yl)benzenesulfonamide

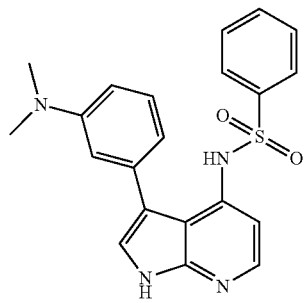 [SMILES: CN(C)c1cccc(-c2c[nH]c3nccc(NS(=O)(=O)c4ccccc4)c23)c1]

The title compound was prepared using the procedure as described for Scheme 1 or Scheme 2. LCMS (A): m/z (M+H)+ 393, C21H20N4O2S requires 392 (acidic).

Example 6

3-chloro-N-(3-(3-(dimethylamino)phenyl)-1H-pyrrolo[2,3-b]pyridin-4-yl)benzenesulfonamide

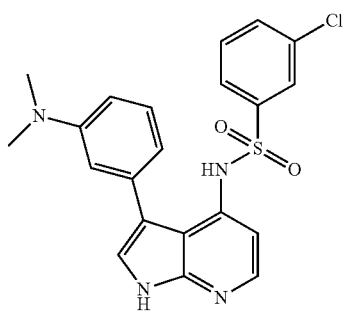 [SMILES: CN(C)c1cccc(-c2c[nH]c3nccc(NS(=O)(=O)c4cccc(Cl)c4)c23)c1]

The title compound was prepared using the procedure as described for Scheme 1. LCMS (A): m/z (M+H)+ 427, C21H19ClN4O2S requires 426 (acidic).

Example 7

N-(3-(4-(dimethylamino)phenyl)-1H-pyrrolo[2,3-b]pyridin-4-yl)benzenesulfonamide

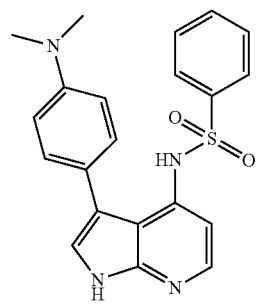 [SMILES: CN(C)c1ccc(-c2c[nH]c3nccc(NS(=O)(=O)c4ccccc4)c23)cc1]

The title compound was prepared using the procedure as described for Scheme 1. LCMS (A): m/z (M+H)+ 393, C21H20N4O2S requires 392 (acidic).

Example 8

N-(3-phenyl-1H-pyrrolo[2,3-b]pyridin-4-yl)benzenesulfonamide

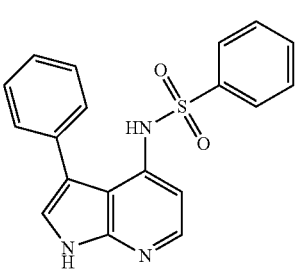 [SMILES: O=S(=O)(Nc1ccnc2[nH]cc(-c3ccccc3)c12)c1ccccc1]

The title compound was prepared using the procedure as described for Scheme 1. LCMS (A): m/z (M+H)+ 350, C19H15N3O2S requires 349 (acidic).

Example 9

N-(3-(3-(pyrrolidin-1-yl)phenyl)-1H-pyrrolo[2,3-b]pyridin-4-yl)benzenesulfonamide

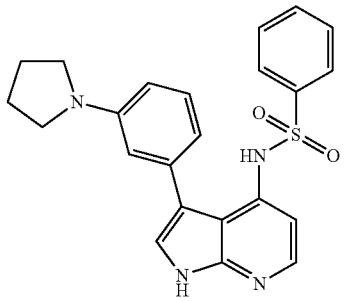 [SMILES: O=S(=O)(Nc1ccnc2[nH]cc(-c3cccc(N4CCCC4)c3)c12)c1ccccc1]

The title compound was prepared using the procedure as described for Scheme 1. LCMS (A): m/z (M+H)+ 419, C23H22N4O2S requires 418 (acidic).

Example 10

N-(3-(5-methylthiophen-2-yl)-1H-pyrrolo[2,3-b]pyridin-4-yl)benzenesulfonamide

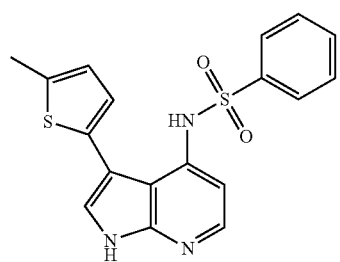 [SMILES: Cc1ccc(-c2c[nH]c3nccc(NS(=O)(=O)c4ccccc4)c23)s1]

The title compound was prepared using the procedure as described for Scheme 1. LCMS (A): m/z (M+H)+ 370, C18H15N3O2S2 requires 369 (acidic).

Example 11

N-(1-methyl-3-(3-(pyrrolidin-1-yl)phenyl)-1H-pyrrolo[2,3-b]pyridin-4-yl)benzenesulfonamide

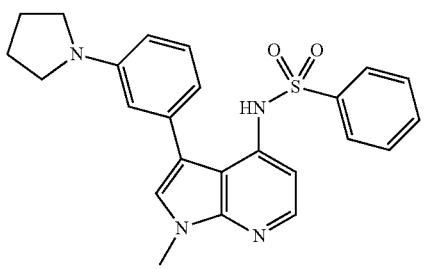 [SMILES: Cn1cc(-c2cccc(N3CCCC3)c2)c2c(NS(=O)(=O)c3ccccc3)ccnc21]

The title compound was prepared using the procedure as described for Scheme 1. LCMS (A): m/z (M+H)+433, C24H24N4O2S requires 432 (acidic).

Example 12

3-chloro-N-(3-(3-methoxyphenyl)-1-methyl-1H-pyrrolo[2,3-b]pyridin-4-yl)benzenesulfonamide

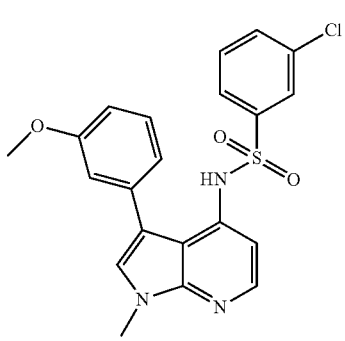 [SMILES: COc1cccc(-c2cn(C)c3nccc(NS(=O)(=O)c4cccc(Cl)c4)c23)c1]

The title compound was prepared using the procedure as described for Scheme 1. LCMS (A): m/z (M+H)+428, C21H18ClN3O3S requires 427 (acidic).

Example 13

N-(3-(3-(dimethylamino)phenyl)-1-ethyl-1H-pyrrolo[2,3-b]pyridin-4-yl) benzenesulfonamide

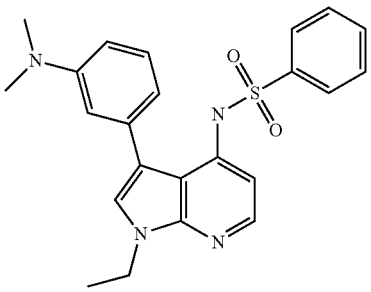 [SMILES: CCn1cc(-c2cccc(N(C)C)c2)c2c(NS(=O)(=O)c3ccccc3)ccnc21]

The title compound was prepared using the procedure as described for Scheme 1. LCMS (A): m/z (M+H)+ 421, C23H24N4O2S requires 420 (acidic).

Example 14

1-methyl-N-(1-methyl-3-(1-methylindolin-6-yl)-1H-pyrrolo[2,3-b]pyridin-4-yl)-1H-pyrazole-3-sulfonamide

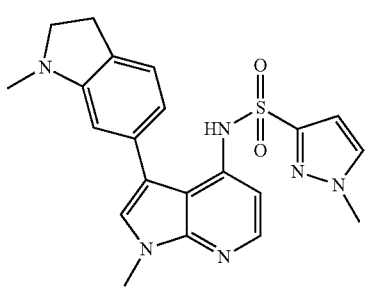 [SMILES: CN1CCc2ccc(-c3cn(C)c4nccc(NS(=O)(=O)c5ccn(C)n5)c34)cc21]

Method A:

To a solution of 4-bromo-1-methyl-3-(1-methylindolin-6-yl)-1H-pyrrolo[2,3-b]pyridine (D8) (100 mg, 0.292 mmol) in 1,4-dioxane (2 mL) was added 1-methyl-1H-pyrazole-3-sulfonamide (D94) (65.9 mg, 0.409 mmol), cesium carbonate (190 mg, 0.584 mmol), Pd$_2$(dba)$_3$ (20.07 mg, 0.022 mmol) and 2-(dimethylamino)-2'-(dicyclohexylphosphino)biphenyl (17.25 mg, 0.044 mmol). The reaction mixture was heated in the microwave at 120° C. for 30 mins. The reaction mixture was filtered through celite washing with ethyl acetate and the resulting solution evaporated to dryness. The residue was purified by column chromatography on silica gel, eluting with a gradient of 0-100% ethyl acetate in cyclohexane to give an impure material which was further triturated with diethylether and followed by a mixture of DMF, MeOH and DCM to afford the title compound (35 mg). LCMS (A): m/z (M+H)$^+$ 423, C21H22N6O2S requires 422 (acidic).

Method B:

A mixture of 4-bromo-1-methyl-3-(1-methylindolin-6-yl)-1H-pyrrolo[2,3-b]pyridine (D8) (3.6 g, 10.52 mmol), 1-methyl-1H-pyrazole-3-sulfonamide (D94) (2.54 g, 15.78 mmol), cesium carbonate (10.28 g, 31.6 mmol), xantphos (0.913 g, 1.578 mmol) and Pd$_2$(dba)$_3$ (0.722 g, 0.789 mmol) in 1,4-dioxane (180 mL) was refluxed for 16 hours. The reaction mixture was filtered through celite, washing with ethyl acetate and the resulting solution was evaporated to dryness to afford a solid, which was triturated with diethyl ether to afford the title compound as material A (3.5 g).

1 g of material A was dissolved in 2:1 acetic acid/water ca. 20 mL and extracted with diethyl ether (50 mL×3), ethyl acetate (50 mL×3) followed by DCM (50 mL×3). The solid precipitated out of the diethyl ether extracts was collected to afford 378 mg of material B. Material B was combined with the ethyl acetate and DCM extracts and once again dissolved in 2:1 acetic acid/water. The solution was further purified by purification on reverse phase eluting with acetonitrile and water (+0.2% formic acid). The desired fractions were extracted with DCM (2×100 mL). The organic layers were combined, passed through a hydrophobic frit and concentrated to afford the title compound (346 mg). LCMS (A): m/z (M+H)$^+$ 423, C21H22N6O2S requires 422 (acidic).

Method C

To a stirred solution of 1-methyl-3-(1-methylindolin-6-yl)-1H-pyrrolo[2,3-b]pyridin-4-amine (D19) (500 mg, 1.796 mmol) in THF (10 mL), cooled to 0° C., was added LiHMDS (1M in THF) (3.59 mL, 3.59 mmol). The resulting mixture was left to stir for 10 minutes at 0° C., after which, 1-methyl-1H-pyrazole-3-sulfonyl chloride (487 mg, 2.69 mmol) was added. The whole mixture left to stir for 45 min at 0° C. The reaction was quenched with saturated aqueous NH$_4$Cl solution (30 mL), extracted with DCM (3×25 mL). The combined organics dried and concentrated. The residue was purified by chromatography on silica, eluting with a gradient of 0-100% ethyl acetate in DCM. The corresponding fractions were combined to give an impure material which was triturated with DMSO and followed by purification by MDAP (acidic condition) to give the title compound (265 mg). LCMS (A): m/z (M+H)$^+$ 423, C21H22N6O2S requires 422 (acidic).

Example 15

N-(1-isopropyl-3-(1-methylindolin-6-yl)-1H-pyrrolo[2,3-b]pyridin-4-yl)-1-methyl-1H-pyrazole-3-sulfonamide

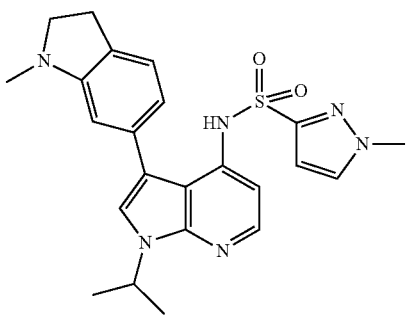

Method A:

A mixture of 4-bromo-1-isopropyl-3-(1-methylindolin-6-yl)-1H-pyrrolo[2,3-b]pyridine (D11) (5.3 g, 14.31 mmol), 1-methyl-1H-pyrazole-3-sulfonamide (D94) (3.00 g, 18.61 mmol), cesium carbonate (9.33 g, 28.6 mmol), xantphos (1.242 g, 2.147 mmol) and Pd$_2$(dba)$_3$ (0.983 g, 1.073 mmol) in 1,4-dioxane (150 mL) were heated at 115° C. overnight. The reaction mixture was filtered through celite, washing with ethyl acetate and the resulting solution was evaporated to dryness. The residue was purified by column chromatography on silica gel, eluting with a gradient of 0-70% ethyl acetate in cyclohexane. This isolated material was combined with another batch (414 mg) prepared via a similar method, starting from 4-bromo-1-isopropyl-3-(1-methylindolin-6-yl)-1H-pyrrolo[2,3-b]pyridine (D11) (500 mg, 1.350 mmol). The combined material was further purified on reverse phase eluting with acetonitrile and water (+0.2% formic acid) in 6 batches. The mixed fractions were recombined and purified again in 3 batches. The isolated product from each batch of purification was combined and further purified on silica, using 0-10% ethyl acetate/DCM to give the title compound (2.2 g). LCMS (A): m/z (M+H)$^+$ 451, C23H26N6O2S requires 450 (acidic).

Method B:

4-bromo-1-isopropyl-3-(1-methylindolin-6-yl)-1H-pyrrolo[2,3-b]pyridine (D11) (1.7 g) was divided into 3 batches of 566 mg each. Each batch was subjected to the following reaction conditions:

A mixture of 1-methyl-1H-pyrazole-3-sulfonamide (D94) (296 mg, 1.834 mmol), cesium carbonate (996 mg, 3.06 mmol), tris(dibenzylideneacetone)dipalladium(0) (140 mg, 0.153 mmol) and 2-dicyclohexylphosphino-2'-(N,N-dimethylamino)biphenyl (120 mg, 0.306 mmol) were suspended in a solution of 4-bromo-1-isopropyl-3-(1-methylindolin-6-yl)-1H-pyrrolo[2,3-b]pyridine (D11) (566 mg, 1.529 mmol) in 1,4-dioxane (10 mL) in a microwave vial and the resulting mixture heated at 150° C. in the microwave reactor for 30 minutes. The reaction mixtures were combined and filtered through celite, washed with ethyl acetate and the filtrate was concentrated in vacuo. The crude residue was purified by chromatography on silica, eluting with ethyl acetate in cyclohexane (0-70%), followed by two purifications using 0-20% ethyl acetate/DCM. The recovered material was then further

Example 16

N-(1,6-dimethyl-3-(3-(pyrrolidin-1-yl)phenyl)-1H-pyrrolo[2,3-b]pyridin-4-yl)-1-methyl-1H-pyrazole-3-sulfonamide

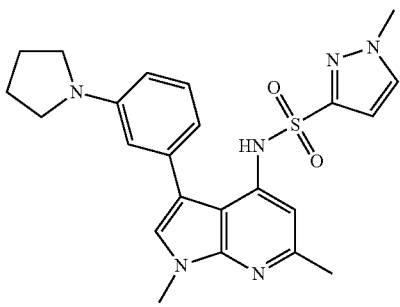 [SMILES: Cc1cc(NS(=O)(=O)c2ccn(C)n2)c2c(-c3cccc(N4CCCC4)c3)cn(C)c2n1]

A microwave vial was charged with 1-methyl-1H-pyrazole-3-sulfonamide (D94) (134 mg, 0.829 mmol), palladium (II) acetate (9.30 mg, 0.041 mmol), xantphos (47.9 mg, 0.083 mmol) and cesium carbonate (270 mg, 0.829 mmol). To this was added 4-chloro-1,6-dimethyl-3-(3-(pyrrolidin-1-yl)phenyl)-1H-pyrrolo[2,3-b]pyridine (D14) (135 mg, 0.414 mmol) dissolved in 1,4-dioxane (2.5 mL). The reaction mixture was heated at 150° C. in the microwave for 30 mins. The crude was purified on normal phase chromatography eluting with ethyl acetate in cyclohexane (0-80%) twice to give an impure material. The material was then dissolved in MeOH and passed through a SCX cartridge eluting with MeOH followed by 2M ammonia in MeOH to give a solid which was triturated with diethyl ether to give the title compound (38.7 mg). LCMS (A): m/z (M+H)+ 451, C23H26N6O2S requires 450 (acidic).

Example 17

N-(1-isopropyl-3-(3-(pyrrolidin-1-yl)phenyl)-1H-pyrrolo[2,3-b]pyridin-4-yl)-1-methyl-1H-pyrazole-3-sulfonamide

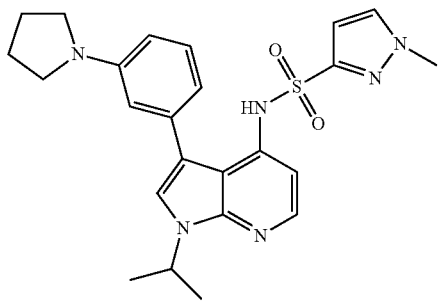 [SMILES: CC(C)n1cc(-c2cccc(N3CCCC3)c2)c2c(NS(=O)(=O)c3ccn(C)n3)ccnc21]

A mixture of 4-bromo-1-isopropyl-3-(3-(pyrrolidin-1-yl)phenyl)-1H-pyrrolo[2,3-b]pyridine (D15) (400 mg, 1.041 mmol), 1-methyl-1H-pyrazole-3-sulfonamide (D94) (252 mg, 1.561 mmol), cesium carbonate (678 mg, 2.082 mmol), Pd2(dba)3 (71.5 mg, 0.078 mmol) and 2-(dimethylamino)-2'-(dicyclohexylphosphino)biphenyl (61.4 mg, 0.156 mmol) in 1,4-dioxane (4.5 mL) was heated under an atmosphere of nitrogen in a microwave at 150° C. for 30 minutes. The mixture was then filtered through celite, washing with ethyl acetate, and evaporated to dryness. The residues were purified on silica eluting with cyclohexane and ethyl acetate (0-100%). The appropriate fractions were combined and evaporated to dryness producing an impure material (327 mg). This was purified via MDAP (acidic) twice. The appropriate fractions were combined and evaporated to dryness to give the title compounds (131 mg). LCMS (A): m/z (M+H)+ 465, C24H28N6O2S requires 464 (acidic).

Example 18

3-chloro-N-(1-methyl-3-(5-(piperazin-1-yl)pyridin-3-yl)-1H-pyrrolo[2,3-b]pyridin-4-yl)benzenesulfonamide

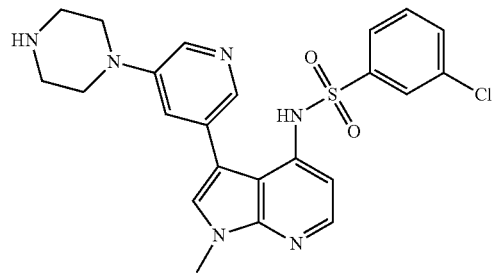 [SMILES: Cn1cc(-c2cncc(N3CCNCC3)c2)c2c(NS(=O)(=O)c3cccc(Cl)c3)ccnc21]

The title compound was prepared using the procedure as described for Scheme 2. LCMS (A): m/z (M+H)+ 483, C23H23ClN6O2S requires 482 (acidic).

Example 19

N-(3-(indolin-6-yl)-1-methyl-1H-pyrrolo[2,3-b]pyridin-4-yl)benzenesulfonamide

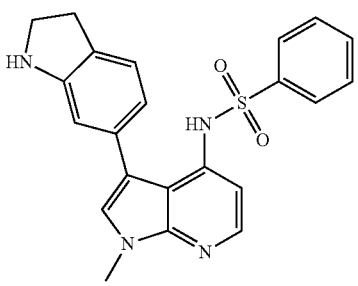 [SMILES: Cn1cc(-c2ccc3c(c2)NCC3)c2c(NS(=O)(=O)c3ccccc3)ccnc21]

The title compound was prepared using the procedure as described for Scheme 2. LCMS (A): m/z (M+H)+405, C22H20N4O2S requires 404 (acidic).

Example 20

3-chloro-N-(1-methyl-3-(3-(piperazin-1-yl)phenyl)-1H-pyrrolo[2,3-b]pyridin-4-yl)benzenesulfonamide

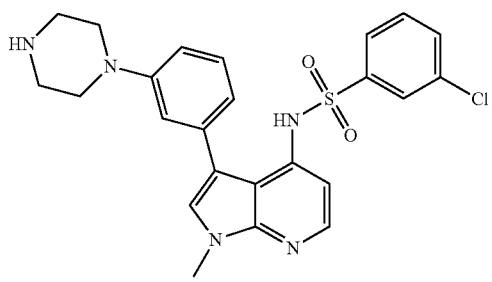 [SMILES: Cn1cc(-c2cccc(N3CCNCC3)c2)c2c(NS(=O)(=O)c3cccc(Cl)c3)ccnc21]

The title compound was prepared using the procedure as described for Scheme 2. LCMS (A): m/z (M+H)+ 483, C23H23ClN6O2S requires 482 (acidic).

Example 21

N-(3-(isoindolin-5-yl)-1-methyl-1H-pyrrolo[2,3-b]pyridin-4-yl)benzenesulfonamide

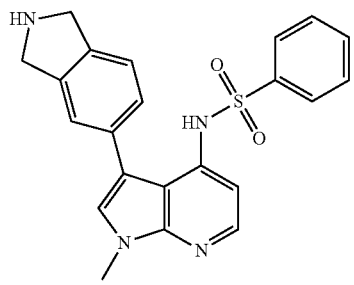 [SMILES: Cn1cc(-c2ccc3c(c2)CNC3)c2c(NS(=O)(=O)c3ccccc3)ccnc21]

The title compound was prepared using the procedure as described for Scheme 2. LCMS (A): m/z (M+H)+405, C22H20N4O2S requires 404 (acidic).

Example 22

N-(3-(3-methoxy-5-(piperazin-1-yl)phenyl)-1-methyl-1H-pyrrolo[2,3-b]pyridin-4-yl)benzenesulfonamide

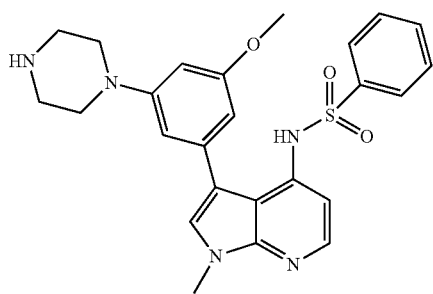 [SMILES: COc1cc(-c2cn(C)c3nccc(NS(=O)(=O)c4ccccc4)c23)cc(N2CCNCC2)c1]

The title compound was prepared using the procedure as described for Scheme 2. LCMS (A): m/z (M+H)+478, C25H27N5O3S requires 477 (acidic).

Example 23

N-(3-(indolin-5-yl)-1-methyl-1H-pyrrolo[2,3-b]pyridin-4-yl)benzenesulfonamide (E6)

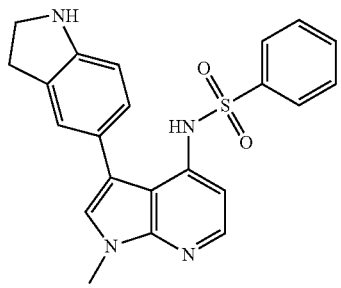 [SMILES: Cn1cc(-c2ccc3c(c2)CCN3)c2c(NS(=O)(=O)c3ccccc3)ccnc21]

The title compound was prepared using the procedure as described for Scheme 2. LCMS (A): m/z (M+H)+405, C22H20N4O2S requires 404 (acidic).

Example 24

N-(1-methyl-3-(1-methylindolin-6-yl)-1H-pyrrolo[2,3-b]pyridin-4-yl)benzenesulfonamide

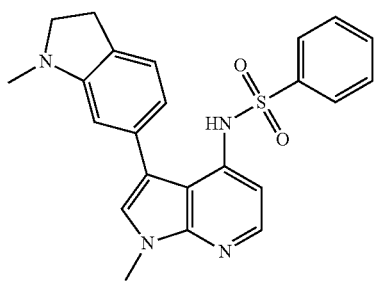 [SMILES: CN1CCc2ccc(-c3cn(C)c4nccc(NS(=O)(=O)c5ccccc5)c34)cc21]

The title compound was prepared using the procedure as described for Scheme 2. LCMS (A): m/z (M+H)+ 419, C23H23ClN6O2S requires 418 (acidic).

Example 25

3-chloro-N-(3-(5-(4-isopropylpiperazin-1-yl)pyridin-3-yl)-1-methyl-1H-pyrrolo[2,3-b]pyridin-4-yl)benzenesulfonamide

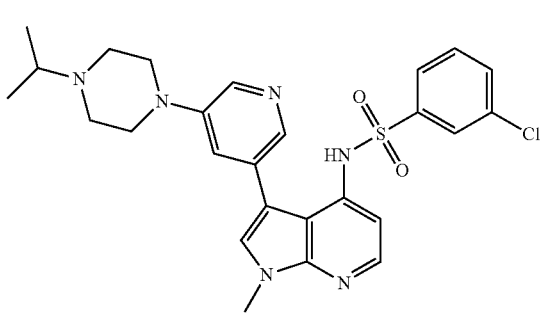 [SMILES: CC(C)N1CCN(c2cncc(-c3cn(C)c4nccc(NS(=O)(=O)c5cccc(Cl)c5)c34)c2)CC1]

The title compound was prepared using the procedure as described for Scheme 2. LCMS (A): m/z (M+H)$^+$526, C26H29ClN6O2S requires 525 (basic).

Example 26

N-(1-methyl-3-(1-methylindolin-5-yl)-1H-pyrrolo[2,3-b]pyridin-4-yl)benzenesulfonamide

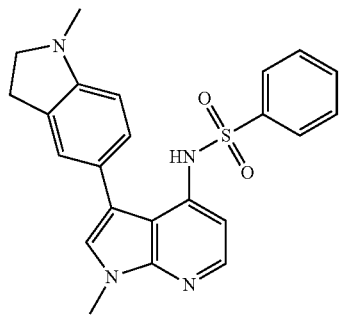 [SMILES: CN1CCc2cc(-c3cn(C)c4nccc(NS(=O)(=O)c5ccccc5)c34)ccc21]

The title compound was prepared using the procedure as described for Scheme 2. LCMS (A): m/z (M+H)$^+$419, C23H23ClN6O2S requires 418 (acidic).

Example 27

3-chloro-N-(1-methyl-3-(3-(4-methylpiperazin-1-yl)phenyl)-1H-pyrrolo[2,3-b]pyridin-4-yl)benzenesulfonamide

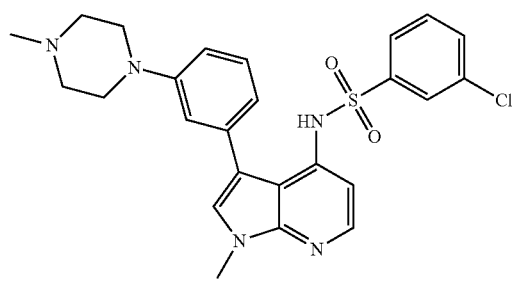 [SMILES: CN1CCN(c2cccc(-c3cn(C)c4nccc(NS(=O)(=O)c5cccc(Cl)c5)c34)c2)CC1]

The title compound was prepared using the procedure as described for Scheme 2. LCMS (A): m/z (M+H)$^+$496, C25H26ClN5O2S requires 495(acidic).

Example 28

N-(3-(3-methoxy-5-(4-methylpiperazin-1-yl)phenyl)-1-methyl-1H-pyrrolo[2,3-b]pyridin-4-yl)benzenesulfonamide

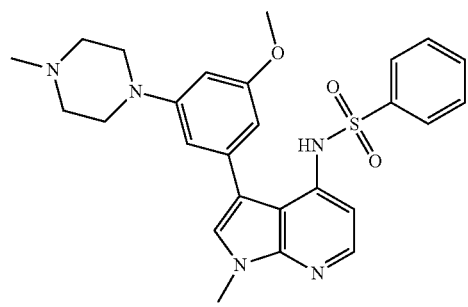 [SMILES: COc1cc(-c2cn(C)c3nccc(NS(=O)(=O)c4ccccc4)c23)cc(N2CCN(C)CC2)c1]

The title compound was prepared using the procedure as described for Scheme 2. LCMS (A): m/z (M+H)$^+$492, C26H29N5O3S requires 491 (acidic).

Example 29

N-(3-(3-(4-isopropylpiperazin-1-yl)-5-methoxyphenyl)-1-methyl-1H-pyrrolo[2,3-b]pyridin-4-yl)benzenesulfonamide

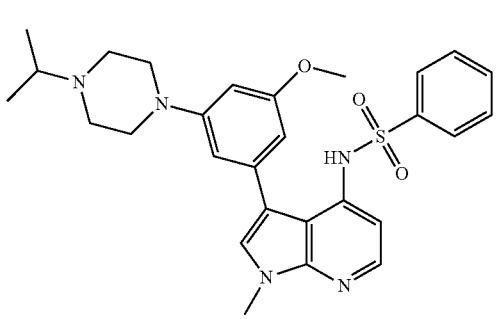 [SMILES: COc1cc(-c2cn(C)c3nccc(NS(=O)(=O)c4ccccc4)c23)cc(N2CCN(C(C)C)CC2)c1]

The title compound was prepared using the procedure as described for Scheme 2. LCMS (A): m/z (M+H)$^+$520, C28H33N5O3S requires 519 (acidic).

Example 30

1-methyl-N-(1-methyl-3-(1-methylindolin-6-yl)-1H-pyrrolo[2,3-b]pyridin-4-yl)-1H-pyrazole-5-sulfonamide

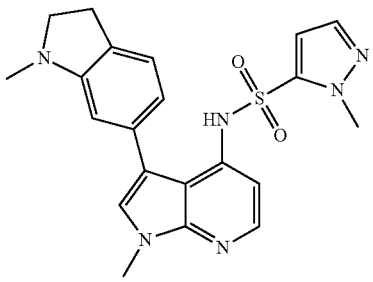 [SMILES: CN1CCc2ccc(-c3cn(C)c4nccc(NS(=O)(=O)c5ccnn5C)c34)cc21]

The title compound was prepared using the procedure as described for Scheme 2. LCMS (A): m/z (M+H)$^+$ 423, C21H22N6O2S requires 422 (acidic).

Example 31

N-(1-methyl-3-(1-methyl-1,2,3,4-tetrahydroquinolin-7-yl)-1H-pyrrolo[2,3-b]pyridin-4-yl)pyridine-3-sulfonamide

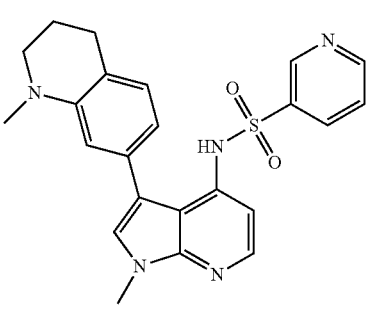 [SMILES: CN1CCCc2ccc(-c3cn(C)c4nccc(NS(=O)(=O)c5cccnc5)c34)cc21]

The title compound was prepared using the procedure as described for Scheme 2. LCMS (A): m/z (M+H)⁺434, C23H23N5O2S requires 433 (acidic).

Example 32

1-methyl-N-(1-methyl-3-(1-methyl-1,2,3,4-tetrahydroquinolin-7-yl)-1H-pyrrolo[2,3-b]pyridin-4-yl)-1H-pyrazole-3-sulfonamide

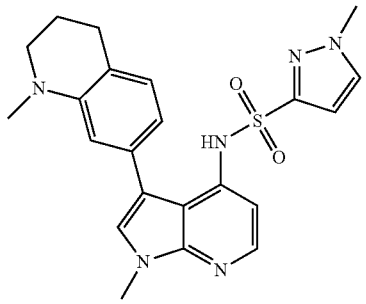 [SMILES: CN1CCCc2ccc(-c3cn(C)c4nccc(NS(=O)(=O)c5ccn(C)n5)c34)cc21]

The title compound was prepared using the procedure as described for Scheme 2. LCMS (A): m/z (M+H)⁺437, C22H24N6O2S requires 436 (acidic).

Example 33

N-(1-methyl-3-(5-methyl-2,3,4,5-tetrahydrobenzo[b][1,4]oxazepin-9-yl)-1H-pyrrolo[2,3-b]pyridin-4-yl)pyridine-3-sulfonamide

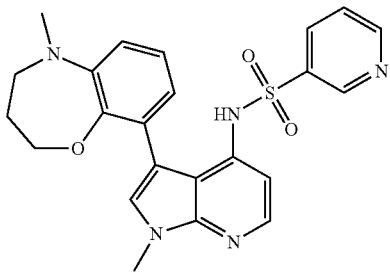 [SMILES: CN1CCCOc2c(-c3cn(C)c4nccc(NS(=O)(=O)c5cccnc5)c34)cccc21]

The title compound was prepared using the procedure as described for Scheme 2. LCMS (A): m/z (M+H)⁺450, C23H23N5O3S requires 449 (acidic).

Example 34

1-methyl-N-(1-methyl-3-(5-methyl-2,3,4,5-tetrahydrobenzo[b][1,4]oxazepin-9-yl)-1H-pyrrolo[2,3-b]pyridin-4-yl)-1H-pyrazole-3-sulfonamide

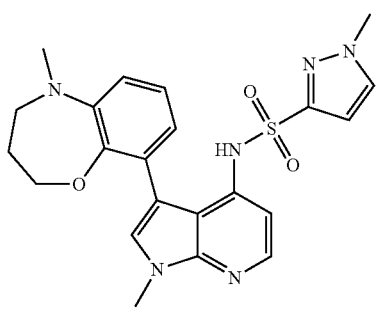 [SMILES: CN1CCCOc2c(-c3cn(C)c4nccc(NS(=O)(=O)c5ccn(C)n5)c34)cccc21]

The title compound was prepared using the procedure as described for Scheme 2. LCMS (A): m/z (M+H)⁺453, C22H24N6O3S requires 452 (acidic).

Example 35

N-(1-methyl-3-(5-methyl-2,3,4,5-tetrahydrobenzo[b][1,4]oxazepin-7-yl)-1H-pyrrolo[2,3-b]pyridin-4-yl)benzenesulfonamide

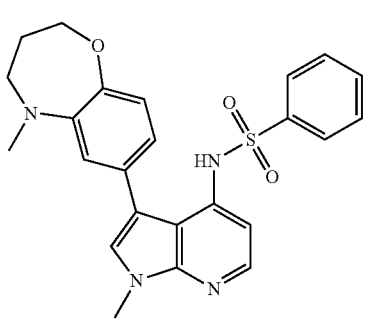 [SMILES: CN1CCCOc2ccc(-c3cn(C)c4nccc(NS(=O)(=O)c5ccccc5)c34)cc21]

The title compound was prepared using the procedure as described for Scheme 2. LCMS (A): m/z (M+H)⁺449, C24H24N4O3S requires 448 (acidic).

Example 36

N-(1-methyl-3-(5-methyl-2,3,4,5-tetrahydrobenzo[b][1,4]oxazepin-7-yl)-1H-pyrrolo[2,3-b]pyridin-4-yl)pyridine-3-sulfonamide

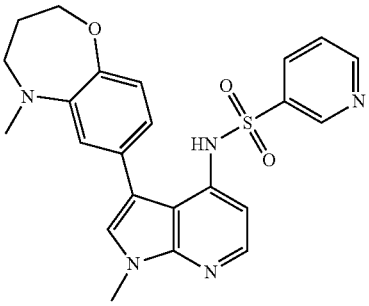 [SMILES: CN1CCCOc2ccc(-c3cn(C)c4nccc(NS(=O)(=O)c5cccnc5)c34)cc21]

The title compound was prepared using the procedure as described for Scheme 2. LCMS (A): m/z (M+H)⁺450, C23H23N5O3S requires 449 (acidic).

Example 37

N-(3-(1-(cyclopropylmethyl)indolin-6-yl)-1-methyl-1H-pyrrolo[2,3-b]pyridin-4-yl)-1-methyl-1H-pyrazole-3-sulfonamide

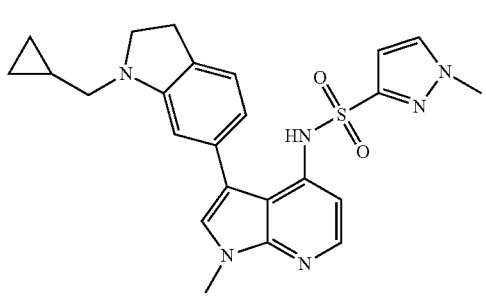 [SMILES: Cn1ccc(S(=O)(=O)Nc2ccnc3c2c(-c2ccc4c(c2)N(CC2CC2)CC4)cn3C)n1]

The title compound was prepared using the procedure as described for Scheme 2. LCMS (A): m/z (M+H)⁺463, C24H26N6O2S requires 462 (acidic).

Example 38

N-(3-(1-isopropylindolin-6-yl)-1-methyl-1H-pyrrolo[2,3-b]pyridin-4-yl)-1-methyl-1H-pyrazole-3-sulfonamide

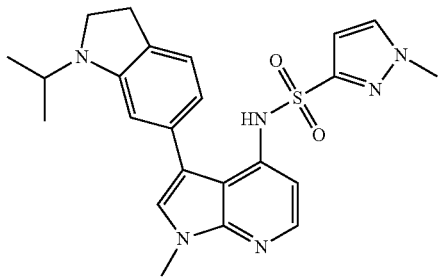 [SMILES: CC(C)N1CCc2ccc(-c3cn(C)c4nccc(NS(=O)(=O)c5ccn(C)n5)c34)cc21]

The title compound was prepared using the procedure as described for Scheme 2. LCMS (A): m/z (M+H)⁺451, C23H26N6O2S requires 450 (acidic).

Example 39

N-(1-methyl-3-(4-methyl-3-oxo-3,4-dihydro-2H-benzo[b][1,4]oxazin-6-yl)-1H-pyrrolo[2,3-b]pyridin-4-yl)benzenesulfonamide

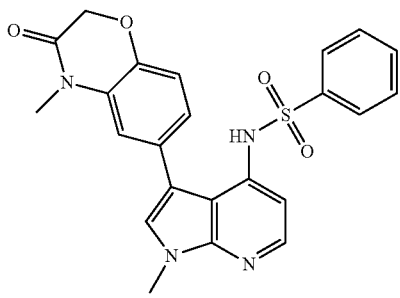 [SMILES: CN1C(=O)COc2ccc(-c3cn(C)c4nccc(NS(=O)(=O)c5ccccc5)c34)cc21]

The title compound was prepared using the procedure as described for Scheme 2. LCMS (A): m/z (M+H)⁺449, C23H20N4O4S requires 448 (acidic).

Example 40

N-(1-methyl-3-(4-methyl-3,4-dihydro-2H-benzo[b][1,4]oxazin-6-yl)-1H-pyrrolo[2,3-b]pyridin-4-yl)benzenesulfonamide

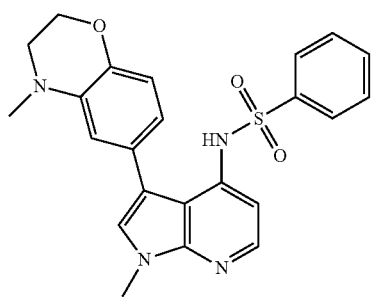

The title compound was prepared using the procedure as described for Scheme 2. LCMS (A): m/z (M+H)⁺435, C23H22N4O3S requires 434 (acidic).

Example 41

N-(1-methyl-3-(2-(pyrrolidin-1-yl)thiazol-5-yl)-1H-pyrrolo[2,3-b]pyridin-4-yl)benzenesulfonamide

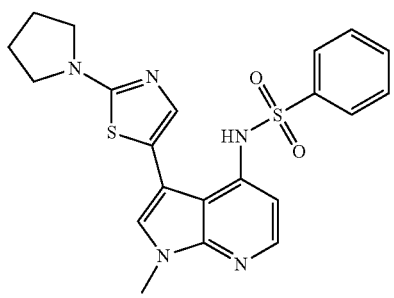 [SMILES: Cn1cc(-c2cnc(N3CCCC3)s2)c2c(NS(=O)(=O)c3ccccc3)ccnc21]

The title compound was prepared using the procedure as described for Scheme 2. LCMS (A): m/z (M+H)⁺ 440, C21H21N5O2S2 requires 439 (acidic).

Example 42

N-(1-methyl-3-(6-(pyrrolidin-1-yl)pyridazin-4-yl)-1H-pyrrolo[2,3-b]pyridin-4-yl)benzenesulfonamide

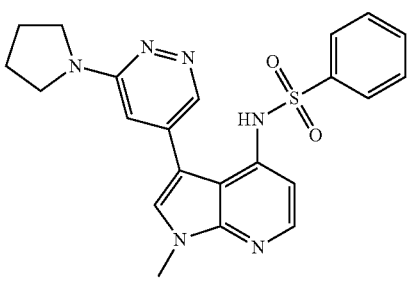 [SMILES: Cn1cc(-c2cnnc(N3CCCC3)c2)c2c(NS(=O)(=O)c3ccccc3)ccnc21]

The title compound was prepared using the procedure as described for Scheme 2. LCMS (A): m/z (M+H)⁺ 435, C22H22N6O2S requires 434 (acidic).

Example 43 tert-butyl 4-(3-(4-(3-chlorophenylsulfonamido)-1-methyl-1H-pyrrolo[2,3-b]pyridin-3-yl)phenyl)piperazine-1-carboxylate

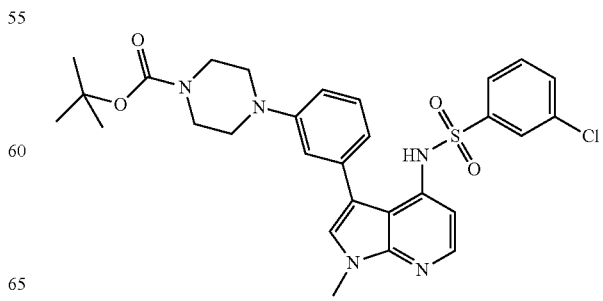

The title compound was prepared using the procedure as described for Scheme 2. LCMS (A): m/z (M+H)+ 582, C29H32ClN5O4S requires 581 (acidic).

Example 44

N-(3-(6-(dimethylamino)pyridin-3-yl)-1-methyl-1H-pyrrolo[2,3-b]pyridin-4-yl)benzenesulfonamide

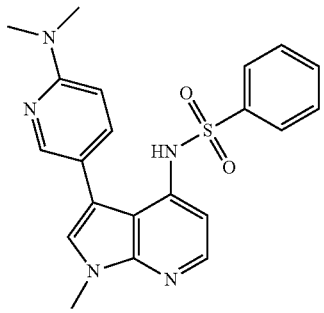 [SMILES: CN(C)c1ccc(-c2cn(C)c3nccc(NS(=O)(=O)c4ccccc4)c23)cn1]

The title compound was prepared using the procedure as described for Scheme 2. LCMS (A): m/z (M+H)+ 408, C21H21N5O2S requires 407 (acidic).

Example 45

N-(1-methyl-3-(4-(4-methylpiperazin-1-yl)phenyl)-1H-pyrrolo[2,3-b]pyridin-4-yl)benzenesulfonamide

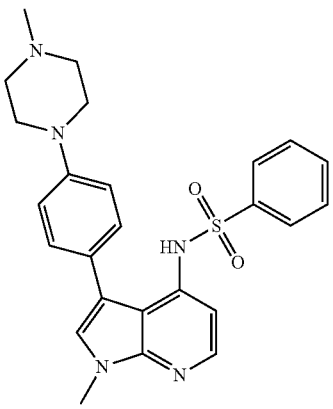 [SMILES: CN1CCN(c2ccc(-c3cn(C)c4nccc(NS(=O)(=O)c5ccccc5)c34)cc2)CC1]

The title compound was prepared using the procedure as described for Scheme 2. LCMS (A): m/z (M+H)+ 462, C25H27N5O2S requires 461 (acidic).

Example 46

N-(1-methyl-3-(4-methyl-3,4-dihydro-2H-pyrido[3,2-b][1,4]oxazin-7-yl)-1H-pyrrolo[2,3-b]pyridin-4-yl)benzenesulfonamide

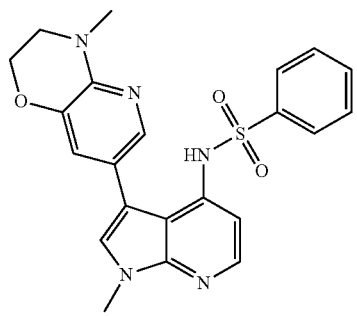 [SMILES: CN1CCOc2cc(-c3cn(C)c4nccc(NS(=O)(=O)c5ccccc5)c34)cnc21]

The title compound was prepared using the procedure as described for Scheme 2. LCMS (A): m/z (M+H)+ 462, C25H27N5O2S requires 461 (acidic).

Example 47

3-chloro-N-(1-methyl-3-(4-methyl-3,4-dihydro-2H-pyrido[3,2-b][1,4]oxazin-7-yl)-1H-pyrrolo[2,3-b]pyridin-4-yl)benzenesulfonamide

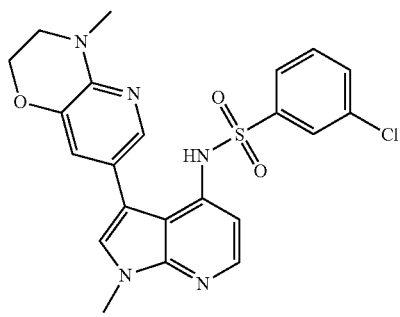 [SMILES: CN1CCOc2cc(-c3cn(C)c4nccc(NS(=O)(=O)c5cccc(Cl)c5)c34)cnc21]

The title compound was prepared using the procedure as described for Scheme 2. LCMS (A): m/z (M+H)+ 470, C22H20ClN5O3S requires 469 (acidic).

Example 48

N-(1-methyl-3-(1-methyl-2,3-dihydro-1H-pyrido[2,3-b][1,4]oxazin-7-yl)-1H-pyrrolo[2,3-b]pyridin-4-yl)benzenesulfonamide

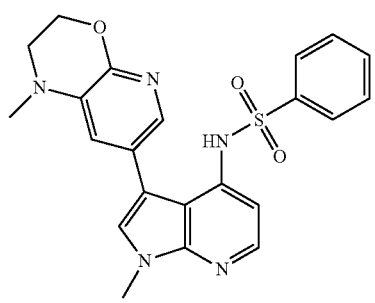 [SMILES: CN1CCOc2ncc(-c3cn(C)c4nccc(NS(=O)(=O)c5ccccc5)c34)cc21]

The title compound was prepared using the procedure as described for Scheme 2. LCMS (A): m/z (M+H)+ 436, C22H21N5O3S requires 435 (acidic).

Example 49

N-(1-methyl-3-(1-methyl-1H-indazol-6-yl)-1H-pyrrolo[2,3-b]pyridin-4-yl)benzenesulfonamide

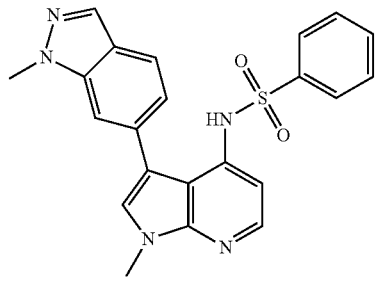 [SMILES: Cn1cc(-c2ccc3cnn(C)c3c2)c2c(NS(=O)(=O)c3ccccc3)ccnc21]

The title compound was prepared using the procedure as described for Scheme 2. LCMS (A): m/z (M+H)+ 418, C22H19N5O2S requires 417 (acidic).

Example 50

3-chloro-N-(1-methyl-3-(1-methyl-1H-indazol-6-yl)-1H-pyrrolo[2,3-b]pyridin-4-yl)benzenesulfonamide

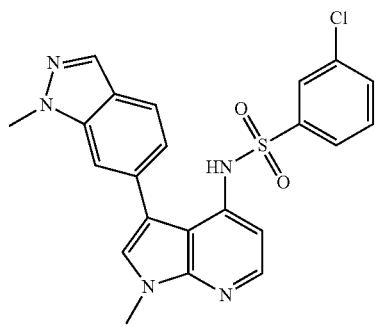 [SMILES: Cn1cc(-c2ccc3cnn(C)c3c2)c2c(NS(=O)(=O)c3cccc(Cl)c3)ccnc21]

The title compound was prepared using the procedure as described for Scheme 2. LCMS (A): m/z (M+H)+ 452, C22H18ClN5O2S requires 451 (acidic).

Example 51

N-(3-(4-fluoro-3-(pyrrolidin-1-yl)phenyl)-1-methyl-1H-pyrrolo[2,3-b]pyridin-4-yl)benzenesulfonamide

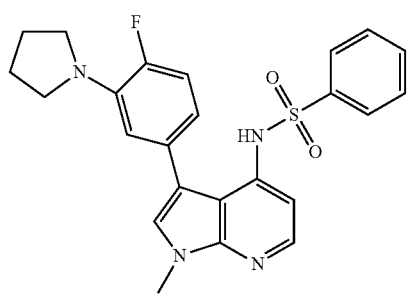 [SMILES: Cn1cc(-c2ccc(F)c(N3CCCC3)c2)c2c(NS(=O)(=O)c3ccccc3)ccnc21]

The title compound was prepared using the procedure as described for Scheme 2. LCMS (A): m/z (M+H)+ 451, C24H23FN4O2S requires 450 (acidic).

Example 52

N-(1-methyl-3-(3-(piperidin-1-yl)phenyl)-1H-pyrrolo[2,3-b]pyridin-4-yl)benzenesulfonamide

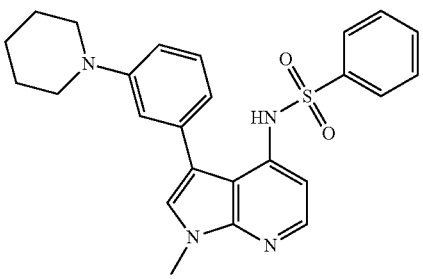 [SMILES: Cn1cc(-c2cccc(N3CCCCC3)c2)c2c(NS(=O)(=O)c3ccccc3)ccnc21]

The title compound was prepared using the procedure as described for Scheme 2. LCMS (A): m/z (M+H)+ 447, C25H26N4O2S requires 446 (acidic).

Example 53

N-(3-(2-fluoro-5-(pyrrolidin-1-yl)phenyl)-1-methyl-1H-pyrrolo[2,3-b]pyridin-4-yl)benzenesulfonamide

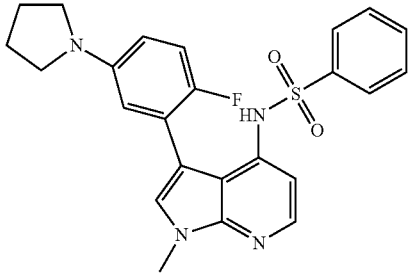 [SMILES: Cn1cc(-c2cc(N3CCCC3)ccc2F)c2c(NS(=O)(=O)c3ccccc3)ccnc21]

The title compound was prepared using the procedure as described for Scheme 2. LCMS (A): m/z (M+H)+ 451, C24H23FN4O2S requires 450 (acidic).

Example 54

N-(3-(3-(azetidin-1-yl)phenyl)-1-methyl-1H-pyrrolo[2,3-b]pyridin-4-yl)benzenesulfonamide

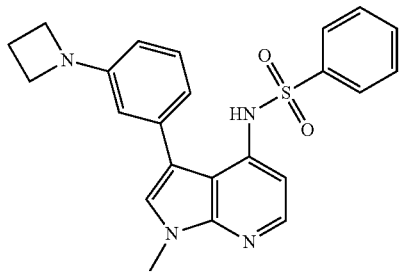 [SMILES: Cn1cc(-c2cccc(N3CCC3)c2)c2c(NS(=O)(=O)c3ccccc3)ccnc21]

The title compound was prepared using the procedure as described for Scheme 2. LCMS (A): m/z (M+H)+ 419, C23H22N4O2S requires 418 (acidic).

Example 55

N-(1-methyl-3-(1-methyl-1H-pyrazol-4-yl)-1H-pyrrolo[2,3-b]pyridin-4-yl)benzenesulfonamide

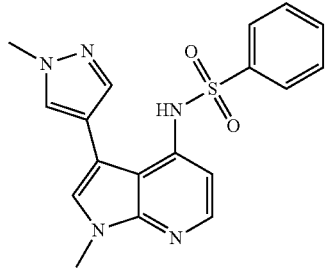 [SMILES: Cn1cc(-c2cn(C)c3nccc(NS(=O)(=O)c4ccccc4)c23)cn1]

The title compound was prepared using the procedure as described for Scheme 2. LCMS (A): m/z (M+H)+ 368, C18H17N5O2S requires 367 (acidic).

Example 56

5-methyl-N-(1-methyl-3-(3-(pyrrolidin-1-yl)phenyl)-1H-pyrrolo[2,3-b]pyridin-4-yl)furan-2-sulfonamide

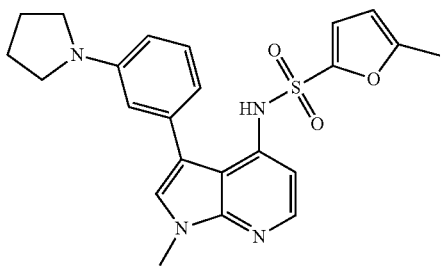 [SMILES: Cc1ccc(S(=O)(=O)Nc2ccnc3c2c(-c2cccc(N4CCCC4)c2)cn3C)o1]

The title compound was prepared using the procedure as described for Scheme 2. LCMS (A): m/z (M+H)+ 437, C23H24N4O3S requires 436 (acidic).

Example 57

2,4-dimethyl-N-(1-methyl-3-(3-(pyrrolidin-1-yl)phenyl)-1H-pyrrolo[2,3-b]pyridin-4-yl)thiazole-5-sulfonamide

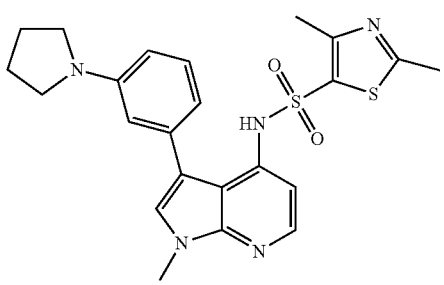 [SMILES: Cc1nc(C)c(S(=O)(=O)Nc2ccnc3c2c(-c2cccc(N4CCCC4)c2)cn3C)s1]

The title compound was prepared using the procedure as described for Scheme 2. LCMS (A): m/z (M+H)+ 468, C23H25N5O2S2 requires 467 (acidic).

Example 58

1-ethyl-N-(1-methyl-3-(3-(pyrrolidin-1-yl)phenyl)-1H-pyrrolo[2,3-b]pyridin-4-yl)-1H-pyrazole-4-sulfonamide

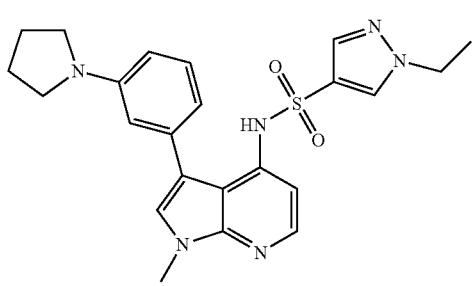 [SMILES: CCn1cc(S(=O)(=O)Nc2ccnc3c2c(-c2cccc(N4CCCC4)c2)cn3C)cn1]

The title compound was prepared using the procedure as described for Scheme 2. LCMS (A): m/z (M+H)+ 451, C23H26N6O2S requires 450 (acidic).

Example 59

1-methyl-N-(1-methyl-3-(3-(pyrrolidin-1-yl)phenyl)-1H-pyrrolo[2,3-b]pyridin-4-yl)-1H-pyrazole-4-sulfonamide

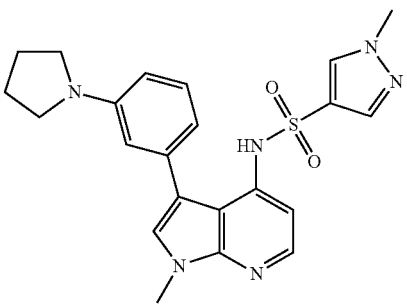 [SMILES: Cn1cc(S(=O)(=O)Nc2ccnc3c2c(-c2cccc(N4CCCC4)c2)cn3C)cn1]

The title compound was prepared using the procedure as described for Scheme 2. LCMS (A): m/z (M+H)+ 437, C22H24N6O2S requires 436 (acidic).

Example 60

1-methyl-N-(1-methyl-3-(3-(pyrrolidin-1-yl)phenyl)-1H-pyrrolo[2,3-b]pyridin-4-yl)-1H-pyrazole-3-sulfonamide

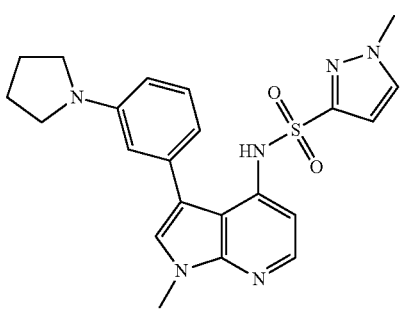 [SMILES: Cn1ccc(S(=O)(=O)Nc2ccnc3c2c(-c2cccc(N4CCCC4)c2)cn3C)n1]

The title compound was prepared using the procedure as described for Scheme 2. LCMS (A): m/z (M+H)+ 437, C22H24N6O2S requires 436 (acidic).

Example 61

1-methyl-N-(1-methyl-3-(3-(pyrrolidin-1-yl)phenyl)-1H-pyrrolo[2,3-b]pyridin-4-yl)-1H-imidazole-4-sulfonamide

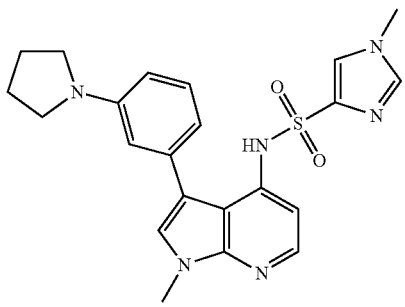 [SMILES: Cn1cnc(S(=O)(=O)Nc2ccnc3c2c(-c2cccc(N4CCCC4)c2)cn3C)c1]

The title compound was prepared using the procedure as described for Scheme 2. LCMS (A): m/z (M+H)+ 437, C22H24N6O2S requires 436 (acidic).

Example 62

N-(3-(1-ethylindolin-6-yl)-1-methyl-1H-pyrrolo[2,3-b]pyridin-4-yl)-1-methyl-1H-pyrazole-3-sulfonamide

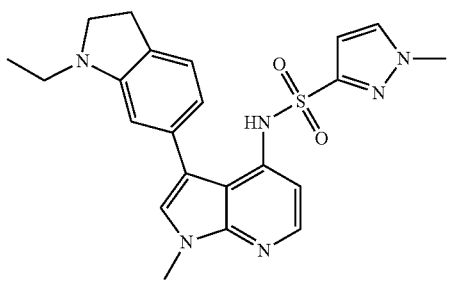 [SMILES: CCN1CCc2ccc(-c3cn(C)c4nccc(NS(=O)(=O)c5ccn(C)n5)c34)cc21]

The title compound was prepared using the procedure as described for Scheme 2. LCMS (A): m/z (M+H)+ 437, C22H24N6O2S requires 436 (basic).

Example 63

N-(3-(4-fluoro-1-methylindolin-6-yl)-1-methyl-1H-pyrrolo[2,3-b]pyridin-4-yl)-1-methyl-1H-pyrazole-3-sulfonamide

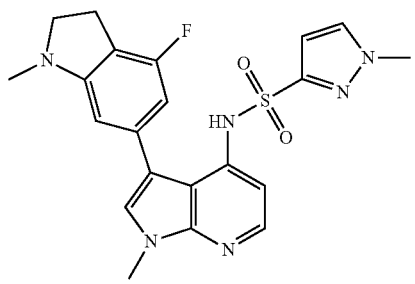

The title compound was prepared using the procedure as described for Scheme 2. LCMS (A): m/z (M+H)+ 441, C21H21FN6O2S requires 440 (acidic).

Example 64

N-(3-(1,5-dimethylindolin-6-yl)-1-methyl-1H-pyrrolo[2,3-b]pyridin-4-yl)benzenesulfonamide

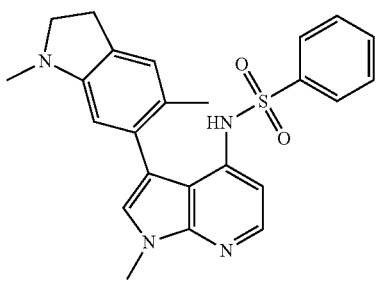 [SMILES: Cc1cc2c(cc1-c1cn(C)c3nccc(NS(=O)(=O)c4ccccc4)c13)N(C)CC2]

The title compound was prepared using the procedure as described for Scheme 2. LCMS (A): m/z (M+H)+ 433, C24H24N4O2S requires 432 (acidic).

Example 65

N-(3-(5-fluoro-1-methylindolin-6-yl)-1-methyl-1H-pyrrolo[2,3-b]pyridin-4-yl)-1-methyl-1H-pyrazole-3-sulfonamide

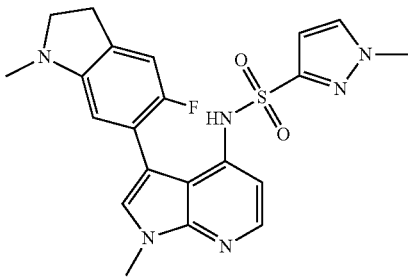

The title compound was prepared using the procedure as described for Scheme 2. LCMS (A): m/z (M+H)+ 441, C21H21FN6O2S requires 440 (acidic).

Example 66

2,4-dimethyl-N-(1-methyl-3-(1-methylindolin-6-yl)-1H-pyrrolo[2,3-b]pyridin-4-yl)thiazole-5-sulfonamide

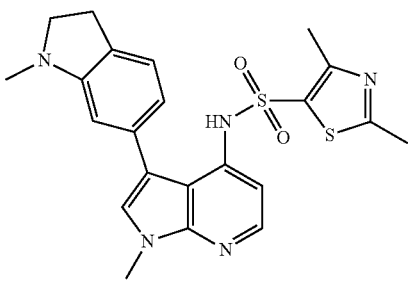

The title compound was prepared using the procedure as described for Scheme 2. LCMS (A): m/z (M+H)+ 454, C22H23N5O2S2 requires 453 (acidic).

Example 67

3,5-dimethyl-N-(1-methyl-3-(1-methylindolin-6-yl)-1H-pyrrolo[2,3-b]pyridin-4-yl)isoxazole-4-sulfonamide

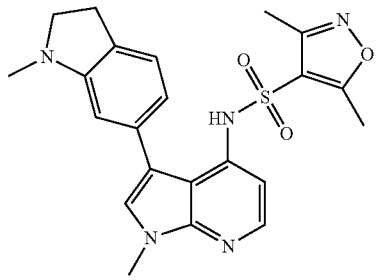 [SMILES: Cc1noc(C)c1S(=O)(=O)Nc1ccnc2c1c(-c1ccc3c(c1)N(C)CC3)cn2C]

The title compound was prepared using the procedure as described for Scheme 2. LCMS (A): m/z (M+H)+ 438, C22H23N5O3S requires 437 (acidic).

Example 68

1-ethyl-5-methyl-N-(1-methyl-3-(1-methylindolin-6-yl)-1H-pyrrolo[2,3-b]pyridin-4-yl)-1H-pyrazole-4-sulfonamide

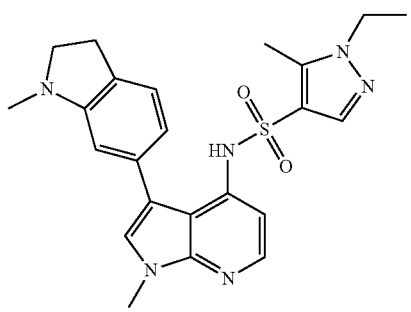 [SMILES: CCn1ncc(S(=O)(=O)Nc2ccnc3c2c(-c2ccc4c(c2)N(C)CC4)cn3C)c1C]

The title compound was prepared using the procedure as described for Scheme 2. LCMS (A): m/z (M+H)+ 451, C23H26N6O2S requires 450 (acidic).

Example 69

1,2-dimethyl-N-(1-methyl-3-(1-methylindolin-6-yl)-1H-pyrrolo[2,3-b]pyridin-4-yl)-1H-imidazole-5-sulfonamide

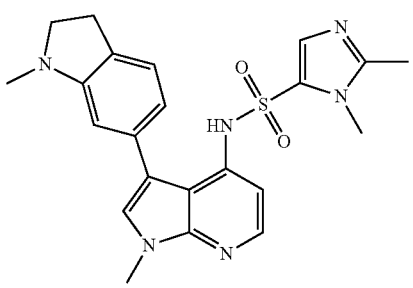

The title compound was prepared using the procedure as described for Scheme 2. LCMS (A): m/z (M+H)+ 437, C22H24N6O2S requires 436 (acidic).

Example 70

1,3-dimethyl-N-(1-methyl-3-(1-methylindolin-6-yl)-1H-pyrrolo[2,3-b]pyridin-4-yl)-1H-pyrazole-4-sulfonamide

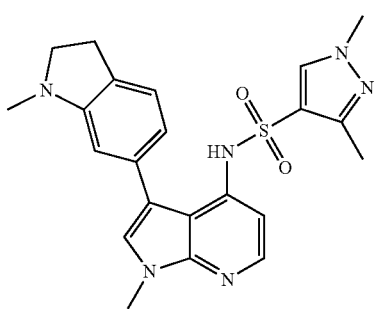 [SMILES: Cc1nn(C)cc1S(=O)(=O)Nc1ccnc2c1c(-c1ccc3c(c1)N(C)CC3)cn2C]

The title compound was prepared using the procedure as described for Scheme 2. LCMS (A): m/z (M+H)+ 437, C22H24N6O2S requires 436 (acidic).

Example 71

1-methyl-N-(1-methyl-3-(1-methylindolin-6-yl)-1H-pyrrolo[2,3-b]pyridin-4-yl)-1H-pyrazole-4-sulfonamide

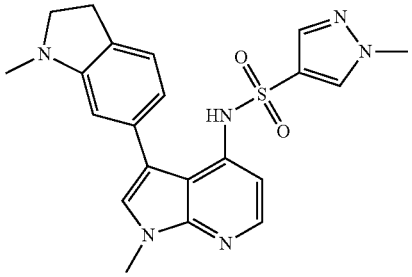

The title compound was prepared using the procedure as described for Scheme 2. LCMS (A): m/z (M+H)+ 423, C21H22N6O2S requires 422 (acidic).

Example 72

1,5-dimethyl-N-(1-methyl-3-(1-methylindolin-6-yl)-1H-pyrrolo[2,3-b]pyridin-4-yl)-1H-pyrazole-4-sulfonamide

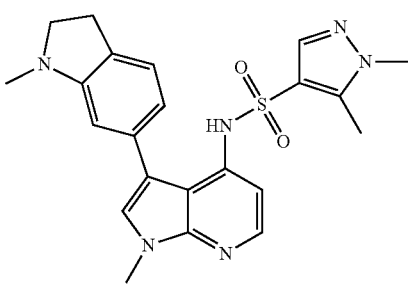

The title compound was prepared using the procedure as described for Scheme 2. LCMS (A): m/z (M+H)+ 437, C22H24N6O2S requires 436 (acidic).

Example 73

1-methyl-N-(1-methyl-3-(1-methylindolin-4-yl)-1H-pyrrolo[2,3-b]pyridin-4-yl)-1H-pyrazole-3-sulfonamide

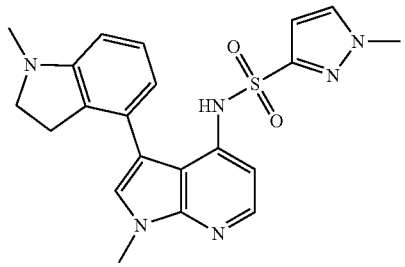

The title compound was prepared using the procedure as described for Scheme 2. LCMS (A): m/z (M+H)+ 423, C21H22N6O2S requires 422 (acidic).

Example 74

1-methyl-N-(1-methyl-3-(1-methyl-1H-indol-6-yl)-1H-pyrrolo[2,3-b]pyridin-4-yl)-1H-pyrazole-3-sulfonamide

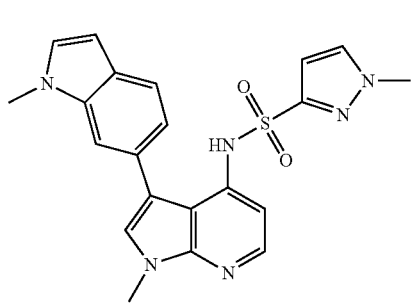

The title compound was prepared using the procedure as described for Scheme 2. LCMS (A): m/z (M+H)+ 421, C21H20N6O2S requires 420 (acidic).

Example 75

N-(3-(5-fluoro-1-methylindolin-6-yl)-1-methyl-1H-pyrrolo[2,3-b]pyridin-4-yl)benzenesulfonamide

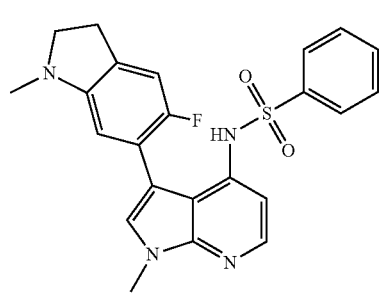 [SMILES: CN1CCc2cc(F)c(-c3cn(C)c4nccc(NS(=O)(=O)c5ccccc5)c34)cc21]

The title compound was prepared using the procedure as described for Scheme 2. LCMS (A): m/z (M+H)+ 437, C23H21FN4O2S requires 436 (acidic).

Example 76

N-(1-methyl-3-(1-methylindolin-6-yl)-1H-pyrrolo[2,3-b]pyridin-4-yl)cyclobutanesulfonamide

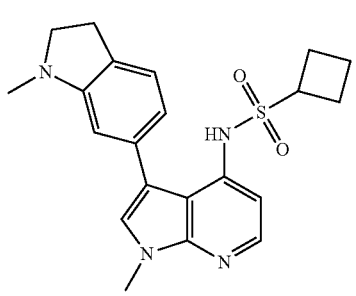 [SMILES: CN1CCc2ccc(-c3cn(C)c4nccc(NS(=O)(=O)C5CCC5)c34)cc21]

The title compound was prepared using the procedure as described for Scheme 2. LCMS (A): m/z (M+H)+ 397, C21H24N4O2S requires 396 (acidic).

Example 77

5-methyl-N-(1-methyl-3-(1-methylindolin-6-yl)-1H-pyrrolo[2,3-b]pyridin-4-yl)pyridine-2-sulfonamide

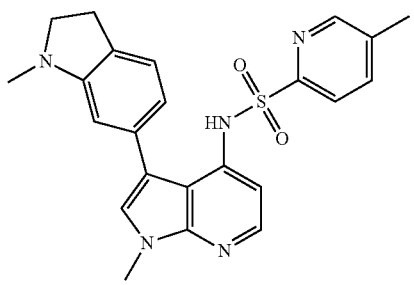

The title compound was prepared using the procedure as described for Scheme 2. LCMS (A): m/z (M+H)+ 434, C23H23N5O2S requires 433 (acidic).

Example 78

1-methyl-N-(1-methyl-3-(1-methyl-2,3,4,5-tetrahydro-1H-benzo[b]azepin-8-yl)-1H-pyrrolo[2,3-b]pyridin-4-yl)-1H-pyrazole-3-sulfonamide

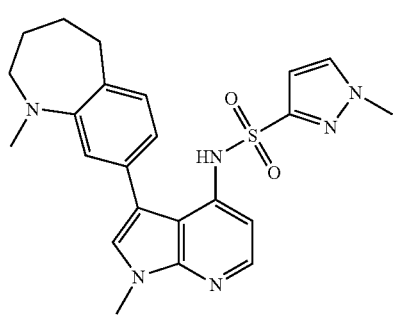 [SMILES: CN1CCCCc2ccc(-c3cn(C)c4nccc(NS(=O)(=O)c5ccn(C)n5)c34)cc21]

The title compound was prepared using the procedure as described for Scheme 2. LCMS (A): m/z (M+H)+ 451, C23H26N6O2S requires 450 (acidic).

Example 79

N-(3-(2-fluoro-5-(pyrrolidin-1-yl)phenyl)-1-methyl-1H-pyrrolo[2,3-b]pyridin-4-yl)-1-methyl-1H-pyrazole-3-sulfonamide

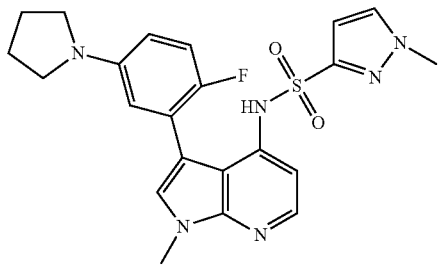 [SMILES: Cn1ccc(S(=O)(=O)Nc2ccnc3c2c(-c2cc(N4CCCC4)ccc2F)cn3C)n1]

The title compound was prepared using the procedure as described for Scheme 2. LCMS (A): m/z (M+H)+ 455, C22H23FN6O2S requires 454 (acidic).

Example 80

N-(3-(3-fluoro-5-(pyrrolidin-1-yl)phenyl)-1-methyl-1H-pyrrolo[2,3-b]pyridin-4-yl)benzenesulfonamide

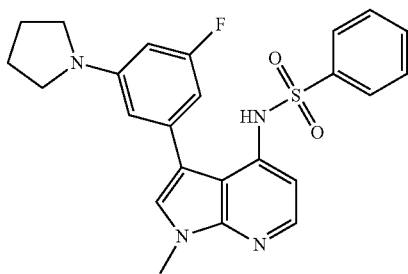 [SMILES: Cn1cc(-c2cc(F)cc(N3CCCC3)c2)c2c(NS(=O)(=O)c3ccccc3)ccnc21]

The title compound was prepared using the procedure as described for Scheme 2. LCMS (A): m/z (M+H)+ 451, C24H23FN4O2S requires 450 (acidic).

Example 81

4-cyano-N-(1-methyl-3-(3-(pyrrolidin-1-yl)phenyl)-1H-pyrrolo[2,3-b]pyridin-4-yl)benzenesulfonamide

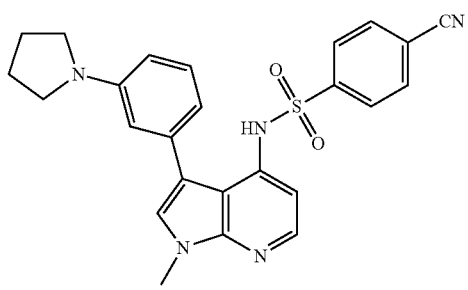 [SMILES: Cn1cc(-c2cccc(N3CCCC3)c2)c2c(NS(=O)(=O)c3ccc(C#N)cc3)ccnc21]

The title compound was prepared using the procedure as described for Scheme 2. LCMS (B): m/z (M+H)+ 458, C25H23N5O2S requires 457 (basic).

Example 82

3-cyano-N-(1-methyl-3-(3-(pyrrolidin-1-yl)phenyl)-1H-pyrrolo[2,3-b]pyridin-4-yl)benzenesulfonamide

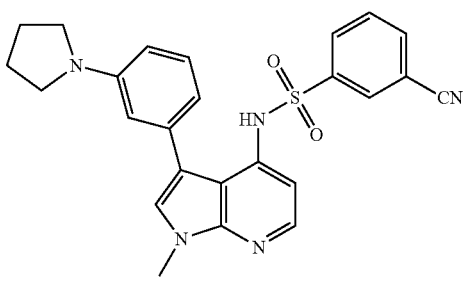 [SMILES: Cn1cc(-c2cccc(N3CCCC3)c2)c2c(NS(=O)(=O)c3cccc(C#N)c3)ccnc21]

The title compound was prepared using the procedure as described for Scheme 2. LCMS (B): m/z (M+H)+ 458, C25H23N5O2S requires 457 (basic).

Example 83

2-cyano-N-(1-methyl-3-(3-(pyrrolidin-1-yl)phenyl)-1H-pyrrolo[2,3-b]pyridin-4-yl)benzenesulfonamide

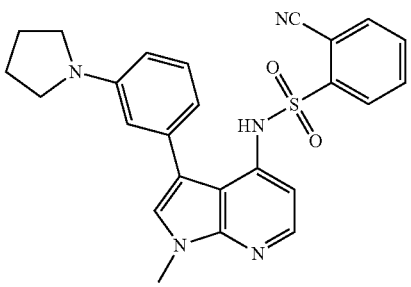 [SMILES: Cn1cc(-c2cccc(N3CCCC3)c2)c2c(NS(=O)(=O)c3ccccc3C#N)ccnc21]

The title compound was prepared using the procedure as described for Scheme 2. LCMS (B): m/z (M+H)+ 458, C25H23N5O2S requires 457 (acidic).

Example 84

N-(1-methyl-3-(3-(2-methylpyrrolidin-1-yl)phenyl)-1H-pyrrolo[2,3-b]pyridin-4-yl)benzenesulfonamide

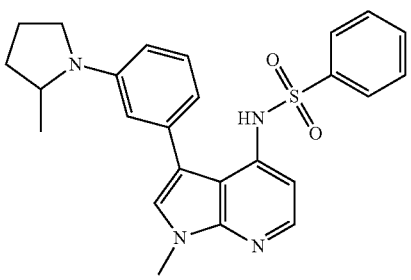 [SMILES: CC1CCCN1c1cccc(-c2cn(C)c3nccc(NS(=O)(=O)c4ccccc4)c23)c1]

The title compound was prepared using the procedure as described for Scheme 2. LCMS (B): m/z (M+H)+ 447, C25H26N4O2S requires 446 (acidic).

Example 85

N-(3-(3-(cyclobutylmethyl)amino)phenyl)-1-methyl-1H-pyrrolo[2,3-b]pyridin-4-yl)benzenesulfonamide

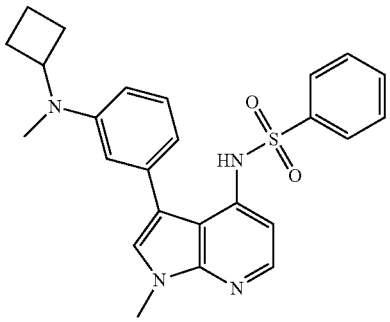 [SMILES: CN(c1cccc(-c2cn(C)c3nccc(NS(=O)(=O)c4ccccc4)c23)c1)C1CCC1]

The title compound was prepared using the procedure as described for Scheme 2. LCMS (A): m/z (M+H)+ 447, C25H26N4O2S requires 446 (acidic).

Example 86

N-(3-(3-(cyclobutylmethyl)amino)phenyl)-1-methyl-1H-pyrrolo[2,3-b]pyridin-4-yl)-1-methyl-1H-pyrazole-3-sulfonamide

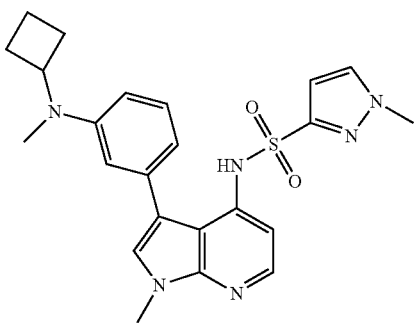 [SMILES: CN(c1cccc(-c2cn(C)c3nccc(NS(=O)(=O)c4ccn(C)n4)c23)c1)C1CCC1]

The title compound was prepared using the procedure as described for Scheme 2. LCMS (A): m/z (M+H)+ 451, C23H26N6O2S requires 450 (acidic).

Example 87

N-(3-(3-(cyclopentyl(methyl)amino)phenyl)-1-methyl-1H-pyrrolo[2,3-b]pyridin-4-yl)-1-methyl-1H-pyrazole-3-sulfonamide

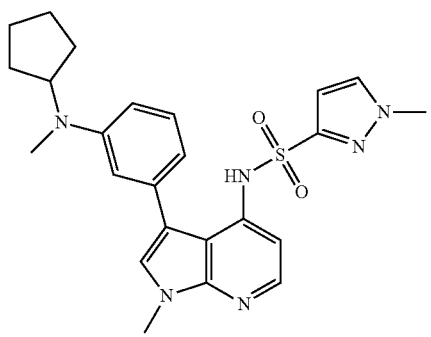 [SMILES: CN(c1cccc(-c2cn(C)c3nccc(NS(=O)(=O)c4ccn(C)n4)c23)c1)C1CCCC1]

The title compound was prepared using the procedure as described for Scheme 2. LCMS (A): m/z (M+H)+ 465, C24H28N6O2S requires 464 (acidic).

Example 88

N-(3-(3-(dimethylamino)phenyl)-1-methyl-1H-pyrrolo[2,3-b]pyridin-4-yl)benzenesulfonamide

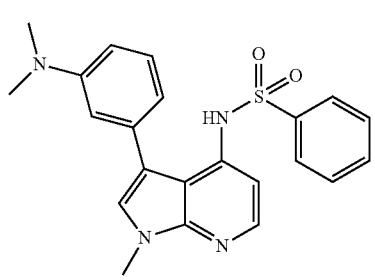 [SMILES: CN(C)c1cccc(-c2cn(C)c3nccc(NS(=O)(=O)c4ccccc4)c23)c1]

The title compound was prepared using the procedure as described for Scheme 2. LCMS (A): m/z (M+H)+ 407, C22H22N4O2S requires 406 (acidic).

Example 89

N-(3-(3-(dimethylamino)phenyl)-1-methyl-1H-pyrrolo[2,3-b]pyridin-4-yl)pyridine-3-sulfonamide

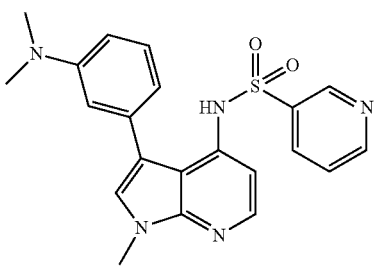 [SMILES: CN(C)c1cccc(-c2cn(C)c3nccc(NS(=O)(=O)c4cccnc4)c23)c1]

The title compound was prepared using the procedure as described for Scheme 2. LCMS (A): m/z (M+H)+ 408, C21H21N5O2S requires 407 (acidic).

Example 90

N-(3-(3-(dimethylamino)phenyl)-1-methyl-1H-pyrrolo[2,3-b]pyridin-4-yl)cyclopentanesulfonamide

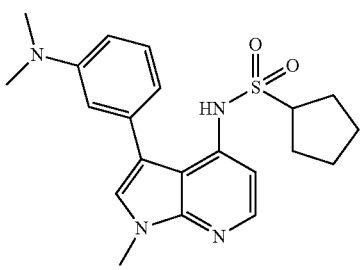 [SMILES: CN(C)c1cccc(-c2cn(C)c3nccc(NS(=O)(=O)C4CCCC4)c23)c1]

The title compound was prepared using the procedure as described for Scheme 2. LCMS (A): m/z (M+H)$^+$ 399, C21H26N4O2S requires 398 (acidic).

Example 91

Benzyl 4-(N-(3-(3-(dimethylamino)phenyl)-1-methyl-1H-pyrrolo[2,3-b]pyridin-4-yl)sulfamoyl)piperidine-1-carboxylate

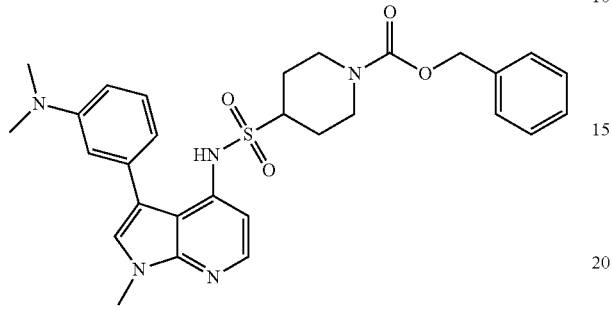

The title compound was prepared using the procedure as described for Scheme 2. LCMS (A): m/z (M+H)$^+$548, C29H33N5O4S requires 547 (acidic).

Example 92

N-(3-(3-(dimethylamino)phenyl)-1-methyl-1H-pyrrolo[2,3-b]pyridin-4-yl)-5-methylthiophene-2-sulfonamide

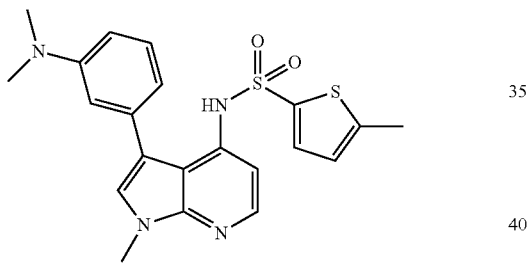

The title compound was prepared using the procedure as described for Scheme 2. LCMS (A): m/z (M+H)$^+$ 427, C21H22N4O2S2 requires 426 (acidic).

Example 93

Benzyl 4-chloro-4-(N-(3-(3-(dimethylamino)phenyl)-1-methyl-1H-pyrrolo[2,3-b]pyridin-4-yl)sulfamoyl)piperidine-1-carboxylate

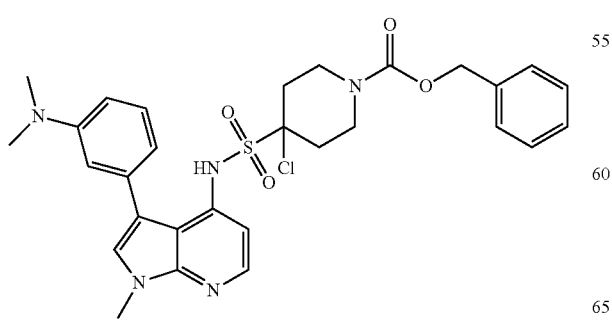

The title compound was prepared using the procedure as described for Scheme 2. LCMS (A): m/z (M+H)$^+$ 582, C29H32ClN5O4S requires 581 (acidic).

Example 94

N-(3-(3-(dimethylamino)phenyl)-1-methyl-1H-pyrrolo[2,3-b]pyridin-4-yl)-1-methyl-1H-pyrazole-3-sulfonamide

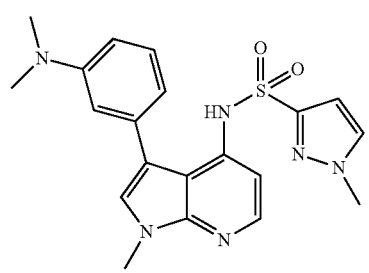 [SMILES: CN(C)c1cccc(-c2cn(C)c3nccc(NS(=O)(=O)c4ccn(C)n4)c23)c1]

The title compound was prepared using the procedure as described for Scheme 2. LCMS (A): m/z (M+H)$^+$ 411, C20H22N6O2S requires 410 (acidic).

Example 95

N-(3-(3-(dimethylamino)phenyl)-1-methyl-1H-pyrrolo[2,3-b]pyridin-4-yl)-1-methyl-1H-imidazole-4-sulfonamide

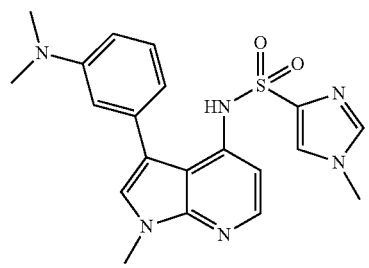 [SMILES: CN(C)c1cccc(-c2cn(C)c3nccc(NS(=O)(=O)c4cn(C)cn4)c23)c1]

The title compound was prepared using the procedure as described for Scheme 2. LCMS (A): m/z (M+H)$^+$ 411, C20H22N6O2S requires 410 (acidic).

Example 96

N-(3-(3-(dimethylamino)phenyl)-1-methyl-1H-pyrrolo[2,3-b]pyridin-4-yl)-3,5-difluorobenzenesulfonamide

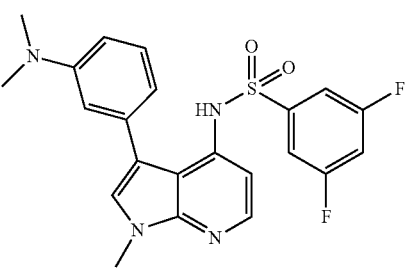 [SMILES: CN(C)c1cccc(-c2cn(C)c3nccc(NS(=O)(=O)c4cc(F)cc(F)c4)c23)c1]

The title compound was prepared using the procedure as described for Scheme 2. LCMS (A): m/z (M+H)+ 443, C22H20F2N4O2S requires 442 (acidic).

Example 97

N-(3-(3-(dimethylamino)phenyl)-1-methyl-1H-pyrrolo[2,3-b]pyridin-4-yl)pyrrolidine-1-sulfonamide

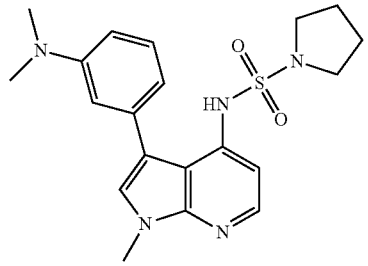 [SMILES: CN(C)c1cccc(-c2cn(C)c3nccc(NS(=O)(=O)N4CCCC4)c23)c1]

The title compound was prepared using the procedure as described for Scheme 2. LCMS (A): m/z (M+H)+ 400, C20H25N5O2S requires 399 (acidic).

Example 98

N-(3-(3-(dimethylamino)phenyl)-1-methyl-1H-pyrrolo[2,3-b]pyridin-4-yl)piperidine-4-sulfonamide

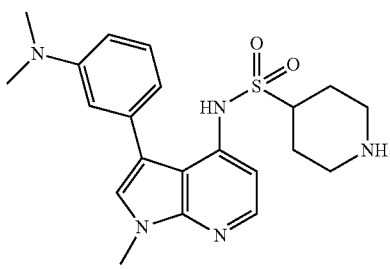 [SMILES: CN(C)c1cccc(-c2cn(C)c3nccc(NS(=O)(=O)C4CCNCC4)c23)c1]

The title compound was prepared using the procedure as described for Scheme 3. LCMS (A): m/z (M+H)+414, C21H27N5O2S requires 413 (acidic).

Example 99

N-(3-(3-(dimethylamino)phenyl)-1-methyl-1H-pyrrolo[2,3-b]pyridin-4-yl)-3-(4-methylpiperazin-1-yl)benzenesulfonamide

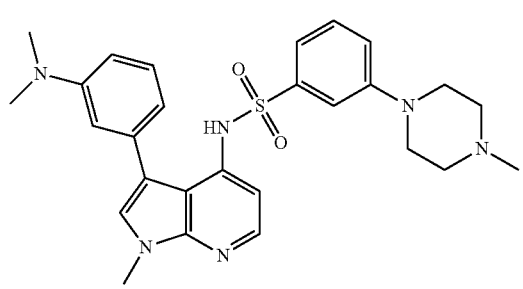

The title compound was prepared using the procedure as described for Scheme 2. LCMS (A): m/z (M+H)+505, C27H32N6O2S requires 504 (acidic).

Example 100

1-isopropyl-N-(1-methyl-3-(1-methylindolin-6-yl)-1H-pyrrolo[2,3-b]pyridin-4-yl)piperidine-4-sulfonamide

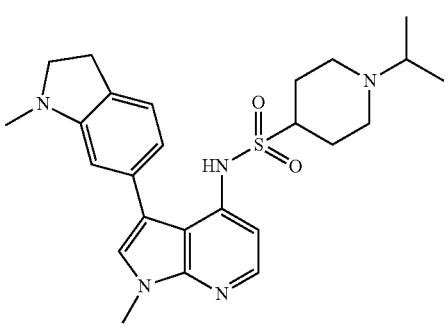 [SMILES: CC(C)N1CCC(S(=O)(=O)Nc2ccnc3c2c(-c2ccc4c(c2)N(C)CC4)cn3C)CC1]

The title compound was prepared using the procedure as described for Scheme 2. LCMS (A): m/z (M+H)+468, C25H33N5O2S requires 467 (acidic).

Example 101

3-chloro-N-(1-methyl-3-(2-(pyrrolidin-1-yl)pyridin-4-yl)-1H-pyrrolo[2,3-b]pyridin-4-yl)benzenesulfonamide

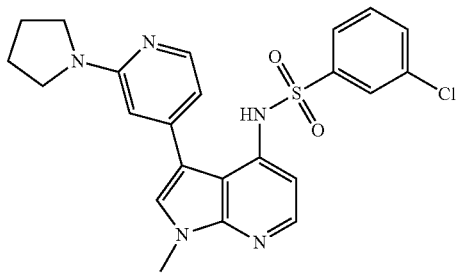 [SMILES: Cn1cc(-c2ccnc(N3CCCC3)c2)c2c(NS(=O)(=O)c3cccc(Cl)c3)ccnc21]

The title compound was prepared using the procedure as described for Scheme 2. LCMS (A): m/z (M+H)+468, C23H22ClN5O2S requires 467 (acidic).

Example 102

3-chloro-N-(3-(2-(cyclopropylamino)pyridin-4-yl)-1-methyl-1H-pyrrolo[2,3-b]pyridin-4-yl)benzenesulfonamide

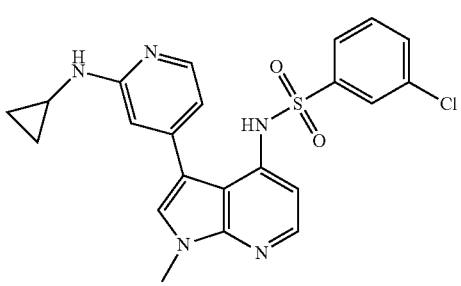 [SMILES: Cn1cc(-c2ccnc(NC3CC3)c2)c2c(NS(=O)(=O)c3cccc(Cl)c3)ccnc21]

The title compound was prepared using the procedure as described for Scheme 2. LCMS (A): m/z (M+H)$^+$454, C22H20ClN5O2S requires 453 (acidic).

Example 103

3-chloro-N-(1-methyl-3-(2-(piperidin-1-yl)pyridin-4-yl)-1H-pyrrolo[2,3-b]pyridin-4-yl)benzenesulfonamide

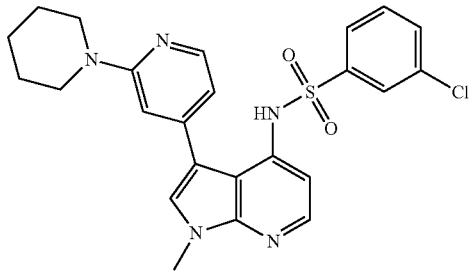 [SMILES: Cn1cc(-c2ccnc(N3CCCCC3)c2)c2c(NS(=O)(=O)c3cccc(Cl)c3)ccnc21]

The title compound was prepared using the procedure as described for Scheme 2. LCMS (A): m/z (M+H)$^+$482, C24H24ClN5O2S requires 481 (acidic).

Example 104

3-chloro-N-(1-methyl-3-(2-(2-methylpyrrolidin-1-yl)pyridin-4-yl)-1H-pyrrolo[2,3-b]pyridin-4-yl)benzenesulfonamide

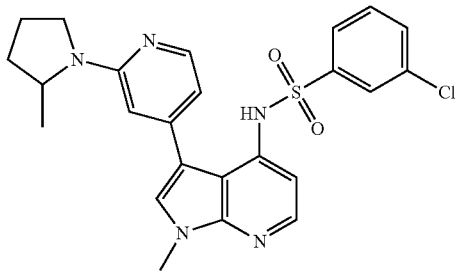 [SMILES: CC1CCCN1c1cc(-c2cn(C)c3nccc(NS(=O)(=O)c4cccc(Cl)c4)c23)ccn1]

The title compound was prepared using the procedure as described for Scheme 2. LCMS (A): m/z (M+H)$^+$482, C24H24ClN5O2S requires 481 (acidic).

Example 105

3-chloro-N-(3-(2-(3-(dimethylamino)pyrrolidin-1-yl)pyridin-4-yl)-1-methyl-1H-pyrrolo[2,3-b]pyridin-4-yl)benzenesulfonamide

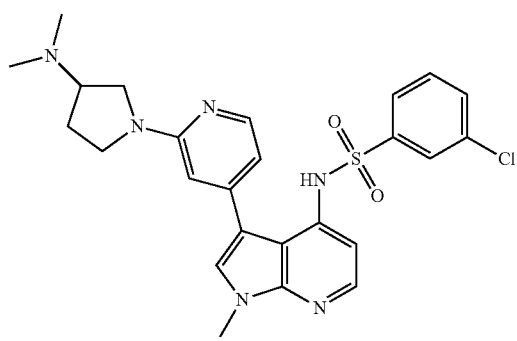 [SMILES: CN(C)C1CCN(c2cc(-c3cn(C)c4nccc(NS(=O)(=O)c5cccc(Cl)c5)c34)ccn2)C1]

The title compound was prepared using the procedure as described for Scheme 2. LCMS (A): m/z (M+H)$^+$511, C25H27ClN6O2S requires 510 (acidic).

Example 106

3-chloro-N-(1-methyl-3-(2-(4-methylpiperazin-1-yl)pyridin-4-yl)-1H-pyrrolo[2,3-b]pyridin-4-yl)benzenesulfonamide

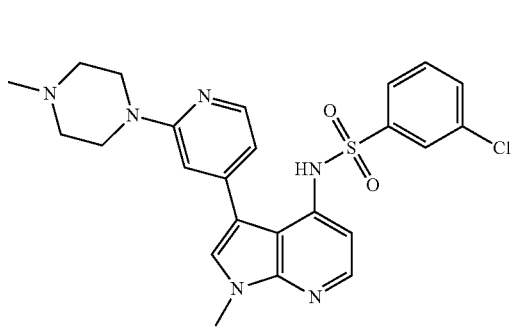 [SMILES: CN1CCN(c2cc(-c3cn(C)c4nccc(NS(=O)(=O)c5cccc(Cl)c5)c34)ccn2)CC1]

The title compound was prepared using the procedure as described for Scheme 2. LCMS (A): m/z (M+H)$^+$ 497, C24H25ClN6O2S requires 496 (acidic).

Example 107

1-methyl-N-(3-(3-(pyrrolidin-1-yl)phenyl)-1H-pyrrolo[2,3-b]pyridin-4-yl)-1H-pyrazole-3-sulfonamide

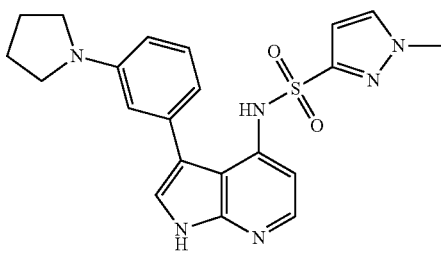 [SMILES: Cn1ccc(S(=O)(=O)Nc2ccnc3[nH]cc(-c4cccc(N5CCCC5)c4)c23)n1]

The title compound was prepared using the procedure as described for Scheme 2. LCMS (A): m/z (M+H)$^+$ 423, C21H22N6O2S requires 422 (acidic).

Example 108

N-(3-(3-(pyrrolidin-1-yl)phenyl)-1H-pyrrolo[2,3-b]pyridin-4-yl)cyclopropanesulfonamide

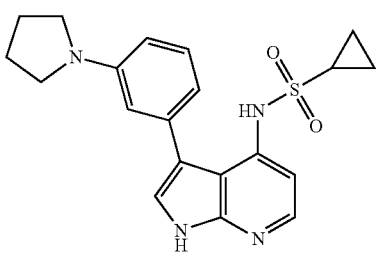 [SMILES: O=S(=O)(Nc1ccnc2[nH]cc(-c3cccc(N4CCCC4)c3)c12)C1CC1]

The title compound was prepared using the procedure as described for Scheme 2. LCMS (A): m/z (M+H)+ 383, C20H22N4O2S requires 382 (acidic).

Example 109

N-(3-(3-(piperazin-1-yl)phenyl)-1H-pyrrolo[2,3-b]pyridin-4-yl)benzenesulfonamide

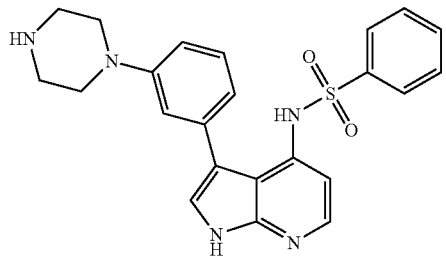 [SMILES: O=S(=O)(Nc1ccnc2[nH]cc(-c3cccc(N4CCNCC4)c3)c12)c1ccccc1]

The title compound was prepared using the procedure as described for Scheme 2. LCMS (A): m/z (M+H)+ 434, C23H23N5O2S requires 433 (acidic).

Example 110

N-(3-(5-(pyrrolidin-1-yl)pyridin-3-yl)-1H-pyrrolo[2,3-b]pyridin-4-yl)benzenesulfonamide

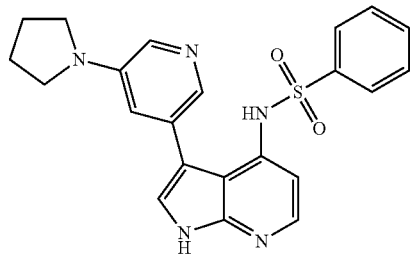 [SMILES: O=S(=O)(Nc1ccnc2[nH]cc(-c3cncc(N4CCCC4)c3)c12)c1ccccc1]

The title compound was prepared using the procedure as described for Scheme 2. LCMS (A): m/z (M+H)+ 420, C22H21N5O2S requires 419 (acidic).

Example 111

N-(3-(3-morpholinophenyl)-1H-pyrrolo[2,3-b]pyridin-4-yl)benzenesulfonamide

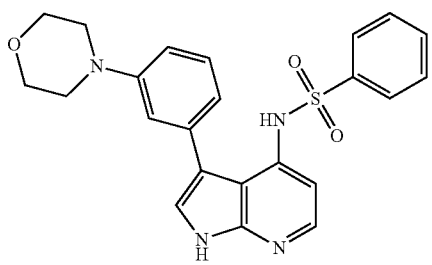 [SMILES: O=S(=O)(Nc1ccnc2[nH]cc(-c3cccc(N4CCOCC4)c3)c12)c1ccccc1]

The title compound was prepared using the procedure as described for Scheme 2. LCMS (A): m/z (M+H)+ 435, C23H22N4O3S requires 434 (acidic).

Example 112

N-(3-(1-methyl-1H-indol-6-yl)-1H-pyrrolo[2,3-b]pyridin-4-yl)benzenesulfonamide

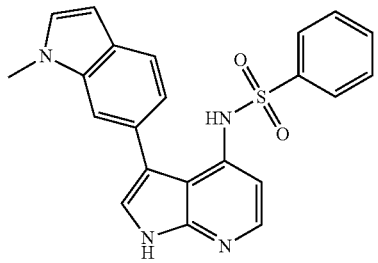 [SMILES: Cn1ccc2ccc(-c3c[nH]c4nccc(NS(=O)(=O)c5ccccc5)c34)cc21]

The title compound was prepared using the procedure as described for Scheme 2. LCMS (A): m/z (M+H)+ 403, C22H18N4O2S requires 402 (acidic).

Example 113

N-(3-(3-(1H-pyrazol-1-yl)phenyl)-1H-pyrrolo[2,3-b]pyridin-4-yl)benzenesulfonamide

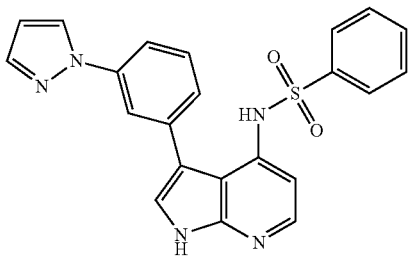 [SMILES: O=S(=O)(Nc1ccnc2[nH]cc(-c3cccc(-n4cccn4)c3)c12)c1ccccc1]

The title compound was prepared using the procedure as described for Scheme 2. LCMS (A): m/z (M+H)+ 416, C22H17N5O2S requires 415 (acidic).

Example 114

N-(3-(3-(2-oxopyrrolidin-1-yl)phenyl)-1H-pyrrolo[2,3-b]pyridin-4-yl)benzenesulfonamide

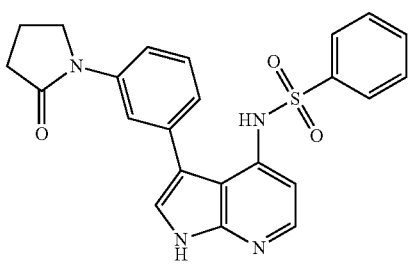 [SMILES: O=C1CCCN1c1cccc(-c2c[nH]c3nccc(NS(=O)(=O)c4ccccc4)c23)c1]

The title compound was prepared using the procedure as described for Scheme 2. LCMS (A): m/z (M+H)+ 433, C23H20N4O3S requires 432 (acidic).

Example 115

N-(3-(4-methyl-3,4-dihydro-2H-benzo[b][1,4]ox-azin-6-yl)-1H-pyrrolo[2,3-b]pyridin-4-yl)benzene-sulfonamide

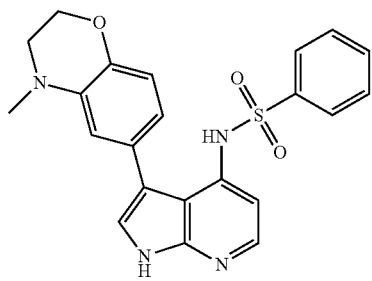 [SMILES: CN1CCOc2ccc(-c3c[nH]c4nccc(NS(=O)(=O)c5ccccc5)c34)cc21]

The title compound was prepared using the procedure as described for Scheme 2. LCMS (A): m/z (M+H)+ 421, C22H20N4O3S requires 420 (acidic).

Example 116

1-methyl-N-(3-(3-(pyrrolidin-1-yl)phenyl)-1H-pyr-rolo[2,3-b]pyridin-4-yl)-1H-imidazole-4-sulfona-mide

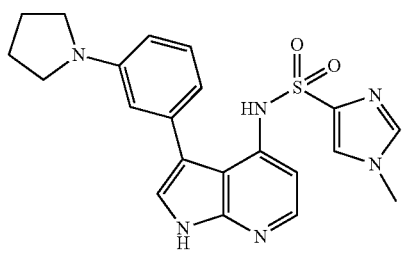 [SMILES: Cn1cnc(S(=O)(=O)Nc2ccnc3[nH]cc(-c4cccc(N5CCCC5)c4)c23)c1]

The title compound was prepared using the procedure as described for Scheme 2. LCMS (A): m/z (M+H)+ 423, C21H22N6O2S requires 422 (acidic).

Example 117

1-methyl-N-(3-(1-methylindolin-6-yl)-1H-pyrrolo[2,3-b]pyridin-4-yl)-1H-pyrazole-3-sulfonamide

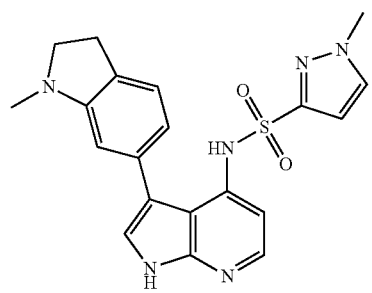 [SMILES: CN1CCc2ccc(-c3c[nH]c4nccc(NS(=O)(=O)c5ccn(C)n5)c34)cc21]

The title compound was prepared using the procedure as described for Scheme 2. LCMS (A): m/z (M+H)+ 409, C20H20N6O2S requires 408 (acidic).

Example 118

N-(3-(3-(dimethylamino)phenyl)-1H-pyrrolo[2,3-b]pyridin-4-yl)-3-fluorobenzenesulfonamide

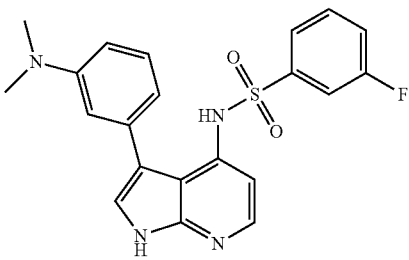 [SMILES: CN(C)c1cccc(-c2c[nH]c3nccc(NS(=O)(=O)c4cccc(F)c4)c23)c1]

The title compound was prepared using the procedure as described for Scheme 2. LCMS (B): m/z (M+H)+ 411, C21H19FN4O2S requires 410 (basic).

Example 119

2-chloro-N-(3-(3-(dimethylamino)phenyl)-1H-pyr-rolo[2,3-b]pyridin-4-yl)benzenesulfonamide

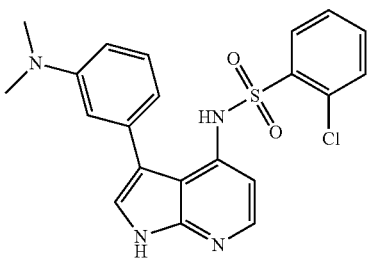 [SMILES: CN(C)c1cccc(-c2c[nH]c3nccc(NS(=O)(=O)c4ccccc4Cl)c23)c1]

The title compound was prepared using the procedure as described for Scheme 2. LCMS (B): m/z (M+H)+ 427, C21H19ClN4O2S requires 426 (basic).

Example 120

N-(3-(3-(dimethylamino)phenyl)-1H-pyrrolo[2,3-b]pyridin-4-yl)-4-methoxybenzenesulfonamide

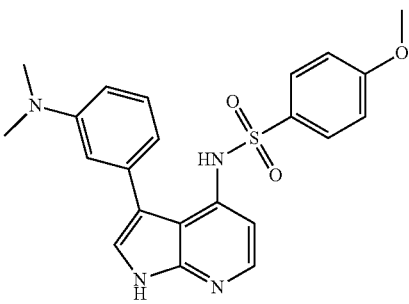

The title compound was prepared using the procedure as described for Scheme 2. LCMS (B): m/z (M+H)+ 423, C22H22N4O3S requires 422 (basic).

Example 121

N-(3-(3-(dimethylamino)phenyl)-1H-pyrrolo[2,3-b]pyridin-4-yl)-4-fluorobenzenesulfonamide

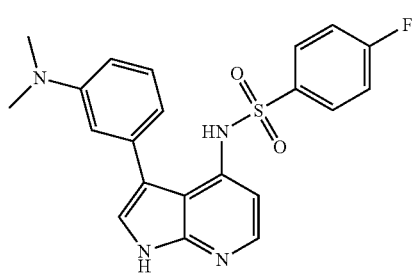 [SMILES: CN(C)c1cccc(-c2c[nH]c3nccc(NS(=O)(=O)c4ccc(F)cc4)c23)c1]

The title compound was prepared using the procedure as described for Scheme 2. LCMS (B): m/z (M+H)+ 411, C21H19FN4O2S requires 410 (basic).

Example 122

4-chloro-N-(3-(3-(dimethylamino)phenyl)-1H-pyrrolo[2,3-b]pyridin-4-yl)benzenesulfonamide

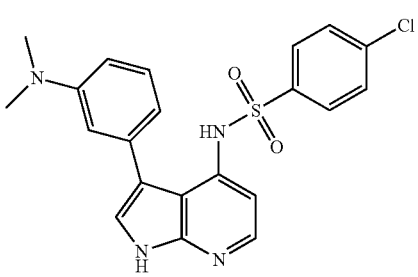 [SMILES: CN(C)c1cccc(-c2c[nH]c3nccc(NS(=O)(=O)c4ccc(Cl)cc4)c23)c1]

The title compound was prepared using the procedure as described for Scheme 2. LCMS (B): m/z (M–H)− 425, C21H19ClN4O2S requires 426 (basic).

Example 123

N-(3-(3-(dimethylamino)phenyl)-1H-pyrrolo[2,3-b]pyridin-4-yl)-2-fluorobenzenesulfonamide

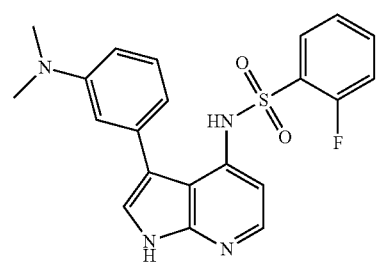 [SMILES: CN(C)c1cccc(-c2c[nH]c3nccc(NS(=O)(=O)c4ccccc4F)c23)c1]

The title compound was prepared using the procedure as described for Scheme 2. LCMS (B): m/z (M–H)− 409, C21H19FN4O2S requires 410 (basic).

Example 124

N-(3-(3-(dimethylamino)phenyl)-1H-pyrrolo[2,3-b]pyridin-4-yl)-3-methoxybenzenesulfonamide

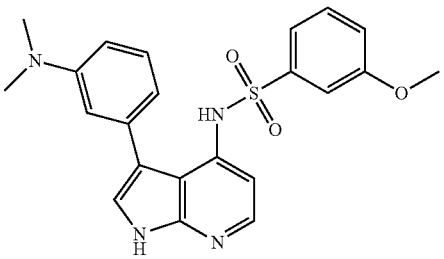

The title compound was prepared using the procedure as described for Scheme 2. LCMS (B): m/z (M–H)− 421, C22H22N4O3S requires 422 (basic).

Example 125

N-(3-(3-(dimethylamino)phenyl)-1H-pyrrolo[2,3-b]pyridin-4-yl)-2-methoxybenzenesulfonamide

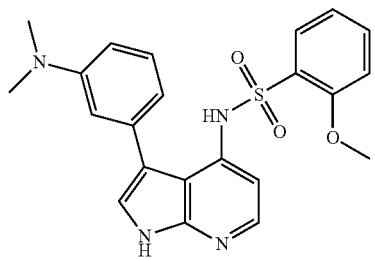

The title compound was prepared using the procedure as described for Scheme 2. LCMS (B): m/z (M–H)− 421, C22H22N4O3S requires 422 (basic).

Example 126

N-(3-(2-(pyrrolidin-1-yl)pyridin-4-yl)-1H-pyrrolo[2,3-b]pyridin-4-yl)benzenesulfonamide

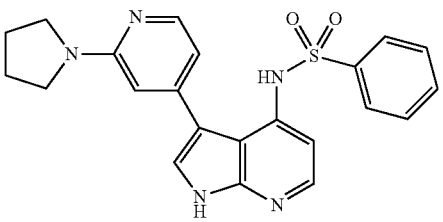 [SMILES: O=S(=O)(Nc1ccnc2[nH]cc(-c3ccnc(N4CCCC4)c3)c12)c1ccccc1]

The title compound was prepared using the procedure as described for Scheme 2. LCMS (A): m/z (M+H)+420, C22H21N5O2S requires 419 (acidic).

Example 127

N-(3-(2-((2-(dimethylamino)ethyl)(methyl)amino)pyridin-4-yl)-1H-pyrrolo[2,3-b]pyridin-4-yl)benzenesulfonamide

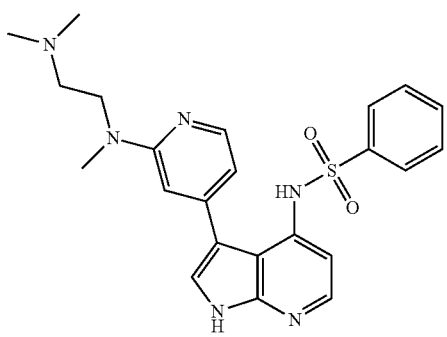 [SMILES: CN(C)CCN(C)c1cc(-c2c[nH]c3nccc(NS(=O)(=O)c4ccccc4)c23)ccn1]

The title compound was prepared using the procedure as described for Scheme 2. LCMS (A): m/z (M+H)+ 451, C23H26N6O2S requires 450 (basic).

Example 128

N-(3-(2-(4-methyl-1,4-diazepan-1-yl)pyridin-4-yl)-1H-pyrrolo[2,3-b]pyridin-4-yl)benzenesulfonamide

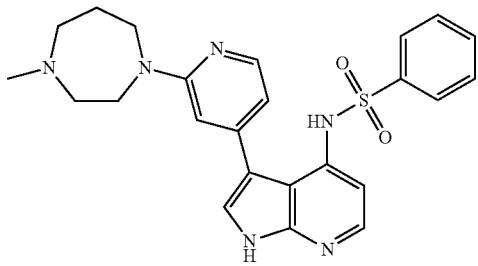 [SMILES: CN1CCCN(c2cc(-c3c[nH]c4nccc(NS(=O)(=O)c5ccccc5)c34)ccn2)CC1]

The title compound was prepared using the procedure as described for Scheme 2. LCMS (A): m/z (M+H)+ 463, C24H26N6O2S requires 462 (basic).

Example 129

N-(3-(2-(methyl(propyl)amino)pyridin-4-yl)-1H-pyrrolo[2,3-b]pyridin-4-yl)benzenesulfonamide

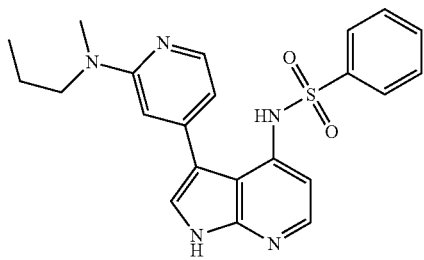 [SMILES: CCCN(C)c1cc(-c2c[nH]c3nccc(NS(=O)(=O)c4ccccc4)c23)ccn1]

The title compound was prepared using the procedure as described for Scheme 2. LCMS (A): m/z (M+H)+ 422, C22H23N5O2S requires 421 (acidic).

Example 130

N-(1-(2-(dimethylamino)ethyl)-3-(3-(pyrrolidin-1-yl)phenyl)-1H-pyrrolo[2,3-b]pyridin-4-yl)benzenesulfonamide

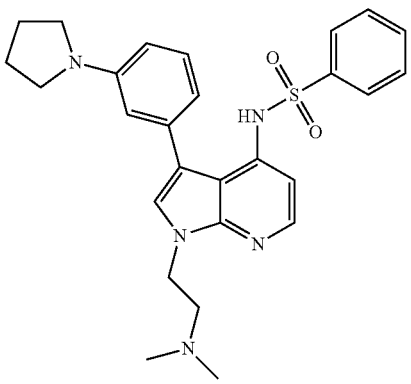 [SMILES: CN(C)CCn1cc(-c2cccc(N3CCCC3)c2)c2c(NS(=O)(=O)c3ccccc3)ccnc21]

The title compound was prepared using the procedure as described for Scheme 1 or 2. LCMS (A): m/z (M+H)+ 490, C27H31N5O2S requires 489 (acidic).

Example 131

N-(1-isopropyl-3-(3-(pyrrolidin-1-yl)phenyl)-1H-pyrrolo[2,3-b]pyridin-4-yl)-1,3-dimethyl-1H-pyrazole-4-sulfonamide

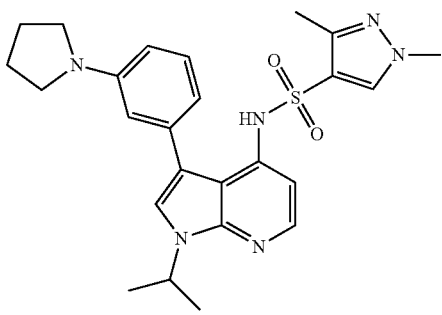 [SMILES: Cc1nn(C)cc1S(=O)(=O)Nc1ccnc2c1c(-c1cccc(N3CCCC3)c1)cn2C(C)C]

The title compound was prepared using the procedure as described for Scheme 2. LCMS (A): m/z (M+H)+ 479, C25H30N6O2S requires 478 (acidic).

Example 132

N-(1-ethyl-3-(1-methylindolin-6-yl)-1H-pyrrolo[2,3-b]pyridin-4-yl)-1-methyl-1H-pyrazole-3-sulfonamide

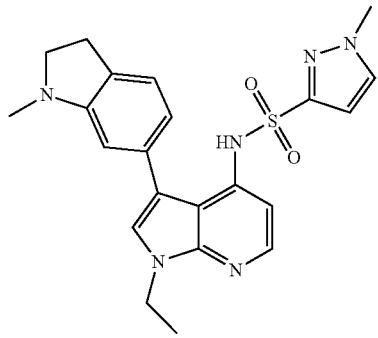 [SMILES: CCn1cc(-c2ccc3c(c2)N(C)CC3)c2c(NS(=O)(=O)c3ccn(C)n3)ccnc21]

The title compound was prepared using the procedure as described for Scheme 2. LCMS (A): m/z (M+H)$^+$ 437, C22H24N6O2S requires 436 (acidic).

Example 133

N-(1-(2-(dimethylamino)ethyl)-3-(4-methyl-3,4-dihydro-2H-benzo[b][1,4]oxazin-6-yl)-1H-pyrrolo[2,3-b]pyridin-4-yl)benzenesulfonamide

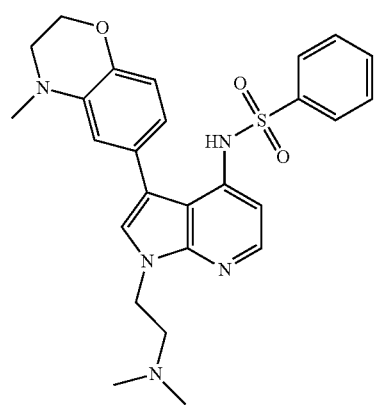 [SMILES: CN(C)CCn1cc(-c2ccc3c(c2)N(C)CCO3)c2c(NS(=O)(=O)c3ccccc3)ccnc21]

The title compound was prepared using the procedure as described for Scheme 2. LCMS (A): m/z (M+H)$^+$ 492, C26H29N5O3S requires 491 (acidic).

Example 134

N-(1-(2-(dimethylamino)ethyl)-3-(5-(pyrrolidin-1-yl)pyridin-3-yl)-1H-pyrrolo[2,3-b]pyridin-4-yl)benzenesulfonamide

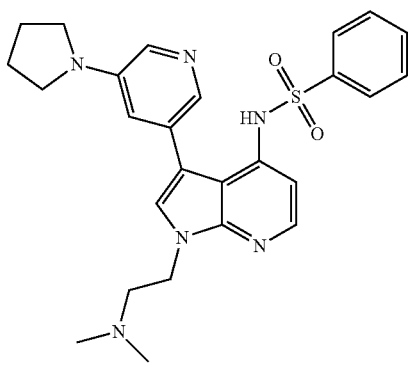 [SMILES: CN(C)CCn1cc(-c2cncc(N3CCCC3)c2)c2c(NS(=O)(=O)c3ccccc3)ccnc21]

The title compound was prepared using the procedure as described for Scheme 2. LCMS (A): m/z (M+H)$^+$ 491, C26H30N6O2S requires 490 (acidic).

Example 135

N-(1-(1-methylpyrrolidin-3-yl)-3-(3-(pyrrolidin-1-yl)phenyl)-1H-pyrrolo[2,3-b]pyridin-4-yl)benzenesulfonamide

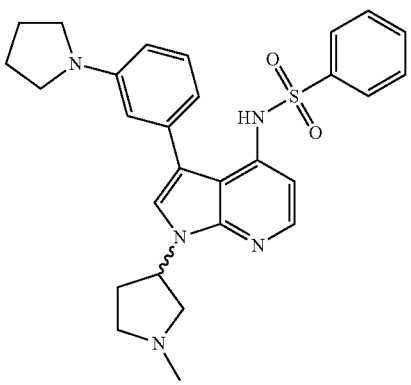 [SMILES: CN1CCC(n2cc(-c3cccc(N4CCCC4)c3)c3c(NS(=O)(=O)c4ccccc4)ccnc32)C1]

The title compound was prepared using the procedure as described for Scheme 2. LCMS (A): m/z (M+H)$^+$ 502, C28H31N5O2S requires 501 (acidic).

Example 136 & Example 137

(R) N-(1-(1-methylpyrrolidin-3-yl)-3-(3-(pyrrolidin-1-yl)phenyl)-1H-pyrrolo[2,3-b]pyridin-4-yl)benzenesulfonamide (S) N-(1-(1-methylpyrrolidin-3-yl)-3-(3-(pyrrolidin-1-yl)phenyl)-1H-pyrrolo[2,3-b]pyridin-4-yl)benzenesulfonamide

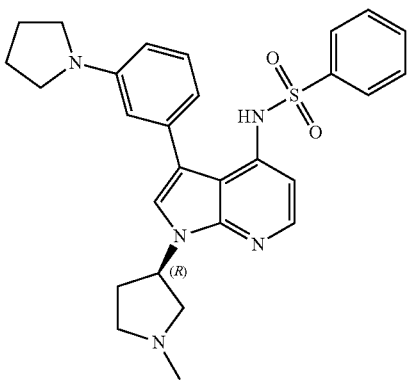

-continued

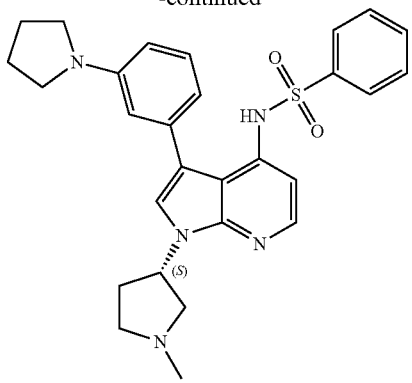

Example 135 was separated by chiral chromatography to give two enantiomers: (R)N-(1-(1-methylpyrrolidin-3-yl)-3-(3-(pyrrolidin-1-yl)phenyl)-1H-pyrrolo[2,3-b]pyridin-4-yl)benzenesulfonamide and (S)N-(1-(1-methylpyrrolidin-3-yl)-3-(3-(pyrrolidin-1-yl)phenyl)-1H-pyrrolo[2,3-b]pyridin-4-yl)benzenesulfonamide. The absolute stereochemistry was not determined LCMS (A): m/z (M+H)+ 502, C28H31N5O2S requires 501 (acidic).

Example 138

N-(1-(4-methoxybenzyl)-3-(3-(pyrrolidin-1-yl)phenyl)-1H-pyrrolo[2,3-b]pyridin-4-yl)benzenesulfonamide

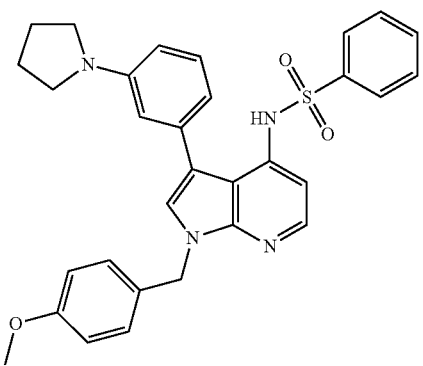 [SMILES: COc1ccc(Cn2cc(-c3cccc(N4CCCC4)c3)c3c(NS(=O)(=O)c4ccccc4)ccnc32)cc1]

The title compound was prepared using the procedure as described for Scheme 2. LCMS (A): m/z (M+H)+ 539, C31H30N4O3S requires 538 (acidic).

Example 139

N-(3-(3-(dimethylamino)phenyl)-1-(2-morpholinoethyl)-1H-pyrrolo[2,3-b]pyridin-4-yl)benzenesulfonamide

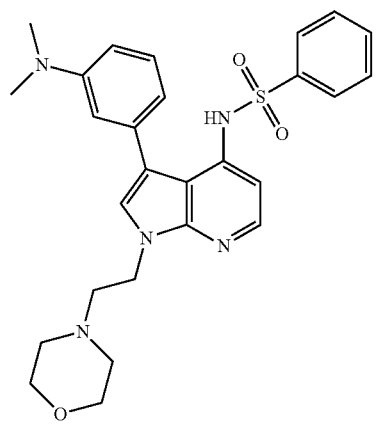 [SMILES: CN(C)c1cccc(-c2cn(CCN3CCOCC3)c3nccc(NS(=O)(=O)c4ccccc4)c23)c1]

The title compound was prepared using the procedure as described for Scheme 2. LCMS (A): m/z (M+H)+ 506, C27H31N5O3S requires 505 (acidic).

Example 140

N-(3-(2-fluoro-5-(pyrrolidin-1-yl)phenyl)-1-isopropyl-1H-pyrrolo[2,3-b]pyridin-4-yl)-1-methyl-1H-pyrazole-3-sulfonamide

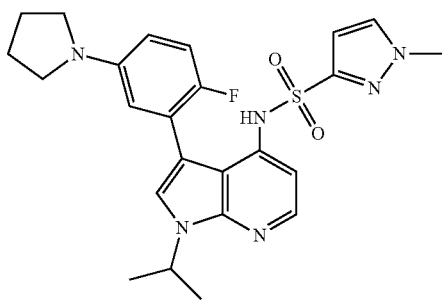 [SMILES: CC(C)n1cc(-c2cc(N3CCCC3)ccc2F)c2c(NS(=O)(=O)c3ccn(C)n3)ccnc21]

The title compound was prepared using the procedure as described for Scheme 2. LCMS (A): m/z (M+H)+ 483, C24H27FN6O2S requires 482 (acidic).

Example 141

N-(3-(3-(dimethylamino)phenyl)-1-isopropyl-1H-pyrrolo[2,3-b]pyridin-4-yl)benzenesulfonamide

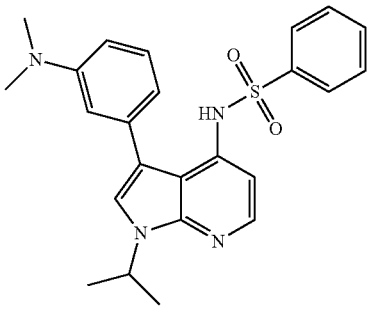 [SMILES: CC(C)n1cc(-c2cccc(N(C)C)c2)c2c(NS(=O)(=O)c3ccccc3)ccnc21]

The title compound was prepared using the procedure as described for Scheme 2. LCMS (B): m/z (M+H)+ 435, C24H26N4O2SS requires 434 (basic).

Example 142

N-(3-(indolin-6-yl)-1-isopropyl-1H-pyrrolo[2,3-b]pyridin-4-yl)-1-methyl-1H-pyrazole-3-sulfonamide

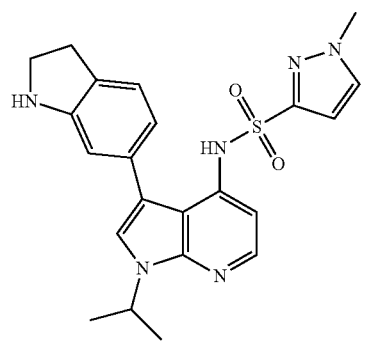 [SMILES: CC(C)n1cc(-c2ccc3c(c2)NCC3)c2c(NS(=O)(=O)c3ccn(C)n3)ccnc21]

Example 143

N-(3-(3-(dimethylamino)phenyl)-1-(piperidin-4-yl)-1H-pyrrolo[2,3-b]pyridin-4-yl)benzenesulfonamide

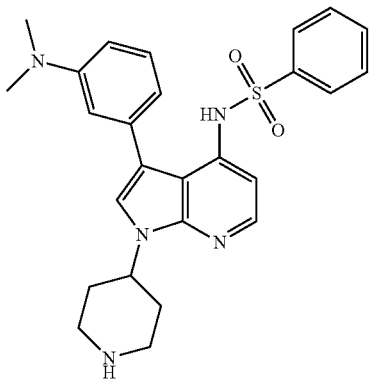 [SMILES: CN(C)c1cccc(-c2cn(C3CCNCC3)c3nccc(NS(=O)(=O)c4ccccc4)c23)c1]

The title compound was prepared using the procedure as described for Scheme 2. LCMS (A): m/z (M+H)+ 476, C26H29N5O2S requires 475 (acidic).

Example 144

N-(1-(azetidin-3-ylmethyl)-3-(3-(dimethylamino)phenyl)-1H-pyrrolo[2,3-b]pyridin-4-yl)benzenesulfonamide

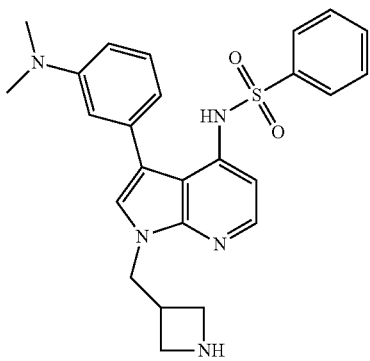 [SMILES: CN(C)c1cccc(-c2cn(CC3CNC3)c3nccc(NS(=O)(=O)c4ccccc4)c23)c1]

The title compound was prepared using the procedure as described for Scheme 2. LCMS (A): m/z (M+H)+ 462, C25H27N5O2S requires 461 (basic).

Example 145 tert-butyl 3-(3-(3-(dimethylamino)phenyl)-4-(phenylsulfonamido)-1H-pyrrolo[2,3-b]pyridin-1-yl)azetidine-1-carboxylate

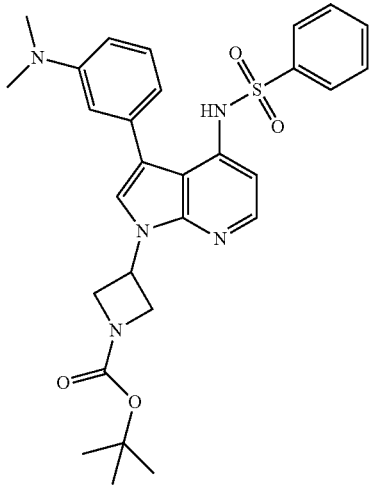 [SMILES: CN(C)c1cccc(-c2cn(C3CN(C(=O)OC(C)(C)C)C3)c3nccc(NS(=O)(=O)c4ccccc4)c23)c1]

The title compound was prepared using the procedure as described for Scheme 2. LCMS (A): m/z (M+H)+ 548, C29H33N5O4S requires 547 (acidic).

Example 146

N-(1-(azetidin-3-yl)-3-(3-(dimethylamino)phenyl)-1H-pyrrolo[2,3-b]pyridin-4-yl)benzenesulfonamide

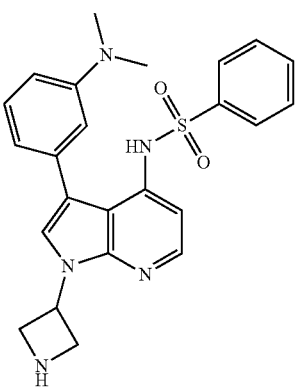 [SMILES: CN(C)c1cccc(-c2cn(C3CNC3)c3nccc(NS(=O)(=O)c4ccccc4)c23)c1]

The title compound was prepared using the procedure as described for Scheme 2. LCMS (A): m/z (M+H)+ 448, C24H25N5O2S requires 447 (acidic).

Example 147

N-(3-(3-(dimethylamino)phenyl)-1-(1-methylazetidin-3-yl)-1H-pyrrolo[2,3-b]pyridin-4-yl)benzenesulfonamide

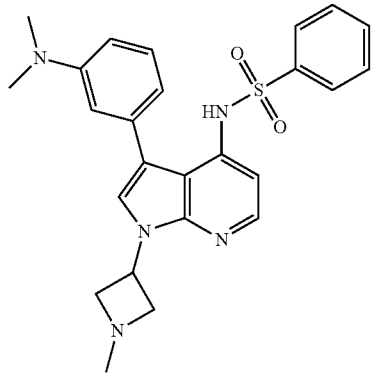 [SMILES: CN1CC(n2cc(-c3cccc(N(C)C)c3)c3c(NS(=O)(=O)c4ccccc4)ccnc32)C1]

The title compound was prepared using the procedure as described for Scheme 2. LCMS (A): m/z (M+H)⁺ 462, C25H27N5O2S requires 461 (acidic).

Example 148

N-(1-isopropyl-3-(1-methyl-1,2,3,4-tetrahydroquinolin-7-yl)-1H-pyrrolo[2,3-b]pyridin-4-yl)-1-methyl-1H-pyrazole-3-sulfonamide

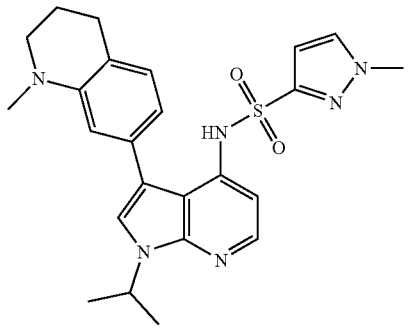

The title compound was prepared using the procedure as described for Scheme 2. LCMS (A): m/z (M+H)⁺ 465, C24H28N6O2S requires 464 (acidic).

Example 149

N-(1-isopropyl-6-methyl-3-(1-methylindolin-6-yl)-1H-pyrrolo[2,3-b]pyridin-4-yl)-1-methyl-1H-pyrazole-3-sulfonamide

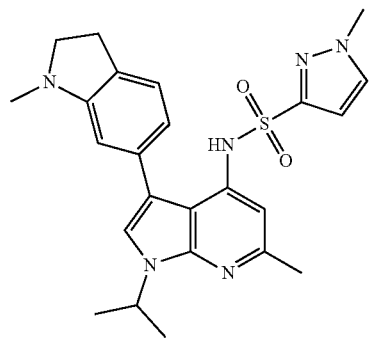 [SMILES: Cc1cc(NS(=O)(=O)c2ccn(C)n2)c2c(-c3ccc4c(c3)N(C)CC4)cn(C(C)C)c2n1]

The title compound was prepared using the procedure as described for Scheme 6. LCMS (A): m/z (M+H)⁺ 465, C24H28N6O2S requires 464 (acidic).

Example 150

N-(1,6-dimethyl-3-(1-methylindolin-6-yl)-1H-pyrrolo[2,3-b]pyridin-4-yl)-1-methyl-1H-pyrazole-3-sulfonamide

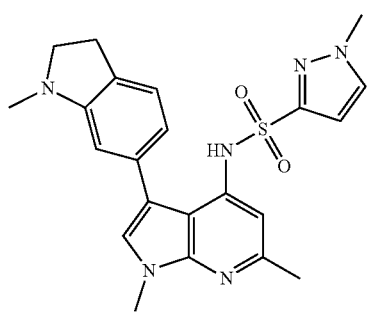 [SMILES: Cc1cc(NS(=O)(=O)c2ccn(C)n2)c2c(-c3ccc4c(c3)N(C)CC4)cn(C)c2n1]

The title compound was prepared using the procedure as described for Scheme 6. LCMS (A): m/z (M+H)⁺ 437, C22H24N6O2S requires 436 (acidic).

Example 151

N-(3-(3-(dimethylamino)phenyl)-6-methyl-1H-pyrrolo[2,3-b]pyridin-4-yl)benzenesulfonamide

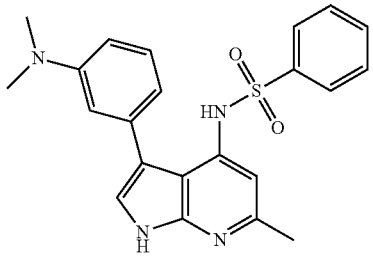 [SMILES: Cc1cc(NS(=O)(=O)c2ccccc2)c2c(-c3cccc(N(C)C)c3)c[nH]c2n1]

The title compound was prepared using the procedure as described for Scheme 6. LCMS (A): m/z (M+H)⁺ 407, C22H22N4O2S requires 406 (acidic).

Example 152

1-methyl-N-(6-methyl-3-(1-methylindolin-6-yl)-1H-pyrrolo[2,3-b]pyridin-4-yl)-1H-pyrazole-3-sulfonamide

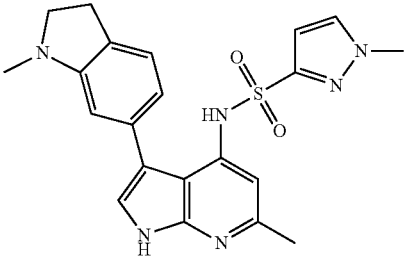

The title compound was prepared using the procedure as described for Scheme 6. LCMS (A): m/z (M+H)+ 423, C21H22N6O2S requires 422 (acidic).

Example 153

3-chloro-N-(6-methyl-3-(3-(pyrrolidin-1-yl)phenyl)-1H-pyrrolo[2,3-b]pyridin-4-yl)benzenesulfonamide

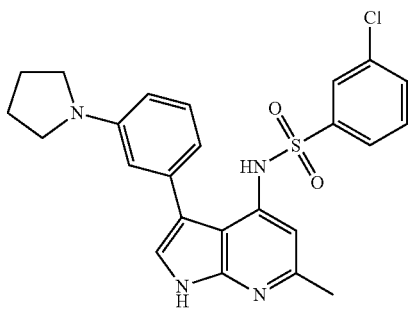 [SMILES: Cc1cc(NS(=O)(=O)c2cccc(Cl)c2)c2c(-c3cccc(N4CCCC4)c3)c[nH]c2n1]

The title compound was prepared using the procedure as described for Scheme 6. LCMS (A): m/z (M+H)+ 467, C24H23ClN4O2S requires 466 (acidic).

Example 154

1-methyl-N-(1-methyl-2-(1-methylindolin-6-yl)-1H-pyrrolo[2,3-b]pyridin-4-yl)-1H-pyrazole-3-sulfonamide

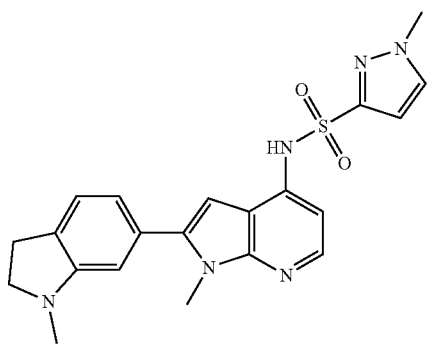 [SMILES: CN1CCc2ccc(-c3cc4c(NS(=O)(=O)c5ccn(C)n5)ccnc4n3C)cc21]

The title compound was prepared using the procedure as described for Scheme 2 (R2 substituted product isolated). LCMS (A): m/z (M+H)+ 423, C21H22N6O2S requires 422 (acidic).

Example 155

N-(1,6-dimethyl-2-(1-methylindolin-6-yl)-1H-pyrrolo[2,3-b]pyridin-4-yl)-1-methyl-1H-pyrazole-3-sulfonamide

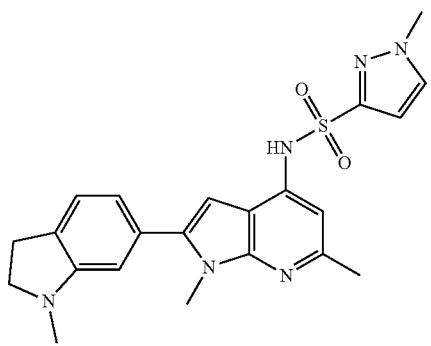 [SMILES: Cc1cc(NS(=O)(=O)c2ccn(C)n2)c2cc(-c3ccc4c(c3)N(C)CC4)n(C)c2n1]

The title compound was prepared using the procedure as described for Scheme 6 (R2 substituted product isolated). LCMS (A): m/z (M+H)+ 437, C22H24N6O2S requires 436 (acidic).

Example 156

N-(1,6-dimethyl-2-(1-methylindolin-6-yl)-1H-pyrrolo[2,3-b]pyridin-4-yl)benzenesulfonamide

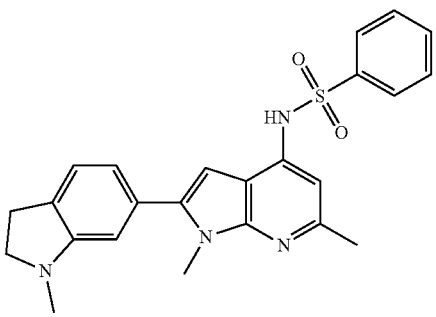 [SMILES: Cc1cc(NS(=O)(=O)c2ccccc2)c2cc(-c3ccc4c(c3)N(C)CC4)n(C)c2n1]

The title compound was prepared using the procedure as described for Scheme 6 (R2 substituted product isolated). LCMS (A): m/z (M+H)+ 433, C24H24N4O2S requires 432 (acidic).

Example 157

N-(6-chloro-3-(3-(dimethylamino)phenyl)-1H-pyrrolo[2,3-b]pyridin-4-yl)benzenesulfonamide

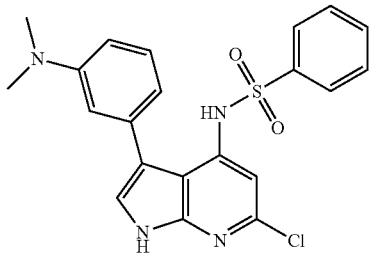

The title compound was prepared using the procedure as described for Scheme 2. LCMS (A): m/z (M+H)+ 427, C21H19ClN4O2S requires 426 (acidic).

Example 158

N-(1-methyl-3-(1-methylindolin-6-yl)-1H-pyrrolo[2,3-b]pyridin-4-yl)cyclopentanesulfonamide

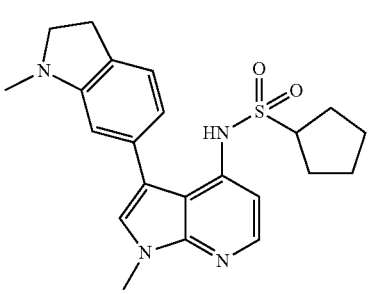 [SMILES: CN1CCc2ccc(-c3cn(C)c4nccc(NS(=O)(=O)C5CCCC5)c34)cc21]

The title compound was prepared using the procedure as described for Scheme 3. LCMS (A): m/z (M+H)⁺411, C22H26N4O2S requires 410 (acidic).

Example 159

1-methyl-N-(1-methyl-3-(1-methylindolin-6-yl)-1H-pyrrolo[2,3-b]pyridin-4-yl)-1H-imidazole-2-sulfonamide

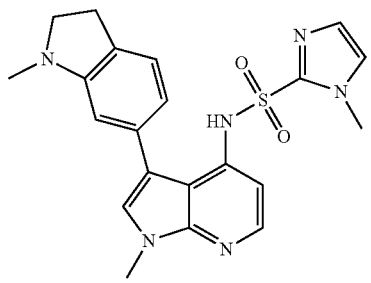 [SMILES: CN1CCc2ccc(-c3cn(C)c4nccc(NS(=O)(=O)c5nccn5C)c34)cc21]

The title compound was prepared using the procedure as described for Scheme 3. LCMS (A): m/z (M+H)⁺423, C21H22N6O2S requires 422 (acidic).

Example 160

N-(1-methyl-3-(1-methylindolin-6-yl)-1H-pyrrolo[2,3-b]pyridin-4-yl)-6-(trifluoromethyl)pyridine-3-sulfonamide

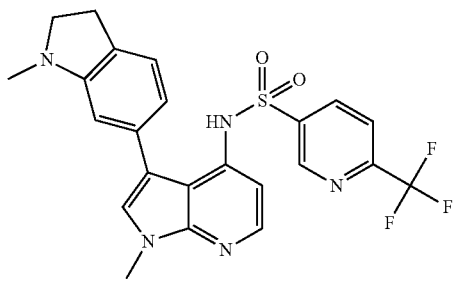 [SMILES: CN1CCc2ccc(-c3cn(C)c4nccc(NS(=O)(=O)c5ccc(C(F)(F)F)nc5)c34)cc21]

The title compound was prepared using the procedure as described for Scheme 3. LCMS (A): m/z (M+H)⁺ 488, C23H20F3N5O2S requires 487 (acidic).

Example 161

N-(1-methyl-3-(1-methylindolin-6-yl)-1H-pyrrolo[2,3-b]pyridin-4-yl)pyridine-3-sulfonamide

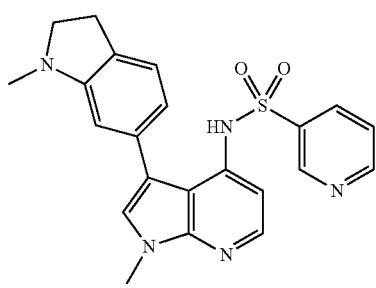 [SMILES: CN1CCc2ccc(-c3cn(C)c4nccc(NS(=O)(=O)c5cccnc5)c34)cc21]

The title compound was prepared using the procedure as described for Scheme 3. LCMS (A): m/z (M+H)⁺ 420, C22H21N5O2S requires 419 (acidic).

Example 162

N-(1,2-dimethyl-3-(1-methylindolin-6-yl)-1H-pyrrolo[2,3-b]pyridin-4-yl)-1-methyl-1H-pyrazole-3-sulfonamide

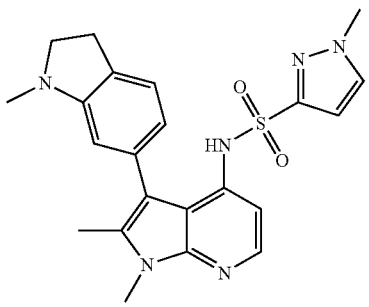 [SMILES: Cc1c(-c2ccc3c(c2)N(C)CC3)c2c(NS(=O)(=O)c3ccn(C)n3)ccnc2n1C]

To a solution of 4-bromo-1,2-dimethyl-3-(1-methylindolin-6-yl)-1H-pyrrolo[2,3-b]pyridine (D28) (85 mg, 0.239 mmol) in 1,4-dioxane (2 mL) was added 1-methyl-1H-pyrazole-3-sulfonamide (D94) (65.4 mg, 0.406 mmol), cesium carbonate (155 mg, 0.477 mmol), Pd₂(dba)₃ (16.39 mg, 0.018 mmol) and 2-(dimethylamino)-2'-(dicyclohexylphosphino)biphenyl (14.08 mg, 0.036 mmol). The reaction mixture was heated in the microwave at 150° C. for 30 mins. The reaction mixture was filtered through celite washing with ethyl acetate and the resulting solution evaporated to dryness. The residue was purified by column chromatography on silica gel, eluting with a gradient of 0-100% ethyl acetate in cyclohexane to afford a material which was further purified by MDAP (basic condition) to afford the title compound (25 mg). LCMS (A): m/z (M+H)⁺ 437, C22H24N6O2S requires 436 (acidic).

or

A mixture of 4-bromo-1,2-dimethyl-3-(1-methylindolin-6-yl)-1H-pyrrolo[2,3-b]pyridine (D28) (390 mg, 1.095 mmol), 1-methyl-1H-pyrazole-3-sulfonamide (D94) (265 mg, 1.642 mmol), (9,9-dimethyl-9H-xanthene-4,5-diyl)bis(diphenylphosphine) (95 mg, 0.164 mmol), cesium carbonate (1070 mg, 3.28 mmol) and Pd₂(dba)₃ (75 mg, 0.082 mmol) in 1,4-dioxane (10 mL) was refluxed for 7 hours. After cooled to RT, the reaction mixture was filtered through celite, washing with DCM and the resulting solution was evaporated to dryness. DCM was added to the residue and the resulting solid was filtered and then taken up in formic acid/DMSO (1:1), purified by MDAP (acidic condition) to give the title compound (155 mg). LCMS (A): m/z (M+H)⁺ 437, C22H24N6O2S requires 436 (acidic).

Example 163

1-methyl-N-(2-methyl-3-(1-methylindolin-6-yl)-1H-pyrrolo[2,3-b]pyridin-4-yl)-1H-pyrazole-3-sulfonamide

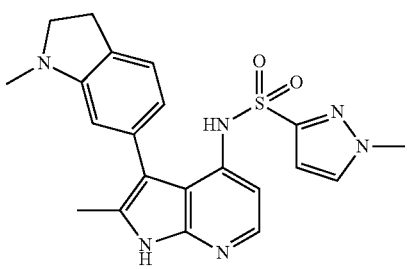

The title compound was prepared using the procedure as described for Scheme 4. LCMS (A): m/z (M+H)+ 423, C21H22N6O2S requires 422 (acidic).

Example 164

N-(3-(5-(dimethylamino)pyridin-3-yl)-2-methyl-1H-pyrrolo[2,3-b]pyridin-4-yl)benzenesulfonamide

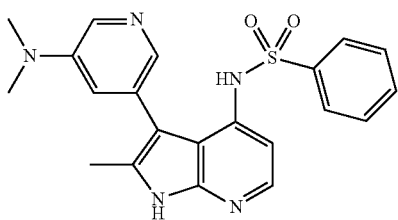 [SMILES: Cc1[nH]c2nccc(NS(=O)(=O)c3ccccc3)c2c1-c1cncc(N(C)C)c1]

The title compound was prepared using the procedure as described for Scheme 4. LCMS (A): m/z (M+H)+ 408, C21H21N5O2S requires 407 (acidic).

Example 165

1-methyl-N-(2-methyl-3-(3-(pyrrolidin-1-yl)phenyl)-1H-pyrrolo[2,3-b]pyridin-4-yl)-1H-pyrazole-3-sulfonamide

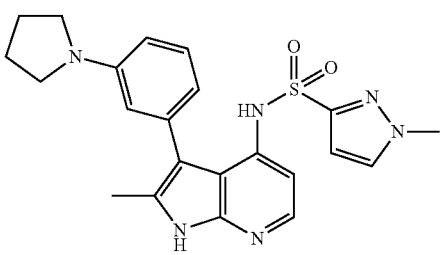 [SMILES: Cc1[nH]c2nccc(NS(=O)(=O)c3ccn(C)n3)c2c1-c1cccc(N2CCCC2)c1]

The title compound was prepared using the procedure as described for Scheme 4. LCMS (A): m/z (M+H)+ 437, C22H24N6O2S requires 436 (acidic).

Example 166

N-(3-(3-(dimethylamino)phenyl)-2-methyl-1H-pyrrolo[2,3-b]pyridin-4-yl)benzenesulfonamide

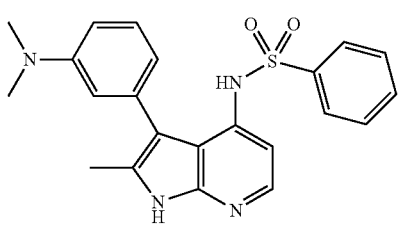 [SMILES: Cc1[nH]c2nccc(NS(=O)(=O)c3ccccc3)c2c1-c1cccc(N(C)C)c1]

The title compound was prepared using the procedure as described for Scheme 4. LCMS (A): m/z (M+H)+ 407, C22H22N4O2S requires 406 (acidic).

Example 167

N-(2-fluoro-3-(3-(pyrrolidin-1-yl)phenyl)-1H-pyrrolo[2,3-b]pyridin-4-yl)benzenesulfonamide

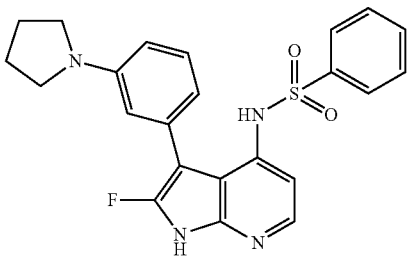 [SMILES: O=S(=O)(Nc1ccnc2[nH]c(F)c(-c3cccc(N4CCCC4)c3)c12)c1ccccc1]

The title compound was prepared using the procedure as described for Scheme 4. LCMS (A): m/z (M+H)+ 437, C23H21FN4O2S requires 436 (acidic).

Example 168

N-(2-(1H-pyrazol-4-yl)-3-(3-(pyrrolidin-1-yl)phenyl)-1H-pyrrolo[2,3-b]pyridin-4-yl)benzenesulfonamide

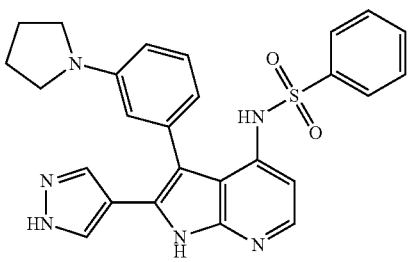 [SMILES: O=S(=O)(Nc1ccnc2[nH]c(-c3cn[nH]c3)c(-c3cccc(N4CCCC4)c3)c12)c1ccccc1]

The title compound was prepared using the procedure as described for Scheme 4. LCMS (A): m/z (M+H)+ 485, C26H24N6O2S requires 484 (acidic).

Example 169

N-(3-(3-(dimethylamino)phenyl)-2-(1-methyl-1H-pyrazol-4-yl)-1H-pyrrolo[2,3-b]pyridin-4-yl)benzenesulfonamide

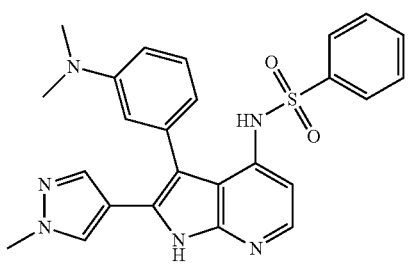 [SMILES: CN(C)c1cccc(-c2c(-c3cnn(C)c3)[nH]c3nccc(NS(=O)(=O)c4ccccc4)c23)c1]

The title compound was prepared using the procedure as described for Scheme 4. LCMS (A): m/z (M+H)+ 473, C25H24N6O2S requires 472 (acidic).

Example 170

Methyl 4-(phenylsulfonamido)-3-(3-(pyrrolidin-1-yl)phenyl)-1H-pyrrolo[2,3-b]pyridine-2-carboxylate

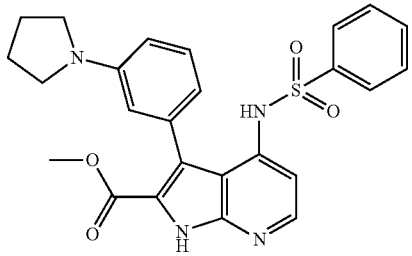 [SMILES: COC(=O)c1[nH]c2nccc(NS(=O)(=O)c3ccccc3)c2c1-c1cccc(N2CCCC2)c1]

The title compound was prepared using the procedure as described for Scheme 4. LCMS (A): m/z (M+H)+ 477, C25H24N4O4S requires 476 (acidic).

Example 171

N-(2-(4-methylpiperazine-1-carbonyl)-3-(3-(pyrrolidin-1-yl)phenyl)-1H-pyrrolo[2,3-b]pyridin-4-yl)benzenesulfonamide

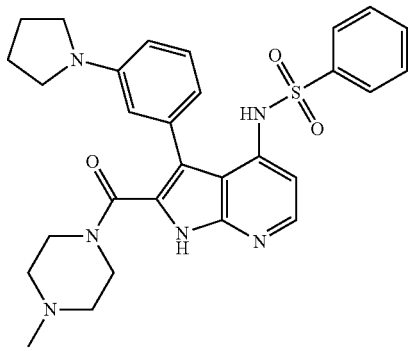 [SMILES: CN1CCN(C(=O)c2[nH]c3nccc(NS(=O)(=O)c4ccccc4)c3c2-c2cccc(N3CCCC3)c2)CC1]

The title compound was prepared using the procedure as described for Scheme 4. LCMS (A): m/z (M+H)+ 545, C29H32N6O3S requires 544 (acidic).

Example 172

N-(1-methyl-2-(pyridin-3-yl)-3-(3-(pyrrolidin-1-yl)phenyl)-1H-pyrrolo[2,3-b]pyridin-4-yl)benzenesulfonamide

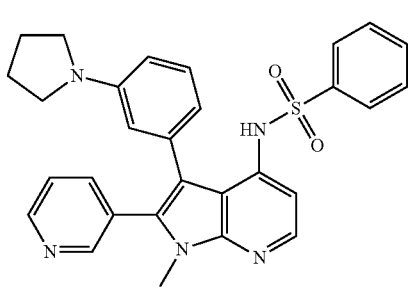 [SMILES: Cn1c(-c2cccnc2)c(-c2cccc(N3CCCC3)c2)c2c(NS(=O)(=O)c3ccccc3)ccnc21]

The title compound was prepared using the procedure as described for Scheme 5. LCMS (A): m/z (M+H)+ 510, C29H27N5O2S requires 509 (acidic).

Example 173

N-(1-methyl-2-(1H-pyrazol-3-yl)-3-(3-(pyrrolidin-1-yl)phenyl)-1H-pyrrolo[2,3-b]pyridin-4-yl)benzenesulfonamide

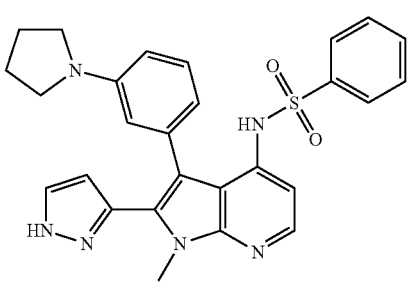 [SMILES: Cn1c(-c2cc[nH]n2)c(-c2cccc(N3CCCC3)c2)c2c(NS(=O)(=O)c3ccccc3)ccnc21]

The title compound was prepared using the procedure as described for Scheme 5. LCMS (A): m/z (M+H)+ 499, C27H26N6O2S requires 498 (acidic).

Example 174

N-(1-isopropyl-2-methyl-3-(1-methylindolin-6-yl)-1H-pyrrolo[2,3-b]pyridin-4-yl)-1-methyl-1H-pyrazole-3-sulfonamide

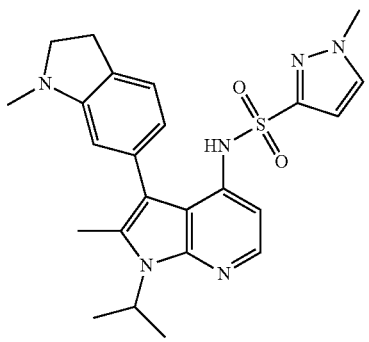 [SMILES: Cc1c(-c2ccc3c(c2)N(C)CC3)c2c(NS(=O)(=O)c3ccn(C)n3)ccnc2n1C(C)C]

The title compound was prepared using the procedure as described for Scheme 4. LCMS (A): m/z (M+H)+ 465, C24H28N6O2S requires 464 (acidic).

Example 175

N-(1,2-dimethyl-3-(3-(pyrrolidin-1-yl)phenyl)-1H-pyrrolo[2,3-b]pyridin-4-yl)-1-methyl-1H-pyrazole-3-sulfonamide

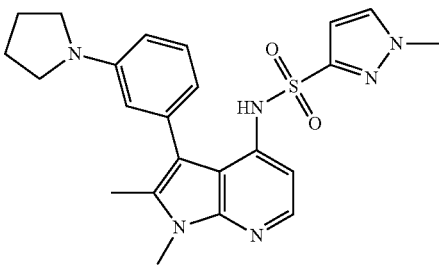 [SMILES: Cc1c(-c2cccc(N3CCCC3)c2)c2c(NS(=O)(=O)c3ccn(C)n3)ccnc2n1C]

The title compound was prepared using the procedure as described for Scheme 4. LCMS (A): m/z (M+H)+ 451, C23H26N6O2S requires 450 (acidic).

Example 176

3-chloro-N-(3-(3-(dimethylamino)phenyl)-1-methyl-2-(morpholinomethyl)-1H-pyrrolo[2,3-b]pyridin-4-yl)benzenesulfonamide

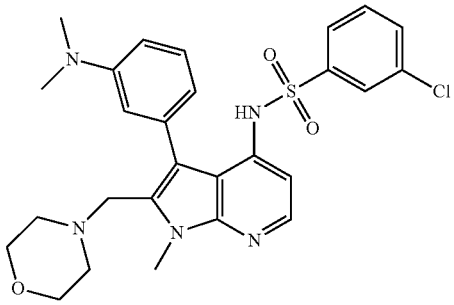 [SMILES: CN(C)c1cccc(-c2c(CN3CCOCC3)n(C)c3nccc(NS(=O)(=O)c4cccc(Cl)c4)c23)c1]

The title compound was prepared using the procedure as described for Scheme 4, starting from 4-chloro-1H-pyrrolo[2,3-b]pyridine rather than 4-bromo-1H-pyrrolo[2,3-b]pyridine. LCMS (A): m/z (M+H)⁺ 540, C27H30ClN5O3S requires 539 (acidic).

Example 177

1-methyl-N-(1-methyl-3-(1,3,3-trimethylindolin-6-yl)-1H-pyrrolo[2,3-b]pyridin-4-yl)-1H-pyrazole-3-sulfonamide

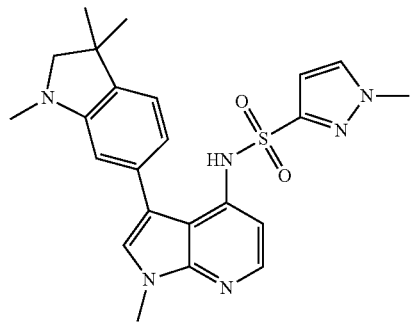

The title compound was prepared using the procedure as described for Scheme 2. LCMS (A): m/z (M+H)⁺ 451, C23H26N6O2S requires 450 (basic).

Example 178

N-(1-isopropyl-3-(1-methylindolin-6-yl)-1H-pyrrolo[2,3-b]pyridin-4-yl)morpholine-4-sulfonamide

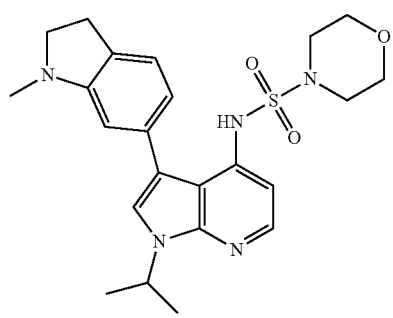 [SMILES: CC(C)n1cc(-c2ccc3c(c2)N(C)CC3)c2c(NS(=O)(=O)N3CCOCC3)ccnc21]

The title compound was prepared using the procedure as described in either Scheme 2 (Method A) or Scheme 3 (Method B). LCMS (A): m/z (M+H)⁺ 456, C23H29N5O3S requires 455 (acidic).

Example 179

5-chloro-N-(1-methyl-3-(1-methylindolin-6-yl)-1H-pyrrolo[2,3-b]pyridin-4-yl)pyridine-2-sulfonamide

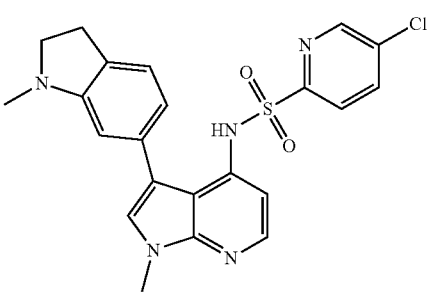 [SMILES: CN1CCc2ccc(-c3cn(C)c4nccc(NS(=O)(=O)c5ccc(Cl)cn5)c34)cc21]

The title compound was prepared using the procedure as described for Scheme 2. LCMS (A): m/z (M+H)⁺ 454, C22H20ClN5O2S requires 453 (acidic).

Example 180

N-(1-methyl-3-(1-methylindolin-6-yl)-1H-pyrrolo[2,3-b]pyridin-4-yl)-5-(4-methylpiperazin-1-yl)pyridine-2-sulfonamide

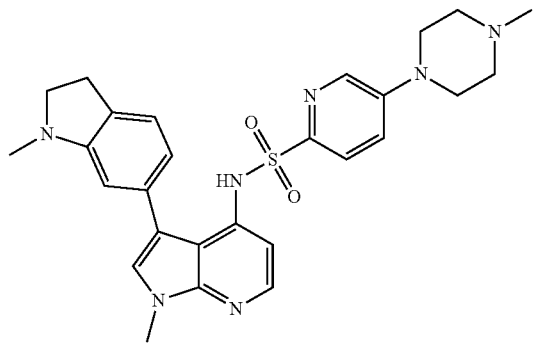

The title compound was prepared using the procedure as described for Scheme 2. LCMS (A): m/z (M−H)⁺ 516, C27H31N7O2S requires 517 (acidic).

Example 181

N-(1-methyl-3-(1-methylindolin-6-yl)-1H-pyrrolo[2,3-b]pyridin-4-yl)methanesulfonamide

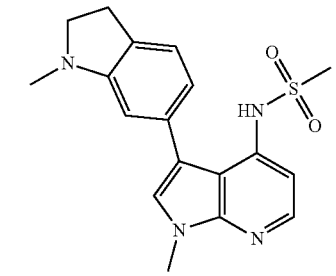

The title compound was prepared using the procedure as described for Scheme 2. LCMS (A): m/z (M+H)+ 357, C18H20N4O2S requires 356 (acidic).

Example 182

N-(3-(4-fluoro-1-methylindolin-6-yl)-1-methyl-1H-pyrrolo[2,3-b]pyridin-4-yl)-5-methylpyridine-2-sulfonamide

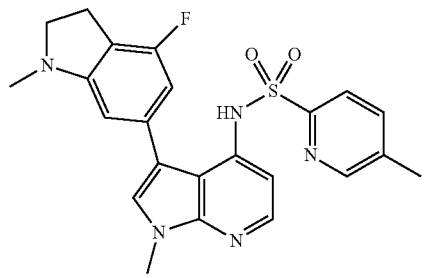

The title compound was prepared using the procedure as described for Scheme 2. LCMS (A): m/z (M+H)+ 452, C18H20N4O2S requires 451 (acidic).

Example 183

N-(3-(5-fluoro-1-methylindolin-6-yl)-1-methyl-1H-pyrrolo[2,3-b]pyridin-4-yl)-5-methylpyridine-2-sulfonamide

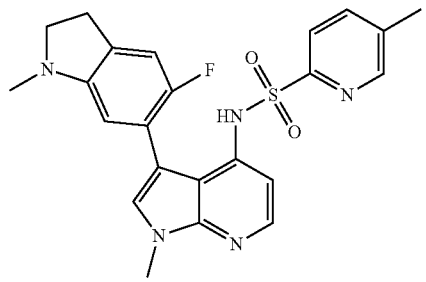

The title compound was prepared using the procedure as described for Scheme 2. LCMS (A): m/z (M+H)+ 452, C18H20N4O2S requires 451 (acidic).

Example 184

4-Isopropyl-N-(1-methyl-3-(1-methylindolin-6-yl)-1H-pyrrolo[2,3-b]pyridin-4-yl)piperazine-1-sulfonamide

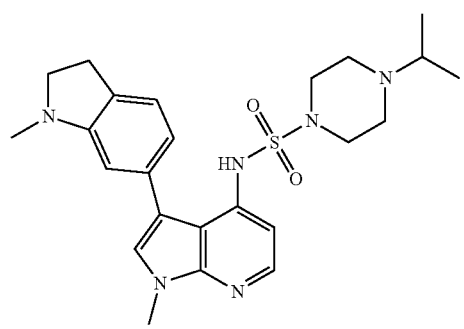 [SMILES: CC(C)N1CCN(S(=O)(=O)Nc2ccnc3c2c(-c2ccc4c(c2)N(C)CC4)cn3C)CC1]

The title compound was prepared using the procedure as described for Scheme 2. LCMS (A): m/z (M+H)+ 469, C24H32N6O2S requires 468 (acidic).

Example 185

N-(3-(3-methoxyphenyl)-1-methyl-1H-pyrrolo[2,3-b]pyridin-4-yl)-1-methyl-1H-pyrazole-3-sulfonamide

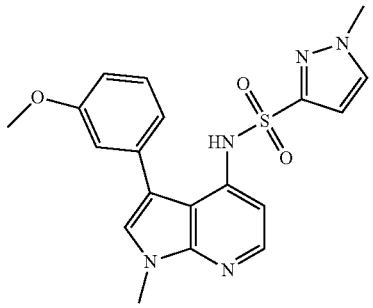 [SMILES: COc1cccc(-c2cn(C)c3nccc(NS(=O)(=O)c4ccn(C)n4)c23)c1]

The title compound was prepared using the procedure as described for Scheme 2. LCMS (A): m/z (M+H)+ 398, C19H19N5O3S requires 397 (acidic).

Example 186

1-methyl-N-(1-methyl-3-(3-(4-methylpiperazin-1-yl)phenyl)-1H-pyrrolo[2,3-b]pyridin-4-yl)-1H-pyrazole-3-sulfonamide

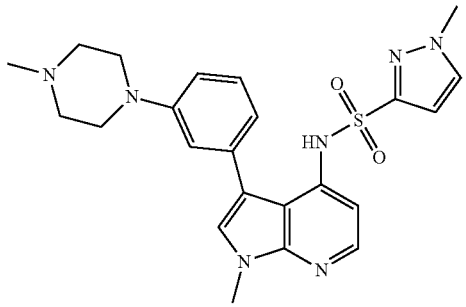 [SMILES: CN1CCN(c2cccc(-c3cn(C)c4nccc(NS(=O)(=O)c5ccn(C)n5)c34)c2)CC1]

The title compound was prepared using the procedure as described for Scheme 2. LCMS (A): m/z (M−H)+ 464, C23H27N7O2S requires 465 (acidic).

Example 187

N-(1-isopropyl-3-(1-methylindolin-6-yl)-1H-pyrrolo[2,3-b]pyridin-4-yl)tetrahydro-2H-pyran-4-sulfonamide

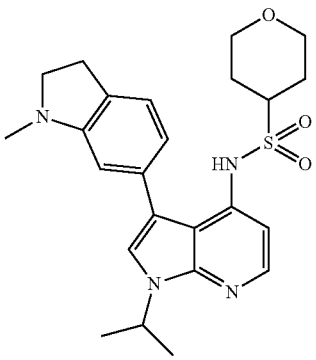 [SMILES: CC(C)n1cc(-c2ccc3c(c2)N(C)CC3)c2c(NS(=O)(=O)C3CCOCC3)ccnc21]

The title compound was prepared using the procedure as described for Scheme 2. LCMS (A): m/z (M+H)+ 455, C24H30N4O3S requires 454 (acidic).

Example 188

6-methyl-N-(1-methyl-3-(1-methylindolin-6-yl)-1H-pyrrolo[2,3-b]pyridin-4-yl)pyridine-2-sulfonamide

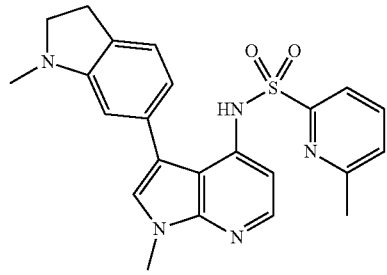 [SMILES: Cc1cccc(S(=O)(=O)Nc2ccnc3c2c(-c2ccc4c(c2)N(C)CC4)cn3C)n1]

The title compound was prepared using the procedure as described for Scheme 2. LCMS (A): m/z (M+H)+ 434, C23H23N5O2S requires 433 (acidic).

Example 189

1-methyl-N-(1-methyl-3-(m-tolyl)-1H-pyrrolo[2,3-b]pyridin-4-yl)-1H-pyrazole-3-sulfonamide

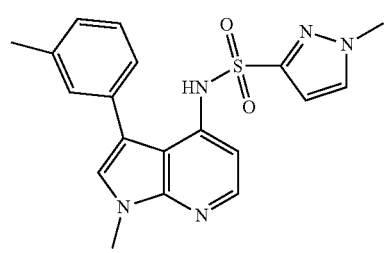

The title compound was prepared using the procedure as described for Scheme 2. LCMS (A): m/z (M+H)+ 382, C19H19N5O2S requires 381 (acidic).

Example 190

N-(1-methyl-3-(1-methylindolin-6-yl)-1H-pyrrolo[2,3-b]pyridin-4-yl)-3-(4-methylpiperazin-1-yl)benzenesulfonamide

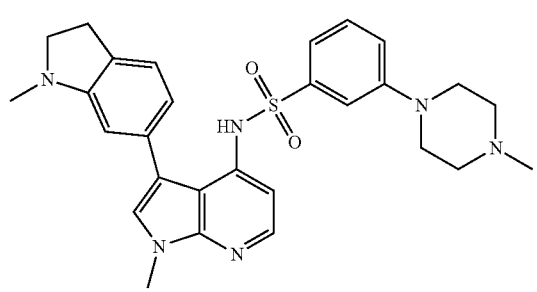

The title compound was prepared using the procedure as described for Scheme 2. LCMS (A): m/z (M+H)+ 517, C28H32N6O2S requires 516 (acidic).

Example 191

N-(1-methyl-3-(1-methylindolin-6-yl)-1H-pyrrolo[2,3-b]pyridin-4-yl)piperidine-4-sulfonamide, hydrochloride

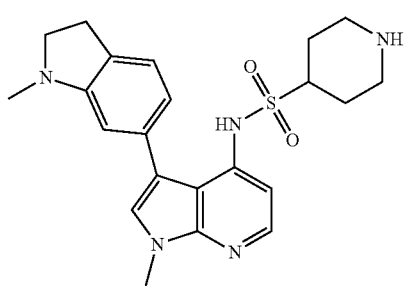 [SMILES: CN1CCc2ccc(-c3cn(C)c4nccc(NS(=O)(=O)C5CCNCC5)c34)cc21]

The title compound was prepared using the procedure as described for Scheme 2. LCMS (A): m/z [(M−HCl)+H]+ 426, C22H27N5O2S.HCl requires 462 (acidic).

Example 192

N-(3-(2-fluoro-5-(pyrrolidin-1-yl)phenyl)-1-methyl-1H-pyrrolo[2,3-b]pyridin-4-yl)-5-methylpyridine-2-sulfonamide

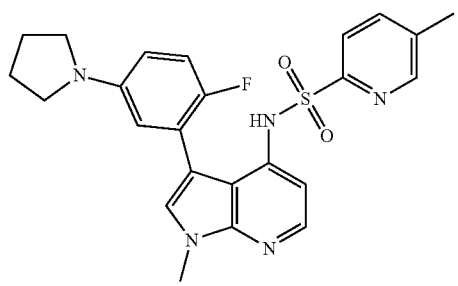 [SMILES: Cc1ccc(S(=O)(=O)Nc2ccnc3c2c(-c2cc(N4CCCC4)ccc2F)cn3C)nc1]

The title compound was prepared using the procedure as described for Scheme 2. LCMS (A): m/z (M+H)+ 466, C24H24FN5O2S requires 465 (acidic).

Example 193

N-(3-(4-fluoro-1-methylindolin-6-yl)-1-isopropyl-1H-pyrrolo[2,3-b]pyridin-4-yl)-5-methylpyridine-2-sulfonamide

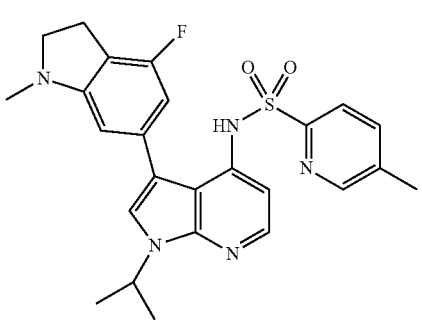

The title compound was prepared using the procedure as described for Scheme 2. LCMS (A): m/z (M+H)+ 480, C25H26FN5O2S requires 479 (acidic).

Example 194

N-(3-(4-fluoro-1-methylindolin-6-yl)-1-isopropyl-1H-pyrrolo[2,3-b]pyridin-4-yl)-1-methyl-1H-pyrazole-3-sulfonamide

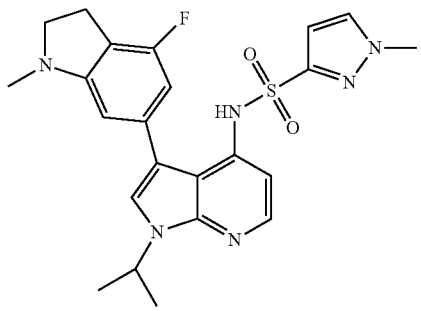

The title compound was prepared using the procedure as described for Scheme 2. LCMS (A): m/z (M+H)+ 469, C23H25FN6O2S requires 468 (acidic).

Example 195

N-(3-(5-fluoro-1-methylindolin-6-yl)-1,2-dimethyl-1H-pyrrolo[2,3-b]pyridin-4-yl)-1-methyl-1H-pyrazole-3-sulfonamide

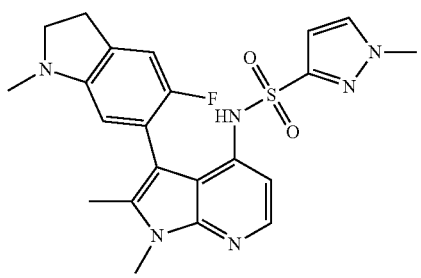

The title compound was prepared using the procedure as described for Scheme 4. LCMS (A): m/z (M+H)+ 455, C22H23FN6O2S requires 454 (acidic).

Example 196

N-(1-ethyl-3-(5-fluoro-1-methylindolin-6-yl)-1H-pyrrolo[2,3-b]pyridin-4-yl)-1-methyl-1H-pyrazole-3-sulfonamide

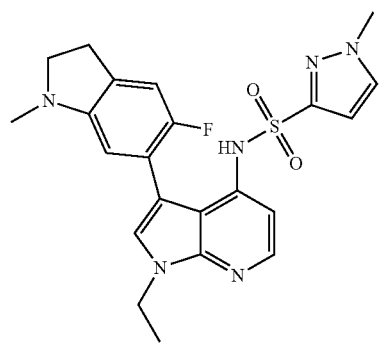 [SMILES: CCn1cc(-c2cc3c(cc2F)CCN3C)c2c(NS(=O)(=O)c3ccn(C)n3)ccnc21]

The title compound was prepared using the procedure as described for Scheme 2. LCMS (A): m/z (M+H)+ 455, C22H23FN6O2S requires 454 (acidic).

Example 197

N-(1,2-dimethyl-3-(1-methylindolin-6-yl)-1H-pyrrolo[2,3-b]pyridin-4-yl)-5-methylpyridine-2-sulfonamide

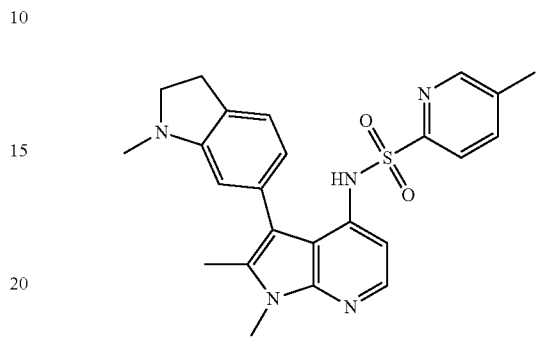

The title compound was prepared using the procedure as described for Scheme 4. LCMS (A): m/z (M+H)+ 448, C24H25N5O2S requires 447 (acidic).

Example 198

N-(1,6-dimethyl-3-(1-methylindolin-6-yl)-1H-pyrrolo[2,3-b]pyridin-4-yl)-5-methylpyridine-2-sulfonamide

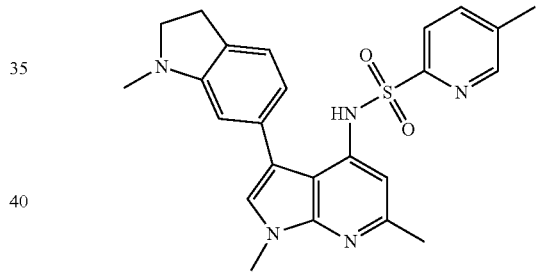

The title compound was prepared using the procedure as described for Scheme 6. LCMS (A): m/z (M+H)+ 448, C24H25N5O2S requires 447 (acidic).

Example 199

N-(1-ethyl-3-(1-methylindolin-6-yl)-1H-pyrrolo[2,3-b]pyridin-4-yl)-5-methylpyridine-2-sulfonamide

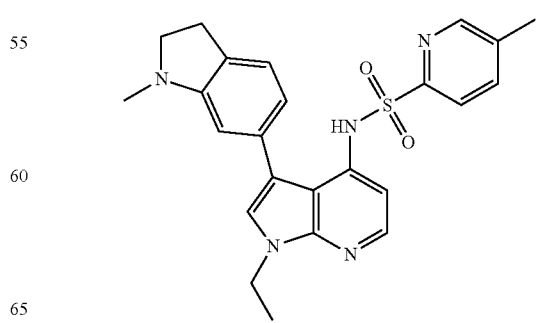

The title compound was prepared using the procedure as described for Scheme 2. LCMS (A): m/z (M+H)+ 448, C24H25N5O2S requires 447 (acidic).

Example 200

2-methyl-N-(1-methyl-3-(1-methylindolin-6-yl)-1H-pyrrolo[2,3-b]pyridin-4-yl)isoindoline-5-sulfonamide

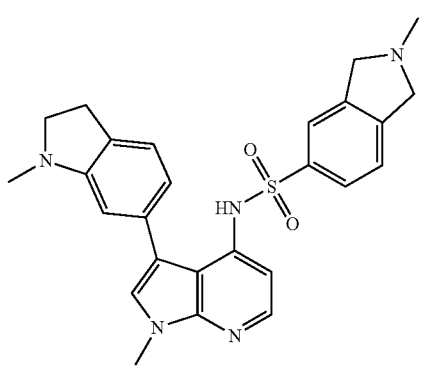

The title compound was prepared using the procedure as described for Scheme 2. LCMS (A): m/z (M+H)+ 474, C26H27N5O2S requires 473 (acidic).

Example 201

N-(3-(5-fluoro-1-methylindolin-6-yl)-1,6-dimethyl-1H-pyrrolo[2,3-b]pyridin-4-yl)-1-methyl-1H-pyrazole-3-sulfonamide

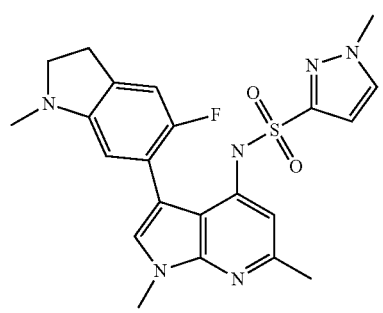 [SMILES: Cc1cc(NS(=O)(=O)c2ccn(C)n2)c2c(-c3cc4c(cc3F)CCN4C)cn(C)c2n1]

The title compound was prepared using the procedure as described for Scheme 6. LCMS (A): m/z (M+H)+ 455, C22H23FN6O2S requires 454 (acidic).

Example 202

N-(3-(1,2-dimethylindolin-6-yl)-1-methyl-1H-pyrrolo[2,3-b]pyridin-4-yl)-1-methyl-1H-pyrazole-3-sulfonamide

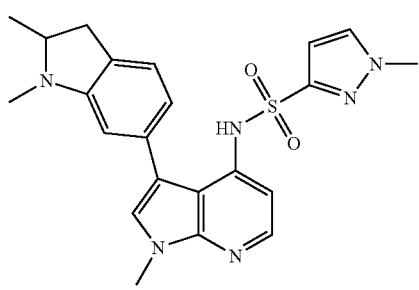

4-Bromo-3-(1,2-dimethylindolin-6-yl)-1-methyl-1H-pyrrolo[2,3-b]pyridine (541 mg, 1.519 mmol), 1-methyl-1H-pyrazole-3-sulfonamide (D94) (367 mg, 2.278 mmol), Pd2(dba)3 (139 mg, 0.152 mmol), xantphos (176 mg, 0.304 mmol) and cesium carbonate (1484 mg, 4.56 mmol) charged into a microwave vial and suspended in 1,4-dioxane (8.0 mL). The reaction mixture was degassed under nitrogen for 10 mins before subjected to microwave heating at 120° C. for 30 mins. The reaction mixture was then partitioned between ethyl acetate/water (ca. 30 mL each). Aqueous layer was separated and re-extracted with ethyl acetate (ca. 25 mL twice). The combined organic layers were dried over MgSO4 and solvent removed in vacuo. The residue was purified using chromatography on silica, eluting with a gradient of 0-100% ethyl acetate in cyclohexane and followed by another purification on silica, eluting with a gradient of 0-40% ethyl acetate in DCM to afford title compound (205 mg). LCMS (A): m/z (M+H)+ 437, C22H24N6O2S requires 436 (acidic).

Example 203

1-methyl-N-(1-methyl-3-(1-(2,2,2-trifluoroethyl)indolin-6-yl)-1H-pyrrolo[2,3-b]pyridin-4-yl)-1H-pyrazole-3-sulfonamide

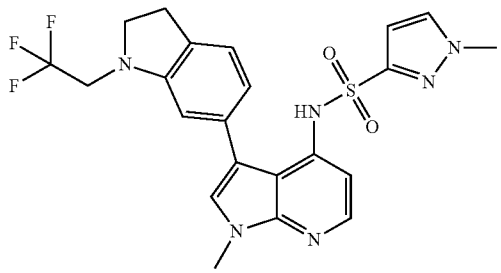 [SMILES: Cn1ccc(S(=O)(=O)Nc2ccnc3c2c(-c2ccc4c(c2)N(CC(F)(F)F)CC4)cn3C)n1]

The title compound was prepared using the procedure as described for Scheme 2. LCMS (A): m/z (M+H)+ 491, C22H21F3N6O2S requires 490 (acidic).

Example 204

N-(3-(1,2-dimethyl-1H-indol-6-yl)-1-methyl-1H-pyrrolo[2,3-b]pyridin-4-yl)-1-methyl-1H-pyrazole-3-sulfonamide

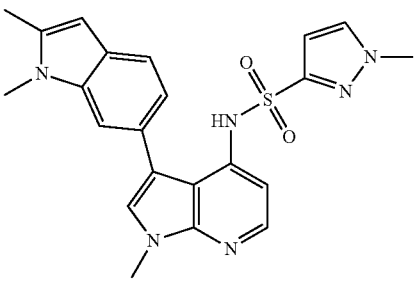

The title compound was prepared using the procedure as described for Scheme 2. LCMS (A): m/z (M+H)+ 435, C22H22N6O2S requires 434 (acidic).

Example 205

N-(3-(3-methoxy-5-(pyrrolidin-1-yl)phenyl)-1-methyl-1H-pyrrolo[2,3-b]pyridin-4-yl)-5-methylpyridine-2-sulfonamide

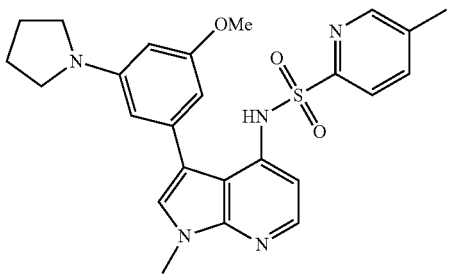 [SMILES: COc1cc(-c2cn(C)c3nccc(NS(=O)(=O)c4ccc(C)cn4)c23)cc(N2CCCC2)c1]

The title compound was prepared using the procedure as described for Scheme 2. LCMS (A): m/z (M+H)+ 478, C25H27N5O3S requires 477 (acidic).

Example 206

N-(3-(5-fluoro-1-methyl-1H-indol-6-yl)-1-methyl-1H-pyrrolo[2,3-b]pyridin-4-yl)-1-methyl-1H-pyrazole-3-sulfonamide

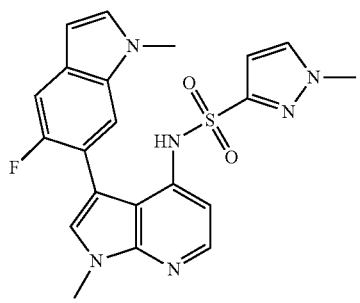 [SMILES: Cn1ccc(S(=O)(=O)Nc2ccnc3c2c(-c2cc4c(ccn4C)cc2F)cn3C)n1]

The title compound was prepared using the procedure as described for Scheme 2. LCMS (A): m/z (M+H)+ 439, C21H19FN6O2S requires 438 (acidic).

Example 207

N-(3-(4-fluoro-1-methyl-1H-indol-6-yl)-1-methyl-1H-pyrrolo[2,3-b]pyridin-4-yl)-1-methyl-1H-pyrazole-3-sulfonamide

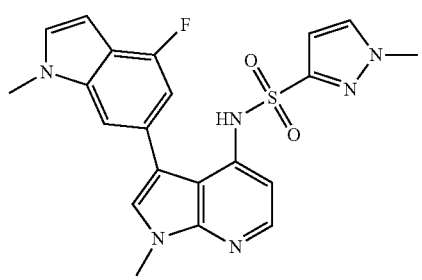

The title compound was prepared using the procedure as described for Scheme 2. LCMS (A): m/z (M+H)+ 439, C21H19FN6O2S requires 438 (acidic).

Example 208

N-(1-methyl-3-(1-methyl-1H-benzo[d]imidazol-6-yl)-1H-pyrrolo[2,3-b]pyridin-4-yl)benzenesulfonamide

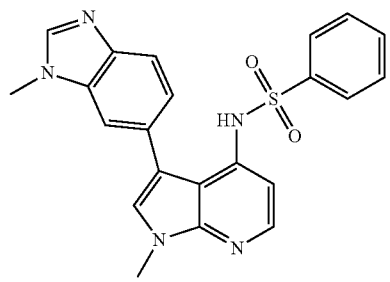 [SMILES: Cn1cnc2ccc(-c3cn(C)c4nccc(NS(=O)(=O)c5ccccc5)c34)cc21]

The title compound was prepared using the procedure as described for Scheme 2. LCMS (A): m/z (M+H)+ 418, C22H19N5O2S requires 417 (acidic).

Example 209

N-(3-(3-chloro-1-methyl-1H-indol-6-yl)-1-methyl-1H-pyrrolo[2,3-b]pyridin-4-yl)-1-methyl-1H-pyrazole-3-sulfonamide

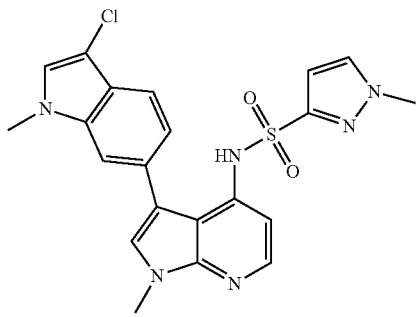

The title compound was prepared using the procedure as described for Scheme 2. LCMS (A): m/z (M+H)+ 455, C21H19ClN6O2S requires 454 (acidic).

Example 210

N-(3-(5-fluoro-1-methylindolin-6-yl)-1-isopropyl-1H-pyrrolo[2,3-b]pyridin-4-yl)-5-methylpyridine-2-sulfonamide

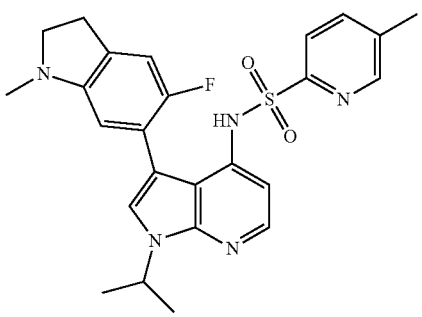

The title compound was prepared using the procedure as described for Scheme 2. LCMS (A): m/z (M+H)+ 480, C25H26FN5O2S requires 479 (acidic).

Example 211

N-(3-(5-methoxy-1,2-dimethyl-1H-indol-6-yl)-1-methyl-1H-pyrrolo[2,3-b]pyridin-4-yl)-1-methyl-1H-pyrazole-3-sulfonamide

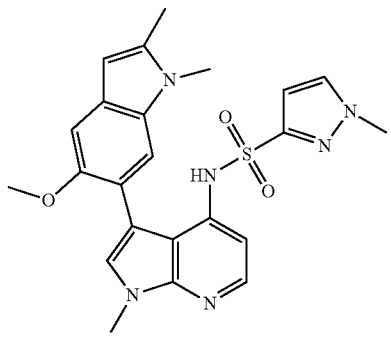

The title compound was prepared using the procedure as described for Scheme 2. LCMS (A): m/z (M+H)+ 465, C23H24N6O3S requires 464 (acidic).

Example 212

N-(3-(5-fluoro-1-methyl-1H-indol-6-yl)-1-methyl-1H-pyrrolo[2,3-b]pyridin-4-yl)-1-isopropylpiperidine-4-sulfonamide

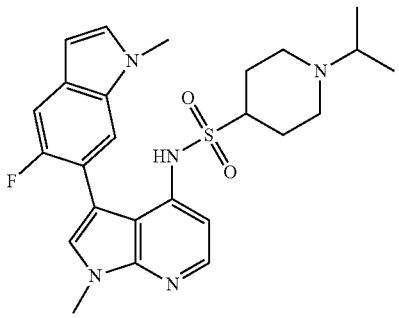 [SMILES: CC(C)N1CCC(S(=O)(=O)Nc2ccnc3c2c(-c2cc4c(ccn4C)cc2F)cn3C)CC1]

The title compound was prepared using the procedure as described for Scheme 2. LCMS (A): m/z (M+H)+ 484, C25H30FN5O2S requires 483 (acidic).

Example 213

N-(3-(5-fluoro-1-methylindolin-6-yl)-1-isopropyl-1H-pyrrolo[2,3-b]pyridin-4-yl)-1-methylpiperidine-4-sulfonamide

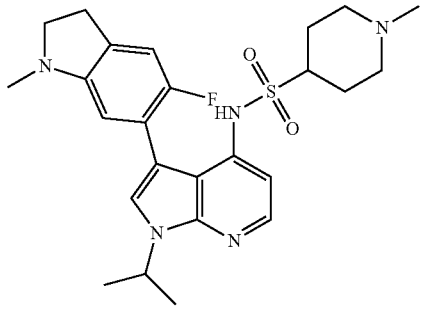

To a stirred solution of N-(3-(5-fluoro-1-methylindolin-6-yl)-1-isopropyl-1H-pyrrolo[2,3-b]pyridin-4-yl)piperidine-4-sulfonamide, hydrochloride (D39) (248 mg, 0.488 mmol) in MeOH (8 mL) at RT was added acetic acid (0.279 mL, 4.88 mmol), formaldehyde (37% solution in water) (0.218 mL, 2.93 mmol) and sodium cyanoborohydride (307 mg, 4.88 mmol). The reaction mixture was stirred at RT for an hour. The reaction mixture was concentrated in vacuo. The residue was passed through SCX cartridge (eluted with MeOH followed by 2M NH3 in MeOH solution; 100 mL each). The basic fractions were concentrated in vacuo to afford a material which was purified using chromatography on silica, eluted with 0-10% MeOH in DCM to afford the title compound (84 mg). LCMS (A): m/z (M+H)+ 486, C25H32FN5O2S requires 485 (acidic).

Example 214

6-methoxy-N-(1-methyl-3-(1-methylindolin-6-yl)-1H-pyrrolo[2,3-b]pyridin-4-yl)pyridine-3-sulfonamide

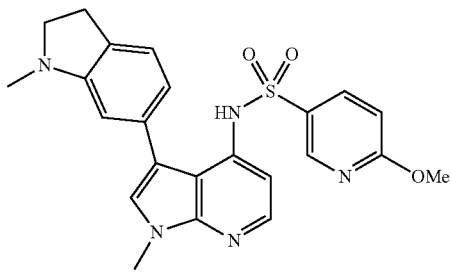 [SMILES: COc1ccc(S(=O)(=O)Nc2ccnc3c2c(-c2ccc4c(c2)N(C)CC4)cn3C)cn1]

The title compound was prepared using the procedure as described for Scheme 2. LCMS (A): m/z (M+H)+ 450, C23H23N5O3S requires 449 (acidic).

Example 215

N-(3-(5-fluoro-1-methylindolin-6-yl)-1-methyl-1H-pyrrolo[2,3-b]pyridin-4-yl)-1-isopropylpiperidine-4-sulfonamide

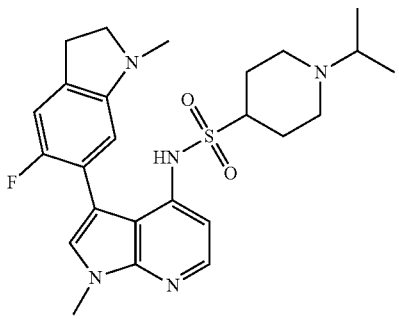

The title compound was prepared using the procedure as described for Scheme 2. LCMS (A): m/z (M+H)+ 486, C25H32FN5O2S requires 485 (acidic).

Example 216

N-(3-(5-fluoro-1-methyl-1H-indol-6-yl)-1-methyl-1H-pyrrolo[2,3-b]pyridin-4-yl)-5-methylpyridine-2-sulfonamide

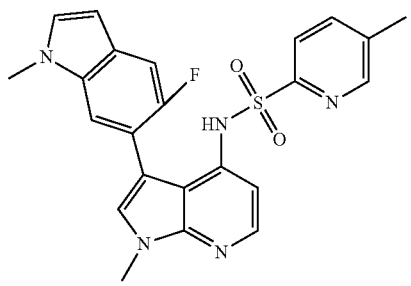

The title compound was prepared using the procedure as described for Scheme 2. LCMS (A): m/z (M+H)+ 450, C23H20FN5O2S requires 449 (acidic).

Example 217

N-(3-(5-fluoro-1-methylindolin-6-yl)-1-methyl-1H-pyrrolo[2,3-b]pyridin-4-yl)tetrahydro-2H-pyran-4-sulfonamide

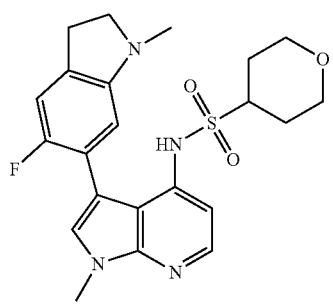 [SMILES: CN1CCc2cc(F)c(-c3cn(C)c4nccc(NS(=O)(=O)C5CCOCC5)c34)cc21]

The title compound was prepared using the procedure as described for Scheme 2. LCMS (A): m/z (M+H)+ 445, C22H25FN4O3S requires 444 (basic).

Example 218

1-acetyl-N-(1-methyl-3-(1-methylindolin-6-yl)-1H-pyrrolo[2,3-b]pyridin-4-yl)piperidine-4-sulfonamide

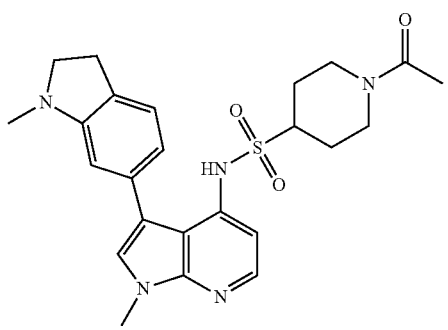 [SMILES: CC(=O)N1CCC(S(=O)(=O)Nc2ccnc3c2c(-c2ccc4c(c2)N(C)CC4)cn3C)CC1]

The title compound was prepared using the procedure as described for Scheme 2. LCMS (A): m/z (M+H)+ 468, C24H29N5O3S requires 467 (acidic).

Example 219

1-methyl-N-(1-methyl-3-(3-(methylthio)phenyl)-1H-pyrrolo[2,3-b]pyridin-4-yl)-1H-pyrazole-3-sulfonamide

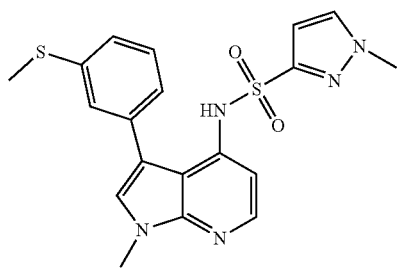

The title compound was prepared using the procedure as described for Scheme 2. LCMS (A): m/z (M+H)+ 414, C19H19N5O2S2 requires 413 (acidic).

Example 220

N-(1-methyl-3-(1-methylindolin-6-yl)-1H-pyrrolo[2,3-b]pyridin-4-yl)-1-(2,2,2-trifluoroethyl)piperidine-4-sulfonamide

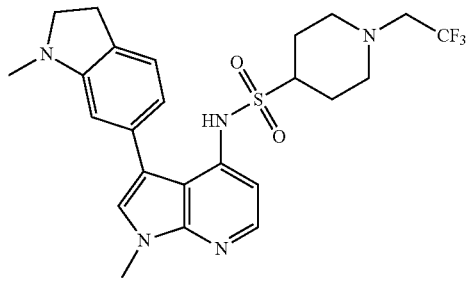 [SMILES: CN1CCc2ccc(-c3cn(C)c4nccc(NS(=O)(=O)C5CCN(CC(F)(F)F)CC5)c34)cc21]

The title compound was prepared using the procedure as described for Scheme 2. LCMS (A): m/z (M+H)+ 508, C24H28F3N5O2S requires 507 (acidic).

Example 221

1-methyl-N-(1-methyl-3-(3-(methylsulfinyl)phenyl)-1H-pyrrolo[2,3-b]pyridin-4-yl)-1H-pyrazole-3-sulfonamide

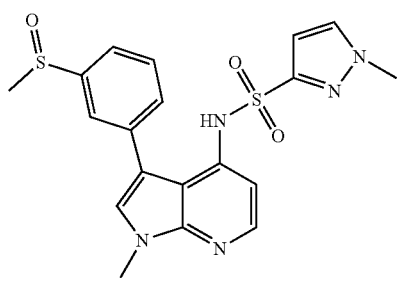

The title compound was prepared using the procedure as described for Scheme 2. LCMS (A): m/z (M+H)⁺ 430, C19H19N5O3S2 requires 429 (acidic).

Example 222

1-acetyl-N-(3-(2-fluoro-5-(pyrrolidin-1-yl)phenyl)-1-isopropyl-1H-pyrrolo[2,3-b]pyridin-4-yl)piperidine-4-sulfonamide

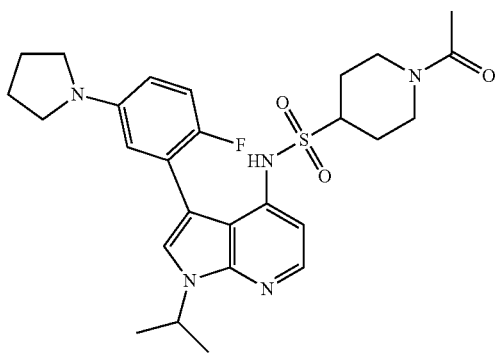 [SMILES: CC(=O)N1CCC(S(=O)(=O)Nc2ccnc3c2c(-c2cc(N4CCCC4)ccc2F)cn3C(C)C)CC1]

The title compound was prepared using the procedure as described for Scheme 2. LCMS (A): m/z (M+H)⁺ 528, C27H34FN5O3S requires 527 (acidic).

Example 223

N-(3-(5-fluoro-1-methylindolin-6-yl)-1-methyl-1H-pyrrolo[2,3-b]pyridin-4-yl)-5-methyl-4,5,6,7-tetrahydropyrazolo[1,5-a]pyrazine-2-sulfonamide

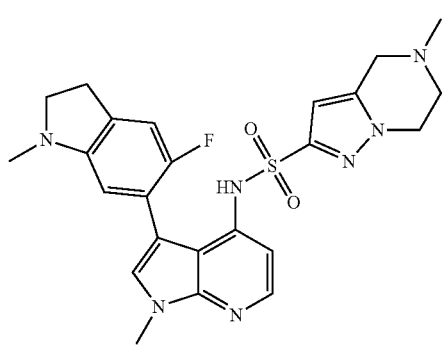

The title compound was prepared using the procedure as described for Scheme 2. LCMS (A): m/z (M+H)⁺ 496, C24H26FN7O2S requires 495 (acidic).

Example 224

N-(3-(5-fluoro-1-(2-methoxyethyl)indolin-6-yl)-1-methyl-1H-pyrrolo[2,3-b]pyridin-4-yl)-1-methyl-1H-pyrazole-3-sulfonamide

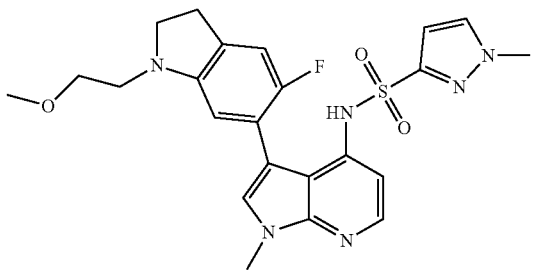

The title compound was prepared using the procedure as described for Scheme 2. LCMS (A): m/z (M+H)⁺ 485, C23H25FN6O3S requires 484 (acidic).

Example 225

N-(3-(5-(7-azabicyclo[2.2.1]heptan-7-yl)-2-fluorophenyl)-1-methyl-1H-pyrrolo[2,3-b]pyridin-4-yl)-1-methyl-1H-pyrazole-3-sulfonamide

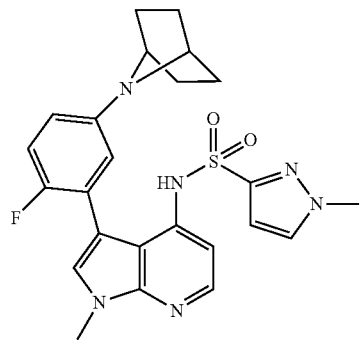 [SMILES: Cn1ccc(S(=O)(=O)Nc2ccnc3c2c(-c2cc(N4C5CCC4CC5)ccc2F)cn3C)n1]

The title compound was prepared using the procedure as described for Scheme 2. LCMS (A): m/z (M+H)⁺ 481, C24H25FN6O2S requires 480 (acidic).

Example 226

N-(3-(5-fluoro-1-(2-hydroxyethyl)indolin-6-yl)-1-methyl-1H-pyrrolo[2,3-b]pyridin-4-yl)-1-methyl-1H-pyrazole-3-sulfonamide

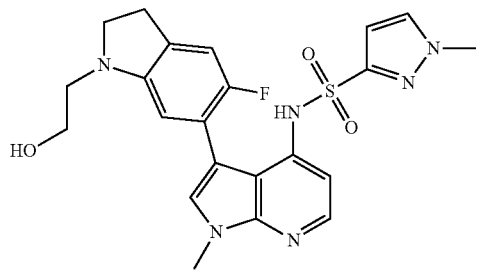 [SMILES: Cn1ccc(S(=O)(=O)Nc2ccnc3c2c(-c2cc4c(cc2F)CCN4CCO)cn3C)n1]

The title compound was prepared using the procedure as described for Scheme 2. LCMS (A): m/z (M+H)+ 471, C22H23FN6O3S requires 470 (acidic).

Example 227

N-(3-(2-fluoro-5-(pyrrolidin-1-yl)phenyl)-1-methyl-1H-pyrrolo[2,3-b]pyridin-4-yl)-5-methyl-4,5,6,7-tetrahydropyrazolo[1,5-a]pyrazine-2-sulfonamide

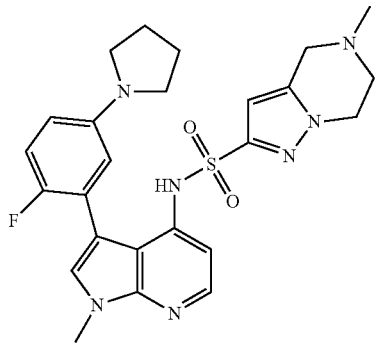 [SMILES: CN1CCn2nc(S(=O)(=O)Nc3ccnc4c3c(-c3cc(N5CCCC5)ccc3F)cn4C)cc2C1]

The title compound was prepared using the procedure as described for Scheme 2. LCMS (A): m/z (M+H)+ 510, C25H28FN7O2S requires 509 (acidic).

Example 228

N-(3-(5-fluoro-1,2,2-trimethyl-3-oxoindolin-6-yl)-1-methyl-1H-pyrrolo[2,3-b]pyridin-4-yl)-1-methyl-1H-pyrazole-3-sulfonamide

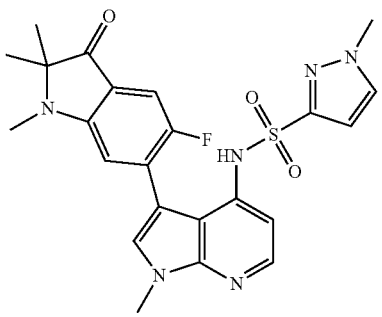 [SMILES: CN1c2cc(-c3cn(C)c4nccc(NS(=O)(=O)c5ccn(C)n5)c34)c(F)cc2C(=O)C1(C)C]

The title compound was prepared using the procedure as described for Scheme 2. LCMS (A): m/z (M+H)+ 483, C23H23FN6O3S requires 482 (acidic).

Example 229

N-(3-(2-fluoro-5-(pyrrolidin-1-yl)phenyl)-1-methyl-1H-pyrrolo[2,3-b]pyridin-4-yl)-1-methylpiperidine-4-sulfonamide

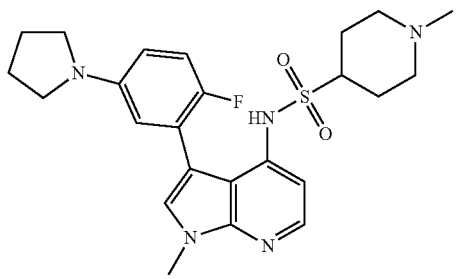 [SMILES: CN1CCC(S(=O)(=O)Nc2ccnc3c2c(-c2cc(N4CCCC4)ccc2F)cn3C)CC1]

The title compound was prepared using the procedure as described for Scheme 2. LCMS (A): m/z (M+H)+ 472, C24H30FN5O2S requires 471 (acidic).

Example 230

Methyl 3-(2-fluoro-5-(pyrrolidin-1-yl)phenyl)-1-methyl-4-(phenylsulfonamido)-1H-pyrrolo[2,3-b]pyridine-2-carboxylate

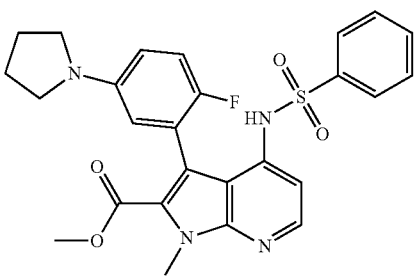 [SMILES: COC(=O)c1c(-c2cc(N3CCCC3)ccc2F)c2c(NS(=O)(=O)c3ccccc3)ccnc2n1C]

The title compound was prepared using the procedure as described for Scheme 4. LCMS (A): m/z (M+H)+ 509, C26H25FN4O4S requires 508 (acidic).

Example 231

3-(2-fluoro-5-(pyrrolidin-1-yl)phenyl)-1-methyl-4-(phenylsulfonamido)-1H-pyrrolo[2,3-b]pyridine-2-carboxylic acid

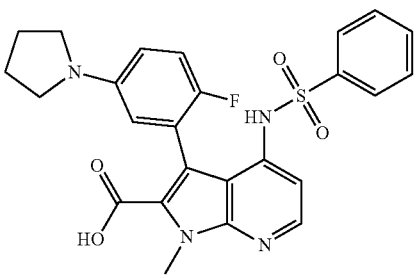 [SMILES: Cn1c(C(=O)O)c(-c2cc(N3CCCC3)ccc2F)c2c(NS(=O)(=O)c3ccccc3)ccnc21]

To a suspension of methyl 3-(2-fluoro-5-(pyrrolidin-1-yl)phenyl)-1-methyl-4-(phenylsulfonamido)-1H-pyrrolo[2,3-b]pyridine-2-carboxylate (47 mg, 0.092 mmol) in MeOH (1 mL) stirred under nitrogen at RT was added a aqueous solution of 6M sodium hydroxide (0.077 mL, 0.462 mmol) in one charge. The reaction mixture was stirred at 80° C. for 2 hours. The reaction mixture was cooled to RT and concentrated. The crude was purified on normal phase silica eluting with 2M ammonia in MeOH and DCM (0-50%) to give the title compound (35 mg). LCMS (A): m/z (M+H)$^+$ 495, C25H23FN4O4S requires 494 (basic).

Example 232

N-(3-(2-fluoro-5-(pyrrolidin-1-yl)phenyl)-1-(1-methylazetidin-3-yl)-1H-pyrrolo[2,3-b]pyridin-4-yl)benzenesulfonamide

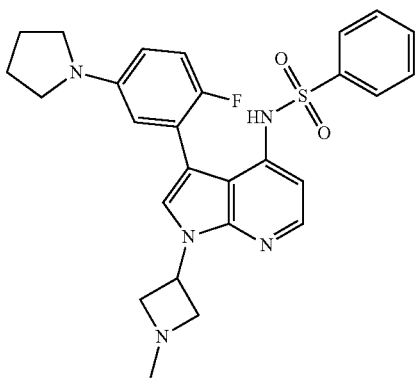 [SMILES: CN1CC(n2cc(-c3cc(N4CCCC4)ccc3F)c3c(NS(=O)(=O)c4ccccc4)ccnc32)C1]

The title compound was prepared using the procedure as described for Scheme 2. LCMS (A): m/z (M+H)$^+$ 506, C27H28FN5O2S requires 505 (acidic).

Example 233

N-(3-(5-fluoro-1-methylindolin-6-yl)-1-(1-methylazetidin-3-yl)-1H-pyrrolo[2,3-b]pyridin-4-yl)benzenesulfonamide

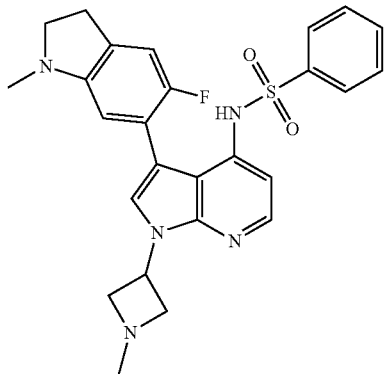 [SMILES: CN1CC(n2cc(-c3cc4c(cc3F)CCN4C)c3c(NS(=O)(=O)c4ccccc4)ccnc32)C1]

To a solution of N-(1-(azetidin-3-yl)-3-(5-fluoro-1-methylindolin-6-yl)-1H-pyrrolo[2,3-b]pyridin-4-yl)benzenesulfonamide D34 (394 mg, 0.825 mmol) in DCM (5 mL) was added formaldehyde (0.307 mL, 4.13 mmol) and sodium cyanoborohydride (104 mg, 1.650 mmol). The final mixture was stirred at RT for 1 h. The mixture was passed through a SCX cartridge eluting with MeOH and followed by 2M ammonia in MeOH. The desired fractions were concentrated and further purified on normal phase silica eluting with 2M ammonia in MeOH and DCM (0-10%) to give the title compound (153 mg). LCMS (A): m/z (M+H)$^+$ 492, C26H26FN5O2S requires 491 (acidic).

Example 234

N-(1-isobutyl-3-(4-methyl-3,4-dihydro-2H-benzo[b][1,4]oxazin-6-yl)-1H-pyrrolo[2,3-b]pyridin-4-yl)-1-methylpiperidine-4-sulfonamide

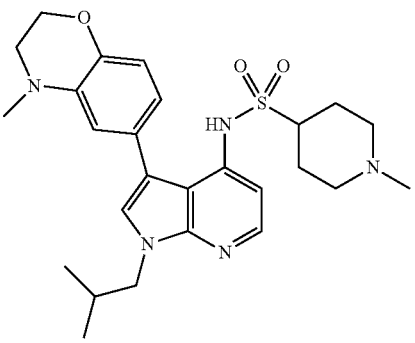

The title compound was prepared using the procedure as described for Scheme 2. LCMS (A): m/z (M+H)$^+$ 498, C26H35N5O3S requires 497 (acidic).

Example 235

N-(3-(2-fluoro-5-(pyrrolidin-1-yl)phenyl)-1-isopropyl-6-methyl-1H-pyrrolo[2,3-b]pyridin-4-yl)-1-methylpiperidine-4-sulfonamide

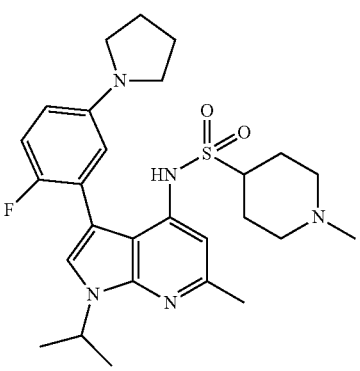 [SMILES: Cc1cc(NS(=O)(=O)C2CCN(C)CC2)c2c(-c3cc(N4CCCC4)ccc3F)cn(C(C)C)c2n1]

The title compound was prepared using the procedure as described for Scheme 6. LCMS (A): m/z (M+H)$^+$ 514, C27H36FN5O2S requires 513 (acidic).

Example 236

N-(3-(2-fluoro-5-(pyrrolidin-1-yl)phenyl)-1-isopropyl-6-methyl-1H-pyrrolo[2,3-b]pyridin-4-yl)-1-methyl-1H-pyrazole-3-sulfonamide

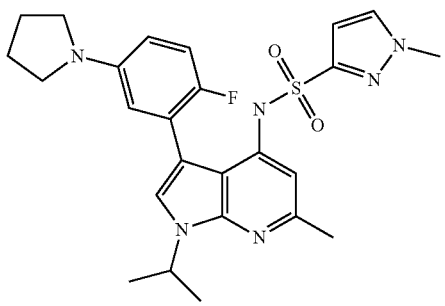 [SMILES: Cc1cc(NS(=O)(=O)c2ccn(C)n2)c2c(-c3cc(N4CCCC4)ccc3F)cn(C(C)C)c2n1]

The title compound was prepared using the procedure as described for Scheme 6. LCMS (A): m/z (M+H)+ 497, C25H29FN6O2S requires 496 (acidic).

Example 237

N-(3-(2-fluoro-5-(pyrrolidin-1-yl)phenyl)-1-isopropyl-6-methyl-1H-pyrrolo[2,3-b]pyridin-4-yl)piperidine-4-sulfonamide

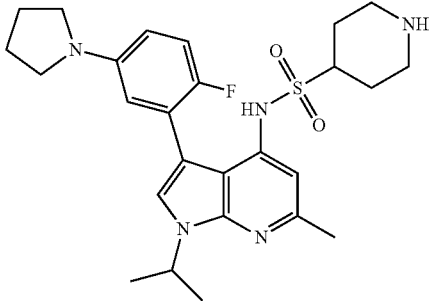 [SMILES: Cc1cc(NS(=O)(=O)C2CCNCC2)c2c(-c3cc(N4CCCC4)ccc3F)cn(C(C)C)c2n1]

The title compound was prepared using the procedure as described for Scheme 6. LCMS (A): m/z (M+H)+ 500, C26H34FN5O2S requires 499 (acidic).

Example 238

N-(3-(2-fluoro-5-(pyrrolidin-1-yl)phenyl)-1,6-dimethyl-1H-pyrrolo[2,3-b]pyridin-4-yl)-1-methyl-1H-pyrazole-3-sulfonamide

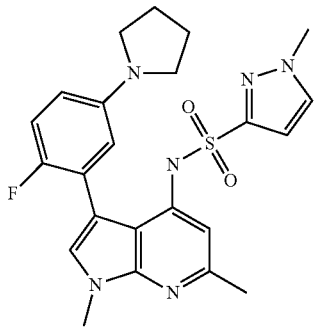 [SMILES: Cc1cc(NS(=O)(=O)c2ccn(C)n2)c2c(-c3cc(N4CCCC4)ccc3F)cn(C)c2n1]

The title compound was prepared using the procedure as described for Scheme 6. LCMS (A): m/z (M+H)+ 469, C23H25FN6O2S requires 468 (acidic).

Example 239

N-(3-(2-fluoro-5-(pyrrolidin-1-yl)phenyl)-1,6-dimethyl-1H-pyrrolo[2,3-b]pyridin-4-yl)-1-methylpiperidine-4-sulfonamide

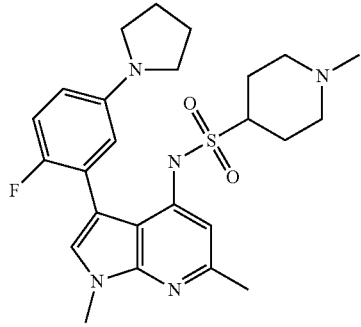 [SMILES: Cc1cc(NS(=O)(=O)C2CCN(C)CC2)c2c(-c3cc(N4CCCC4)ccc3F)cn(C)c2n1]

The title compound was prepared using the procedure as described for Scheme 6. LCMS (A): m/z (M+H)+ 486, C25H32FN5O2S requires 485 (acidic).

Example 240

N-(3-(2-fluoro-5-(pyrrolidin-1-yl)phenyl)-1,6-dimethyl-1H-pyrrolo[2,3-b]pyridin-4-yl)-1-isopropylpiperidine-4-sulfonamide

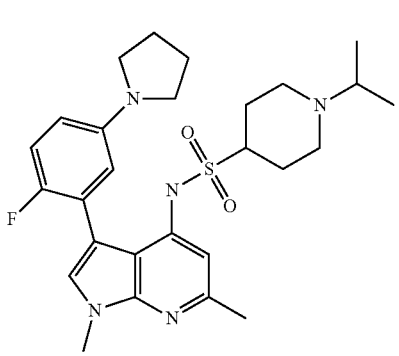 [SMILES: Cc1cc(NS(=O)(=O)C2CCN(C(C)C)CC2)c2c(-c3cc(N4CCCC4)ccc3F)cn(C)c2n1]

The title compound was prepared using the procedure as described for Scheme 6. LCMS (A): m/z (M+H)+ 514, C27H36FN5O2S requires 513 (acidic).

Example 241

1-methyl-N-(1-methyl-3-(4-methyl-3,4-dihydro-2H-benzo[b][1,4]oxazin-6-yl)-1H-pyrrolo[2,3-b]pyridin-4-yl)-1H-pyrazole-3-sulfonamide

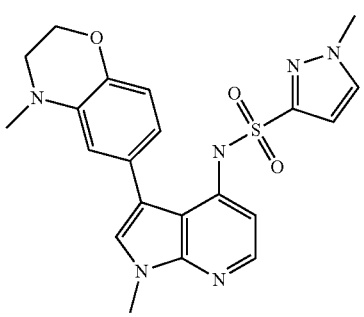 [SMILES: CN1CCOc2ccc(-c3cn(C)c4nccc(NS(=O)(=O)c5ccn(C)n5)c34)cc21]

6-(4-Bromo-1-methyl-1H-pyrrolo[2,3-b]pyridin-3-yl)-4-methyl-3,4-dihydro-2H-benzo[b][1,4]oxazine (344 mg, 0.960 mmol), 1-methyl-1H-pyrazole-3-sulfonamide (D94) (186 mg, 1.152 mmol), xantphos (111 mg, 0.192 mmol), palladium(II) acetate (21.56 mg, 0.096 mmol) and cesium carbonate (939 mg, 2.88 mmol) were dissolved in 1,4-dioxane (10 mL) and refluxed at 130° C. overnight. The mixture was cooled and then acidified with 1M HCl till pH7-8. Water (50 mL) was added and extracted with ethyl acetate (3×50 mL). The combined organics were dried over magnesium sulfate, filtered and concentrated. The residue was purified on normal phase silica eluting with a gradient of 0-100% ethyl acetate in cyclohexane to give an impure fraction which was further triturated with MeOH and followed by purification on reverse phase eluting with acetonitrile and water (+0.2% formic acid) to give the title compound (191 mg). LCMS (A): m/z (M+H)+ 439, C21H22N6O3S requires 438 (acidic).

Alternatively, a mixture of 6-(4-bromo-1-methyl-1H-pyrrolo[2,3-b]pyridin-3-yl)-4-methyl-3,4-dihydro-2H-benzo[b][1,4]oxazine (130 mg, 0.363 mmol), 1-methyl-1H-pyrazole-3-sulfonamide (D94) (88 mg, 0.544 mmol), 2-(dimethylamino)-2'-(dicyclohexylphosphino)biphenyl (21.42 mg, 0.054 mmol), Pd$_2$(dba)$_3$ (24.92 mg, 0.027 mmol), cesium carbonate (355 mg, 1.089 mmol) in 1,4-dioxane (2.7 mL) was heated at 120° C. for 55 mins using a microwave reactor. The reaction mixture was partitioned between ethyl acetate and water. The organic phase was separated, washed with brine, dried and concentrated. The residue was then purified on silica eluting with a gradient of 0-100% ethyl acetate in cyclohexane to afford a material which was further purified by MDAP (acidic condition) to afford the title compound (35 mg). LCMS (A): m/z (M+H)$^+$ 439, C21H22N6O3S requires 438 (acidic).

Example 242

1-ethyl-3-methyl-N-(1-methyl-3-(3-(pyrrolidin-1-yl)phenyl)-1H-pyrrolo[2,3-b]pyridin-4-yl)-1H-pyrazole-4-sulfonamide

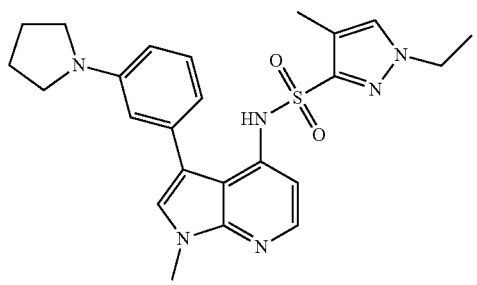 [SMILES: CCn1cc(C)c(S(=O)(=O)Nc2ccnc3c2c(-c2cccc(N4CCCC4)c2)cn3C)n1]

The title compound was prepared using the procedure as described for Scheme 2. LCMS (A): m/z (M+H)$^+$ 465, C24H28N6O2S requires 464 (acidic).

Example 243

N-(3-(2-fluoro-5-(pyrrolidin-1-yl)phenyl)-1,2-dimethyl-1H-pyrrolo[2,3-b]pyridin-4-yl)-1-methyl-1H-pyrazole-3-sulfonamide

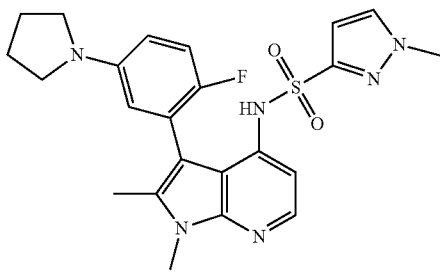 [SMILES: Cc1c(-c2cc(N3CCCC3)ccc2F)c2c(NS(=O)(=O)c3ccn(C)n3)ccnc2n1C]

The title compound was prepared using the procedure as described for Scheme 4. LCMS (A): m/z (M+H)$^+$ 469, C23H25FN6O2S requires 468 (acidic).

Example 244

N-(1-methyl-3-(1-methylindolin-6-yl)-1H-pyrrolo[2,3-b]pyridin-4-yl)tetrahydro-2H-pyran-4-sulfonamide

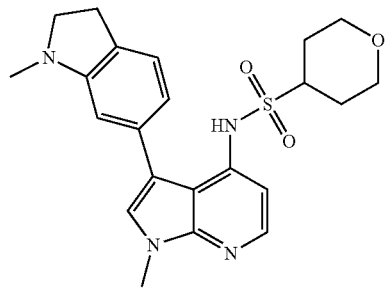 [SMILES: CN1CCc2ccc(-c3cn(C)c4nccc(NS(=O)(=O)C5CCOCC5)c34)cc21]

The title compound was prepared using the procedure as described for Scheme 2. LCMS (A): m/z (M+H)$^+$ 427, C22H26N4O3S requires 426 (acidic).

Example 245

N-(1-methyl-3-(1-methylindolin-6-yl)-1H-pyrrolo[2,3-b]pyridin-4-yl)pyridine-2-sulfonamide

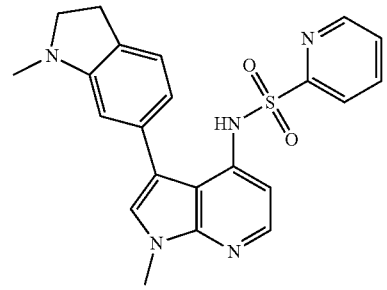 [SMILES: CN1CCc2ccc(-c3cn(C)c4nccc(NS(=O)(=O)c5ccccn5)c34)cc21]

Method A:
The title compound was prepared using the procedure as described for Scheme 2. LCMS (A): m/z (M+H)$^+$ 420, C22H21N5O2S requires 419 (acidic).
Method B:
The title compound was prepared using the procedure as described for Example 180. LCMS (A): m/z (M+H)$^+$ 420, C22H21N5O2S requires 419 (acidic).

Example 246

4-methyl-N-(1-methyl-3-(1-methylindolin-6-yl)-1H-pyrrolo[2,3-b]pyridin-4-yl)pyridine-2-sulfonamide

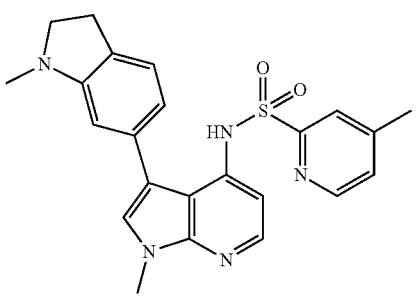

The title compound was prepared using the procedure as described for Scheme 2. LCMS (A): m/z (M+H)+ 434, C23H23N5O2S requires 433 (acidic).

Example 247

N-(3-(5-fluoro-1-methylindolin-6-yl)-1-isopropyl-1H-pyrrolo[2,3-b]pyridin-4-yl)-1-methyl-1H-pyrazole-3-sulfonamide

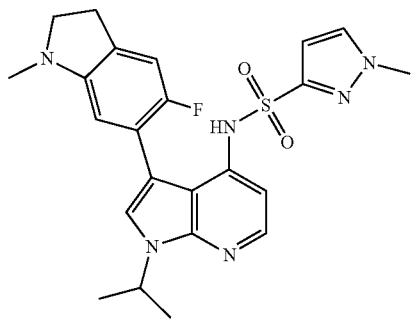

The title compound was prepared using the procedure as described for Scheme 2. LCMS (A): m/z (M+H)+ 469, C23H25FN6O2S requires 468 (acidic).

Example 248 & Example 249

(R)—N-(3-(1,2-dimethylindolin-6-yl)-1-methyl-1H-pyrrolo[2,3-b]pyridin-4-yl)-1-methyl-1H-pyrazole-3-sulfonamide (S)—N-(3-(1,2-dimethylindolin-6-yl)-1-methyl-1H-pyrrolo[2,3-b]pyridin-4-yl)-1-methyl-1H-pyrazole-3-sulfonamide

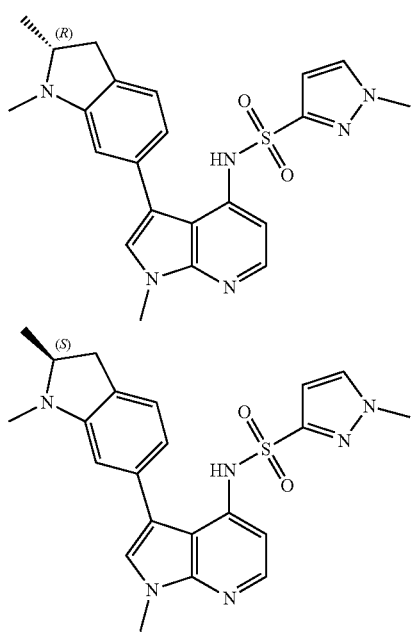

Example 202 was separated by chiral chromatography to give two enantiomers: (R)—N-(3-(1,2-dimethylindolin-6-yl)-1-methyl-1H-pyrrolo[2,3-b]pyridin-4-yl)-1-methyl-1H-pyrazole-3-sulfonamide and (S)—N-(3-(1,2-dimethylindolin-6-yl)-1-methyl-1H-pyrrolo[2,3-b]pyridin-4-yl)-1-methyl-1H-pyrazole-3-sulfonamide. The absolute stereochemistry was not determined LCMS (A): m/z (M+H)+ 437, C22H24N6O2S requires 436 (acidic).

Example 250

N-[1-methyl-3-(2-methyl-1,3-benzoxazol-5-yl)-1H-pyrrolo[2,3-b]pyridin-4-yl]benzenesulfonamide

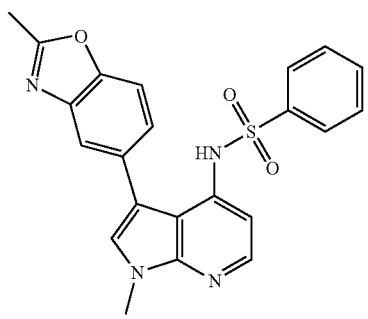 [SMILES: Cc1nc2cc(-c3cn(C)c4nccc(NS(=O)(=O)c5ccccc5)c34)ccc2o1]

The title compound was prepared using the procedure as described for Scheme 2. LCMS (A): m/z (M+H)+ 419, C22H18N4O3S requires 418 (acidic).

Example 251

N-[1-methyl-3-(2-methyl-2,3-dihydro-1H-isoindol-5-yl)-1H-pyrrolo[2,3-b]pyridin-4-yl]benzenesulfonamide

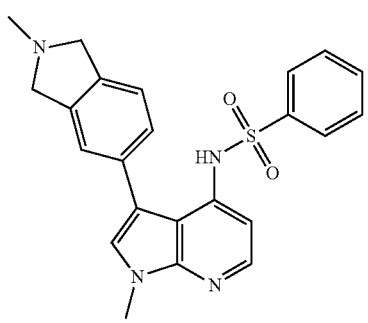 [SMILES: CN1Cc2ccc(-c3cn(C)c4nccc(NS(=O)(=O)c5ccccc5)c34)cc2C1]

The title compound was prepared using the procedure as described for Scheme 2. LCMS (A): m/z (M+H)+ 419, C23H22N4O2S requires 418 (acidic).

Example 252

N-(1-isopropyl-3-(1-methyl-1H-indol-6-yl)-1H-pyrrolo[2,3-b]pyridin-4-yl)-1-methyl-1H-pyrazole-3-sulfonamide

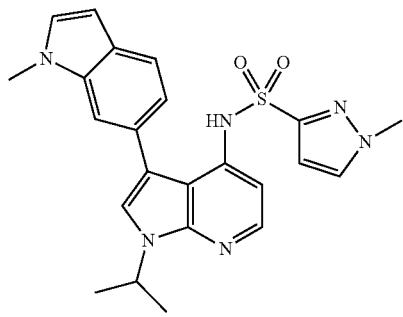

The title compound was prepared using the procedure as described for Scheme 3. LCMS (A): m/z (M–H)⁻ 447, C23H24N6O2S requires 448 (acidic).

Example 253

1-ethyl-N-(1-isopropyl-3-(1-methylindolin-6-yl)-1H-pyrrolo[2,3-b]pyridin-4-yl)-1H-pyrazole-4-sulfonamide

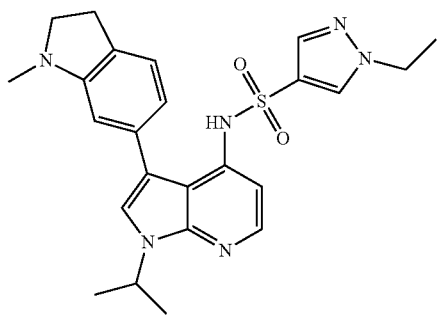 [SMILES: CCn1cc(S(=O)(=O)Nc2ccnc3c2c(-c2ccc4c(c2)N(C)CC4)cn3C(C)C)cn1]

The title compound was prepared using the procedure as described for Scheme 2. LCMS (A): m/z (M–H)⁻ 463, C24H28N6O2S requires 464 (acidic).

Example 254

N-(1-isopropyl-3-(1-methylindolin-6-yl)-1H-pyrrolo[2,3-b]pyridin-4-yl)-1-methyl-1H-pyrazole-4-sulfonamide

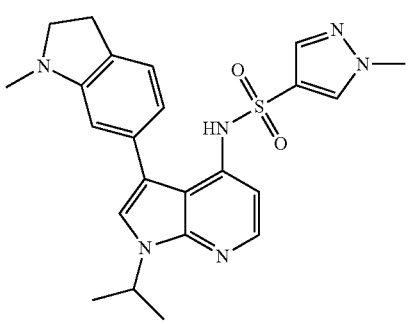

The title compound was prepared using the procedure as described for Scheme 2. LCMS (A): m/z (M–H)⁻ 449, C23H26N6O2S requires 450 (acidic).

Example 255

N-(1-isopropyl-3-(4-methyl-3,4-dihydro-2H-benzo[b][1,4]oxazin-6-yl)-1H-pyrrolo[2,3-b]pyridin-4-yl)-1-methyl-1H-pyrazole-3-sulfonamide

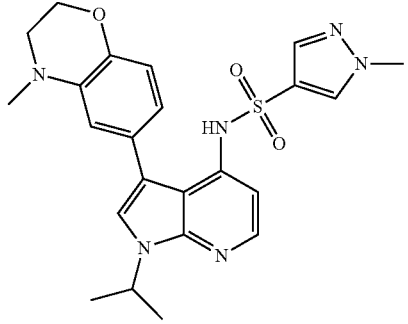

The title compound was prepared using the procedure as described for Scheme 2. LCMS (A): m/z (M+H)⁺ 467, C23H26N6O3S requires 466 (acidic).

Example 256

N-(1-isopropyl-3-(1-methyl-1H-indol-6-yl)-1H-pyrrolo[2,3-b]pyridin-4-yl)morpholine-4-sulfonamide

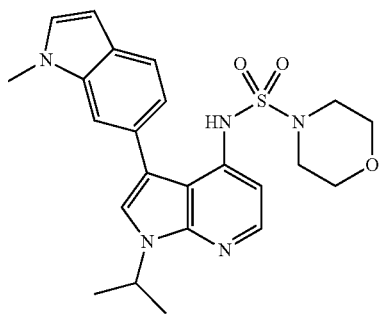 [SMILES: CC(C)n1cc(-c2ccc3ccn(C)c3c2)c2c(NS(=O)(=O)N3CCOCC3)ccnc21]

The title compound was prepared using the procedure as described for Scheme 3. LCMS (A): m/z (M–H)⁻ 452, C23H27N5O3S requires 453 (acidic).

Example 257

N-(3-(2-fluoro-5-(pyrrolidin-1-yl)phenyl)-1-methyl-1H-pyrrolo[2,3-b]pyridin-4-yl)-1-methyl-1H-pyrazole-4-sulfonamide

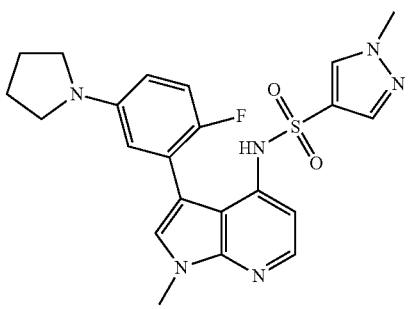 [SMILES: Cn1cc(S(=O)(=O)Nc2ccnc3c2c(-c2cc(N4CCCC4)ccc2F)cn3C)cn1]

The title compound was prepared using the procedure as described for Scheme 2. LCMS (A): m/z (M+H)+ 455, C22H23FN6O2S requires 454 (acidic).

Example 258

N-(1-isopropyl-3-(3-(pyrrolidin-1-yl)phenyl)-1H-pyrrolo[2,3-b]pyridin-4-yl)-1-methyl-1H-pyrazole-5-sulfonamide

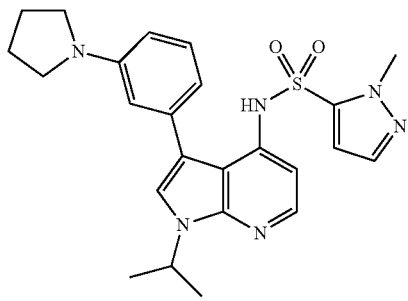 [SMILES: CC(C)n1cc(-c2cccc(N3CCCC3)c2)c2c(NS(=O)(=O)c3ccnn3C)ccnc21]

The title compound was prepared using the procedure as described for Scheme 2. LCMS (A): m/z (M+H)+ 465, C24H28N6O2S requires 464 (acidic).

Example 259

N-(3-(4-isopropyl-3,4-dihydro-2H-benzo[b][1,4]oxazin-6-yl)-1-methyl-1H-pyrrolo[2,3-b]pyridin-4-yl)-1-methyl-1H-pyrazole-3-sulfonamide

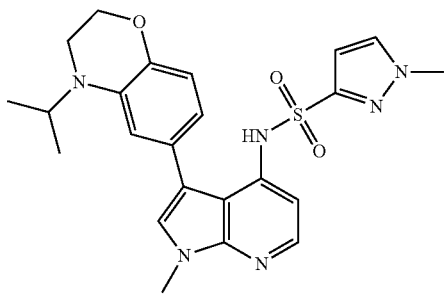 [SMILES: CC(C)N1CCOc2ccc(-c3cn(C)c4nccc(NS(=O)(=O)c5ccn(C)n5)c34)cc21]

The title compound was prepared using the procedure as described for Scheme 2. LCMS (A): m/z (M+H)+ 467, C23H26N6O3S requires 466 (acidic).

Example 260

N-(3-(3-(azetidin-1-yl)phenyl)-1-isopropyl-1H-pyrrolo[2,3-b]pyridin-4-yl)-1-methyl-1H-pyrazole-3-sulfonamide

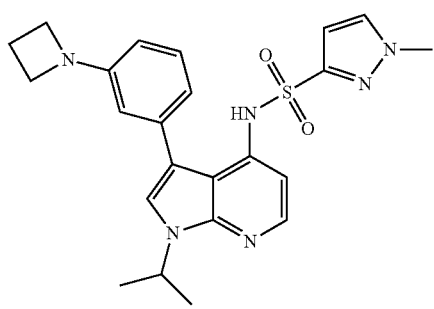 [SMILES: CC(C)n1cc(-c2cccc(N3CCC3)c2)c2c(NS(=O)(=O)c3ccn(C)n3)ccnc21]

The title compound was prepared using the procedure as described for Scheme 2. LCMS (A): m/z (M+H)+ 451, C23H26N6O2S requires 450 (acidic).

Example 261

N-(1-ethyl-3-(3-(pyrrolidin-1-yl)phenyl)-1H-pyrrolo[2,3-b]pyridin-4-yl)-1-methyl-1H-pyrazole-3-sulfonamide

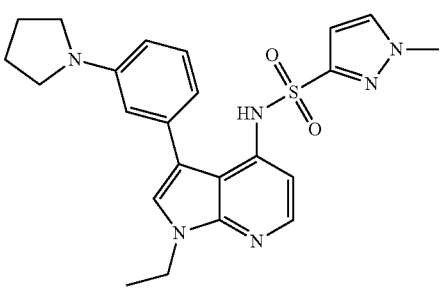 [SMILES: CCn1cc(-c2cccc(N3CCCC3)c2)c2c(NS(=O)(=O)c3ccn(C)n3)ccnc21]

The title compound was prepared using the procedure as described for Scheme 2. LCMS (A): m/z (M−H)− 449, C23H26N6O2S requires 450 (acidic).

Example 262

N-(3-(2-fluoro-5-(pyrrolidin-1-yl)phenyl)-1,2-dimethyl-1H-pyrrolo[2,3-b]pyridin-4-yl)-1-methyl-1H-pyrazole-4-sulfonamide

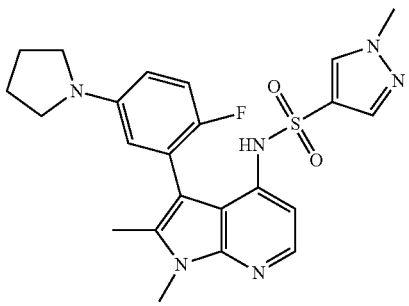 [SMILES: Cc1c(-c2cc(N3CCCC3)ccc2F)c2c(NS(=O)(=O)c3cnn(C)c3)ccnc2n1C]

The title compound was prepared using the procedure as described for Scheme 2. LCMS (A): m/z (M+H)+ 469, C23H25FN6O2S requires 468 (acidic).

Example 263

N-(3-(3-(azetidin-1-yl)phenyl)-1-isopropyl-1H-pyrrolo[2,3-b]pyridin-4-yl)cyclopentanesulfonamide

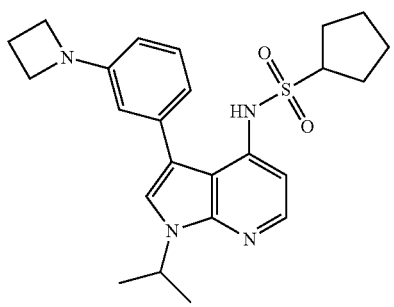 [SMILES: CC(C)n1cc(-c2cccc(N3CCC3)c2)c2c(NS(=O)(=O)C3CCCC3)ccnc21]

The title compound was prepared using the procedure as described for Scheme 2. LCMS (A): m/z (M−H)⁻ 437, C24H30N4O2S requires 438 (acidic).

Example 264

N-(1-methyl-3-(1-methylindolin-6-yl)-1H-pyrrolo[2,3-b]pyridin-4-yl)morpholine-4-sulfonamide

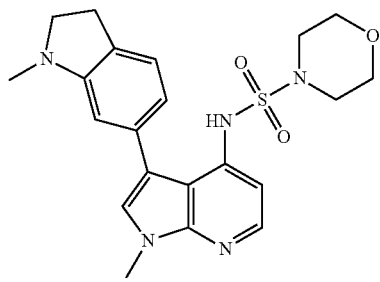 [SMILES: CN1CCc2ccc(-c3cn(C)c4nccc(NS(=O)(=O)N5CCOCC5)c34)cc21]

The title compound was prepared using the procedure as described for Scheme 2. LCMS (A): m/z (M+H)⁺ 428, C21H25N5O3S requires 427 (acidic).

Example 265

N-(1-methyl-3-(1-methylindolin-6-yl)-1H-pyrrolo[2,3-b]pyridin-4-yl)pyrrolidine-1-sulfonamide

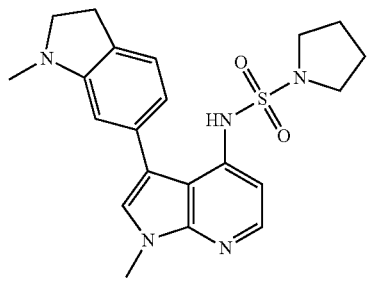 [SMILES: CN1CCc2ccc(-c3cn(C)c4nccc(NS(=O)(=O)N5CCCC5)c34)cc21]

The title compound was prepared using the procedure as described for Scheme 2. LCMS (A): m/z (M+H)⁺ 412, C21H25N5O2S requires 411 (acidic).

Biological Data

Fluorescence Assay

In the high throughput fluorescence assay, superoxide production by NOX2 is measured by coupling the disproportionation of superoxide, which forms $H_2O_2$, to horse radish peroxidase (HRP) and amplex red. The final product is a fluorescent resorufin signal at an excitation and emission of 560 nm and 590 nm, respectively.

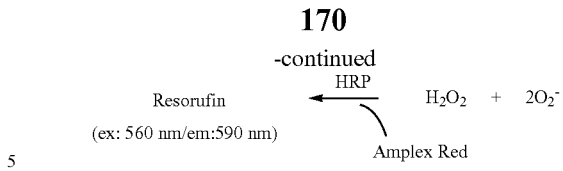

Materials

Baby Hamster Kidney (BHK) cells were transfected with the NOX 2 enzyme complex membrane bound subunits gp91$^{phox}$ and p22$^{phox}$ and membranes prepared using a Waring Blender. Stocks were prepared in a storage buffer of 50 mM Hepes, 1 mM EDTA, 25 ug/ml Bacitracin and 0.1 mM Leupeptin. Native Human-H6-P47, Human-H6-P67 and Human-H6-RAC2 were each baculovirus expressed and purified from 10 L of Sf9 cells freshly harvested by NiNTA agarose and Superdex 200 and prepared in a storage buffer of 25 mM Hepes pH7.4, 150 mM NaCl, 0.5 mM DTT, 1 mM MgCl2 with estimated purity of 90% by gel densitometry.

Flavin Adenine Dinucleotide (FAD), Catalase-Agarose, Dibasic and Monobasic Potassium Phosphate, EGTA, MgCl2, NADPH, Horseradish Peroxidase (HRP), Glycerol, Arachidonic Acid (from Porcine Liver) were purchased from Sigma (St. Louis, Mo.; catalog #s F6625, C9284-50KU, P8584, P5379, E4378, M-1028, N-0411, P-8250, G-5516 and A3555, respectively). GTP-γ-S (Guanosine-5'-O-(3-thiotriphosphate), tetralithium salt, powder) was purchased from Roche Diagnostics (catalog #10220647001). Amplex Red was purchased from Molecular Probes, Inc. (Invitrogen catalog #A12222). Diphenyleneiodonium chloride (DPI) was purchased from Biomol International (Plymouth Meeting, Pa.; catalog #CN-240). Dimethyl sulfoxide (DMSO) from EMD Chemicals (VWR catalog #MX1456-1). 384 well and 1536 well micro-titer plates were purchased from Greiner Bio-One Inc (Monroe, N.C.; catalog #s784076 and 782076, respectively). 50, 250 and 500 ml Conical Centrifuge Tubes were supplied by Corning Life Sciences (Lowell, Mass.). Eppendorf Centrifuge 5804 was supplied by Eppendorf SA, (Hamburg Germany). Multidrop Combi liquid dispenser was supplied by Thermo Electron Corporation (Waltham, Mass.). Cybi-Well liquid dispenser was supplied by Cybio Inc. (Jena, Germany) Hummingbird nanoliter liquid dispenser was supplied by Genomic Solutions (Ann Arbor, Mich.). Viewlux Imager Plate Reader and Envision Plate Reader were supplied by Perkin Elmer (Waltham, Mass.). Infinite F500 Reader and Freedom Evo liquid handler were supplied by Tecan Group Ltd (Switzerland). Spectromax spectrophotometer was supplied by Molecular Devices (Silicon Valley, Calif.).

Assay 1

1×NOX2 Fluorescence Assay Buffer:

All stock solutions were placed on ice, except for the FAD solution, which was placed at RT. The final concentrations in the 1×NOX2 fluorescence assay buffer were 50 mM KPO4 pH 7, 10 uM FAD, 1 mM EGTA, 4 mM MgCl2, 1 uM GTPgS.

2× Substrate Solution:

Catalase-Agarose beads were kept on ice, Amplex Red solution was kept on a 37° C. heat block, 1×NOX2 assay buffer was kept at room temperature. The 2× substrate solution was made by mixing 1×NOX2 fluorescence assay buffer with catalase beads and NADPH. The 2× substrate solution with catalase beads were incubated for 30 minutes at RT and filtered using a 0.2 micron Nalgene filter. Homogenized Amplex Red was then added in the dark. Final 2× substrate solution concentrations in 1× assay buffer were 50 U/mL catalase beads, 100 uM NADPH, 40 uM Amplex Red.

2× Enzyme/NOX2 Complex Solution:

1×NOX2 fluorescence assay buffer at RT was mixed with HRP, Human-H6-RAC2, Human-H6-P47, Human-H6-P67 and gp91/p22 BHK membranes. Arachidonic acid was then added. Final 2× enzyme/NOX2 Complex solution concentrations in 1×NOX2 fluorescence assay buffer were 4 U/mL HRP, 40 nM RAC2, 200 nM P47, 300 nM P67, 0.0092 ug/uL gp91/p22 BHK membranes and 40 uM arachidonic acid.

Reaction Mixture and Assay:

50 mL or 100 mL volumes of 100× stock compounds prepared as 10 mM stock in DMSO for single-shot and dose response testing were dispensed from source plates into black 1536 well or 384 well assay plates, respectively, with a Hummingbird nanoliter liquid dispenser. Full inhibition controls were dispensed using 100 nL/well of 5 mM DPI to column 18 of a 384 well plate or 50 nL/well 5 mM DPI to columns 35 and 36 of a 1536 well plate. Full activity controls were dispensed using 100 nL/well of 100% DMSO to column 6 of a 384 well plate or 50 nL/well 100% DMSO to columns 11 and 12 of a 1536 well plate. 2.5 uL or 5 uL volumes of 2× enzyme solution were dispensed using Cybi-well or Multidrop Combi into black 1536 well or 384 well assay plates, respectively, and allowed to pre-incubate with compound/DMSO for 15 minutes at room temperature. The substrate addition was performed in a dark environment as follows: 2.5 uL or 5 uL volumes of 2× substrate solution were dispensed using Cybi-well or Multidrop Combi into black 1536 well or 384 well assay plates, respectively, and centrifuged for approximately 10 seconds at 1000 rpm. Fluorescence readings were taken following 5 minutes at room temperature with a Viewlux imager plate reader using excitation at 525/20 nm and emission at 598/25 nm.

Assay 2

1×NOX2 Fluorescence Assay Buffer:

Same as described in Assay 1 above.

2.5× Enzyme Solution:

Final concentrations in the 2.5× enzyme solution: 5 U/mL HRP, 50 nM RAC2, 250 nM p47, 375 nM p67, 0.0115 ug/uL gp91/p22 BHK membranes, 50 uM arachidonic Acid 2.5× Substrate Solution Preparation:

Final concentrations in the 2.5× substrate solution: 125 U/mL catalase beads, 125 uM NADPH, 50 uM Amplex Red.

Compound Dilution and Assay:

Serial dilution (1:3.16 fold serial dilution) of the compound was performed in 100% DMSO in 96 well plate—Rows B-H, Col 1-10. Row A=DPI. Starting concentration was 10E-2M (10 mM). Final maximum compound concentration in the assay was 10E-4M (100 uM). DPI (5 mM) in column 11 and 100% DMSO in column 12 provide the positive and negative controls respectively with regards to NOX inhibition. Compounds were diluted 20 fold in 1× buffer using Tecan Freedom Evo. 10 ul of compounds were transferred to 190 ul/well 1× assay buffer. 4 ul compounds from 96 well compound plates were added to 384 well assay plate using Tecan Freedom Evo.

8 ul/well of 2.5× enzyme solution was added to the 384 well assay plate using Combi Multidrop dispensed using the micro-cassette. The plate was centrifuged for approximately 10 seconds up to 1000 rpm. Enzyme was pre-incubated with compound for 15 minutes at room temperature in the dark after which time 8 ul/well of 2.5× substrate solution was added to the 384 well assay plate using Combi Multidrop using the micro-cassette. The plate was centrifuged for approximately 10 seconds up to 1000 rpm. Fluorescence at excitation at 535 nm/25 nm and emission at 590 nm/20 nm was read using the Tecan Infinite F500 plate reader.

Absorbance Assay

In the orthogonal absorbance assay, superoxide production by NOX2 is measured via the reduction of Cytochrome C at an absorbance wavelength of 550 nm (Abo et al. (1992) *J. Biol. Chem.* 267:16767-16770).

Materials

Corning Low Volume 384 Well Black with Clear Flat Bottom Polystyrene Not Treated Microplate, Non-Sterile, Corning Life Sciences Inc. (Big Flats, N.Y.). Cytochrome C (from horse heart), and CHAPS were purchased from Sigma (St. Louis, Mo.; catalog #s C7752 and C3023, respectively).

1×NOX2 Absorbance Assay Buffer:

Same as described in Assay 1 above.

2× Substrate Solution:

6 mL of HPLC grade water was added to 5 mg of NADPH to dilute to a 1 mM stock. 1×NOX2 absorbance assay buffer was mixed with 1.0 mL 1 mM NADPH at RT. Final 2× substrate solution concentrations in 1× assay buffer was 100 uM NADPH.

2× Enzyme/NOX2 Complex Solution:

The following were added to a Corning tube: 1×NOX2 absorbance assay buffer at RT, Human-H6-RAC2, Human-H6-P47, Human-H6-P67, gp91/p22 BHK membranes. Arachidonic acid was then added. Final 2× enzyme/NOX2 Complex solution concentrations in 1×NOX2 absorbance assay buffer were: 80 nM RAC2, 400 nM P47, 600 nM P67, 0.0184 ug/ul gp91/p22 BHK membranes and 40 uM arachidonic Acid.

Reaction Mixture and Assay:

100 nl volumes of 200× stock compounds in DMSO for single-shot and dose response testing were dispensed from source plates into black clear bottom Corning 384 well assay plates with a Hummingbird nanoliter liquid dispenser. Full inhibition controls were dispensed using 100 nL/well of 5 mM DPI to column 18 of a 384 well plate. Full activity controls were dispensed using 100 nL/well of 100% DMSO to column 6 of a 384 well plate. 10 uL volumes of 2× enzyme solution were dispensed using Cybi-well into black clear bottom Corning 384 well assay plates, and allowed to pre-incubate with compound/DMSO for 15 minutes at room temperature. 10 uL volumes of 2× substrate solution were dispensed using Cybi-well into black clear bottom Corning 384 well assay plates and centrifuged for approximately 10 seconds at 1000 rpm. Absorbance readings were measured kinetically on the SpectrMax plate reader for 20 minutes (1 read/minute) at 550 nm. The slope from data points from reads time=4 minutes to 19 minutes were obtained and used for calculations.

Substrate Depletion Assay

In the substrate depletion assay, inhibition of NOX2 is measured by monitoring levels of the substrate, NADPH, at 340 nm.

Materials

1×NOX2 Assay Buffer

Same as described in the fluorescence assay Assay 1 above.

2.5× Enzyme Solution:

Final concentrations in the 2.5× enzyme solution: 50 nM rac2, 250 nM p4'7, 375 nM p67, 0.0115 ug/uL gp91/p22 BHK membranes, 50 uM Arachidonic Acid 2.5× Substrate Solution Preparation:

Final concentrations in the 2.5× substrate solution: 125 uM NADPH

Compound Dilution:

Same as described in the fluorescence assay Assay 1 above.

Assay

Same as described in the fluorescence assay Assay 2 with the exception that post final centrifugation, absorbance at 340 nm is measured using the Tecan Infinite F500 plate reader at t=0 and again at t=60 mins Abs/time is calculated to determine rate of substrate depletion.

Results

All exemplified compounds except Examples 238, 239 and 240 were tested in at least one of the assays described above (Fluorescence Assay, Absorbance Assay, Substrate Depletion Assay). All tested compounds exhibited a pIC50 equal or greater than 4 in at least one of the assays.

Cell-Based Assays

In the cell-based assay, superoxide production by NOX2 was measured in differentiated HL60 cells, a human myelomonocytic leukemia cell line, using either Oxyburst (Assay1) or L012 (Assay2). Differentiation of HL-60 cells to granulocytes increases NOX2 expression. The phorbol 12-myristate 13-acetate (PMA) was used to stimulate the production of superoxide in HL60 cells by activating protein kinase C, which then activated the NADPH oxidase (NOX) enzymes. Inhibition of NOX2 enzyme was detected by the reversal of fluorescence signal (Assay 1) or luminescence signal (Assay2). The control inhibitor used was diphenyleneiodonium chloride (DPI), a flavonoid inhibitor capable of non-selectively inhibiting superoxide produced by NOX enzymes.

Assay 1: in this high-throughput screening assay, oxyburst green bovine serum albumin (BSA) was used to detect superoxide production in HL60 cells. Oxidation of Oxyburst green BSA by hydrogen peroxide as a result of the activation of NOX2 by PMA. Oxyburst green BSA fluorescence was measured at excitation 485 nm and emission 530 nm.

Assay 2: in this assay, a chemiluminescence probe, L-012 was used to detect superoxide production in HL60 cells. L-012 reacted with various types of reactive oxygen species generated by PMA-activated HL60 cells. Luminescence was measured using Tecan Infinite 500.

Materials

The HL60 cells were differentiated into neutrophil-like cells by adding 1.3% DMSO in the media for 3-7 days (Hua, J et al. (2000) *Journal of Leukocyte Biology.* 68:216-224). Iscove's Modified Dulbecco's Media (IMDM) with L-Glutamine and 25 mM HEPES buffer, Fetal Bovine Serum (FBS), Penicillin/Streptomycin, Oxyburst Green BSA, PBS, and HBSS buffer with Calcium Chloride and Magnesium Chloride were purchased from Invitrogen (Catalog #s: 12440-061, 10500-064, 15140-163, O-13291, 14190-250, and 14025-134 respectively). Phorbol 12-myristate 13-acetate (PMA), glucose, and CHAPS were purchased from Sigma (Catalog #s: 79346, D-9434, and C5070 respectively). Diphenyleneiodonium chloride (DPI) was purchased from Toronto Research Chemicals (Catalog #: D491500). L-012 was purchased from Wako Chemical (Catalog #: 120-04891). Dimethyl sulfoxide (DMSO) was purchased EMD Chemicals (VWR Catalog #: MX1456-1). Multidrop combi was purchased from Thermo Electron Corporation (Waltham, Mass., USA). Hummingbird nanoliter liquid dispenser was purchased from Genomics Solution (Ann Arbor, Mich., USA). 384 well low-volume plates and polypropylene 384 well clear plates were purchased from Greiner (Catalog #: 784076 and 781280 respectively). 96 well plate and 384 well plate black assay plates were purchased from Greiner (Catalog #: 655094 and 781098). 96 well plate for compound serial dilution was purchased from Corning (Catalog #: 9017). Acquest or Analyst fluorescence plate reader was purchased from LJL Biosystems/Molecular Devices (California, USA). Tecan Infinite 500 was purchased from Tecan (Switzerland).

Cells Media:

Media for HL60 cells were kept at 4° C. for storage and were warmed to 37° C. in a water bath before use. The media components were IMDM media with 20% FBS and 1% Penicillin/Streptomycin.

Compound Buffer:

Buffer to be used for compound addition and compound dilution consisted of HBSS buffer with 0.1% glucose.

Cells Buffer:

Buffer to be used for cells consisted of HBSS buffer with 0.1% glucose and 0.01% CHAPS.

HL60 cells were thawed and resuspended in Cells media. The cells were centrifuged at 1200 rpm for 5 minutes. Media was aspirated and the cells were resuspended in Cells buffer. The cells were counted and resuspended to $0.5 \times 10^6$ cells/mL.

Assay1

Compound Dilution and Assay:

Full inhibition controls were dispensed using 100 nL/well of 1 mM DPI in DMSO to column 18 of a 384 well plate. Compounds were dispensed using 100 nL/well. Full activity controls were dispensed using 100 nL/well of 4 uM PMA in DMSO. Oxyburst Green BSA was added to cell solution at 10 ug/mL. Using the Multidrop, 10 uL cell solution was added to the entire assay plate. The assay plate was incubated at room temperature for 100 minutes. Fluorescence reading was taken after 100 minutes at excitation 485 and emission 530 using 505 Dichroic on the Acquest or Analyst.

Assay 2

Compound Dilution:

Serial dilution (1:3.16 fold serial dilution) of the compounds was performed in 100% DMSO in 96 well plate—Row B-H Column 1-10. Row A, Column 1-10 contained DPI serial dilution. Starting concentration was $10^{-2}$ M (10 mM). Final concentration in assay was $10^{-4}$ M (100 uM). Compounds were diluted 10 fold in compounds buffer by transferring 10 uL/well of compounds sample in DMSO into 90 uL/well of compounds buffer using Tecan Freedom Evo.

For Assay in 96 Well Plate:

12.5 uL of compounds were dispensed into assay plate column 1-10 using Tecan Freedom Evo. Full inhibition controls were dispensed manually at 12.5 uL/well of 500 uM DPI in DMSO to column 11. 10% DMSO was dispensed to column 12, at 12.5 uL/well. Cells were dispensed to all wells at density $0.5 \times 10^6$ cells/mL, 50 uL/well, using Multidrop Combi large dispensing head. Cells with compounds were incubated in assay plates for 10 minutes at room temperature. 12.5 uL of 120 nM PMA were dispensed to the entire assay plate. Detection reagent, L012, was dispensed as 2.5× solution, 50 uL/well, to the entire assay plate. Luminescence reading was taken at 60 min time point using Tecan Infinite 500.

For Assay in 384 Well Plates:

5 uL of compounds were dispensed into assay plate column 1-10 using Tecan Freedom Evo. Full inhibition controls were dispensed at 5 uL/well of 500 uM DPI in DMSO to column 21 and 22. 10% DMSO was dispensed to column 23 and 24, at 5 uL/well. Cells were dispensed to all wells at density $0.5 \times 10^6$ cells/mL, 20 uL/well, using Multidrop Combi small dispensing head. Cells with compounds were incubated in assay plates for 10 minutes at room temperature. 5 uL of 120 nM PMA were dispensed to the entire assay plate. Detection reagent, L012, was dispensed as 2.5× solution, 20 uL/well, to the entire assay plate. Luminescence reading was taken at 60 min time point using Tecan Infinite 500.

Results

All exemplified compounds except Examples 2, 23 and 129 were tested in at least one of the HL60 assays described above. All tested compounds except Examples 25, 28, 29, 39, 173 and 251 were found to exhibit a pIC50 equal or greater than 4 in at least one of the assays.

Methods of Use

The compounds of the invention are inhibitors of NOX2 and can be useful in the treatment of diseases mediated by NOX enzymes including NOX2. Examples of such diseases include neurodegenerative diseases such as amyotrophic lateral sclerosis, Parkinson's disease, Alzheimer's disease and Huntington's disease; neuroinflammatory diseases such as multiple sclerosis; cardiovascular diseases such as hypertension, atherosclerosis, cardiac hypertrophy, cardiac fibrosis and stroke; ocular diseases such as diabetic macular edema, diabetic retinopathy, age-related macular degeneration and glaucoma; spinal cord injury; traumatic brain injury; reproduction diseases such as prostate cancer and preeclampsia; liver diseases such as hepatic carcinogenesis, non-alcoholic fatty liver disease, liver ischemia, liver necrosis, liver reperfusion injury; kidney diseases such as diabetic nephropathy, chronic renal failure and acute renal failure. Accordingly, in another aspect the invention is directed to methods of treating such diseases.

The methods of treatment of the invention comprise administering a safe and effective amount of a compound according to Formula I or a pharmaceutically-acceptable salt thereof to a patient in need thereof.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

As indicated above, "treatment" of a condition includes prevention of the condition. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human or other animal.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion, intradermal, extraocular and intraocular administration. Intraocular administration includes intravitreal, subretinal, subscleral, intrachoroidal and subconjuctival administration. Inhalation refers to administration into the patient's lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical daily dosages for oral administration range from 0.1 mg to 1000 mg.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

In one embodiment, the invention relates to the use of the compounds of the invention in the preparation of a medicament for the treatment of diseases mediated by NOX enzymes including NOX2. In another embodiment, the invention relates to the compounds of the invention for use in the treatment of diseases mediated by NOX enzymes including NOX2. Examples of such diseases include neurodegenerative diseases such as amyotrophic lateral sclerosis, Parkinson's disease, Alzheimer's disease and Huntington's disease; neuroinflammatory diseases such as multiple sclerosis; cardiovascular diseases such as hypertension, atherosclerosis, cardiac hypertrophy, cardiac fibrosis and stroke; ocular diseases such as diabetic macular edema, diabetic retinopathy, age-related macular degeneration and glaucoma; spinal cord injury; traumatic brain injury; reproduction diseases such as prostate cancer and preeclampsia; liver diseases such as hepatic carcinogenesis, non-alcoholic fatty liver disease, liver ischemia, liver necrosis, liver reperfusion injury; kidney diseases such as diabetic nephropathy, chronic renal failure and acute renal failure.

Compositions

The compounds of the invention will normally, but not necessarily, be formulated into pharmaceutical compositions prior to administration to a patient. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 0.1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesuim stearate, calcium stearate, and talc.

The invention claimed is:
1. A compound of Formula (I) or a pharmaceutically acceptable salt thereof

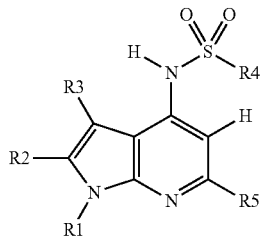

Formula (I)

wherein:
R1 is selected from the group consisting of:
  H,
  C1-C6 alkyl optionally substituted with cycloalkyl or C1-C3 alkoxy substituted with trimethylsilyl,
  $(CH_2)_k$NRaRa, wherein Ra is optionally substituted with halo or NRaRa,
  $(CH_2)_m$Rb, wherein Rb is optionally substituted with C1-C3 alkyl, C1-C3 alkoxy or C(O)ORa, and
  benzyl optionally substituted with C1-C3 alkoxy, halo or C1-C3 alkyl;
R2 is selected from the group consisting of:
  H, halo, CN, $(CH_2)_n$NRaRa, C(O)NRaRa, C(O)ORa, NRaC(O)Ra, $(CH_2)_s$ORa,
  C1-C6 alkyl optionally substituted with Rb,
  indoline optionally substituted with C1-C3 alkyl or halo,
  C2-C6 alkynyl optionally substituted with OH, C1-C3 alkoxy, NRaRa or Rb,
  $(CH_2)_n$Rb, wherein Rb is optionally substituted with C1-C3 alkyl,
  C(O)Rb, wherein Rb is optionally substituted with C1-C3 alkyl,
  $(CH_2)_n$Rc wherein Rc is optionally substituted with one or more substituents selected from the group consisting of C1-C3 alkoxy, C1-C3 alkyl, NRaRa and halo, and
  $(CH_2)_n$Rd wherein Rd is optionally substituted with one or more substituents selected from the group consisting of C1-C3 alkoxy, C1-C3 alkyl, NRaRa and halo;
R3 is selected from the group consisting of:
  H,
  indoline, wherein said indoline is optionally substituted with one or more substituents selected from the group consisting of 1) C1-C6 alkyl optionally substituted with C3-C5 cycloalkyl or halo, 2) cycloalkyl substituted with C1-C3 alkyl, 3) halo, 4) C1-C3 alkoxy, 5) $(CH_2)_t$OH, and 6) =O,
  indole optionally substituted with one or more 1) C1-C3 alkyl optionally substituted with halo, 2) halo, or 3) C1-C3 alkoxy,
  indazole optionally substituted with C1-C3 alkyl or halo,
  $(CH_2)_t$Rc wherein Rc is optionally substituted with one or more substituents selected from the group consisting of:
    1) Rb optionally substituted with C1-C3 alkyl, C(O)ORa or =O,
    2) C1-C3 alkoxy,
    3) C1-C4 alkyl optionally substituted with one to three F,
    4) $(CH_2)_t$NRaC(O)ORa,
    5) $(CH_2)_t$NRaRa,
    6) halo,
    7) —S—$CH_3$,
    8) —S(O)$CH_3$, and
    9) Rd,
  $(CH_2)_t$Rd wherein Rd is optionally substituted with one or more substituents selected from the group consisting of C1-C4 alkyl, C1-C3 alkoxy, halo, Rb, and $(CH_2)_t$NRaRa optionally substituted with dimethylamino;
R4 is selected from the group consisting of:
  C1-C3 alkyl optionally substituted with cycloalkyl,
  C3-C5 cycloalkyl,
  Rb optionally substituted with one or more substituents selected from the group consisting of: 1) C1-C3 alkyl, 2) halo, 3) $(CH_2)_v$NRaRa, 4) $(CH_2)_v$$CF_3$, 5) C(O)$CH_3$ and
  6) benzylcarboxylate,
  Rc optionally substituted with one or more substituents selected from the group consisting of: 1) halo, 2) CN, 3) C1-C3 alkoxy, 4) Rb optionally substituted with C1-C3 alkyl, and 5) $(CH_2)_v$NRaRa, and
  Rd optionally substituted with one or more substituents selected from the group consisting of: 1) C1-C3 alkyl, 2) C1-C3 alkoxy, 3) $CF_3$, 4) halo, and 5) Rb optionally substituted with C1-C3 alkyl;
R5 is H, C1-C3 alkyl or halo;
each Ra is C1-C6 alkyl, C3-C5 cycloalkyl or H;
each Rb is heterocycloalkyl;
each Rc is phenyl;
each Rd is heteroaryl;
s is 1 or 2;
k is 2 or 3;
m is 0, 1, 2 or 3;
n is 0, 1, 2 or 3;
t is 0, 1, 2 or 3; and
v is 0, 1, 2 or 3.

2. A compound or salt according to claim 1, wherein R1 is methyl, ethyl or isopropyl.
3. A compound or salt according to claim 1, wherein R1 is H.
4. A compound or salt according to claim 1, wherein R2 is H.
5. A compound or salt according to claim 1, wherein R2 is methyl.
6. A compound or salt according to claim 1, wherein R3 is indoline substituted with one or more substituents selected from the group consisting of methyl, F and methoxy.
7. A compound or salt according to claim 1, wherein R3 is phenyl substituted with one or two substituents selected from the group consisting of pyrrolidinyl, dimethylamino and F.
8. A compound or salt according to claim 1, wherein R3 is heteroaryl substituted with methyl or heterocycloalkyl.
9. A compound or salt according to claim 1, wherein R4 is piperidine substituted with C1-C3 alkyl.
10. A compound or salt according to claim 1, wherein R4 is heteroaryl optionally substituted with methyl.
11. A compound or salt according to claim 1, wherein R4 is phenyl optionally substituted with halo.
12. A compound or salt according to claim 1, wherein R5 is H or methyl.
13. A pharmaceutical composition which comprises a compound of Formula (I) according to claim 1 and a pharmaceutically acceptable carrier or excipient.

14. A compound or salt according to claim 1 wherein the compound is selected from:
- N-(1-isopropyl-3-(1-methylindolin-6-yl)-1H-pyrrolo[2,3-b]pyridin-4-yl)-1-methyl-1H-pyrazole-3-sulfonamide (E15);
- N-(1-ethyl-3-(5-fluoro-1-methylindolin-6-yl)-1H-pyrrolo[2,3-b]pyridin-4-yl)-1-methyl-1H-pyrazole-3-sulfonamide (E196);
- N-(3-(5-fluoro-1-methylindolin-6-yl)-1,6-dimethyl-1H-pyrrolo[2,3-b]pyridin-4-yl)-1-methyl-1H-pyrazole-3-sulfonamide (E201);
- N-(3-(1,2-dimethylindolin-6-yl)-1-methyl-1H-pyrrolo[2,3-b]pyridin-4-yl)-1-methyl-1H-pyrazole-3-sulfonamide (E202); and
- N-(3-(5-fluoro-1-methylindolin-6-yl)-1-isopropyl-1H-pyrrolo[2,3-b]pyridin-4-yl)-1-methyl-1H-pyrazole-3-sulfonamide (E247).

* * * * *